United States Patent
Ringheim

(10) Patent No.: US 10,766,958 B2
(45) Date of Patent: Sep. 8, 2020

(54) METHODS OF TREATING VITILIGO USING PD-1 BINDING ANTIBODIES

(71) Applicant: CELGENE CORPORATION, Summit, NJ (US)

(72) Inventor: Garth E. Ringheim, Belle Mead, NJ (US)

(73) Assignee: Celgene Corporation, Summit, NJ (US)

( * ) Notice: Subject to any disclaimer, the term of this patent is extended or adjusted under 35 U.S.C. 154(b) by 51 days.

(21) Appl. No.: 15/707,906

(22) Filed: Sep. 18, 2017

(65) Prior Publication Data

US 2018/0094057 A1 Apr. 5, 2018

Related U.S. Application Data

(60) Provisional application No. 62/396,720, filed on Sep. 19, 2016.

(51) Int. Cl.
| | | |
|---|---|---|
| C07K 16/28 | (2006.01) | |
| A61K 47/68 | (2017.01) | |
| A61P 17/00 | (2006.01) | |
| A61K 39/00 | (2006.01) | |

(52) U.S. Cl.
CPC ...... *C07K 16/2818* (2013.01); *A61K 47/6849* (2017.08); *A61P 17/00* (2018.01); *A61K 2039/505* (2013.01); *C07K 2317/21* (2013.01); *C07K 2317/24* (2013.01); *C07K 2317/33* (2013.01); *C07K 2317/34* (2013.01); *C07K 2317/51* (2013.01); *C07K 2317/515* (2013.01); *C07K 2317/52* (2013.01); *C07K 2317/56* (2013.01); *C07K 2317/565* (2013.01); *C07K 2317/567* (2013.01); *C07K 2317/71* (2013.01); *C07K 2317/732* (2013.01); *C07K 2317/734* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,301,144 A | 11/1981 | Iwashita et al. |
| 4,496,689 A | 1/1985 | Mitra |
| 4,526,938 A | 7/1985 | Churchill et al. |
| 4,640,835 A | 2/1987 | Shimizu et al. |
| 4,670,417 A | 6/1987 | Iwasaki et al. |
| 4,676,980 A | 6/1987 | Segal et al. |
| 4,791,192 A | 12/1988 | Nakagawa et al. |
| 4,816,567 A | 3/1989 | Cabilly et al. |
| 4,946,778 A | 8/1990 | Ladner et al. |
| 5,112,946 A | 5/1992 | Maione |
| 5,128,326 A | 7/1992 | Balazs et al. |
| 5,208,020 A | 5/1993 | Chari et al. |
| 5,260,203 A | 11/1993 | Ladner et al. |
| 5,336,603 A | 8/1994 | Capon et al. |
| 5,349,053 A | 10/1994 | Rogers et al. |
| 5,359,046 A | 10/1994 | Capon et al. |
| 5,447,851 A | 9/1995 | Beutler et al. |
| 5,476,786 A | 12/1995 | Huston |
| 5,482,858 A | 1/1996 | Huston et al. |
| 5,500,362 A | 3/1996 | Robinson et al. |
| 5,545,807 A | 8/1996 | Surani et al. |
| 5,565,332 A | 10/1996 | Hoogenboom et al. |
| 5,571,894 A | 11/1996 | Wels et al. |
| 5,587,458 A | 12/1996 | King et al. |
| 5,605,793 A | 2/1997 | Stemmer |
| 5,622,929 A | 4/1997 | Willner et al. |
| 5,629,204 A | 5/1997 | Honjo et al. |
| 5,679,377 A | 10/1997 | Bernstein et al. |
| 5,698,520 A | 12/1997 | Honjo et al. |
| 5,723,125 A | 3/1998 | Chang et al. |
| 5,739,277 A | 4/1998 | Presta et al. |
| 5,750,373 A | 5/1998 | Garrard et al. |
| 5,766,886 A | 6/1998 | Studnicka et al. |
| 5,770,196 A | 6/1998 | Studnicka |
| 5,783,181 A | 7/1998 | Browne et al. |
| 5,811,238 A | 9/1998 | Stemmer et al. |
| 5,821,123 A | 10/1998 | Studnicka |
| 5,821,337 A | 10/1998 | Carter et al. |
| 5,827,690 A | 10/1998 | Meade et al. |
| 5,830,721 A | 11/1998 | Stemmer et al. |
| 5,834,252 A | 11/1998 | Stemmer et al. |
| 5,837,242 A | 11/1998 | Holliger et al. |
| 5,837,458 A | 11/1998 | Minshull et al. |
| 5,844,095 A | 12/1998 | Linsley et al. |

(Continued)

FOREIGN PATENT DOCUMENTS

| | | |
|---|---|---|
| CN | 107137712 A | 9/2017 |
| EP | 0367166 A1 | 5/1990 |

(Continued)

OTHER PUBLICATIONS

Lloyd et al. (Protein Engineering, Design & Selection 2009, 22:159-168 (Year: 2009).*
The Merck Manuals Online Medical Library, [online]. Whitehouse Station, NJ: Merck Research Laboratories, 2006-2007. [retrieved on Sep. 20, 2019]. Retrieved from the Internet: < https://www.merckmanuals.com/professional/dermatologic-disorders/pigmentation-disorders/vitiligo?query=vitiligo#>. Psoriasis. pp. 1-4.*
U.S. Appl. No. 15/707,902, (filed Sep. 18, 2017), 2018/0092975 (Apr. 5, 2018), Methods of Treating Immune Disorders Using PD-1 Binding Proteins, Pending.
U.S. Appl. No. 15/939,177 (filed Mar. 28, 2018), 2018/0289802 (Oct. 11, 2018), Formulations Comprising PD-1 Binding Proteins and Methods of Making Thereof, Pending.
U.S. Appl. No. 15/278,425 (filed Sep. 28, 2016), 2017/0088618 (Mar. 30, 2017), PD-1 Binding Proteins and Methods of Use Thereof, Pending.

(Continued)

*Primary Examiner* — Sharon X Wen
(74) *Attorney, Agent, or Firm* — Jones Day

(57) ABSTRACT

Provided herein are methods for managing, treating, or preventing vitiligo using proteins that specifically bind to Programmed Death-1 (PD-1) and modulate the expression and/or activity of PD-1.

66 Claims, 15 Drawing Sheets

Specification includes a Sequence Listing.

(56) References Cited

U.S. PATENT DOCUMENTS

| | | |
|---|---|---|
| 5,869,046 A | 2/1999 | Presta et al. |
| 5,869,619 A | 2/1999 | Studnicka |
| 5,897,862 A | 4/1999 | Hardy et al. |
| 5,908,626 A | 6/1999 | Chang et al. |
| 5,912,015 A | 6/1999 | Bernstein et al. |
| 5,916,597 A | 6/1999 | Lee et al. |
| 5,989,463 A | 11/1999 | Tracy et al. |
| 6,054,297 A | 4/2000 | Carter et al. |
| 6,075,181 A | 6/2000 | Kucherlapati et al. |
| 6,150,584 A | 11/2000 | Kucherlapati et al. |
| 6,194,551 B1 | 2/2001 | Idusogie et al. |
| 6,407,213 B1 | 6/2002 | Carter et al. |
| 6,492,123 B1 | 12/2002 | Holliger et al. |
| 6,639,055 B1 | 10/2003 | Carter et al. |
| 6,719,971 B1 | 4/2004 | Carter et al. |
| 6,800,738 B1 | 10/2004 | Carter et al. |
| 6,808,710 B1 | 10/2004 | Wood et al. |
| 6,989,250 B2 | 1/2006 | Soderlind et al. |
| 7,029,674 B2 | 4/2006 | Carreno et al. |
| 7,105,328 B2 | 9/2006 | Wood et al. |
| 7,183,387 B1 | 2/2007 | Presta et al. |
| 7,332,581 B2 | 2/2008 | Presta et al. |
| 7,332,582 B2 | 2/2008 | Hardy et al. |
| 7,335,742 B2 | 2/2008 | Presta et al. |
| 7,432,059 B2 | 10/2008 | Freeman et al. |
| 7,488,802 B2 | 2/2009 | Collins et al. |
| 7,521,051 B2 | 4/2009 | Collins et al. |
| 7,524,498 B2 | 4/2009 | Hardy et al. |
| 7,563,869 B2 | 7/2009 | Honjo et al. |
| 7,595,048 B2 | 9/2009 | Honjo et al. |
| 7,612,181 B2 | 11/2009 | Wu et al. |
| 7,612,183 B2 | 11/2009 | Ellis et al. |
| 7,638,492 B2 | 12/2009 | Wood et al. |
| 7,700,301 B2 | 4/2010 | Wood et al. |
| 7,851,598 B2 | 12/2010 | Davis |
| 7,858,746 B2 | 12/2010 | Honjo et al. |
| 7,981,416 B2 | 7/2011 | Hardy et al. |
| 7,985,840 B2 | 7/2011 | Fuh et al. |
| 7,998,479 B2 | 8/2011 | Honjo et al. |
| 8,008,449 B2 | 8/2011 | Korman et al. |
| 8,088,905 B2 | 1/2012 | Collins et al. |
| 8,168,757 B2 | 5/2012 | Finnefrock et al. |
| 8,246,955 B2 | 8/2012 | Honjo et al. |
| 8,354,509 B2 | 1/2013 | Carven et al. |
| 8,409,577 B2 | 4/2013 | Thompson et al. |
| 8,603,930 B2 | 12/2013 | Doesburg et al. |
| 8,685,897 B2 | 4/2014 | Bowers et al. |
| 8,686,119 B2 | 4/2014 | Rotem-Yehudar et al. |
| 8,728,474 B2 | 5/2014 | Honjo et al. |
| 8,735,553 B1 | 5/2014 | Li et al. |
| 8,747,847 B2 | 6/2014 | Rotem-Yehudar et al. |
| 8,779,105 B2 | 7/2014 | Korman et al. |
| 8,900,587 B2 | 12/2014 | Carven et al. |
| 8,927,697 B2 | 1/2015 | Davis et al. |
| 8,945,561 B2 | 2/2015 | Davis |
| 8,951,518 B2 | 2/2015 | Honjo et al. |
| 8,952,136 B2 | 2/2015 | Carven et al. |
| 8,993,731 B2 | 3/2015 | Tyson |
| 9,067,998 B1 | 6/2015 | Clube |
| 9,067,999 B1 | 6/2015 | Honjo et al. |
| 9,073,994 B2 | 7/2015 | Honjo et al. |
| 9,084,776 B2 | 7/2015 | Korman et al. |
| 9,085,625 B2 | 7/2015 | Labrijn et al. |
| 9,102,727 B2 | 8/2015 | Freeman et al. |
| 9,102,728 B2 | 8/2015 | Tyson |
| 9,181,342 B2 | 11/2015 | Davis |
| 9,205,148 B2 | 12/2015 | Langermann et al. |
| 9,217,034 B2 | 12/2015 | Li et al. |
| 9,220,776 B2 | 12/2015 | Sharma et al. |
| 9,243,052 B2 | 1/2016 | Olive et al. |
| 9,309,308 B2 | 4/2016 | Rotem-Yehudar et al. |
| 9,358,289 B2 | 6/2016 | Korman et al. |
| 9,387,247 B2 | 7/2016 | Korman et al. |
| 9,394,365 B1 | 7/2016 | Eisenbach-Schwartz et al. |
| 9,416,175 B2 | 8/2016 | Rotem-Yehudar et al. |
| 9,457,080 B2 | 10/2016 | Freeman et al. |
| 9,492,539 B2 | 11/2016 | Korman et al. |
| 9,492,540 B2 | 11/2016 | Korman et al. |
| 9,499,603 B2 | 11/2016 | Tyson |
| 9,676,853 B2 | 6/2017 | Zhou et al. |
| 9,683,048 B2 | 6/2017 | Freeman et al. |
| 9,701,749 B2 | 7/2017 | Shibayama et al. |
| 2003/0186374 A1 | 10/2003 | Hufton et al. |
| 2004/0005709 A1 | 1/2004 | Hoogenboom et al. |
| 2006/0029600 A1 | 2/2006 | Rubin et al. |
| 2006/0110394 A1 | 5/2006 | Bendig et al. |
| 2009/0075378 A1 | 3/2009 | Horlick et al. |
| 2009/0280116 A1 | 11/2009 | Smith et al. |
| 2011/0177074 A1 | 7/2011 | Sivakumar et al. |
| 2011/0183855 A1 | 7/2011 | Horlick et al. |
| 2011/0229461 A1 | 9/2011 | Tyson |
| 2012/0028301 A1 | 2/2012 | Horlick et al. |
| 2012/0100139 A1 | 4/2012 | Thompson et al. |
| 2013/0202623 A1 | 8/2013 | Chomont et al. |
| 2013/0345406 A1 | 12/2013 | van de Winkel et al. |
| 2014/0094392 A1 | 4/2014 | Bowers et al. |
| 2014/0141022 A1 | 5/2014 | Thompson et al. |
| 2014/0154252 A1 | 6/2014 | Thompson et al. |
| 2014/0161794 A1 | 6/2014 | Lugovskoy et al. |
| 2014/0170705 A1 | 6/2014 | Bowers et al. |
| 2014/0212427 A1 | 7/2014 | Song |
| 2014/0220012 A1 | 8/2014 | Noelle et al. |
| 2014/0220021 A1 | 8/2014 | Shibayama et al. |
| 2014/0234331 A1 | 8/2014 | Korman et al. |
| 2014/0294759 A1 | 10/2014 | Chu et al. |
| 2014/0302070 A1 | 10/2014 | Chen et al. |
| 2014/0335093 A1 | 11/2014 | Olive |
| 2014/0341933 A1 | 11/2014 | Riley et al. |
| 2014/0348743 A1 | 11/2014 | Korman et al. |
| 2014/0377253 A1 | 12/2014 | Harding et al. |
| 2014/0377334 A1 | 12/2014 | Irvine et al. |
| 2015/0004161 A1 | 1/2015 | Zhu |
| 2015/0079192 A1 | 3/2015 | Felder |
| 2015/0086584 A1 | 3/2015 | Gilboa et al. |
| 2015/0118234 A1 | 4/2015 | Honjo et al. |
| 2015/0125955 A1 | 5/2015 | Chomont et al. |
| 2015/0152180 A1 | 6/2015 | Davis et al. |
| 2015/0203579 A1 | 7/2015 | Papadopoulos et al. |
| 2015/0210769 A1* | 7/2015 | Freeman ............ C07K 16/2896 424/136.1 |
| 2015/0252107 A1 | 9/2015 | Stevis et al. |
| 2015/0299322 A1 | 10/2015 | Freeman et al. |
| 2015/0315274 A1 | 11/2015 | Li et al. |
| 2015/0368345 A1 | 12/2015 | Labrijn et al. |
| 2016/0000909 A1 | 1/2016 | Eisenbach-Schwartz et al. |
| 2016/0017051 A1 | 1/2016 | Clube |
| 2016/0068586 A1 | 3/2016 | Tyson |
| 2016/0075783 A1 | 3/2016 | King et al. |
| 2016/0083472 A1 | 3/2016 | Noelle et al. |
| 2016/0130348 A1 | 5/2016 | Langermann et al. |
| 2016/0137731 A1 | 5/2016 | Freeman et al. |
| 2016/0159905 A1 | 6/2016 | Abdiche et al. |
| 2016/0222113 A1 | 8/2016 | Buchanan et al. |
| 2016/0251436 A1 | 9/2016 | Amirina et al. |
| 2016/0251437 A1 | 9/2016 | Dong et al. |
| 2016/0264667 A1 | 9/2016 | Chen et al. |
| 2016/0272708 A1 | 9/2016 | Chen |
| 2016/0280786 A1 | 9/2016 | Hermans et al. |
| 2016/0304606 A9 | 10/2016 | Carven et al. |
| 2016/0319019 A1 | 11/2016 | Amirina et al. |
| 2016/0362492 A1 | 12/2016 | Freeman et al. |
| 2016/0375149 A1 | 12/2016 | Irvine et al. |
| 2016/0376367 A1 | 12/2016 | Yuan et al. |
| 2017/0029508 A1 | 2/2017 | Eisenbach-Schwartz et al. |
| 2017/0029521 A1 | 2/2017 | van de Winkel et al. |
| 2017/0044259 A1 | 2/2017 | Tipton et al. |
| 2017/0044260 A1 | 2/2017 | Baruah et al. |
| 2017/0051060 A1 | 2/2017 | Honjo et al. |
| 2017/0073414 A1 | 3/2017 | Weiskopf et al. |
| 2017/0081409 A1 | 3/2017 | van Dijk et al. |
| 2017/0088615 A1 | 3/2017 | Korman et al. |
| 2017/0088618 A1 | 3/2017 | Bennett et al. |

(56) References Cited

U.S. PATENT DOCUMENTS

| | | | |
|---|---|---|---|
| 2018/0092975 | A1 | 4/2018 | Chan et al. |
| 2018/0289802 | A1 | 10/2018 | Banks et al. |

FOREIGN PATENT DOCUMENTS

| | | | |
|---|---|---|---|
| EP | 0394827 | A1 | 10/1990 |
| EP | 0307434 | B1 | 9/1993 |
| WO | WO 91/05548 | A1 | 5/1991 |
| WO | WO 91/06570 | A1 | 5/1991 |
| WO | WO 92/09690 | A2 | 6/1992 |
| WO | WO 93/06213 | A1 | 4/1993 |
| WO | WO 93/11161 | A1 | 6/1993 |
| WO | WO 93/11794 | A1 | 6/1993 |
| WO | WO 93/16185 | A2 | 8/1993 |
| WO | WO 96/04388 | A1 | 2/1996 |
| WO | WO 96/20698 | A2 | 7/1996 |
| WO | WO 96/22024 | A1 | 7/1996 |
| WO | WO 97/34631 | A1 | 9/1997 |
| WO | WO 99/04813 | A1 | 2/1999 |
| WO | WO 99/15154 | A1 | 4/1999 |
| WO | WO 99/20253 | A1 | 4/1999 |
| WO | WO 99/51642 | A1 | 10/1999 |
| WO | WO 2000/042072 | A2 | 7/2000 |
| WO | WO 2008/047914 | A1 | 4/2008 |
| WO | WO 2010/040105 | A2 | 4/2010 |
| WO | WO 2014/116846 | A2 | 7/2014 |
| WO | WO 2014/121085 | A1 | 8/2014 |
| WO | WO 2014/122271 | A1 | 8/2014 |
| WO | WO 2014/134165 | A1 | 9/2014 |
| WO | WO 2015/038538 | A1 | 3/2015 |
| WO | WO 2015/048520 | A1 | 4/2015 |
| WO | WO 2015/058573 | A1 | 4/2015 |
| WO | WO 2015/103072 | A1 | 7/2015 |
| WO | WO 2015/103139 | A1 | 7/2015 |
| WO | WO 2015/119841 | A1 | 8/2015 |
| WO | WO 2015/120421 | A1 | 8/2015 |
| WO | WO 2015/145360 | A1 | 10/2015 |
| WO | WO 2015/195163 | A1 | 12/2015 |
| WO | WO 2015/200119 | A1 | 12/2015 |
| WO | WO 2016/011069 | A1 | 1/2016 |
| WO | WO 2016/014688 | A2 | 1/2016 |
| WO | WO 2016/014799 | A1 | 1/2016 |
| WO | WO 2016/015685 | A1 | 2/2016 |
| WO | WO 2016/020856 | A2 | 2/2016 |
| WO | WO 2016/068801 | A1 | 5/2016 |
| WO | WO 2016/077397 | A2 | 5/2016 |
| WO | WO 2016/127179 | A2 | 8/2016 |
| WO | WO 2016/137850 | A1 | 9/2016 |
| WO | WO 2016/168716 | A1 | 10/2016 |
| WO | WO 2016/197497 | A1 | 12/2016 |
| WO | WO 2016/210129 | A1 | 12/2016 |
| WO | WO 2017/016497 | A1 | 2/2017 |
| WO | WO 2017/019846 | A1 | 2/2017 |
| WO | WO 2017/021910 | A1 | 2/2017 |
| WO | WO 2017/024515 | A1 | 2/2017 |
| WO | WO 2017/025051 | A1 | 2/2017 |
| WO | WO 2017/042336 | A1 | 3/2017 |
| WO | WO 2017/042633 | A2 | 3/2017 |
| WO | WO2017/054646 | A1 | 4/2017 |
| WO | WO 2017/055443 | A1 | 4/2017 |
| WO | WO 2017/055547 | A1 | 4/2017 |
| WO | WO 2017/058115 | A1 | 4/2017 |
| WO | WO 2017/066561 | A2 | 4/2017 |
| WO | WO 2018/006881 | A1 | 1/2018 |

OTHER PUBLICATIONS

Boyd et al., "Deep sequencing and human antibody repertoire analysis," *Curr. Opin. Immunol.*, 40:103-109 (2016).
Conroy et al., "Antibodies: From novel repertoires to defining and refining the structure of biologically important targets," *Methods*, 116:12-22 (2017).
Damschroder et al., "Analysis of human and primate CD2 molecules by protein sequence and epitope mapping with anti-human CD2 antibodies," *Mol. Immunol.*, 41:985-1000 (2004).
Ferrara et al., "Recombinant renewable polyclonal antibodies," *mAbs*, 7(1):32-41 (2015).
Kasagi et al., "Anti-programmed cell death 1 antibody reduces CD4+PD-1+ T cells and relieves the lupus-like nephritis of NZB/W FI mice," *J. Immunol.*, 184(5):2337-2347 (2010).
Khan et al., "Cross-neutralizing anti-HIV-1 human single chain variable fragments (scFvs) against CD4 binding site and N332 glycan identified from a recombinant phage library," *Sci. Rep.*, 7:45163, 12 pages (2017).
Könitzer et al., "Generation of a highly diverse panel of antagonistic chicken monoclonal antibodies against the GIP receptor," *mAbs*, 9(3):536-549 (2017).
Lazar-Molnar et al., "Crystal structure of the complex between programmed death-1 (PD-1) and its ligand PD-L2," *Proc. Natl. Acad. Sci, USA*, 105(30):10483-10488 (2008).
Lee et al., "Molecular-level analysis of the serum antibody repertoire in young adults before and after seasonal influenza vaccination," *Nature Med.*, 22(12):1456-1464 (2016).
Parola et al., "Integrating high-throughput screening and sequencing for monoclonal antibody discovery and engineering," *Immunology*, 153(1):31-41 (2018).
Perez De La Lastra et al., "Epitope mapping of 10 monoclonal antibodies against the pig analogue of human membrane cofactor protein (MCP)," *Immunology*, 96(4):663-670 (1999).
Seko et al., "Roles of programmed death-1 (PD-1)/PD-1 ligands pathway in the development of murine acute myocarditis caused by coxsackievirus B3," *Cardiovasc. Res.*, 75(1):158-167 (2007).
Sheehan et al., "Phage and yeast display," *Microbiol. Spectr.*, 3(1):AID-0028-2014, 17 pages (2015).
Subudhi et al., "Local expression of B7-H1 promotes organ specific autoimmunity and transplant rejection," *J. Clin. Invest.*, 113(5):694-700 (2004).
Van Regenmortel, "Development of a preventive HIV vaccine requires solving inverse problems which is unattainable by rational vaccine design," *Front Immunol.*, 8:2009 (2018).
Wang et al., "Protective role of programmed death 1 ligand (PD-L1)in nonobese diabetic mice," *Diabetes*, 57(7):1861-1869 (2008).
Zhou et al., "Structural repertoire of HIV-1-neutralizing antibodies targeting the CD4 supersite in 14 donors," *Cell.*, 161(6):1280-1292 (2015).
Ahlmen et al., "Influence of gender on assessments of disease activity and function in early rheumatoid arthritis in relation to radiographic joint damage," *Ann. Rheum. Dis.*, 69:230-233 (2010).
Akkaya et al., "In vivo characterization of inhibitory anti-PD-1 antibody superagonists," Abstracts of the Annual Congreess of the British Society for Immunology, Liverpool, UK, ed., Daniel Altman, Dec. 5-8, 2011, *BSI Oral Abstracts*, Abstract 80.
Aletaha et al., "The Simplified Disease Activity Index (SDAI) and the Clinical Disease Activity Index (CDAI): a Review of Their Usefulness and Validity in Rheumatoid Arthritis," *Clin. Exp. Rheumatol.*, 23(Suppl 39): S100-S108 (2005).
Aletaha et al., "2010 Rheumatoid Arthritis Classification Criteria: An American College of Rheumatology/European League Against Rheumatism Collaborative Initiative," *Arthritis Rheum.*, 62(9):2569-2581 (2010).
Amarnath et al., "Regulatory T cells and human myeloid dendritic cells promote tolerance via programmed death ligand-I," *PLoS Biology*, 8(2):e1000302 (2010).
Amarnath et al., "The PDL1-PD1 axis converts human $T_H1$ cells into regulatory T cells," *Sci. Transl. Med.*, 3(111):111ra120 (2011).
Ashkenazi et al., "Protection against endotoxic shock by a tumor necrosis factor receptor immunoadhesin," *Proc. Natl. Acad. Sci. USA*, 88:10535-10539 (1991).
Barton et al., "Genetic Susceptibility to Rheumatoid Arthritis: An Emerging Picture," *Arthritis Rheum.*, 61(10):1441-1446 (2009).
Bennett et al., "Program death-1 engagement upon TCR activation has distinct effects on costimulation and cytokine-driven proliferation: attenuation of ICOS, IL-4, and IL-21, but not CD28, IL-7, and IL-15 responses," *J. Immunol.*, 170:711-718 (2003).

(56) References Cited

OTHER PUBLICATIONS

Bertsias et al., "Genetic, Immunologic, and Immunohistochemical Analysis of the Programmed Death 1/Programmed Death Ligand 1 Pathway in Human Systemic Lupus Erythematosus," *Arthritis Rheum.*, 60(1):207-218 (2009).

Bommarito et al., "Inflammatory cytokines compromise programmed cell death-1 (PD-1)-mediated T cell suppression in inflammatory arthritis through up-regulation of soluble PD-1," *Clin. Exp. Immunol.*, 188:455-466 (2017).

Bour-Jordan et al., "Intrinsic and Extrinsic Control of Peripheral T-cell Tolerance by Costimulatory Molecules of the CD28/ B7 Family," *Immuno.1 Rev.*, 24(1):180-205 (2011).

Bowman et al., "Sjogren's Systemic Clinical Activity Index (SCAI)—a Systemic Disease Activity Measure for Use in Clinical Trials in Primary Sjogren's Syndrome," *Rheumatology*, 46:1845-1851 (2007).

Brito-Zeron et al., "Systemic activity and mortality in primary Sjögren syndrome: predicting survival using the EULAR-SS Disease Activity Index (ESSDAI) in 1045 patients," *Ann. Rheum. Dis.*, Published Online First: Nov. 28, 2014, doi:10.1136/annrheumdis-2014-206418 (2014).

Burmester et al., "Emerging cell and cytokine targets in rheumatoid arthritis," *Nat. Rev. Rheumatol.*, Advanced Online Publication: Nov. 13, 2012, doi:10.1038/nrrheum.2013.168 (2013).

Choi et al., "Selection Bias in Rheumatic Disease Research," *Nat. Rev. Rheumatol.*, Advanced Online Publication: Apr. 1, 2014, doi:10.1038/nrrheum.2014.36 (2014).

Doran et al., "Trends in Incidence and Mortality in Rheumatoid Arthritis in Rochester, Minnesota, Over a Forty-Year Period," *Arthritis Rheum.*, 46(3):625-631 (2002).

Fazaa et al., "Classification Criteria and Treatment Modalities in Primary Sjogren's Syndrome," *Expert Rev. Clin. Immunol.*, 10(4):543-551 (2014).

Feldman et al., "Psoriasis Assessment Tools in Clinical Trials," *Ann. Rheum. Dis.*,64(Supl II):ii65-ii68 (2005).

Felson et al., "American College of Rheumatology. Preliminary Definition of Improvement in Rheumatoid Arthritis." *Arthritis Rheum.*, 38(6):727-735 (1995).

Fife et al., "The Role of the PD-1 Pathway in Autoimmunity and Peripheral Tolerance," *Ann. N.Y. Acad. Sci.*, 1217:45-59 (2011).

Francisco et al., "PD-L1 regulates the development, maintenance, and function of induced regulatory T cells," *J. Exp. Med.*, 206(13):3015-3029 (2009).

Francisco et al., "The PD-1 Pathway in Tolerance and Autoimmunity," *Immunol. Rev.*, 236:219-242 (2010).

Fransen et al., "Performance of Response Criteria for Assessing Peripheral Arthritis in Patients with Psoriatic Arthritis: Analysis of Data from Randomised Controlled Trials of Two Tumour Necrosis Factor Inhibitors," *Ann. Rheum. Dis.*, 65:1373-1378 (2006).

Fransen et al., "The Disease Activity Score and the EULAR Response Criteria," *Clin. Exp. Rheumatol.*, (5 Suppl 39):Abstract (2005).

Fuentes-Duculan et al., "A Subpopulation of CD163-positive Macrophages is Classically Activated in Psoriasis," *J. Invest. Dermatol.*, 130:2412-2422 (2010).

Gabriel et al., "Epidemiological studies in incidence, prevalence, mortality, and comorbidity of the rheumatic diseases," *Arthritis Res. Ther.*, 11(3):229 (2009).

Gallo et al., "Discovery and Validation of Novel microRNAs in Sjogren's Syndrome Salivary Glands," *Clin. Exp. Rheumatol.*, 32(5):761-762 (2014).

Gay et al., "Molecular and Cellular Mechanisms of Joint Destruction in Rheumatoid Arthritis: Two Cellular Mechanisms Explain Joint Destruction?" *Ann. Rheum. Dis.*, 52(Suppl 1):S39-S47 (1993).

Hatachi et al., "CD4+ PD-1+ T Cells Accumulate as Unique Anergic Cells in Rheumatoid Arthritis Synovial Fluid," *J. Rheumatol.*, 30(7):1410-1419 (2003).

Hirata et al., "Prevention of experimental autoimmune encephalomyelitis by transfer of embryonic stem cell-derived dendritic cells expressing myelin oligodendrocyte glycoprotein peptide along with TRAIL or programmed death-1 ligand," *J. Immunol.*, 174:1888-1897 (2005).

Idusogie et al., "Mapping of the Clq Binding Site on Rituxan, a Chimeric Antibody with a Human IgGl Fc," *J. Immunol.*, 164:4178-4184 (2000).

Kabat et al., "Identical V Region Amino Acid Sequences and Segments of Sequences in Antibodies of Different Specificities. Relative Contributions of VH and VL Genes, Minigenes, and Complementarity-determining Regions to Binding of Antibody-combining Sites," *J. Immunol.*, 147(5):Abstract (1991).

Keir et al., "Programmed death-1 (PD-1):PD-ligand 1 interactions inhibit TCR-mediated positive selection of thymocytes," *J. Immunol.*, 175:7372-7379 (2005).

Konsta et al., "The Contribution of Epigenetics in Sjogren's Syndrome," *Front. Genet.*, 5(7):1-9 (2014).

Kroner et al., "A PD-1 Polymorphism is Associated with Disease Progression in Multiple Sclerosis," *Ann. Neurol.*, 58:50-57 (2005).

Kurko et al., "Genetics of Rheumatoid Arthritis—A Comprehensive Review," *Clinic. Rev. Allerg. Immunol.*, 45(2):170-179 (2013).

Lee et al., "Association of the Programmed Cell Death 1 (PDCD1) Gene Polymorphism with Ankylosing Spondylitis in the Korean Population," *Arthritis Res. Ther.*, 8:R163 (2006).

Li et al., "Human antibodies for immunotherapy development generated via a human B cell hybridoma technology," *Proc. Natl. Acad. Sci. USA*, 103(10):3557-3562 (2006).

Liu et al., "A Promoter Region Polymorphism in PDCD-1 Gene is Associated with Risk of Rheumatoid Arthritis in the Han Chinese Population of Southeastern China," *Int. J Genomics*, 2014:247637 (2014).

Liu et al., "Soluble PD-1 aggravates progression of collagen-induced arthritis through Th1 and Th17 pathways," *Arthritis Res. Ther.*, 17:340 (2015).

Lowes et al., "Pathogenesis and Therapy of Psoriasis," *Nature*, 445:866-873 (2007).

Ma et al., "Human T Follicular Helper (Tfh) Cells and Disease," *Immunol. Cell Biol.*, 92:64-71 (2014).

Maksymowych et al., "14-3-3eta is a Novel Mediator Associated with the Pathogenesis of Rheumatoid Arthritis and Joint Damage," *Arthritis Res. Ther.*, 16:R99 (2014).

Maksymowych et al., "Serum 14-3-3eta is a Novel Marker That Complements Current Serological Measurements to Enhance Detection of Patients with Rheumatoid Arthritis," *J. Rheumatol.*, 41(11):2104-2113 (2014).

Maksymowych et al.,"14-3-3eta: a Novel Biomarker Platform for Rheumatoid Arthritis," *Clin. Exp. Rheumatol.*, 32(Suppl 85):S35-S39 (2014).

Maria et al., "MxA as a Clinically Applicable Biomarker for Identifying Systemic Interferon Type I in Primary Sjogren's Syndrome," *Ann. Rheum. Dis.*, 73:1052-1059 (2014).

Mohammad et al., "Dual Phosphorylation of Btk by Akt/protein Kinase b Provides Docking for 14-3-3zeta, Regulates Shuttling, and Attenuates Both Tonic and Induced Signaling in B Cells," *Mol. Cell. Biol.*, 33(16):3214-3226 (2013).

Moret et al., "Synovial T Cell Hypo-responsiveness to Myeloid Dendritic Cells is Reversed by Preventing PD-1/PD-L1 Interactions," *Arthritis Res. Ther.*, 16:497 (2014).

Nielsen et al., "Association of a Putative Regulatory Polymorphism in the PD-1 Gene with Susceptibility to Type 1 Diabetes," *Tissue Antigens*, 62:492-497 (2003).

Nishimura et al., "Autoimmune Dilated Cardiomyopathy in PD-1 Receptor-Deficient Mice," *Science*, 293:319-322 (2001).

Nishimura et al., "Development of Lupus-like Autoimmune Diseases by Disruption of the PD-1 Gene Encoding an ITIM Motif-carrying Immunoreceptor," *Immunity*, 11(2):141-51 (1999).

Okazaki et al., "A Rheostat for Immune Responses: The Unique Properties of PD-1 and Their Advantages for Clinical Application," *Nat. Immunol.*, 14(12):1212-1218 (2013).

Okazaki et al., "PD-1 and PD-1 Ligands: From Discovery to Clinical Application," *Int. Immunol.*, 19(7):813-824 (2007).

Overdijk et al., "Crosstalk Between Human IgG Isotypes and Murine Effector Cells," *J. Immonol.*, 189:3430-3438 (2012).

(56) References Cited

OTHER PUBLICATIONS

Patel et al., "The Epidemiology of Sjogren's Syndrome," *Clin. Epidemiol.*, 6:247-55 (2014).
Rao et al., "Pathologically expanded peripheral T helper cell subset drives B cells in rheumatoid arthritis," *Nature*, 542:110-114, with supplemental data (2017).
Raptopoulou et al., "The Programmed Death 1/Programmed Death Ligand 1 Inhibitory Pathway is Up-Regulated in Rheumatoid Synovium and Regulates Peripheral T Cell Responses in Human and Murine Arthritis," *Arthritis Rheum.*, 62(7):1870-1880 (2010).
Ray et al., "Autoimmune disorders: An overview of molecular and cellular basis in today's perspective," *J. Clin. Cell. Immunol.*, S10:003 (2012).
Reynolds et al., "Stimulation of the PD-1/PDL-1 T-cell co-inhibitory pathway is effective in treatment of experimental autoimmune glomerulonephritis," *Nephrol. Dial Transplant.*, 27:1343-1350 (2012).
Roy et al., "The role of PD-1 in regulation of macrophage apoptosis and its subversion by Leishmania donovani," *Clin. Transl. Immunology*, 6:e137 (2017).
Sada et al., "Biologic Treatment in Sjogren's Syndrome," *Rheumatology*, 54(2):219-230, doi:10.1093/rheumatology/keu417 (2015).
Salama et al., "Critical role of the programmed death-1 (PD-1) pathway in regulation of experimental autoimmune encephalomyelitis," *J. Exp. Med.*, 198(1):71-78 (2003).
San Jose et al., "Triggering the TCR Complex Causes the Downregulation of Nonengaged Receptors by a Signal Transduction-dependent Mechanism," *Immunity*, 12(2):161-70 (2000).
Saunders et al., "PD-L2:PD-1 involvement in T cell proliferation cytokine production, and integrin-mediated adhesion," *Eur. J. Immunol.*, 35:3561-3569 (2005).
Seror et al., "EULAR Sjogren's Syndrome Disease Activity Index: Development of a Consensus Systemic Disease Activity Index for Primary Sjogren's Syndrome," *Ann. Rheum. Dis.*, 69:1103-1109 (2010).
Seror et al., "EULAR Sjogren's Syndrome Patient Reported Index (ESSPRI): Development of a Consensus Patient Index for Primary Sjogren's Syndrome," *Ann. Rheum. Dis.*, 70:968-972 (2011).
Seror et al., "Outcome Measures for Primary Sjogren's Syndrome: a Comprehensive Review," *J. Autoimmun.*, 51:1-6, doi:10.1016/j.jaut.2013.12.010 (2013).
Shiboski et al., "American College of Rheumatology Classification Criteria for Sjogren's Syndrome: a Data-driven, Expert Consensus Approach in the Sjogren's International Collaborative Clinical Alliance Cohort.," *Arthritis Care Res.*, 64(4):475-487 (2012).
Shields et al., "High resolution mapping of the binding site on human IgG1 for Fc gamma RI, Fc gamma RII, Fc gamma RIII, and FcRn and design of IgG1 variants with improved binding to the Fc gamma R," *J. Biol. Chem.*, 276(9):6591-6604 (2001).
Smolen et al., "EULAR Recommendations for the Management of Rheumatoid Arthritis with Synthetic and Biological Disease-modifying Antirheumatic Drugs," *Ann. Rheum. Dis*, 69:964-975 (2010).
Soleimanifar et al., "Study of Programmed Cell Death 1 (PDCD1) Gene Polymorphims in Iranian Patients with Ankylosing Spondylitis," *Inflammation*, 34(6):707-712 (2011).
Song et al., "Protective effects of Fc-fused PD-L1 on two different animal models of colitis," *Gut*, doi: 10.1136/gutjnl-2014-307311 (2014).
Sullivan et al., "Influence of Rheumatoid Arthritis on Employment, Function, and Productivity in a Nationally Representative Sample in the United States," *J. Rheumatol.*, 37(3):544-549 (2010).
Swindell et al., "Cellular Dissection of Psoriasis for Transcriptome Analyses and the Post-GWAS Era," *BMC Med. Genomics*, 7:27 (2014).
Tan et al., "'Superhumanized' antibodies: reduction of immunogenic potential by complementarity-determining region grafting with human germline sequences: application to an anti-CD28," *J. Immunol.*, 169(2):1119-1125 (2002).
Tan et al., "Quality of life issues and measurement in patients with psoriasis," *Psoriasis: Targets and Therapy*, 2:13-23 (2012).
Taylor et al., "A Systematic Review of Serum Biomarkers Anti-cyclic Citrullinated Peptide and Rheumatoid Factor as Tests for Rheumatoid Arthritis," *Autoimmune Dis.*, doi:10.4061/2011/815038, 1-18 (2011).
Tincani et al., "Novel Aspects of Sjogren's Syndrome in 2012," *BMC Medicine*, 11:93 (2013).
Vitali et al., "Sjogren's Syndrome Disease Damage Index and Disease Activity Index: Scoring Systems for the Assessment of Disease Damage and Disease Activity in Sjogren's Syndrome, Derived from an Analysis of a Cohort of Italian Patients," *Arthritis Rheum.*, 56(7):2223-2231 (2007).
Wan et al., "Aberrant Regulation of Synovial T Cell Activation by Soluble Costimulatory Molecules in Rheumatoid Arthritis," *J. Immunol.*, 177: 8844-8850 (2006).
Wang et al., "Phenotype, Effector Function, and Tissue Localization of PD-1-expressing Human Follicular Helper T Cell Subsets," *BMC Immunol.*, 12:53 (2011).
Wang et al., "The effects of PDL-Ig on collagen-induced arthritis," *Rheumatol. Int.*, 31:513-519 (2011).
Westhoff et al., "Fatigue and Depression Predict Physician Visits and Work Disability in Women with Primary Sjogren's Syndrome: Results from a Cohort Study," *Rheumatology*, 51(2):262-269 (2012).
Yang et al., "Association of Polymorphisms in the Programmed Cell Death 1 (PD-1) and PD-1 Ligand Genes with Ankylosing Spondylitis in a Chinese Population," *Clin. Exp. Rheumatol.* 29:13-18 (2011).
Zhou et al., "Treatment of murine lupus with PD-LIg," *Clin. Immunol.*, doi: 10.1016/j.clim.2015.10.006 (2015).
Abdiche et al., "Assessing kinetic and epitopic diversity across orthogonal monoclonal antibody generation platforms," mAbs, 8(2):264-277 (2016).
Kehry et al., "Discovery of a PD-1 Checkpoint Agonist Antibody for Autoimmune/Inflammatory Disease" Anaptys Bio (2019).
Paluch et al., "Immune Checkpoints as Therapeutic Targets in Autoimmunity," *Frontiers in Immunology.*, 9:2306 (2018).

* cited by examiner

>LC_PD1AB-6-IgG1
DIVMTQSPDSLAVSLGERATINCKSGQSVLYSSNQKNFLAWYQQKPGQPPKLLIYWASTRESGVPDRFSGSGSGTDFTLTISSLQAE
DVAVYYCHQYLYSWTFGQGTKLEIKRTVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC

>HC_PD1AB-6-IgG1
EVQLVQSGAEVKKPGATVKISCKASGFNIKDTYMHWVQQAPGKGLEWMGRIDPANGDRKYDPKFQGRVTITADTSTDTAYMELS
SLRSEDTAVYYCARSGPVYYGSSYVMDYWGQGTTVVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVEPKSCDKTHTCPPCPAPELLGGPSVFLFPPKPKD
TLMISRTPEVTCVVVDVSHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLDSDGSFFLYSKLTVDKSRWQ
QGNVFSCSVMHEALHNHYTQKSLSLSPGK

>HC_PD1AB-6-IgG1-K322A
EVQLVQSGAEVKKPGATVKISCKASGFNIKDTYMHWVQQAPGKGLEWMGRIDPANGDRKYDPKFQGRVTITADTSTDTAYMELS
SLRSEDTAVYYCARSGPVYYGSSYVMDYWGQGTTVVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKKVEPKSCDKTHTCPPCPAPELLGGPSVFLFPPKPKD
TLMISRTPEVTCVVVDVSHEDPEVKFNWYVDGVEVHNAKTKPREEQYNSTYRVVSVLTVLHQDWLNGKEYKCAVSNKALPAPI
EKTISKAKGQPREPQVYTLPPSRDELTKNQVSLTCLVKGFYPSDIAVEWESNGQPENNYKTTPPVLDSDGSFFLYSKLTVDKSRWQ
QGNVFSCSVMHEALHNHYTQKSLSLSPGK

>HC_PD1AB-6-IgG4P
EVQLVQSGAEVKKPGATVKISCKASGFNIKDTYMHWVQQAPGKGLEWMGRIDPANGDRKYDPKFQGRVTITADTSTDTAYMELS
SLRSEDTAVYYCARSGPVYYGSSYVMDYWGQGTTVVSSASTKGPSVFPLAPCSRSTSESTAALGCLVKDYFPEPVTVSWNSGALTS
GVHTFPAVLQSSGLYSLSSVVTVPSSSLGTKTYTCNVDHKPSNTKVDKRVESKYGPPCPPCPAPEFLGGPSVFLFPPKPKDTLMISRTPEVT
CVVVDVSQEDPEVQFNWYVDGVEVHNAKTKPREEQFNSTYRVVSVLTVLHQDWLNGKEYKCKVSNKGLPSSIEKTISKAKGQPREPQVY
TLPPSQEEMTKNQVSLTCLVKGFYPSDIAVEWESNGQPENNYKTTPPVLDSDGSFFLYSRLTVDKSRWQEGNVFSCSVMHEALHNHYTQ
KSLSLSPGK

FIG. 4

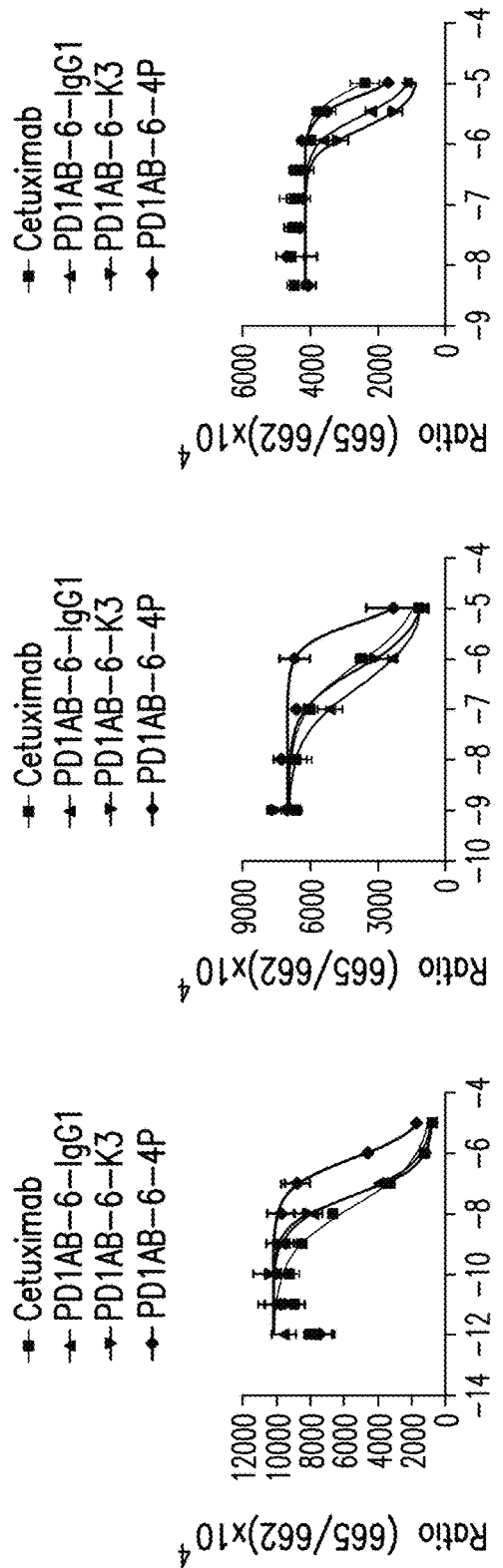

ID NO:8 and a heavy chain variable region having an amino acid sequence of SEQ ID NO:13.

```
                        SEQUENCE LISTING

<160> NUMBER OF SEQ ID NOS: 44

<210> SEQ ID NO 1
<211> LENGTH: 17
<212> TYPE: PRT
<213> ORGANISM: Artificial Sequence
<220> FEATURE:
<223> OTHER INFORMATION: VL CDR1 of Antibodies PD1AB-1, PD1AB-3 and
      PD1AB-6

<400> SEQUENCE: 1

Lys Ser Gly Gln Ser Val Leu Tyr Ser Ser Asn Gln Lys Asn Phe Leu
1               5                   10                  15

Ala

<210> SEQ ID NO 2
<211> LENGTH: 7
<212> TYPE: PRT
<213> ORGANISM: Artificial Sequence
<220> FEATURE:
<223> OTHER INFORMATION: VL CDR2 of Antibodies PD1AB-1, PD1AB-2,
      PD1AB-3, PD1AB-4, PD1AB-5 and PD1AB-6

<400> SEQUENCE: 2

Trp Ala Ser Thr Arg Glu Ser
1               5

<210> SEQ ID NO 3
<211> LENGTH: 8
<212> TYPE: PRT
<213> ORGANISM: Artificial Sequence
<220> FEATURE:
```

```
<223> OTHER INFORMATION: VL CDR3 of Antibodies PD1AB-1, PD1AB-2,
      PD1AB-3, PD1AB-4, PD1AB-5 and PD1AB-6

<400> SEQUENCE: 3

His Gln Tyr Leu Tyr Ser Trp Thr
1               5

<210> SEQ ID NO 4
<211> LENGTH: 10
<212> TYPE: PRT
<213> ORGANISM: Artificial Sequence
<220> FEATURE:
<223> OTHER INFORMATION: VH CDR1 of Antibodies PD1AB-1, PD1AB-2,
      PD1AB-3, PD1AB-4, PD1AB-5 and PD1AB-6

<400> SEQUENCE: 4

Gly Phe Asn Ile Lys Asp Thr Tyr Met His
1               5                   10

<210> SEQ ID NO 5
<211> LENGTH: 10
<212> TYPE: PRT
<213> ORGANISM: Artificial Sequence
<220> FEATURE:
<223> OTHER INFORMATION: VH CDR2 of Antibodies PD1AB-1, PD1AB-2,
      PD1AB-3, PD1AB-4, PD1AB-5 and PD1AB-6

<400> SEQUENCE: 5

Arg Ile Asp Pro Ala Asn Gly Asp Arg Lys
1               5                   10

<210> SEQ ID NO 6
<211> LENGTH: 15
<212> TYPE: PRT
<213> ORGANISM: Artificial Sequence
<220> FEATURE:
<223> OTHER INFORMATION: VH CDR3 of Antibodies PD1AB-1, PD1AB-2,
      PD1AB-3, PD1AB-4, PD1AB-5 and PD1AB-6

<400> SEQUENCE: 6

Ser Gly Pro Val Tyr Tyr Tyr Gly Ser Ser Tyr Val Met Asp Tyr
1               5                   10                  15

<210> SEQ ID NO 7
<211> LENGTH: 17
<212> TYPE: PRT
<213> ORGANISM: Artificial Sequence
<220> FEATURE:
<223> OTHER INFORMATION: VL CDR1 of Antibodies PD1AB-2, PD1AB-4, and
      PD1AB-5

<400> SEQUENCE: 7

Lys Ser Ser Gln Ser Val Leu Tyr Ser Ser Asn Asn Lys Asn Tyr Leu
1               5                   10                  15

Ala

<210> SEQ ID NO 8
<211> LENGTH: 113
<212> TYPE: PRT
<213> ORGANISM: Artificial Sequence
<220> FEATURE:
<223> OTHER INFORMATION: VL domain of Antibodies PD1AB-1 and PD1AB-6

<400> SEQUENCE: 8

Asp Ile Val Met Thr Gln Ser Pro Asp Ser Leu Ala Val Ser Leu Gly
1               5                   10                  15
```

```
Glu Arg Ala Thr Ile Asn Cys Lys Ser Gly Gln Ser Val Leu Tyr Ser
            20                  25                  30

Ser Asn Gln Lys Asn Phe Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Leu Tyr Ser Trp Thr Phe Gly Gln Gly Thr Lys Leu Glu Ile Lys
            100                 105                 110

Arg
```

<210> SEQ ID NO 9
<211> LENGTH: 113
<212> TYPE: PRT
<213> ORGANISM: Artificial Sequence
<220> FEATURE:
<223> OTHER INFORMATION: VL domain of Antibodies PD1AB-2, PD1AB-4 and
    PD1AB-5

<400> SEQUENCE: 9

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Leu Tyr Ser Trp Thr Phe Gly Gln Gly Thr Lys Leu Glu Ile Lys
            100                 105                 110

Arg
```

<210> SEQ ID NO 10
<211> LENGTH: 113
<212> TYPE: PRT
<213> ORGANISM: Artificial Sequence
<220> FEATURE:
<223> OTHER INFORMATION: VL domain of Antibody PD1AB-3

<400> SEQUENCE: 10

```
Asp Ile Val Met Thr Gln Ser Pro Asp Ser Leu Ala Val Ser Leu Gly
1               5                   10                  15

Glu Arg Ala Thr Ile Asn Cys Lys Ser Gly Gln Ser Val Leu Tyr Ser
            20                  25                  30

Ser Asn Gln Lys Asn Phe Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80
```

Ile Ser Asn Leu Gln Ala Glu Asp Val Ala Val Tyr Tyr Cys His Gln
                85                  90                  95

Tyr Leu Tyr Ser Trp Thr Phe Gly Gln Gly Thr Lys Leu Glu Ile Lys
            100                 105                 110

Arg

<210> SEQ ID NO 11
<211> LENGTH: 124
<212> TYPE: PRT
<213> ORGANISM: Artificial Sequence
<220> FEATURE:
<223> OTHER INFORMATION: VH domain of Antibodies PD1AB-1 and PD1AB-2

<400> SEQUENCE: 11

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Thr
            20                  25                  30

Tyr Met His Trp Val Gln Gln Ala Pro Gly Lys Gly Leu Glu Trp Met
        35                  40                  45

Gly Arg Ile Asp Pro Ala Asn Gly Asp Arg Lys Tyr Asp Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Pro Val Tyr Tyr Gly Ser Ser Tyr Val Met Asp
            100                 105                 110

Tyr Trp Gly Gln Gly Thr Thr Val Thr Val Ser Ser
        115                 120

<210> SEQ ID NO 12
<211> LENGTH: 124
<212> TYPE: PRT
<213> ORGANISM: Artificial Sequence
<220> FEATURE:
<223> OTHER INFORMATION: VH domain of Antibodies PD1AB-3 and PD1AB-4

<400> SEQUENCE: 12

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Thr
            20                  25                  30

Tyr Met His Trp Val Gln Gln Ala Pro Gly Lys Gly Leu Glu Trp Met
        35                  40                  45

Gly Arg Ile Asp Pro Ala Asn Gly Asp Arg Lys Tyr Asp Pro Lys Phe
    50                  55                  60

Gln Gly Arg Val Thr Ile Thr Ala Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Pro Val Tyr Tyr Gly Ser Ser Tyr Val Met Asp
            100                 105                 110

Tyr Trp Gly Gln Gly Thr Thr Val Thr Val Ser Ser
        115                 120

<210> SEQ ID NO 13
<211> LENGTH: 124

```
<212> TYPE: PRT
<213> ORGANISM: Artificial Sequence
<220> FEATURE:
<223> OTHER INFORMATION: VH domain of Antibodies PD1AB-5 and PD1AB-6

<400> SEQUENCE: 13

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Thr
            20                  25                  30

Tyr Met His Trp Val Gln Gln Ala Pro Gly Lys Gly Leu Glu Trp Met
        35                  40                  45

Gly Arg Ile Asp Pro Ala Asn Gly Asp Arg Lys Tyr Asp Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Pro Val Tyr Tyr Gly Ser Ser Tyr Val Met Asp
            100                 105                 110

Tyr Trp Gly Gln Gly Thr Thr Val Thr Val Ser Ser
        115                 120

<210> SEQ ID NO 14
<211> LENGTH: 23
<212> TYPE: PRT
<213> ORGANISM: Artificial Sequence
<220> FEATURE:
<223> OTHER INFORMATION: VL FR1 of Antibodies PD1AB-1, PD1AB-2, PD1AB-3,
      PD1AB-4, PD1AB-5 and PD1AB-6

<400> SEQUENCE: 14

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 15
<211> LENGTH: 15
<212> TYPE: PRT
<213> ORGANISM: Artificial Sequence
<220> FEATURE:
<223> OTHER INFORMATION: VL FR2 of Antibodies PD1AB-1, PD1AB-2, PD1AB-3,
      PD1AB-4, PD1AB-5 and PD1AB-6

<400> SEQUENCE: 15

Trp Tyr Gln Gln Lys Pro Gly Gln Pro Pro Lys Leu Leu Ile Tyr
1               5                   10                  15

<210> SEQ ID NO 16
<211> LENGTH: 32
<212> TYPE: PRT
<213> ORGANISM: Artificial Sequence
<220> FEATURE:
<223> OTHER INFORMATION: VL FR3 of Antibodies PD1AB-1, PD1AB-2, PD1AB-4,
      PD1AB-5 and PD1AB-6

<400> SEQUENCE: 16

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30
```

<210> SEQ ID NO 17
<211> LENGTH: 11
<212> TYPE: PRT
<213> ORGANISM: Artificial Sequence
<220> FEATURE:
<223> OTHER INFORMATION: VL FR4 of Antibodies PD1AB-1, PD1AB-2, PD1AB-3,
      PD1AB-4, PD1AB-5 and PD1AB-6

<400> SEQUENCE: 17

Phe Gly Gln Gly Thr Lys Leu Glu Ile Lys Arg
1               5                   10

<210> SEQ ID NO 18
<211> LENGTH: 32
<212> TYPE: PRT
<213> ORGANISM: Artificial Sequence
<220> FEATURE:
<223> OTHER INFORMATION: VL FR3 of Antibody PD1AB-3

<400> SEQUENCE: 18

Gly Val Pro Asp Arg Phe Ser Gly Ser Gly Ser Gly Thr Asp Phe Thr
1               5                   10                  15

Leu Thr Ile Ser Asn Leu Gln Ala Glu Asp Val Ala Val Tyr Tyr Cys
            20                  25                  30

<210> SEQ ID NO 19
<211> LENGTH: 25
<212> TYPE: PRT
<213> ORGANISM: Artificial Sequence
<220> FEATURE:
<223> OTHER INFORMATION: VH FR1 of Antibodies PD1AB-1, PD1AB-2, PD1AB-3
      and PD1AB-4

<400> SEQUENCE: 19

Glu Val Gln Leu Val Gln Ser Gly Ala Glu Val Lys Lys Pro Gly Ala
1               5                   10                  15

Thr Val Lys Ile Ser Cys Lys Val Ser
            20                  25

<210> SEQ ID NO 20
<211> LENGTH: 14
<212> TYPE: PRT
<213> ORGANISM: Artificial Sequence
<220> FEATURE:
<223> OTHER INFORMATION: VH FR2 of Antibodies PD1AB-1, PD1AB-2, PD1AB-3,
      PD1AB-4, PD1AB-5 and PD1AB-6

<400> SEQUENCE: 20

Trp Val Gln Gln Ala Pro Gly Lys Gly Leu Glu Trp Met Gly
1               5                   10

<210> SEQ ID NO 21
<211> LENGTH: 39
<212> TYPE: PRT
<213> ORGANISM: Artificial Sequence
<220> FEATURE:
<223> OTHER INFORMATION: VH FR3 of Antibodies PD1AB-1, PD1AB-2, PD1AB-5
      and PD1AB-6

<400> SEQUENCE: 21

Tyr Asp Pro Lys Phe Gln Gly Arg Val Thr Ile Thr Ala Asp Thr Ser
1               5                   10                  15

Thr Asp Thr Ala Tyr Met Glu Leu Ser Ser Leu Arg Ser Glu Asp Thr
            20                  25                  30

Ala Val Tyr Tyr Cys Ala Arg

<210> SEQ ID NO 22
<211> LENGTH: 11
<212> TYPE: PRT
<213> ORGANISM: Artificial Sequence
<220> FEATURE:
<223> OTHER INFORMATION: VH FR4 of Antibodies PD1AB-1, PD1AB-2, PD1AB-3, PD1AB-4, PD1AB-5 and PD1AB-6

<400> SEQUENCE: 22

Trp Gly Gln Gly Thr Thr Val Thr Val Ser Ser
1               5                   10

<210> SEQ ID NO 23
<211> LENGTH: 39
<212> TYPE: PRT
<213> ORGANISM: Artificial Sequence
<220> FEATURE:
<223> OTHER INFORMATION: VH FR3 of Antibodies PD1AB-3 and PD1AB-4

<400> SEQUENCE: 23

Tyr Asp Pro Lys Phe Gln Gly Arg Val Thr Ile Thr Ala Asp Thr Ser
1               5                   10                  15

Thr Asn Thr Ala Tyr Met Glu Leu Ser Ser Leu Arg Ser Glu Asp Thr
            20                  25                  30

Ala Val Tyr Tyr Cys Ala Arg
        35

<210> SEQ ID NO 24
<211> LENGTH: 25
<212> TYPE: PRT
<213> ORGANISM: Artificial Sequence
<220> FEATURE:
<223> OTHER INFORMATION: VH FR1 of Antibodies PD1AB-5 and PD1AB-6

<400> SEQUENCE: 24

Glu Val Gln Leu Val Gln Ser Gly Ala Glu Val Lys Lys Pro Gly Ala
1               5                   10                  15

Thr Val Lys Ile Ser Cys Lys Ala Ser
            20                  25

<210> SEQ ID NO 25
<211> LENGTH: 341
<212> TYPE: DNA
<213> ORGANISM: Artificial Sequence
<220> FEATURE:
<223> OTHER INFORMATION: VL of Antibodies PD1AB-1 and PD1AB-6

<400> SEQUENCE: 25
gacatcgtga tgacccagtc tccagactcc ctggctgtgt ctctgggcga gagggccacc        60
atcaactgca agtccggtca aagtgtttta tacagttcaa atcagaagaa cttcttggcc       120
tggtaccagc agaaaccagg acagcctcct aagctgctca tttactgggc atccactagg       180
gaatctgggg tccctgaccg attcagtggc agcgggtctg ggacagattt cactctcacc       240
atcagcagcc tgcaagctga agatgtggca gtttattact gtcatcaata cctctactcg       300
tggacgtttg gccaggggac caagctggag atcaaacgga c                           341

<210> SEQ ID NO 26
<211> LENGTH: 341
<212> TYPE: DNA
<213> ORGANISM: Artificial Sequence
<220> FEATURE:

<223> OTHER INFORMATION: VL of Antibodies PD1AB-2, PD1AB-4 and PD1AB-5

<400> SEQUENCE: 26

```
gacatcgtga tgacccagtc tccagactcc ctggctgtgt ctctgggcga gagggccacc      60
atcaactgca gtccagcca gagtgtttta tacagctcca acaataagaa ctacttagct      120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaagctga agatgtggca gtttattact gtcatcaata cctctactcg    300
tggacgtttg gccaggggac caagctggag atcaaacgga c                         341
```

<210> SEQ ID NO 27
<211> LENGTH: 341
<212> TYPE: DNA
<213> ORGANISM: Artificial Sequence
<220> FEATURE:
<223> OTHER INFORMATION: VL of Antibody PD1AB-3

<400> SEQUENCE: 27

```
gacatcgtga tgacccagtc tccagactcc ctggctgtgt ctctgggcga gagggccacc      60
atcaactgca gtccggtca agtgtttta tacagttcaa atcagaagaa cttcttggcc       120
tggtaccagc agaaaccagg acagcctcct aagctgctca tttactgggc atccactagg    180
gaatctgggg tccctgaccg attcagtggc agcgggtctg ggacagattt cactctcacc    240
atcagcaacc tgcaagctga agatgtggca gtttattact gtcatcaata cctctactcg    300
tggacgtttg gccaggggac caagctggag atcaaacgga c                         341
```

<210> SEQ ID NO 28
<211> LENGTH: 372
<212> TYPE: DNA
<213> ORGANISM: Artificial Sequence
<220> FEATURE:
<223> OTHER INFORMATION: VH of Antibodies PD1AB-1 and PD1AB-2

<400> SEQUENCE: 28

```
gaggtccagc tggtacagtc tggggctgag gtgaagaagc ctggggctac agtgaaaatc      60
tcctgcaagg tttctggatt caacattaaa gacacgtata tgcactgggt gcaacaggcc    120
cctggaaaag ggcttgagtg gatgggaagg attgatcctg cgaatggtga taggaaaatat  180
gacccgaagt tccagggcag agtcaccata accgcggaca cgtctacaga cacagcctac   240
atggagctga gcagcctgag atctgaggac acggccgtgt attactgtgc tagatcaggc   300
cctgtttatt actacggtag tagctacgtt atggactact ggggtcaagg aaccacagtc   360
accgtctcct ca                                                        372
```

<210> SEQ ID NO 29
<211> LENGTH: 372
<212> TYPE: DNA
<213> ORGANISM: Artificial Sequence
<220> FEATURE:
<223> OTHER INFORMATION: VH of Antibodies PD1AB-3 and PD1AB-4

<400> SEQUENCE: 29

```
gaggtccagc tggtacagtc tggggctgag gtgaagaagc ctggggctac agtgaaaatc      60
tcctgcaagg tttctggatt caacattaaa gacacgtata tgcactgggt gcaacaggcc    120
cctggaaaag ggcttgagtg gatgggaagg attgatcctg cgaatggtga taggaaaatat  180
gacccgaagt tccagggcag agtcaccata accgcggaca cgtctacaaa cacagcctac   240
```

```
atggagctga gcagcctgag atctgaggac acggccgtgt attactgtgc tagatcaggc    300
cctgtttatt actacggtag tagctacgtt atggactact ggggtcaagg aaccacagtc    360
accgtctcct ca                                                        372
```

<210> SEQ ID NO 30
<211> LENGTH: 372
<212> TYPE: DNA
<213> ORGANISM: Artificial Sequence
<220> FEATURE:
<223> OTHER INFORMATION: VH of Antibodies PD1AB-5 and PD1AB-6

<400> SEQUENCE: 30

```
gaggtccagc tggtacagtc tggggctgag gtgaagaagc ctggggctac agtgaaaatc    60
tcctgcaagg cttctggatt caacattaaa gacacgtata tgcactgggt gcaacaggcc   120
cctggaaaag ggcttgagtg gatgggaagg attgatcctg cgaatggtga taggaaatat   180
gacccgaagt tccagggcag agtcaccata accgcggaca cgtctacaga cacagcctac   240
atggagctga gcagcctgag atctgaggac acggccgtgt attactgtgc tagatcaggc   300
cctgtttatt actacggtag tagctacgtt atggactact ggggtcaagg aaccacagtc   360
accgtctcct ca                                                       372
```

<210> SEQ ID NO 31
<211> LENGTH: 219
<212> TYPE: PRT
<213> ORGANISM: Artificial Sequence
<220> FEATURE:
<223> OTHER INFORMATION: light chain of Antibody PD1AB-6-IgG1

<400> SEQUENCE: 31

Asp Ile Val Met Thr Gln Ser Pro Asp Ser Leu Ala Val Ser Leu Gly
1               5                  10                  15

Glu Arg Ala Thr Ile Asn Cys Lys Ser Gly Gln Ser Val Leu Tyr Ser
            20                  25                  30

Ser Asn Gln Lys Asn Phe Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Leu Tyr Ser Trp Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

```
Pro Val Thr Lys Ser Phe Asn Arg Gly Glu Cys
    210                 215

<210> SEQ ID NO 32
<211> LENGTH: 454
<212> TYPE: PRT
<213> ORGANISM: Artificial Sequence
<220> FEATURE:
<223> OTHER INFORMATION: heavy chain of Antibody PD1AB-6-IgG1

<400> SEQUENCE: 32

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Thr
            20                  25                  30

Tyr Met His Trp Val Gln Ala Pro Gly Lys Gly Leu Glu Trp Met
        35                  40                  45

Gly Arg Ile Asp Pro Ala Asn Gly Asp Arg Lys Tyr Asp Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Pro Val Tyr Tyr Gly Ser Ser Tyr Val Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350
```

```
Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 33
<211> LENGTH: 454
<212> TYPE: PRT
<213> ORGANISM: Artificial Sequence
<220> FEATURE:
<223> OTHER INFORMATION: heavy chain of Antibody PD1AB-6-K3

<400> SEQUENCE: 33

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Thr
            20                  25                  30

Tyr Met His Trp Val Gln Gln Ala Pro Gly Lys Gly Leu Glu Trp Met
        35                  40                  45

Gly Arg Ile Asp Pro Ala Asn Gly Asp Arg Lys Tyr Asp Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Pro Val Tyr Tyr Gly Ser Ser Tyr Val Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255
```

```
Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Ala Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 34
<211> LENGTH: 451
<212> TYPE: PRT
<213> ORGANISM: Artificial Sequence
<220> FEATURE:
<223> OTHER INFORMATION: heavy chain of Antibody PD1AB-6-4P

<400> SEQUENCE: 34

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Thr
            20                  25                  30

Tyr Met His Trp Val Gln Gln Ala Pro Gly Lys Gly Leu Glu Trp Met
        35                  40                  45

Gly Arg Ile Asp Pro Ala Asn Gly Asp Arg Lys Tyr Asp Pro Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Pro Val Tyr Tyr Gly Ser Ser Tyr Val Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160
```

Val Thr Val Ser Trp Asn Ser Gly Ala Leu Thr Ser Gly Val His Thr
            165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
            195                 200                 205

Val Asp His Lys Pro Ser Asn Thr Lys Val Asp Lys Arg Val Glu Ser
        210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
450

<210> SEQ ID NO 35
<211> LENGTH: 451
<212> TYPE: PRT
<213> ORGANISM: Artificial Sequence
<220> FEATURE:
<223> OTHER INFORMATION: heavy chain of Antibody PD1AB-6-4PE

<400> SEQUENCE: 35

Glu Val Gln Leu Val Gln Ser Gly Ala Glu Val Lys Lys Pro Gly Ala
1               5                   10                  15

Thr Val Lys Ile Ser Cys Lys Ala Ser Gly Phe Asn Ile Lys Asp Thr
            20                  25                  30

Tyr Met His Trp Val Gln Gln Ala Pro Gly Lys Gly Leu Glu Trp Met
        35                  40                  45

Gly Arg Ile Asp Pro Ala Asn Gly Asp Arg Lys Tyr Asp Pro Lys Phe
    50                  55                  60

Gln Gly Arg Val Thr Ile Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Gly Pro Val Tyr Tyr Gly Ser Ser Tyr Val Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
210                 215                 220

Lys Tyr Gly Pro Pro Cys Pro Pro Cys Pro Ala Pro Glu Phe Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 36
<211> LENGTH: 330

```
<212> TYPE: PRT
<213> ORGANISM: Homo sapiens
<220> FEATURE:
<223> OTHER INFORMATION: Fc region of a human IgG1

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 37
<211> LENGTH: 330
<212> TYPE: PRT
<213> ORGANISM: Artificial Sequence
<220> FEATURE:
<223> OTHER INFORMATION: Fc region of a human IgG1 with K322A
      substitution, also named as IgG1-K322A Fc region
```

<400> SEQUENCE: 37

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 38
<211> LENGTH: 327
<212> TYPE: PRT
<213> ORGANISM: Homo sapiens
<220> FEATURE:
<223> OTHER INFORMATION: Fc region of a human IgG4

<400> SEQUENCE: 38

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr

```
                  20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 39
<211> LENGTH: 327
<212> TYPE: PRT
<213> ORGANISM: Artificial Sequence
<220> FEATURE:
<223> OTHER INFORMATION: Fc region of a human IgG4 with S228P
      substitution, also named as IgG4P Fc region

<400> SEQUENCE: 39

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

```
Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 40
<211> LENGTH: 327
<212> TYPE: PRT
<213> ORGANISM: Artificial Sequence
<220> FEATURE:
<223> OTHER INFORMATION: Fc region of a human IgG4 with S228P and L235E
      substitutions, also named as IgG4PE Fc region

<400> SEQUENCE: 40

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
 65                  70                  75                  80
```

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 41
<211> LENGTH: 106
<212> TYPE: PRT
<213> ORGANISM: Artificial Sequence
<220> FEATURE:
<223> OTHER INFORMATION: constant region of the light chain of Antibody
      PD1AB-6-IgG1

<400> SEQUENCE: 41

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys

```
            100                 105

<210> SEQ ID NO 42
<211> LENGTH: 198
<212> TYPE: PRT
<213> ORGANISM: Homo sapiens
<220> FEATURE:
<223> OTHER INFORMATION: human PD-1

<400> SEQUENCE: 42

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly
        195

<210> SEQ ID NO 43
<211> LENGTH: 10
<212> TYPE: PRT
<213> ORGANISM: Artificial Sequence
<220> FEATURE:
<223> OTHER INFORMATION: amino acid 100-109 of human PD-1 encoding an
      epitope for anti-PD-1 antibody binding

<400> SEQUENCE: 43

Leu Pro Asn Gly Arg Asp Phe His Met Ser
1               5                   10

<210> SEQ ID NO 44
<211> LENGTH: 6
<212> TYPE: PRT
<213> ORGANISM: Artificial Sequence
<220> FEATURE:
<223> OTHER INFORMATION: amino acid 100-105 of human PD-1 encoding an
      epitope for anti-PD-1 antibody binding

<400> SEQUENCE: 44

Leu Pro Asn Gly Arg Asp
1               5
```

METHODS OF TREATING VITILIGO USING PD-1 BINDING ANTIBODIES

CROSS REFERENCE TO RELATED APPLICATIONS

This application claims the benefit of priority to U.S. Provisional Patent Application No. 62/396,720, filed Sep. 19, 2016, the disclosure of which is incorporated by reference herein in its entirety.

1. FIELD

Provided herein are methods for managing, treating, or preventing vitiligo using proteins that specifically bind to Programmed Death-1 (PD-1) and modulate the expression and/or activity of PD-1.

2. SUMMARY

The present disclosure provides methods of managing, preventing, or treating vitiligo in a subject comprising administering to a subject a therapeutically effective amount of proteins that bind to PD-1 (e.g., human PD-1, SEQ ID NO:43), including binding proteins such as antibodies that bind to PD-1. Such binding proteins, including antibodies, can bind to a PD-1 polypeptide, a PD-1 fragment, and/or a PD-1 epitope. Such binding proteins, including antibodies, can be agonists (e.g., induce PD-1 ligand-like signaling). In some embodiments, the binding proteins do not compete with PD-1 ligand (e.g., PD-L1 and PD-L2) for the interaction with PD-1 (e.g., a non-blocking antibody).

The present disclosure also provides, in certain embodiments, methods of managing, preventing, or treating vitiligo in a subject comprising administering to a subject a therapeutically effective amount of binding proteins, including antibodies or fragments thereof, that (i) bind to human PD-1, (ii) induce PD-1 ligand-like signaling, and (iii) do not compete with PD-L1 and/or PD-L2 for the interaction with PD-1.

In some embodiments, a binding protein (e.g., an anti-PD-1 antibody) for use in the methods provided herein comprises six complementarity determining regions (CDRs) or fewer than six CDRs. In other embodiments, a binding protein (e.g., an anti-PD-1 antibody) comprises one, two, three, four, five, or six CDRs selected from heavy chain variable region (VH) CDR1, VH CDR2, VH CDR3, light chain variable region (VL) CDR1, VL CDR2, and/or VL CDR3. In certain embodiments, a binding protein (e.g., an anti-PD-1 antibody) comprises one, two, three, four, five, or six CDRs selected from VH CDR1, VH CDR2, VH CDR3, VL CDR1, VL CDR2, and/or VL CDR3 of a monoclonal antibody designated as PD1AB-1, PD1AB-2, PD1AB-3, PD1AB-4, PD1AB-5, or PD1AB-6 as described herein, or a humanized variant thereof. In some embodiments, a binding protein (e.g., an anti-PD-1 antibody) further comprises a scaffold region or framework region (FR), including a VH FR1, VH FR2, VH FR3, VH FR4, VL FR1, VL FR2, VL FR3, and/or VL FR4 of a human immunoglobulin amino acid sequence or a variant thereof.

In some embodiments of the methods, the antibody or antigen-binding fragment thereof binds to an epitope of human PD-1 recognized by an antibody comprising a light chain variable region having an amino acid sequence of SEQ ID NO:8 and a heavy chain variable region having an amino acid sequence of SEQ ID NO:13.

In other embodiments of the methods, the antibody or antibody fragment thereof competes for the binding to human PD-1 with an antibody comprising a light chain variable region having an amino acid sequence of SEQ ID NO:8 and a heavy chain variable region having an amino acid sequence of SEQ ID NO:13.

In some embodiments of the methods, the antibody or antigen-binding fragment thereof comprises a VL comprising VL CDR1, VL CDR2, and VL CDR3 of any one of antibodies PD1AB-1, PD1AB-2, PD1AB-3, PD1AB-4, PD1AB-5, or PD1AB-6 as set forth in Table 1.

In other embodiments of the methods, the antibody or antigen-binding fragment thereof comprises a VH comprising VH CDR1, VH CDR2, and VH CDR3 of any one of antibodies PD1AB-1, PD1AB-2, PD1AB-3, PD1AB-4, PD1AB-5, or PD1AB-6 as set forth in Table 2.

In still other embodiments of the methods, the antibody or antigen-binding fragment thereof comprises:
(a) a VL comprising VL FR1, VL FR2, VL FR3, and VL FR4 of any one of antibodies PD1AB-1, PD1AB-2, PD1AB-3, PD1AB-4, PD1AB-5, or PD1AB-6 as set forth in Table 3; and
(b) a VH comprising VH FR1, VH FR2, VH FR3, and VH FR4 of any one of antibodies PD1AB-1, PD1AB-2, PD1AB-3, PD1AB-4, PD1AB-5, or PD1AB-6 as set forth in Table 4.

In certain embodiments of the methods, the VL CDR1, VL CDR2, and VL CDR3 of the antibody or antigen-binding fragment thereof comprise amino acid sequences of SEQ ID NOS:1, 2, and 3, respectively, and the VH CDR1, VH CDR2, and VH CDR3 of the antibody or antigen-binding fragment thereof comprise amino acid sequences of SEQ ID NOS:4, 5, and 6, respectively.

In yet another embodiment of the methods, the VL CDR1, VL CDR2, and VL CDR3 of the antibody or antigen-binding fragment thereof comprise amino acid sequences of SEQ ID NOS:7, 2, and 3, respectively, and the VH CDR1, VH CDR2, and VH CDR3 of the antibody or antigen-binding fragment thereof comprise amino acid sequences of SEQ ID NOS:4, 5, and 6, respectively.

In another embodiment of the methods, the antibody or antigen-binding fragment thereof comprises a VL comprising an amino acid sequence of SEQ ID NO:8. In some embodiments, the amino acid sequence comprises one or more conservative modifications thereof.

In certain embodiments of the methods, the antibody or antigen-binding fragment thereof comprises a VL comprising an amino acid sequence of SEQ ID NO:9. In some embodiments, the amino acid sequence comprises one or more conservative modifications thereof.

In some embodiments of the methods, the antibody or antigen-binding fragment thereof comprises a VL comprising an amino acid sequence of SEQ ID NO:10. In some embodiments, the amino acid sequence comprises one or more conservative modifications thereof.

In certain embodiments of the methods, the antibody or antigen-binding fragment thereof comprises a VH comprising an amino acid sequence of SEQ ID NO:11. In some embodiments, the amino acid sequence comprises one or more conservative modifications thereof.

In other embodiments of the methods, the antibody or antigen-binding fragment thereof comprises a VH comprising an amino acid sequence of SEQ ID NO:12. In some embodiments, the amino acid sequence comprises one or more conservative modifications thereof.

In another embodiment of the methods, the antibody or antigen-binding fragment thereof comprises a VH comprising an amino acid sequence of SEQ ID NO:13. In some embodiments, the amino acid sequence comprises one or more conservative modifications thereof.

In certain embodiments of the methods, the antibody or antigen-binding fragment thereof comprises: (a) a VL comprising an amino acid sequence of SEQ ID NO:8; and (b) a VH comprising an amino acid sequence of SEQ ID NO:11.

In some embodiments of the methods, the antibody or antigen-binding fragment thereof comprises: (a) a VL comprising an amino acid sequence of SEQ ID NO:9; and (b) a VH comprising an amino acid sequence of SEQ ID NO:11.

In other embodiments of the methods, the antibody or antigen-binding fragment thereof comprises: (a) a VL comprising an amino acid sequence of SEQ ID NO:10; and (b) a VH comprising an amino acid sequence of SEQ ID NO:11.

In one embodiment of the methods, the antibody or antigen-binding fragment thereof comprises: (a) a VL comprising an amino acid sequence of SEQ ID NO:8; and (b) a VH comprising an amino acid sequence of SEQ ID NO:12.

In another embodiment of the methods, the antibody or antigen-binding fragment thereof comprises: (a) a VL comprising an amino acid sequence of SEQ ID NO:9; and (b) a VH comprising an amino acid sequence of SEQ ID NO:12.

In certain embodiments of the methods, the antibody or antigen-binding fragment thereof comprises: (a) a VL comprising an amino acid sequence of SEQ ID NO:10; and (b) a VH comprising an amino acid sequence of SEQ ID NO:12.

In some embodiments of the methods, the antibody or antigen-binding fragment thereof comprises: (a) a VL comprising an amino acid sequence of SEQ ID NO:8; and (b) a VH comprising an amino acid sequence of SEQ ID NO:13.

In other embodiments of the methods, the antibody or antigen-binding fragment thereof comprises: (a) a VL comprising an amino acid sequence of SEQ ID NO:9; and (b) a VH comprising an amino acid sequence of SEQ ID NO:13.

In certain embodiments of the methods, the antibody or antigen-binding fragment thereof comprises: (a) a VL comprising an amino acid sequence of SEQ ID NO:10; and (b) a VH comprising an amino acid sequence of SEQ ID NO:13.

In some embodiments, the amino acid sequence of the VL comprises one or more conservative modifications thereof. In some embodiments, the amino acid sequence of the VH comprises one or more conservative modifications thereof. In some embodiments, the amino acid sequence of the VL and the VH comprises one or more conservative modifications thereof.

In some embodiments of the methods, the antibody comprises a human IgG1 Fc region. In other embodiments, the antibody comprises a variant human IgG1 Fc region.

In one embodiment of the methods, the antibody comprises a human IgG1-K322A Fc region.

In some embodiments of the methods, the antibody comprises a human IgG4 Fc region. In other embodiments, the antibody comprises a variant human IgG4 Fc region.

In another embodiment of the methods, the antibody comprises a human IgG4P Fc region.

In still another embodiment of the methods, the antibody comprises a human IgG4PE Fc region.

In some embodiments of the methods, the antibody or antigen-binding fragment thereof further comprises a light chain constant region comprising an amino acid sequence of SEQ ID NO:41.

In other embodiments of the methods, the antibody or antigen-binding fragment thereof further comprises a heavy chain Fc region comprising an amino acid sequence selected from the group consisting of SEQ ID NOS:36-40.

In yet another embodiment of the methods, the antibody or antigen-binding fragment thereof further comprises a light chain constant region comprising an amino acid sequence of SEQ ID NO:41; and a heavy chain Fc region comprising an amino acid sequence selected from the group consisting of SEQ ID NOS:36-40.

In some embodiments of the methods, the antibody or antigen-binding fragment thereof comprises a light chain comprising an amino acid sequence of SEQ ID NO:31.

In another embodiment of the methods, the antibody or antigen-binding fragment thereof comprises a heavy chain comprising an amino acid sequence of SEQ ID NO:32.

In other embodiments of the methods, the antibody or antigen-binding fragment thereof comprises: (a) a light chain comprising an amino acid sequence of SEQ ID NO:31; and (b) a heavy chain comprising an amino acid sequence of SEQ ID NO:32.

In certain embodiments of the methods, the antibody or antigen-binding fragment thereof comprises a heavy chain comprising an amino acid sequence of SEQ ID NO:33.

In other embodiments of the methods, the antibody or antigen-binding fragment thereof comprises: (a) a light chain comprising an amino acid sequence of SEQ ID NO:31; and (b) a heavy chain comprising an amino acid sequence of SEQ ID NO:33.

In one embodiment of the methods, the antibody or antigen-binding fragment thereof comprises a heavy chain comprising an amino acid sequence of SEQ ID NO:34.

In yet another embodiment of the methods, the antibody or antigen-binding fragment thereof comprises: (a) a light chain comprising an amino acid sequence of SEQ ID NO:31; and (b) a heavy chain comprising an amino acid sequence of SEQ ID NO:34.

In some embodiments of the methods, the antibody or antigen-binding fragment thereof comprises a heavy chain comprising an amino acid sequence of SEQ ID NO:35.

In other embodiments of the methods, the antibody or antigen-binding fragment thereof comprises: (a) a light chain comprising an amino acid sequence of SEQ ID NO:31; and (b) a heavy chain comprising an amino acid sequence of SEQ ID NO:35.

In certain embodiments of the methods, the antibody or antigen-binding fragment thereof, when bound to PD-1, binds to at least one of residues 100-109 within an amino acid sequence of SEQ ID NO:42.

In some embodiments of the methods, the antibody or antigen-binding fragment thereof, when bound to PD-1, binds to at least one of residues 100-105 within an amino acid sequence of SEQ ID NO:42.

In particular embodiments of the methods, the antibody or antigen-binding fragment thereof, when bound to PD-1, binds to at least one residue selected from the group consisting of N33, T51, S57, L100, N102, G103, R104, D105, H107, and S109 within an amino acid sequence of SEQ ID NO:42.

In some embodiments of the methods, the antibody or antigen-binding fragment thereof, when bound to PD-1, binds to two or more residues selected from the group consisting of N33, T51, S57, L100, N102, G103, R104, D105, H107, and S109 within an amino acid sequence of SEQ ID NO:42.

In other embodiments of the methods, the antibody or antigen-binding fragment thereof, when bound to PD-1, binds to three or more residues selected from the group consisting of N33, T51, S57, L100, N102, G103, R104, D105, H107, and S109 within an amino acid sequence of SEQ ID NO:42.

In certain embodiments of the methods, the antibody or antigen-binding fragment thereof, when bound to PD-1, binds to four or more residues selected from the group consisting of N33, T51, S57, L100, N102, G103, R104, D105, H107, and S109 within an amino acid sequence of SEQ ID NO:42.

In one embodiment of the methods, the antibody or antigen-binding fragment thereof, when bound to PD-1, binds to five or more residues selected from the group consisting of N33, T51, S57, L100, N102, G103, R104, D105, H107, and S109 within an amino acid sequence of SEQ ID NO:42.

In another embodiment of the methods, the antibody or antigen-binding fragment thereof, when bound to PD-1, binds to six or more residues selected from the group consisting of N33, T51, S57, L100, N102, G103, R104, D105, H107, and S109 within an amino acid sequence of SEQ ID NO:42.

In yet another embodiment of the methods, the antibody or antigen-binding fragment thereof, when bound to PD-1, binds to seven or more residues selected from the group consisting of N33, T51, S57, L100, N102, G103, R104, D105, H107, and S109 within an amino acid sequence of SEQ ID NO:42.

In still another embodiment of the methods, the antibody or antigen-binding fragment thereof, when bound to PD-1, binds to eight or more residues selected from the group consisting of N33, T51, S57, L100, N102, G103, R104, D105, H107, and S109 within an amino acid sequence of SEQ ID NO:42.

In certain embodiments of the methods, the antibody or antigen-binding fragment thereof, when bound to PD-1, binds to nine or more residues selected from the group consisting of N33, T51, S57, L100, N102, G103, R104, D105, H107, and S109 within an amino acid sequence of SEQ ID NO:42.

In other embodiments of the methods, the antibody or antigen-binding fragment thereof, when bound to PD-1, binds to all ten residues from the group consisting of N33, T51, S57, L100, N102, G103, R104, D105, H107, and S109 within an amino acid sequence of SEQ ID NO:42.

In one embodiment of the methods, the antibody or antigen-binding fragment thereof, when bound to PD-1, binds to N33 within an amino acid sequence of SEQ ID NO:42.

In another embodiment of the methods, the antibody or antigen-binding fragment thereof, when bound to PD-1, binds to T51 within an amino acid sequence of SEQ ID NO:42.

In a particular embodiment of the methods, the antibody or antigen-binding fragment thereof, when bound to PD-1, binds to S57 within an amino acid sequence of SEQ ID NO:42.

In one specific embodiment of the methods, the antibody or antigen-binding fragment thereof, when bound to PD-1, binds to L100 within an amino acid sequence of SEQ ID NO:42.

In some embodiments of the methods, the antibody or antigen-binding fragment thereof, when bound to PD-1, binds to N102 within an amino acid sequence of SEQ ID NO:42.

In other embodiments of the methods, the antibody or antigen-binding fragment thereof, when bound to PD-1, binds to G103 within an amino acid sequence of SEQ ID NO:42.

In another embodiment of the methods, the antibody or antigen-binding fragment thereof, when bound to PD-1, binds to R104 within an amino acid sequence of SEQ ID NO:42.

In yet another embodiment of the methods, the antibody or antigen-binding fragment thereof, when bound to PD-1, binds to G103 and R104 within an amino acid sequence of SEQ ID NO:42.

In still another embodiment of the methods, the antibody or antigen-binding fragment thereof, when bound to PD-1, binds to D105 within an amino acid sequence of SEQ ID NO:42.

In some embodiments of the methods, the antibody or antigen-binding fragment thereof, when bound to PD-1, binds to H107 within an amino acid sequence of SEQ ID NO:42.

In certain embodiments of the methods, the antibody or antigen-binding fragment thereof, when bound to PD-1, binds to S109 within an amino acid sequence of SEQ ID NO:42.

In one embodiment of the methods, the epitope of human PD-1 is distinct from the PD-L1 binding site. In another embodiment, the epitope of human PD-1 is distinct from the PD-L2 binding site. In a specific embodiment, the epitope of human PD-1 is distinct from both the PD-L1 binding site and the PD-L2 binding site.

In an embodiment of the methods, the antibody or antigen-binding fragment thereof specifically binds to human PD-1 and/or monkey PD-1 (for example, cynomolgus monkey), but not rodent PD-1.

In certain embodiments of the methods, the antibody or antigen-binding fragment thereof has attenuated antibody dependent cellular cytotoxicity (ADCC) activity. In other embodiments, the antibody or antigen-binding fragment thereof has attenuated complement dependent cytotoxicity (CDC) activity. In some embodiments, the antibody or antigen-binding fragment thereof has attenuated ADCC and/or attenuated CDC activity.

In one aspect, provided herein is a method of managing, preventing, or treating vitiligo in a subject, comprising administering to a subject a therapeutically effective amount of an antibody or antigen-binding fragment thereof that binds to an epitope of human PD-1, wherein the antibody or antigen-binding fragment thereof: (a) attenuates T cell activity; and/or (b) downregulates PD-1 expression on the surface of T cells.

In one embodiment of the methods, the antibody attenuates T cell activity. In another embodiment, the antibody downregulates PD-1 expression on the surface of T cells.

In certain embodiments, the attenuation of T cell activity is measured by a T cell effector function.

In some embodiments of the methods, the attenuation of T cell activity is measured by inhibition of cytokine production.

In certain embodiments of the methods, the cytokine that is inhibited by the antibody or antigen-binding fragment thereof comprises IL-2, IL-17, and/or IFN-γ. In some embodiments, the cytokine is selected from the group consisting of IL-1, IL-2, IL-6, IL-12, IL-17, IL-22, IL-23, GM-CSF, IFN-γ, and TNF-α. In certain embodiments, the cytokine is IL-1. In some embodiments, the cytokine is IL-2. In other embodiments, the cytokine is IL-6. In another embodiment, the cytokine is IL-12. In some other embodiments, the cytokine is IL-17. In yet other embodiments, the cytokine is IL-22. In still other embodiments, the cytokine is IL-23. In some embodiments, the cytokine is GM-CSF. In other embodiments, the cytokine is IFN-γ. In yet other embodiments, the cytokine is TNF-α. In certain embodiments, the cytokine is IL-2 and IL-17. In some embodiments, the cytokine is IL-2 and IFN-γ. In yet other embodiments, the cytokine is IL-17 and IFN-γ. In still other embodiments, the cytokine is IL-2, IL-17, and IFN-γ. Other combinations of two, three or more of the above-mentioned cytokines are also contemplated.

In some embodiments of the methods, the attenuation of T cell activity is measured by inhibition of T cell proliferation.

In some embodiments of the methods, the attenuation of T cell activity is measured by downregulation of T cell activation markers.

In some embodiments of the methods, the attenuation of T cell activity is measured by upregulation of regulatory T cell biomarkers.

In some embodiments of the methods, the attenuation of T cell activity is measured by increase of regulatory T cell numbers.

In certain embodiments of the methods, the downregulation of PD-1 expression on the surface of T cells occurs as early as 4 hours after the contact with the antibody or antigen-binding fragment thereof. In another embodiment, the downregulation occurs as early as 6 hours after the contact. In yet another embodiment, the downregulation occurs as early as 8 hours after the contact. In still another embodiment, the downregulation occurs as early as 10 hours after the contact. In one embodiment, the downregulation occurs as early as 12 hours after the contact. In another embodiment, the downregulation occurs as early as 14 hours after the contact. In yet another embodiment, the downregulation occurs as early as 16 hours after the contact. In still another embodiment, the downregulation occurs as early as 18 hours after the contact. In one embodiment, the downregulation occurs as early as 20 hours after the contact. In another embodiment, the downregulation occurs as early as 22 hours after the contact. In yet another embodiment, the downregulation occurs as early as 24 hours after the contact. In some embodiments, the contact is with the antibody. In other embodiments, the contact is with an antigen-binding fragment thereof.

In some embodiments, the downregulation of PD-1 expression on the surface of T cells precedes cytokine inhibition. In one embodiment, the downregulation of PD-1 expression on the surface of T cells occurs as early as 4 hours after the contact with the antibody or antigen-binding fragment thereof, and precedes cytokine inhibition. In another embodiment, the downregulation occurs as early as 6 hours after the contact with the antibody or antigen-binding fragment thereof, and precedes cytokine inhibition. In yet another embodiment, the downregulation occurs as early as 8 hours after the contact with the antibody or antigen-binding fragment thereof, and precedes cytokine inhibition. In still another embodiment, the downregulation occurs as early as 10 hours after the contact with the antibody or antigen-binding fragment thereof, and precedes cytokine inhibition. In one embodiment, the downregulation occurs as early as 12 hours after the contact with the antibody or antigen-binding fragment thereof, and precedes cytokine inhibition. In another embodiment, the downregulation occurs as early as 14 hours after the contact with the antibody or antigen-binding fragment thereof, and precedes cytokine inhibition. In yet another embodiment, the downregulation occurs as early as 16 hours after the contact with the antibody or antigen-binding fragment thereof, and precedes cytokine inhibition. In still another embodiment, the downregulation occurs as early as 18 hours after the contact with the antibody or antigen-binding fragment thereof, and precedes cytokine inhibition. In one embodiment, the downregulation occurs as early as 20 hours after the contact with the antibody or antigen-binding fragment thereof, and precedes cytokine inhibition. In another embodiment, the downregulation occurs as early as 22 hours after the contact with the antibody or antigen-binding fragment thereof, and precedes cytokine inhibition. In yet another embodiment, the downregulation occurs as early as 24 hours after the contact with the antibody or antigen-binding fragment thereof, and precedes cytokine inhibition.

In other embodiments, the downregulation of PD-1 expression on the surface of T cells is concurrent with cytokine inhibition. In one embodiment, the downregulation of PD-1 expression on the surface of T cells occurs as early as 4 hours after the contact with the antibody or antigen-binding fragment thereof, and is concurrent with cytokine inhibition. In another embodiment, the downregulation occurs as early as 6 hours after the contact with the antibody or antigen-binding fragment thereof, and is concurrent with cytokine inhibition. In yet another embodiment, the downregulation occurs as early as 8 hours after the contact with the antibody or antigen-binding fragment thereof, and is concurrent with cytokine inhibition. In still another embodiment, the downregulation occurs as early as 10 hours after the contact with the antibody or antigen-binding fragment thereof, and is concurrent with cytokine inhibition. In one embodiment, the downregulation occurs as early as 12 hours after the contact with the antibody or antigen-binding fragment thereof, and is concurrent with cytokine inhibition. In another embodiment, the downregulation occurs as early as 14 hours after the contact with the antibody or antigen-binding fragment thereof, and is concurrent with cytokine inhibition. In yet another embodiment, the downregulation occurs as early as 16 hours after the contact with the antibody or antigen-binding fragment thereof, and is concurrent with cytokine inhibition. In still another embodiment, the downregulation occurs as early as 18 hours after the contact with the antibody or antigen-binding fragment thereof, and is concurrent with cytokine inhibition. In one embodiment, the downregulation occurs as early as 20 hours after the contact with the antibody or antigen-binding fragment thereof, and is concurrent with cytokine inhibition. In another embodiment, the downregulation occurs as early as 22 hours after the contact with the antibody or antigen-binding fragment thereof, and is concurrent with cytokine inhibition. In yet another embodiment, the downregulation occurs as early as 24 hours after the contact with the antibody or antigen-binding fragment thereof, and is concurrent with cytokine inhibition.

In yet other embodiments, the downregulation of PD-1 expression on the surface of T cells is after cytokine inhibition. In one embodiment, the downregulation of PD-1 expression on the surface of T cells occurs as early as 4 hours after the contact with the antibody or antigen-binding fragment thereof, and is after cytokine inhibition. In another embodiment, the downregulation occurs as early as 6 hours after the contact with the antibody or antigen-binding fragment thereof, and is after cytokine inhibition. In yet another embodiment, the downregulation occurs as early as 8 hours after the contact with the antibody or antigen-binding fragment thereof, and is after cytokine inhibition. In still another embodiment, the downregulation occurs as early as 10 hours after the contact with the antibody or antigen-binding fragment thereof, and is after cytokine inhibition. In one embodiment, the downregulation occurs as early as 12 hours after the contact with the antibody or antigen-binding fragment thereof, and is after cytokine inhibition. In another embodiment, the downregulation occurs as early as 14 hours after the contact with the antibody or antigen-binding fragment thereof, and is after cytokine inhibition. In yet another embodiment, the downregulation occurs as early as 16 hours after the contact with the antibody or antigen-binding fragment thereof, and is after cytokine inhibition. In still another embodiment, the downregulation occurs as early as 18 hours after the contact with the antibody or antigen-binding fragment thereof, and is after cytokine inhibition. In one embodiment, the downregulation occurs as early as 20 hours after the contact with the antibody or antigen-binding fragment thereof, and is after cytokine inhibition. In another embodiment, the downregulation occurs as early as 22 hours after the contact with the antibody or antigen-binding fragment thereof, and is after cytokine inhibition. In yet another embodiment, the downregulation occurs as early as 24 hours after the contact with the antibody or antigen-binding fragment thereof, and is after cytokine inhibition.

In one embodiment of the methods, the $K_D$ of the antibody or antigen-binding fragment thereof for binding to purified human PD-1 is from about 1 nM to about 100 nM. In another embodiment of the methods, the $K_D$ of the antibody or antigen-binding fragment thereof for binding to human PD-1 expressed on cell surface and monkey PD-1 expressed on cell surface is from about 100 pM to about 10 nM.

In some embodiments of the methods, the $EC_{50}$ of the antibody or antigen-binding fragment thereof for attenuating T cell activity is from about 1 pM to about 10 pM, from about 10 pM to about 100 pM, from about 100 pM to about 1 nM, from about 1 nM to about 10 nM, or from about 10 nM to about 100 nM.

In other embodiments of the methods, the maximal percent attenuation of T cell activity by the antibody or antigen-binding fragment thereof is at least about 10%, 20%, 30%, 40%, 45%, 50%, 55%, 60%, 65%, 70%, 75%, 80%, 85%, 90%, 95%, or 100%.

In another embodiment of the methods, the maximal percent downregulation of PD-1 expression by the antibody or antigen-binding fragment thereof is at least about 10%, 20%, 30%, 40%, 45%, 50%, 55%, 60%, 65%, 70%, 75%, 80%, 85%, 90%, 95%, or 100%.

In certain embodiments of the methods, the antibody is a monoclonal antibody. In some embodiments, the antibody is a humanized, human, or chimeric antibody. In another embodiment, the humanized antibody is a deimmunized antibody or a composite human antibody. In certain embodiments, the antibody is a humanized antibody. In specific embodiments, the antibody is a humanized antibody that specifically binds human PD-1.

In certain embodiments of the methods, the antibody or antigen-binding fragment thereof is a Fab, a Fab', a F(ab')$_2$, a Fv, a scFv, a dsFv, a diabody, a triabody, or a tetrabody. In some embodiments, the antibody or antigen-binding fragment thereof is a multispecific antibody formed from antibody fragments. In other embodiments, the antibody or antigen-binding fragment thereof is a bispecific antibody.

In some embodiments of the methods, the antibody or antigen-binding fragment thereof is conjugated to an agent. In one embodiment, the agent is a radioisotope, a metal chelator, an enzyme, a fluorescent compound, a bioluminescent compound, or a chemiluminescent compound.

In another embodiment of the methods, the antibody or antigen-binding fragment thereof attenuates T cell activity. In one embodiment, the maximal percent attenuation of T cell activity is at least about 10%, 20%, 30%, 40%, 45%, 50%, 55%, 60%, 65%, 70%, 75%, 80%, 85%, 90%, 95%, or 100%. In some embodiments, the attenuation of T cell activity is measured by inhibition of T cell proliferation. In some embodiments, the attenuation of T cell activity is measured by inhibition of cytokine production. In some embodiments, the cytokine is selected from the group consisting of IL-2, IL-17, IFN-γ, or any combination thereof. In certain embodiments, the cytokine is selected from the group consisting of IL-1, IL-2, IL-6, IL-12, IL-17, IL-22, IL-23, GM-CSF, IFN-γ, and TNF-α. In certain embodiments, the cytokine is IL-1. In some embodiments, the cytokine is IL-2. In other embodiments, the cytokine is IL-6. In another embodiment, the cytokine is IL-12. In some other embodiments, the cytokine is IL-17. In yet other embodiments, the cytokine is IL-22. In still other embodiments, the cytokine is IL-23. In some embodiments, the cytokine is GM-CSF. In other embodiments, the cytokine is IFN-γ. In yet other embodiments, the cytokine is TNF-α. In certain embodiments, the cytokine is IL-2 and IL-17. In some embodiments, the cytokine is IL-2 and IFN-γ. In yet other embodiments, the cytokine is IL-17 and IFN-γ. In still other embodiments, the cytokine is IL-2, IL-17, and IFN-γ. Other combinations of two, three or more of the above-mentioned cytokines are also contemplated. In certain embodiments, the inhibition of cytokine production follows downregulation of PD-1 expression on the surface of the T cell. In other embodiments, the downregulation of PD-1 expression on the surface of T cells occurs as early as 4 hours, 6 hours, 8 hours, 10 hours, 12 hours, 14 hours, 16 hours, 18 hours, 20 hours, 22 hours, or 24 hours after the contact with the antibody or antigen-binding fragment thereof. In one embodiment, the downregulation occurs as early as 4 hours after the contact, and precedes cytokine inhibition. In one embodiment, the downregulation occurs as early as 6 hours after the contact, and precedes cytokine inhibition. In one embodiment, the downregulation occurs as early as 8 hours after the contact, and precedes cytokine inhibition. In one embodiment, the downregulation occurs as early as 10 hours after the contact, and precedes cytokine inhibition. In another embodiment, the downregulation occurs as early as 12 hours after the contact, and precedes cytokine inhibition. In an embodiment, the downregulation occurs as early as 14 hours after the contact, and precedes cytokine inhibition. In other embodiments, the downregulation occurs as early as 16 hours after the contact, and precedes cytokine inhibition. In one embodiment, the downregulation occurs as early as 18 hours after the contact, and precedes cytokine inhibition. In another embodiment, the downregulation occurs as early as 20 hours after the contact, and precedes cytokine inhibition. In one embodiment, the downregulation occurs as early as 22 hours after the contact, and precedes cytokine inhibition. In some embodiments, the downregulation occurs as early as 24 hours after the contact, and precedes cytokine inhibition. In some embodiments, the inhibition of cytokine production is concurrent with downregulation of PD-1 expression on the surface of the T cell. In one embodiment, the downregulation occurs as early as 4 hours after the contact, and is concurrent with cytokine inhibition. In one embodiment, the downregulation occurs as early as 6 hours after the contact, and is concurrent with cytokine inhibition. In one embodiment, the downregulation occurs as early as 8 hours after the contact, and is concurrent with cytokine inhibition. In one embodiment, the downregulation occurs as early as 10 hours after the contact, and is concurrent with cytokine inhibition. In another embodiment, the downregulation occurs as early as 12 hours after the contact, and is concurrent with cytokine inhibition. In an embodiment, the downregulation occurs as early as 14 hours after the contact, and is concurrent with cytokine inhibition. In other embodiments, the downregulation occurs as early as 16 hours after the contact, and is concurrent with cytokine inhibition. In one embodiment, the downregulation occurs as early as 18 hours after the contact, and is concurrent with cytokine inhibition. In another embodiment, the downregulation occurs as early as 20 hours after the contact, and is concurrent with cytokine inhibition. In one embodiment, the downregulation occurs as early as 22 hours after the contact, and is concurrent with cytokine inhibition. In some embodiments, the downregulation occurs as early as 24 hours after the contact, and is concurrent with cytokine inhibition. In some embodiments, the inhibition of cytokine production proceeds downregulation of PD-1 expression on the surface of the T cell. In one embodiment, the downregulation occurs as early as 4 hours after the contact, and is after cytokine inhibition. In one embodiment, the downregulation occurs as early as 6 hours after the contact, and is after cytokine inhibition. In one embodiment, the downregulation occurs as early as 8 hours after the contact, and is after cytokine inhibition. In one embodiment, the downregulation occurs as early as 10 hours after the contact, and is after cytokine inhibition. In another embodiment, the downregulation occurs as early as 12 hours after the contact, and is after cytokine inhibition. In an embodiment, the downregulation occurs as early as 14 hours after the contact, and is after cytokine inhibition. In other embodiments, the downregulation occurs as early as 16 hours after the contact, and is after cytokine inhibition. In one embodiment, the downregulation occurs as early as 18 hours after the contact, and is after cytokine inhibition. In another embodiment, the downregulation occurs as early as 20 hours after the contact, and is after cytokine inhibition. In one embodiment, the downregulation occurs as early as 22 hours after the contact, and is after cytokine inhibition. In some embodiments, the downregulation occurs as early as 24 hours after the contact, and is after cytokine inhibition.

In yet another embodiment of the methods, the antibody or antigen-binding fragment thereof downregulates PD-1 expression on the surface of a T cell. In one embodiment, the maximal percent downregulation of PD-1 expression by the antibody or antigen-binding fragment thereof is at least about 10%, 20%, 30%, 40%, 45%, 50%, 55%, 60%, 65%, 70%, 75%, 80%, 85%, 90%, 95%, or 100%. In another embodiment, the downregulation of PD-1 expression on the surface of the T cell occurs as early as 4 hours after the contact with the antibody or antigen-binding fragment thereof. In one embodiment, the downregulation of PD-1 expression on the surface of the T cell precedes cytokine inhibition. In one embodiment, the downregulation of PD-1 expression on the surface of the T cell is concurrent with cytokine inhibition. In one embodiment, the downregulation of PD-1 expression on the surface of the T cell follows cytokine inhibition. In certain embodiments, the cytokine is IL-2, IL-17, IFN-γ, or any combination thereof. In certain embodiments, the cytokine is selected from the group consisting of IL-1, IL-2, IL-6, IL-12, IL-17, IL-22, IL-23, GM-CSF, IFN-γ, and TNF-α. In certain embodiments, the cytokine is IL-1. In some embodiments, the cytokine is IL-2. In other embodiments, the cytokine is IL-6. In another embodiment, the cytokine is IL-12. In other embodiments, the cytokine is IL-17. In yet other embodiments, the cytokine is IL-22. In still other embodiments, the cytokine is IL-23. In some embodiments, the cytokine is GM-CSF. In other embodiments, the cytokine is IFN-γ. In other embodiments, the cytokine is TNF-α. In certain embodiments, the cytokine is IL-2 and IL-17. In some embodiments, the cytokine is IL-2 and IFN-γ. In yet other embodiments, the cytokine is IL-17 and IFN-γ. In still other embodiments, the cytokine is IL-2, IL-17, and IFN-γ.

In another embodiment of the methods, the antibody or antigen-binding fragment thereof attenuates T cell activity by inhibiting cytokine production. In some embodiments, the cytokine that is inhibited by the antibody or antigen-binding fragment thereof is selected from the group consisting of IL-2, IL-17, IFN-γ, or any combination thereof. In certain embodiments, the cytokine is selected from the group consisting of IL-1, IL-2, IL-6, IL-12, IL-17, IL-22, IL-23, GM-CSF, IFN-γ, and TNF-α. In certain embodiments, the cytokine is IL-1. In some embodiments, the cytokine is IL-2. In other embodiments, the cytokine is IL-6. In another embodiment, the cytokine is IL-12. In other embodiments, the cytokine is IL-17. In yet other embodiments, the cytokine is IL-22. In still other embodiments, the cytokine is IL-23. In some embodiments, the cytokine is GM-CSF. In other embodiments, the cytokine is IFN-γ. In yet other embodiments, the cytokine is TNF-α. In certain embodiments, the cytokine is IL-2 and IL-17. In some embodiments, the cytokine is IL-2 and IFN-γ. In yet other embodiments, the cytokine is IL-17 and IFN-γ. In still other embodiments, the cytokine is IL-2, IL-17, and IFN-γ. Other combinations of two, three or more of the above-mentioned cytokines are also contemplated.

Also provided herein is a method of managing, preventing, or treating vitiligo in a subject, comprising administering to a subject a therapeutically effective amount of a composition comprising an antibody or antigen-binding fragment thereof described herein. In certain embodiments of the methods, the composition further comprises a pharmaceutically acceptable carrier.

In certain embodiments, the subject has vitiligo, or is being treated for vitiligo with an anti-inflammatory therapeutic.

In certain other embodiments, the immune cells in the subject express PD-1.

3. BRIEF DESCRIPTION OF THE FIGURES

FIG. 4 shows the amino acid sequences of heavy chain (HC) and light chain (LC) of PD1AB-6-IgG1 and HC of its variants PD1AB-6-K3 and PD1AB-6-4P.

FIGS. 8A-8D show the PD1AB-6 variants binding to FcγRI (A), FcγRIIIa (V158) (B), or FcγRIIb (C) expressed on HEK293 cells using Cisbio Tag-lite™ detection, and (D) the $EC_{50}$ values of the PD1AB-6 variants binding to FcγRI, FcγRIIIa (V158), or FcγRIIb.

Figure 13:
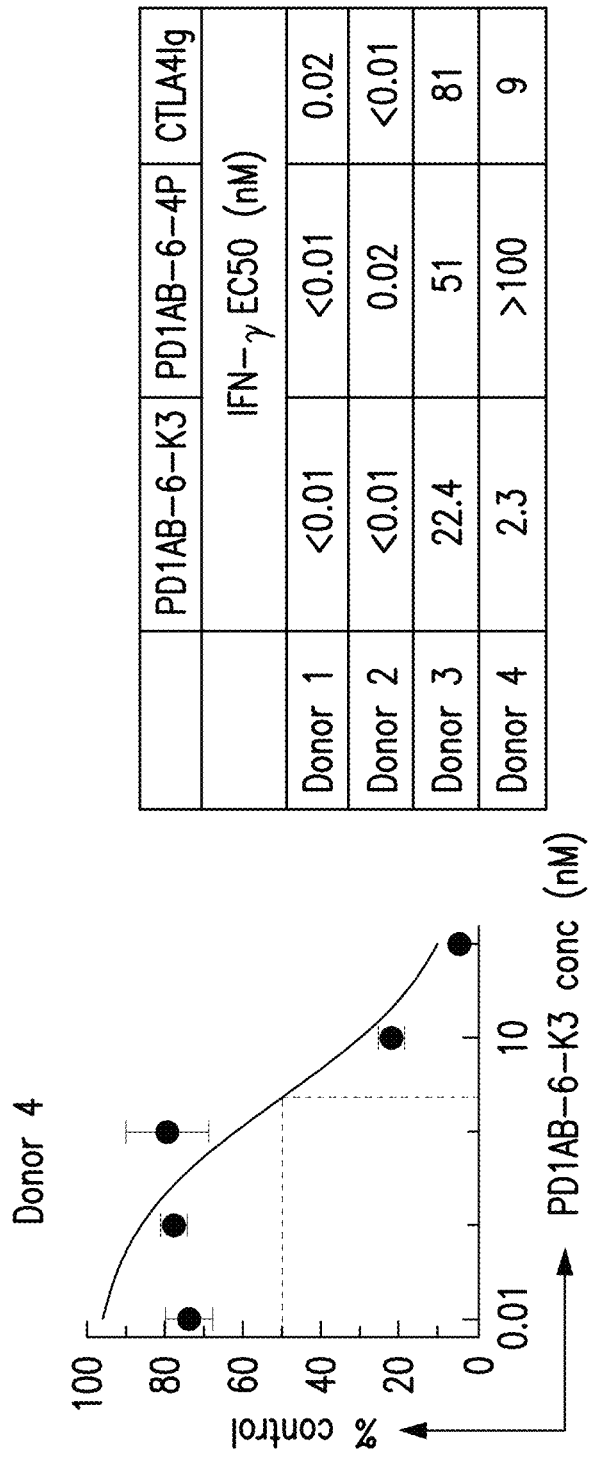

FIG. 13 depicts the activity of PD1AB-6-K3 in human whole blood assay. The graph shows a representative curve from donor 4 used to calculate $EC_{50}$ of IFN-γ inhibition. The table shows $EC_{50}$ values of IFN-γ inhibition for 4 healthy donors with PD1AB-6 variants and CTLA4Ig.

Figure 14A:
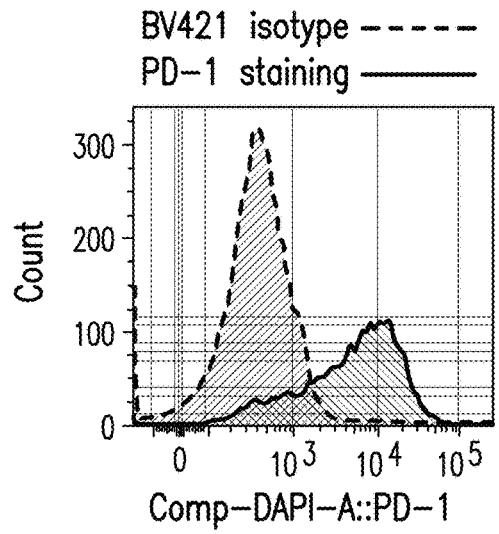
Figure 14B:
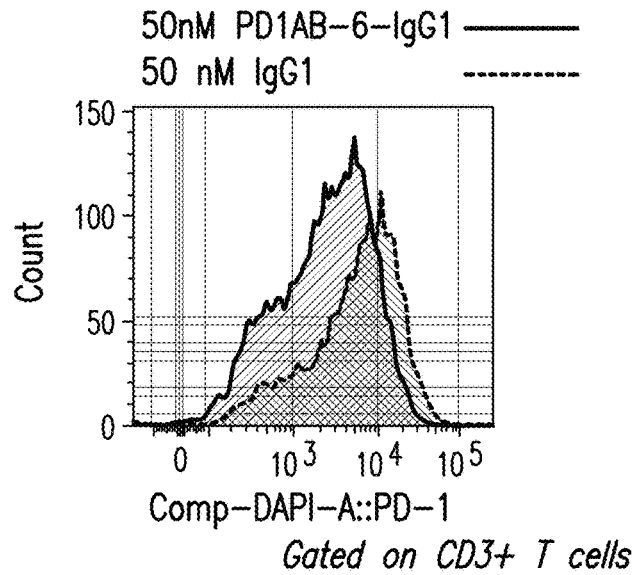
Figure 14C:
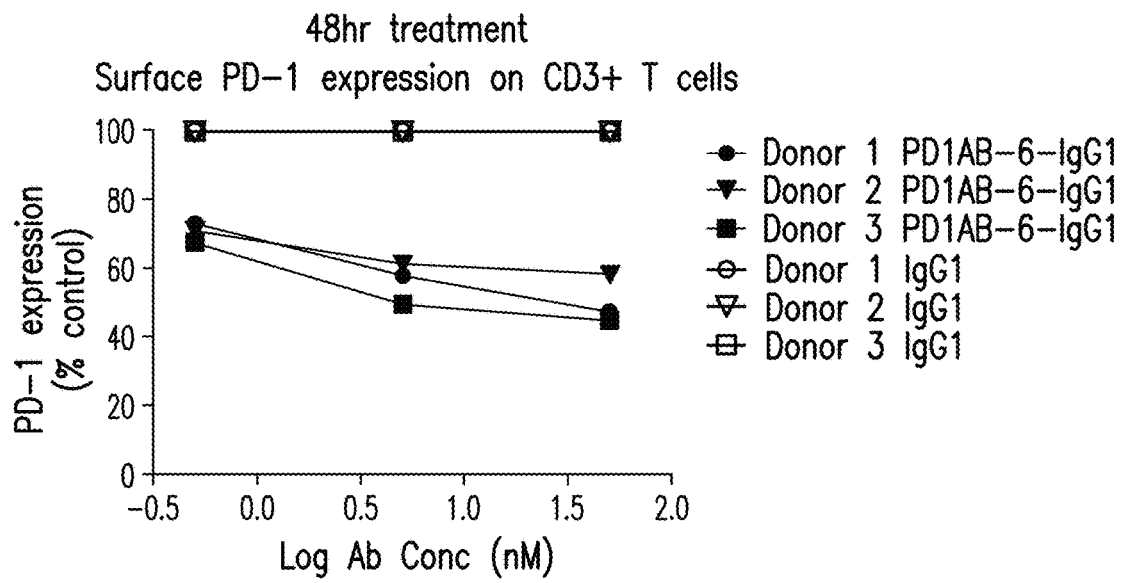

FIGS. 14A-14C depict downregulation of PD-1 expression by PD1AB-6-IgG1 as determined by (A) isotype vs. PD-1 staining on CD3+ T cells in human PBMC activated with anti-CD3+ anti-CD28 for 48 hours, (B) PD-1 expression in isotype IgG1 vs. PD1AB-6-IgG1 treated PBMC (the detection anti-PD-1 antibody is not blocked by PD1AB-6), and (C) PD-1 expression on CD3+ T cells in human PBMC from 3 different donors, activated with anti-CD3+ anti-CD28 and three different concentrations of either isotype IgG1 or PD1AB-6-IgG1.

Figures 15A, 15B, 15C:
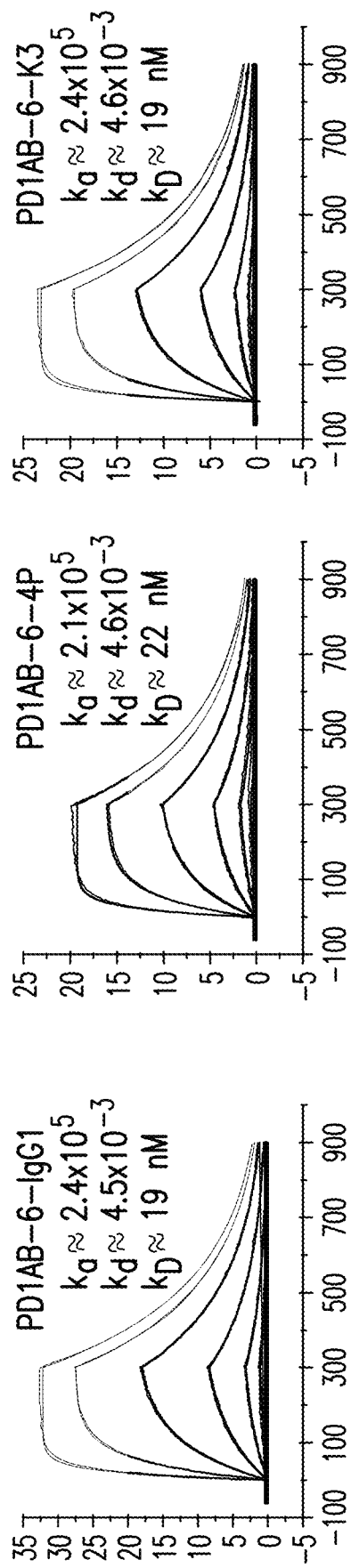

FIGS. 15A-15C show (A) PD1AB-6-IgG1, (B) PD1AB-6-4P, and (C) PD1AB-6-K3 binding to PD-1 antigen on Biacore® T200.

4. DETAILED DESCRIPTION

Provided herein are methods of managing, preventing, or treating vitiligo in a subject, comprising administering to a subject an effective amount of binding proteins, such as antibodies that bind to PD-1. In one embodiment, provided herein is a method of managing vitiligo in a subject, comprising administering to a subject an effective amount of a PD-1 binding protein. In one embodiment, provided herein is a method of preventing vitiligo in a subject, comprising administering to a subject an effective amount of a PD-1 binding protein. In one embodiment, provided herein is a method of treating vitiligo in a subject, comprising administering to a subject an effective amount of a PD-1 binding protein. In a specific embodiment, the PD-1 binding protein is an antibody that binds to PD-1. Exemplary PD-1 antibodies useful in these methods are provided herein.

In some embodiments of the various methods provided herein, the antibodies bind to human and/or cyno PD-1. In some embodiments, the binding proteins, such as antibodies that bind to human and/or cyno PD-1, do not bind to rodent PD-1. In certain embodiments, the PD-1 binding proteins, including antibodies disclosed herein, are agonists (e.g., can mimic the effect of PD-1 ligand and induce PD-1 signaling). In some embodiments, the binding proteins such as antibodies to PD-1 described herein (i) bind to human and/or cyno PD-1, (ii) do not compete for binding with PD-1 ligand (e.g., PD-L1 and/or PD-L2), and/or (iii) induce PD-1 signaling. In one embodiment, the PD-1 antibodies bind to human PD-1. In one embodiment, the PD-1 antibodies bind to cyno PD-1. In one embodiment, the PD-1 antibodies bind to both human PD-1 and cyno PD-1. In some embodiments, the PD-1 antibodies do not compete with PD-L1 for binding to PD-1. In other embodiments, the PD-1 antibodies do not compete with PD-L2 for binding to PD-1. In yet other embodiments, the PD-1 antibodies do not compete with either PD-L1 or PD-L2 for binding to PD-1. In other embodiments, the PD-1 antibodies induce PD-1 signaling. In specific embodiments, the PD-1 antibodies provided herein bind to both human PD-1 and cyno PD-1, do not compete for binding to PD-1 with either PD-L1 or PD-L2, and induce PD-1 signaling. In some embodiments, the binding, competition, and/or signaling is assayed in vitro, e.g., in a cell-based assay. In other embodiments, the binding, competition, and/or signaling is assayed ex vivo, e.g., in a T cell function assay. In other embodiments, the binding, competition, and/or signaling is assayed using a sample from a subject (e.g., a human subject). In certain embodiments, assays and measurements include (1) a human or cyno PBMC assay (see, e.g., Examples 5.2.1 and 5.2.2) and (2) a human whole blood sample assay (see, e.g., Example 5.2.1). In certain embodiments, binding proteins, such as anti-PD-1 antibodies, as described herein, exhibit activities that are consistent with the natural biological function of PD-L1 and/or PD-L2. In some embodiments, the activities are exhibited in vitro. In other embodiments, the activities are exhibited ex vivo.

In other embodiments, the binding, competition and/or signaling is assayed in vivo, e.g., in a mouse model of vitiligo (see, e.g., Example 5.4). In certain embodiments, binding proteins, such as anti-PD-1 antibodies, as described herein, exhibit activities that are consistent with the natural biological function of PD-L1 and/or PD-L2. In some embodiments, the activities are exhibited in vitro. In other embodiments, the activities are exhibited in vivo.

The discovery that such binding proteins, including anti-PD-1 antibodies, induce PD-1 signaling make them viable therapeutics for the treatment of vitiligo.

In specific embodiments of the various methods provided herein, the binding proteins, such as antibodies that bind to PD-1, described herein share the common feature of competing with each other for the binding of PD-1. This competitive inhibition can indicate that each antibody binds to the same region of PD-1 (e.g., the same epitope), thereby asserting similar effects. In certain embodiments, anti-PD-1 antibodies provided herein include humanized anti-PD-1 antibodies, such as those derived from or based on antibodies PD1AB-1, PD1AB-2, PD1AB-3, PD1AB-4, PD1AB-5, and/or PD1AB-6. In other embodiments, anti-PD-1 antibodies provided herein compete for binding with an antibody derived from or based on PD1AB-1, PD1AB-2, PD1AB-3, PD1AB-4, PD1AB-5, and/or PD1AB-6. In some embodiments, the anti-PD-1 antibodies have CDR sequences as described in Tables 1-2. In certain embodiments, the anti-PD-1 antibodies bind to a specific domain or epitope of human PD-1 (e.g., residues 100-105; see Example 5.1.4). Moreover, such binding can be largely attributed to particular amino acid residues within the region (e.g., G103 and R104; see Example 5.1.4), which comprise the epitope recognized by the anti-PD-1 antibodies provided herein. Taken together, the results described herein demonstrate that the effects observed for an anti-PD-1 antibody that is derived from or based on PD1AB-6, including an antibody having one or more CDRs described in Tables 1-2, can be extrapolated to other anti-PD-1 antibodies provided herein having the same or similar epitope specificity (e.g., the same or similar CDRs). For example, the activities of antibodies as shown in Examples 5.1.2-3, 5.1.7-10, 5.2.1-3, and 5.3.1, for an exemplary humanized anti-PD-1 antibody, are representative of the activities and effects of the anti-PD-1 antibodies provided herein.

In some embodiments of the various methods provided herein, the binding proteins such as anti-PD-1 antibodies may comprise immunoglobulin variable regions which comprise one or more CDRs as described in Tables 1-2. In such binding proteins (e.g., anti-PD-1 antibodies), the CDRs may be joined with one or more scaffold regions or framework regions (FRs), which orient(s) the CDR(s) such that the proper antigen binding properties of the CDR(s) is achieved. Such binding proteins, including anti-PD-1 antibodies as described herein, can induce PD-1 signaling.

4.1 General Techniques

Techniques and procedures described or referenced herein include those that are generally well understood and/or commonly employed using conventional methodology by those skilled in the art, such as, for example, the widely utilized methodologies described in Sambrook et al., *Molecular Cloning: A Laboratory Manual* (3d ed. 2001); *Current Protocols in Molecular Biology* (Ausubel et al. eds., 2003); *Therapeutic Monoclonal Antibodies: From Bench to Clinic* (An ed. 2009); *Monoclonal Antibodies: Methods and Protocols* (Albitar ed. 2010); and *Antibody Engineering* Vols 1 and 2 (Kontermann and Dithel eds., 2d ed. 2010).

4.2 Terminology

Unless described otherwise, all technical and scientific terms used herein have the same meaning as is commonly understood by one of ordinary skill in the art. For purposes of interpreting this specification, the following description of terms will apply and whenever appropriate, terms used in the singular will also include the plural and vice versa. All patents, applications, published applications, and other publications are incorporated by reference in their entirety. In the event that any description of terms set forth conflicts with any document incorporated herein by reference, the description of term set forth below shall control.

The terms "Programmed Death 1," "Programmed Cell Death 1," "Protein PD-1," "PD-1," "PD-1 polypeptide," or "PD1" encompasses a polypeptide ("polypeptide" and "protein" are used interchangeably herein), including any native PD-1 polypeptide, from any vertebrate source, including mammals such as primates (e.g., humans and cynomolgus monkeys (cynos)), dogs, and rodents (e.g., mice and rats), unless otherwise indicated. In certain embodiments, the terms include "related PD-1 polypeptides," including SNP variants thereof. The term "PD-1" also encompasses "full-length," unprocessed PD-1 as well as any form of PD-1 that results from processing in the cell. In some embodiments, the PD1 has an amino acid sequence of SEQ ID NO:43. GenBank™ accession number U64863 provides another exemplary human PD-1 nucleic acid sequence.

"Related PD-1 polypeptides" include allelic variants (e.g., SNP variants); splice variants; fragments; derivatives; substitution, deletion, and insertion variants; fusion polypeptides; and interspecies homologs, which can retain PD-1 activity. As those skilled in the art will appreciate, an anti-PD-1 antibody provided herein can bind to a PD-1 polypeptide, a PD-1 polypeptide fragment, a PD-1 antigen, and/or a PD-1 epitope. An "epitope" may be part of a larger PD-1 antigen, which may be part of a larger PD-1 polypeptide fragment, which, in turn, may be part of a larger PD-1 polypeptide. PD-1 may exist in a native or denatured form. PD-1 polypeptides described herein may be isolated from a variety of sources, such as from human tissue types or from another source, or prepared by recombinant or synthetic methods. Orthologs to the PD-1 polypeptide are also well known in the art.

The terms "PD1AB-6-IgG1," "PD1AB-6 IgG1," "PD1AB-6_IgG1," "IgG1_PD1AB-6," and "IgG1-PD1AB-6" are used interchangeably, and refer to the antibody PD1AB-6 having an IgG1 Fc region. In certain embodiments, the antibody PD1AB-6 comprises a light chain amino acid sequence of LC_PD1AB-6-IgG1 (SEQ ID NO:31) and a heavy chain amino acid sequence of HC_PD1AB-6-IgG1 (SEQ ID NO:32), e.g., as shown in FIG. 4.

The terms "PD1AB-6-K3," "PD1AB-6-IgG1-K322A," "PD1AB-6-K322A," "IgG1_PD1AB-6 K322A," "IgG1_PD1AB-6 K3," "IgG1-PD1AB-6-K322A," and "IgG1-PD1AB-6-K3" are used interchangeably and refer to the PD1AB-6 variant having a K322A substitution in the IgG1 Fc region. In certain embodiments, the PD1AB-6 variant has a heavy chain amino acid sequence of HC_PD1AB-6-IgG1-K322A (SEQ ID NO:33), e.g., as shown in FIG. 4.

The terms "PD1AB-6-4P," "IgG4P_PD1AB-6," "IgG4P-PD1AB-6," "PD1AB-6_IgG4P," and "PD1AB-6-IgG4P" are used interchangeably and refer to the PD1AB-6 variant having an IgG4P Fc region. In certain embodiments, the PD-1 antibody variant has a heavy chain amino acid sequence of HC_PD1AB-6-IgG4P (SEQ ID NO:34), e.g., as shown in FIG. 4.

The terms "PD1AB-6-4PE," "IgG4PE_PD1AB-6," "IgG4PE-PD1AB-6," and "PD1AB-6_IgG4PE," and "PD1AB-6-IgG4PE" are used interchangeably and refer to the PD1AB-6 variant having an IgG4PE heavy chain amino acid sequence as HC_PD1AB-6-IgG4PE (SEQ ID NO:35).

The term "PD-1 ligand" refers to a molecule that binds to PD-1, e.g., in vivo or in vitro. Non-limiting examples of PD-1 ligand include naturally occurring ligands, e.g., PD-1 ligand 1 (PD-L1, also known as B7-H1 or CD274) and PD-1 ligand 2 (PD-L2, also known as B7-DC or CD273), and artificially generated ligands.

The terms "PD-L1" and "PDL-1" are used interchangeably herein and refer to PD-1 ligand 1 (also known as B7-H1 or CD274).

The terms "PD-1 activity," "PD-1 signaling," and "PD-1 ligand-like signaling" when applied to a binding protein such as an antibody that binds to PD-1 of the present disclosure, means that the binding protein (e.g., antibody) mimics or modulates a biological effect induced by the binding of PD-1 ligand, and induces a biological response that otherwise would result from PD-1 ligand binding to PD-1, e.g., in vivo or in vitro. In assessing the binding specificity of anti-PD-1 antibody, for example, an antibody or fragment thereof that binds to PD-1 (e.g., human PD-1), the antibody is deemed to induce a biological response when the response is equal to or greater than 5%, such as equal to or greater than 10%, 15%, 20%, 25%, 30%, 35%, 40%, 45%, 50%, 55%, 60%, 65%, 70%, 75%, 80%, 85%, 90%, 95%, 100%, 125%, 150%, 175%, or 200% of the activity of a wild type PD-1 ligand standard. In one embodiment, the anti-PD-1 antibody or the PD-1 ligand is immobilized (for example, on a plastic surface or bead). In certain embodiments, the antibody has the following properties: exhibits an efficacy level of equal to or more than 5% of a PD-1 ligand standard, with an $EC_{50}$ of equal to or less than 100 nM, e.g., 90 nM, 80 nM, 70 nM, 60 nM, 50 nM, 40 nM, 30 nM, 20 nM, 10 nM, 5 nM, 2 nM, 1 nM, 0.5 nM, 0.2 nM, or 0.1 nM in a (1) human or cyno PBMC assay (see, e.g., Examples 5.2.1 and 5.2.2) or (2) human whole blood sample assay (see, e.g., Example 5.2.1).

The term "binding protein" refers to a protein comprising a portion (e.g., one or more binding regions such as CDRs) that binds to PD-1, including human and/or cyno PD-1 and, optionally, a scaffold or framework portion (e.g., one or more scaffold or framework regions) that allows the binding portion to adopt a conformation that promotes binding of the binding protein to a PD-1 polypeptide, fragment, or epitope. Examples of such binding proteins include antibodies, such as a human antibody, a humanized antibody, a chimeric antibody, a recombinant antibody, a single chain antibody, a diabody, a triabody, a tetrabody, a Fab fragment, a F(ab')$_2$ fragment, an IgD antibody, an IgE antibody, an IgM antibody, an IgG1 antibody, an IgG2 antibody, an IgG3 antibody, or an IgG4 antibody, and fragments thereof. The binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the binding protein as well as wholly synthetic scaffolds comprising, for example, a biocompatible polymer. See, e.g., Korndorfer et al., 2003, Proteins: Structure, Function, and Bioinformatics 53(1):121-29; and Roque et al., 2004, Biotechnol. Prog. 20:639-54. In addition, peptide antibody mimetics ("PAMs") can be used, as well as scaffolds based on antibody mimetics utilizing fibronectin components as a scaffold. In the context of the present disclosure, a binding protein is said to specifically bind or selectively bind to PD-1, for example, when the dissociation constant ($K_D$) is $\leq 10^{-7}$ M. In some embodiments, the binding proteins (e.g., antibodies) may specifically bind to PD-1 with a $K_D$ of from about $10^{-7}$ M to about $10^{-12}$ M. In certain embodiments, the binding protein (e.g., antibody) may specifically bind to PD-1 with high affinity when the $K_D$ is $\leq 10^{-8}$ M or $K_D$ is $\leq 10^{-9}$ M. In one embodiment, the binding proteins (e.g., antibodies) may specifically bind to purified human PD-1 with a $K_D$ of from $1 \times 10^{-9}$ M to $10 \times 10^{-9}$ M as measured by Biacore®. In another embodiment, the binding proteins (e.g., antibodies) may specifically bind to purified human PD-1 with a $K_D$ of from $0.1 \times 10^{-9}$ M to $1 \times 10^{-9}$ M as measured by KinExA™ (Sapidyne, Boise, Id.). In yet another embodiment, the binding proteins (e.g., antibodies) specifically bind to human PD-1 expressed on cells with a $K_D$ of from $0.1 \times 10^{-9}$ M to $10 \times 10^{-9}$ M. In certain embodiments, the binding proteins (e.g., antibodies) specifically bind to human PD-1 expressed on cells with a $K_D$ of from $0.1 \times 10^{-9}$ M to $1 \times 10^{-9}$ M. In some embodiments, the binding proteins (e.g., antibodies) specifically bind to human PD-1 expressed on cells with a $K_D$ of $1 \times 10^{-9}$ M to $10 \times 10^{-9}$ M. In certain embodiments, the binding proteins (e.g., antibodies) specifically bind to human PD-1 expressed on cells with a $K_D$ of about $0.1 \times 10^{-9}$ M, about $0.5 \times 10^{-9}$ M, about $1 \times 10^{-9}$ M, about $5 \times 10^{-9}$ M, about $10 \times 10^{-9}$ M, or any range or interval thereof. In still another embodiment, the binding proteins (e.g., antibodies) may specifically bind to cyno PD-1 expressed on cells with a $K_D$ of $0.1 \times 10^{-9}$ M to $10 \times 10^{-9}$ M. In certain embodiments, the binding proteins (e.g., antibodies) specifically bind to cyno PD-1 expressed on cells with a $K_D$ of from $0.1 \times 10^{-9}$ M to $1 \times 10^{-9}$ M. In some embodiments, the binding proteins (e.g., antibodies) specifically bind to cyno PD-1 expressed on cells with a $K_D$ of $1 \times 10^{-9}$ M to $10 \times 10^{-9}$ M. In certain embodiments, the binding proteins (e.g., antibodies) specifically bind to cyno PD-1 expressed on cells with a $K_D$ of about $0.1 \times 10^{-9}$ M, about $0.5 \times 10^{-9}$ M, about $1 \times 10^{-9}$ M, about $5 \times 10^{-9}$ M, about $10 \times 10^{-9}$ M, or any range or interval thereof.

The term "antibody," "immunoglobulin," or "Ig" is used interchangeably herein, and is used in the broadest sense and specifically covers, for example, individual anti-PD-1 monoclonal antibodies (including agonist, antagonist, neutralizing antibodies, full length or intact monoclonal antibodies), anti-PD-1 antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain anti-PD-1 antibodies, and fragments of anti-PD-1 antibodies, as described below. An antibody can be human, humanized, chimeric and/or affinity matured, as well as an antibody from other species, for example, mouse and rabbit, etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa), each amino-terminal portion of each chain includes a variable region of about 100 to about 130 or more amino acids, and each carboxy-terminal portion of each chain includes a constant region. See, e.g., *Antibody Engineering* (Borrebaeck ed., 2d ed. 1995); and Kuby, *Immunology* (3d ed. 1997). In specific embodiments, the specific molecular antigen can be bound by an antibody provided herein, including a PD-1 polypeptide, a PD-1 fragment, or a PD-1 epitope. Antibodies also include, but are not limited to, synthetic antibodies, recombinantly produced antibodies, camelized antibodies, intrabodies, anti-idiotypic (anti-Id) antibodies, and functional fragments (e.g., antigen-binding fragments such as PD-1-binding fragments) of any of the above, which refers to a portion of an antibody heavy or light chain polypeptide that retains some or all of the binding activity of the antibody from which the fragment was derived. Non-limiting examples of functional fragments (e.g., antigen-binding fragments such as PD-1-binding fragments) include single-chain Fvs (scFv) (e.g., including monospecific, bispecific, etc.), Fab fragments, F(ab') fragments, F(ab)$_2$ fragments, F(ab')$_2$ fragments, disulfide-linked Fvs (dsFv), Fd fragments, Fv fragments, diabody, triabody, tetrabody, and minibody. In particular, antibodies provided herein include immunoglobulin molecules and immunologically active portions of immunoglobulin molecules, for example, antigen-binding domains or molecules that contain an antigen-binding site that binds to a PD-1 antigen (e.g., one or more CDRs of an anti-PD-1 antibody). Such antibody fragments can be found in, for example, Harlow and Lane, *Antibodies: A Laboratory Manual* (1989); *Mol. Biology and Biotechnology: A Comprehensive Desk Reference* (Myers ed., 1995); Huston et al., 1993, Cell Biophysics 22:189-224; Plückthun and Skerra, 1989, Meth. Enzymol. 178:497-515; and Day, *Advanced Immunochemistry* (2d ed. 1990). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule. Anti-PD-1 antibodies may be agonistic antibodies or antagonistic antibodies. Described herein are agonistic antibodies to PD-1, including antibodies that induce PD-1 signaling. In specific embodiments, agonistic antibodies to PD-1 do not compete for the binding of PD-L1 and/or PD-L2 to PD-1.

An "antigen" is a predetermined antigen to which an antibody can selectively bind. A target antigen may be a polypeptide, carbohydrate, nucleic acid, lipid, hapten, or other naturally occurring or synthetic compound. In some embodiments, the target antigen is a polypeptide.

The terms "antigen-binding fragment," "antigen-binding domain," "antigen-binding region," and similar terms refer to that portion of an antibody, which comprises the amino acid residues that interact with an antigen and confer on the binding agent its specificity and affinity for the antigen (e.g., the CDRs).

The terms "binds" or "binding" refer to an interaction between molecules including, for example, to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions, or forces. The strength of the total non-covalent interactions between a single antigen-binding site on an antibody and a single epitope of a target molecule, such as PD-1, is the affinity of the antibody or functional fragment for that epitope. The ratio of dissociation rate ($k_{off}$) to association rate ($k_{on}$) of an antibody to a monovalent antigen ($k_{off}/k_{on}$) is the dissociation constant $K_D$, which is inversely related to affinity. The lower the $K_D$ value, the higher the affinity of the antibody. The value of $K_D$ varies for different complexes of antibody and antigen and depends on both $k_{on}$ and $k_{off}$. The dissociation constant $K_D$ for an antibody provided herein can be determined using any method provided herein or any other method well known to those skilled in the art. The affinity at one binding site does not always reflect the true strength of the interaction between an antibody and an antigen. When complex antigens containing multiple, repeating antigenic determinants, such as a polyvalent PD-1, come in contact with antibodies containing multiple binding sites, the interaction of antibody with antigen at one site will increase the probability of a reaction at a second site. The strength of such multiple interactions between a multivalent antibody and antigen is called the avidity. The avidity of an antibody can be a better measure of its binding capacity than is the affinity of its individual binding sites. For example, high avidity can compensate for low affinity as is sometimes found for pentameric IgM antibodies, which can have a lower affinity than IgG, but the high avidity of IgM, resulting from its multivalence, enables it to bind antigen effectively.

The terms "antibodies that specifically bind to PD-1," "antibodies that specifically bind to a PD-1 epitope," and analogous terms are also used interchangeably herein and refer to antibodies that specifically bind to a PD-1 polypeptide, such as a PD-1 antigen, or fragment, or epitope (e.g., human PD-1 such as a human PD-1 polypeptide, antigen, or epitope). An antibody that specifically binds to PD-1 (e.g., human PD-1) may bind to the extracellular domain or peptide derived from the extracellular domain of PD-1. An antibody that specifically binds to a PD-1 antigen (e.g., human PD-1) may be cross-reactive with related antigens (e.g., cyno PD-1). In certain embodiments, an antibody that specifically binds to a PD-1 antigen does not cross-react with other antigens. An antibody that specifically binds to a PD-1 antigen can be identified, for example, by immunoassays, Biacore®, or other techniques known to those of skill in the art. An antibody binds specifically to a PD-1 antigen when it binds to a PD-1 antigen with higher affinity than to any cross-reactive antigen as determined using experimental techniques, such as radioimmunoassays (MA) and enzyme linked immunosorbent assays (ELISAs). Typically a specific or selective reaction will be at least twice background signal or noise and may be more than 10 times background. See, e.g., *Fundamental Immunology* 332-36 (Paul ed., 2d ed. 1989) for a discussion regarding antibody specificity. An antibody which "binds an antigen of interest" (e.g., a target antigen such as PD-1) is one that binds the antigen with sufficient affinity such that the antibody is useful as a therapeutic agent in targeting a cell or tissue expressing the antigen, and does not significantly cross-react with other proteins. In such embodiments, the extent of binding of the antibody to a "non-target" protein will be less than about 10% of the binding of the antibody to its particular target protein, for example, as determined by fluorescence activated cell sorting (FACS) analysis or MA. With regard to the binding of an antibody to a target molecule, the term "specific binding," "specifically binds to," or "is specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "anti-PD-1 antibody" or "an antibody that binds to PD-1" includes an antibody that is capable of binding PD-1 with sufficient affinity such that the antibody is useful, for example, as a diagnostic agent in targeting PD-1. The term "specific binding," "specifically binds to," or "is specific for" a particular polypeptide or an epitope on a particular polypeptide target as used herein refers to binding where a molecule binds to a particular polypeptide or epitope on a particular polypeptide without substantially binding to any other polypeptide or polypeptide epitope. In certain embodiments, an antibody that binds to PD-1 has a dissociation constant ($K_D$) of less than or equal to 10 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. In certain embodiments, anti-PD-1 antibody binds to an epitope of PD-1 that is conserved among PD-1 from different species (e.g., between human and cyno PD-1).

The term "compete" when used in the context of anti-PD-1 antibodies (e.g., agonistic antibodies and binding proteins that bind to PD-1 and compete for the same epitope or binding site on a target) means competition as determined by an assay in which the antibody (or binding fragment) thereof under study prevents or inhibits the specific binding of a reference molecule (e.g., a reference ligand or reference antigen-binding protein, such as a reference antibody) to a common antigen (e.g., PD-1 or a fragment thereof). Numerous types of competitive binding assays can be used to determine if a test antibody competes with a reference antibody for binding to PD-1 (e.g., human PD-1). Examples of assays that can be employed include solid phase direct or indirect RIA, solid phase direct or indirect enzyme immunoassay (EIA), sandwich competition assay (see, e.g., Stahli et al., 1983, Methods in Enzymology 9:242-53), solid phase direct biotin-avidin EIA (see, e.g., Kirkland et al., 1986, J. Immunol. 137:3614-19), solid phase direct labeled assay, solid phase direct labeled sandwich assay (see, e.g., Harlow and Lane, *Antibodies, A Laboratory Manual* (1988)), solid phase direct label RIA using I-125 label (see, e.g., Morel et al., 1988, Mol. Immunol. 25:7-15), and direct labeled RIA (Moldenhauer et al., 1990, Scand. J. Immunol. 32:77-82). Typically, such an assay involves the use of a purified antigen (e.g., PD-1 such as human PD-1) bound to a solid surface, or cells bearing either of an unlabelled test antigen-binding protein (e.g., test anti-PD-1 antibody) or a labeled reference antigen-binding protein (e.g., reference anti-PD-1 antibody). Competitive inhibition may be measured by determining the amount of label bound to the solid surface or cells in the presence of the test antigen-binding protein. Usually the test antigen-binding protein is present in excess. Antibodies identified by competition assay (competing antibodies) include antibodies binding to the same epitope as the reference antibody and/or antibodies binding to an adjacent epitope sufficiently proximal to the epitope bound by the reference for antibodies steric hindrance to occur. Additional details regarding methods for determining competitive binding are described herein. Usually, when a competing antibody protein is present in excess, it will inhibit specific binding of a reference antibody to a common antigen by at least 30%, for example 40%, 45%, 50%, 55%, 60%, 65%, 70%, or 75%. In some instance, binding is inhibited by at least 80%, 85%, 90%, 95%, 96%, 97%, 98%, 99%, or more.

An "isolated" antibody is substantially free of cellular material or other contaminating proteins from the cell or tissue source and/or other contaminant components from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 25%, 20%, 15%, 10%, 5%, or 1% (by dry weight) of heterologous protein (also referred to herein as a "contaminating protein"). In certain embodiments, when the antibody is recombinantly produced, it is substantially free of culture medium, e.g., culture medium represents less than about 20%, 15%, 10%, 5%, or 1% of the volume of the protein preparation. In certain embodiments, when the antibody is produced by chemical synthesis, it is substantially free of chemical precursors or other chemicals, for example, it is separated from chemical precursors or other chemicals that are involved in the synthesis of the protein. Accordingly such preparations of the antibody have less than about 30%, 25%, 20%, 15%, 10%, 5%, or 1% (by dry weight) of chemical precursors or compounds other than the antibody of interest. Contaminant components can also include, but are not limited to, materials that would interfere with therapeutic uses for the antibody, and may include enzymes, hormones, and other proteinaceous or nonproteinaceous solutes. In certain embodiments, the antibody will be purified (1) to greater than 95% by weight of antibody as determined by the Lowry method (Lowry et al., 1951, J. Bio. Chem. 193:265-75), such as 96%, 97%, 98%, or 99%, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step. In specific embodiments, antibodies provided herein are isolated.

A 4-chain antibody unit is a heterotetrameric glycoprotein composed of two identical light (L) chains and two identical heavy (H) chains. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH, and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, for example, *Basic and Clinical Immunology* 71 (Stites et al. eds., 8th ed. 1994).

The term "variable region," "variable domain," "V region," or "V domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" that are each about 9-12 amino acids long. The variable regions of heavy and light chains each comprise four FRs, largely adopting a β sheet configuration, connected by three hypervariable regions, which form loops connecting, and in some cases form part of, the β sheet structure. The hypervariable regions in each chain are held together in close proximity by the FRs and, with the hypervariable regions from the other chain, contribute to the formation of the antigen-binding site of antibodies (see, e.g., Kabat et al., *Sequences of Proteins of Immunological Interest* (5th ed. 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. In specific embodiments, the variable region is a human variable region.

The term "variable region residue numbering as in Kabat" or "amino acid position numbering as in Kabat", and variations thereof, refer to the numbering system used for heavy chain variable regions or light chain variable regions of the compilation of antibodies in Kabat et al., supra. Using this numbering system, the actual linear amino acid sequence may contain fewer or additional amino acids corresponding to a shortening of, or insertion into, an FR or CDR of the variable domain. For example, a heavy chain variable domain may include a single amino acid insert (residue 52a according to Kabat) after residue 52 and three inserted residues (e.g., residues 82a, 82b, and 82c, etc. according to Kabat) after residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., supra). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Other numbering systems have been described, for example, by AbM, Chothia, Contact, IMGT, and AHon.

An "intact" antibody is one comprising an antigen-binding site as well as a CL and at least heavy chain constant regions, CH1, CH2 and CH3. The constant regions may include human constant regions or amino acid sequence variants thereof. In certain embodiments, an intact antibody has one or more effector functions.

"Antibody fragments" comprise a portion of an intact antibody, such as the antigen-binding or variable region of the intact antibody. Examples of antibody fragments include, without limitation, Fab, Fab', F(ab')$_2$, and Fv fragments; diabodies and di-diabodies (see, e.g., Holliger et al., 1993, Proc. Natl. Acad. Sci. 90:6444-48; Lu et al., 2005, J. Biol. Chem. 280:19665-72; Hudson et al., 2003, Nat. Med. 9:129-34; WO 93/11161; and U.S. Pat. Nos. 5,837,242 and 6,492,123); single-chain antibody molecules (see, e.g., U.S. Pat. Nos. 4,946,778; 5,260,203; 5,482,858; and 5,476,786); dual variable domain antibodies (see, e.g., U.S. Pat. No. 7,612,181); single variable domain antibodies (sdAbs) (see, e.g., Woolven et al., 1999, Immunogenetics 50: 98-101; and Streltsov et al., 2004, Proc Natl Acad Sci USA. 101:12444-49); and multispecific antibodies formed from antibody fragments.

A "functional fragment," "binding fragment," or "antigen-binding fragment" of a therapeutic antibody will exhibit at least one if not some or all of the biological functions attributed to the intact antibody, the function comprising at least binding to the target antigen (e.g., a PD-1 binding fragment or fragment that binds to PD-1).

The term "fusion protein" as used herein refers to a polypeptide that comprises an amino acid sequence of an antibody and an amino acid sequence of a heterologous polypeptide or protein (e.g., a polypeptide or protein not normally a part of the antibody (e.g., a non-anti-PD-1 antigen-binding antibody)). The term "fusion" when used in relation to PD-1 or to an anti-PD-1 antibody refers to the joining of a peptide or polypeptide, or fragment, variant, and/or derivative thereof, with a heterologous peptide or polypeptide. In certain embodiments, the fusion protein retains the biological activity of the PD-1 or anti-PD-1 antibody. In certain embodiments, the fusion protein comprises a PD-1 antibody VH region, VL region, VH CDR (one, two, or three VH CDRs), and/or VL CDR (one, two, or three VL CDRs), wherein the fusion protein binds to a PD-1 epitope, a PD-1 fragment, and/or a PD-1 polypeptide.

The term "heavy chain" when used in reference to an antibody refers to a polypeptide chain of about 50-70 kDa, wherein the amino-terminal portion includes a variable region of about 120 to 130 or more amino acids, and a carboxy-terminal portion includes a constant region. The constant region can be one of five distinct types, (e.g., isotypes) referred to as alpha (α), delta (δ), epsilon (ε), gamma (γ), and mu (μ), based on the amino acid sequence of the heavy chain constant region. The distinct heavy chains differ in size: α, δ, and γ contain approximately 450 amino acids, while μ and ε contain approximately 550 amino acids. When combined with a light chain, these distinct types of heavy chains give rise to five well known classes (e.g., isotypes) of antibodies, IgA, IgD, IgE, IgG, and IgM, respectively, including four subclasses of IgG, namely IgG1, IgG2, IgG3, and IgG4. A heavy chain can be a human heavy chain.

The term "light chain" when used in reference to an antibody refers to a polypeptide chain of about 25 kDa, wherein the amino-terminal portion includes a variable region of about 100 to about 110 or more amino acids, and a carboxy-terminal portion includes a constant region. The approximate length of a light chain is 211 to 217 amino acids. There are two distinct types, referred to as kappa (κ) or lambda (λ) based on the amino acid sequence of the constant domains. Light chain amino acid sequences are well known in the art. A light chain can be a human light chain.

The term "host" as used herein refers to an animal, such as a mammal (e.g., a human).

The term "host cell" as used herein refers to a particular subject cell that may be transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "monoclonal antibody" as used herein refers to an antibody obtained from a population of substantially homogeneous antibodies, e.g., the individual antibodies comprising the population are identical except for possible naturally occurring mutations that may be present in minor amounts, and each monoclonal antibody will typically recognize a single epitope on the antigen. In specific embodiments, a "monoclonal antibody," as used herein, is an antibody produced by a single hybridoma or other cell, wherein the antibody binds to only a PD-1 epitope as determined, for example, by ELISA or other antigen-binding or competitive binding assay known in the art. The term "monoclonal" is not limited to any particular method for making the antibody. For example, the monoclonal antibodies useful in the present disclosure may be prepared by the hybridoma methodology first described by Kohler et al., 1975, Nature 256:495, or may be made using recombinant DNA methods in bacterial or eukaryotic animal or plant cells (see, e.g., U.S. Pat. No. 4,816,567). The "monoclonal antibodies" may also be isolated from phage antibody libraries using the techniques described in Clackson et al., 1991, Nature 352:624-28 and Marks et al., 1991, J. Mol. Biol. 222:581-97, for example. Other methods for the preparation of clonal cell lines and of monoclonal antibodies expressed thereby are well known in the art. See, e.g., *Short Protocols in Molecular Biology* (Ausubel et al. eds., 5th ed. 2002). Exemplary methods of producing monoclonal antibodies are provided in the Examples herein.

The term "native" when used in connection with biological materials such as nucleic acid molecules, polypeptides, host cells, and the like, refers to those which are found in nature and not manipulated, modified, and/or changed (e.g., isolated, purified, selected) by a human being.

The antibodies provided herein can include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., 1984, Proc. Natl. Acad. Sci. USA 81:6851-55).

"Humanized" forms of nonhuman (e.g., murine) antibodies are chimeric antibodies that include human immunoglobulins (e.g., recipient antibody) in which the native CDR residues are replaced by residues from the corresponding CDR of a nonhuman species (e.g., donor antibody) such as mouse, rat, rabbit, or nonhuman primate having the desired specificity, affinity, and capacity. In some instances, one or more FR region residues of the human immunoglobulin are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., 1986, Nature 321:522-25; Riechmann et al., 1988, Nature 332:323-29; Presta, 1992, Curr. Op. Struct. Biol. 2:593-96; Carter et al., 1992, Proc. Natl. Acad. Sci. USA 89:4285-89; U.S. Pat. Nos. 6,800,738; 6,719,971; 6,639,055; 6,407,213; and 6,054,297.

A "human antibody" is one that possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries (Hoogenboom and Winter, 1991, J. Mol. Biol. 227:381; Marks et al., 1991, J. Mol. Biol. 222:581) and yeast display libraries (Chao et al., 2006, Nature Protocols 1: 755-68). Also available for the preparation of human monoclonal antibodies are methods described in Cole et al., *Monoclonal Antibodies and Cancer Therapy* 77 (1985); Boerner et al., 1991, J. Immunol. 147(1):86-95; and van Dijk and van de Winkel, 2001, Curr. Opin. Pharmacol. 5: 368-74. Human antibodies can be prepared by administering the antigen to a transgenic animal that has been modified to produce such antibodies in response to antigenic challenge, but whose endogenous loci have been disabled, e.g., mice (see, e.g., Jakobovits, 1995, Curr. Opin. Biotechnol. 6(5): 561-66; Bruggemann and Taussing, 1997, Curr. Opin. Biotechnol. 8(4):455-58; and U.S. Pat. Nos. 6,075,181 and 6,150,584 regarding XENOMOUSE™ technology). See also, for example, Li et al., 2006, Proc. Natl. Acad. Sci. USA 103:3557-62 regarding human antibodies generated via a human B-cell hybridoma technology.

A "CDR" refers to one of three hypervariable regions (H1, H2 or H3) within the non-framework region of the immunoglobulin (Ig or antibody) VH β-sheet framework, or one of three hypervariable regions (L1, L2, or L3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., 1997, J. Biol. Chem. 252:6609-16; Kabat, 1978, Adv. Prot. Chem. 32:1-75). CDR region sequences also have been defined structurally by Chothia as those residues that are not part of the conserved β-sheet framework, and thus are able to adapt different conformations (Chothia and Lesk, 1987, J. Mol. Biol. 196:901-17). Both terminologies are well recognized in the art. CDR region sequences have also been defined by AbM, Contact, and IMGT. The positions of CDRs within a canonical antibody variable region have been determined by comparison of numerous structures (Al-Lazikani et al., 1997, J. Mol. Biol. 273:927-48; Morea et al., 2000, Methods 20:267-79). Because the number of residues within a hypervariable region varies in different antibodies, additional residues relative to the canonical positions are conventionally numbered with a, b, c and so forth next to the residue number in the canonical variable region numbering scheme (Al-Lazikani et al., supra). Such nomenclature is similarly well known to those skilled in the art.

The term "hypervariable region," "HVR," or "HV," when used herein refers to the regions of an antibody variable region that are hypervariable in sequence and/or form structurally defined loops. Generally, antibodies comprise six hypervariable regions, three in the VH (H1, H2, H3) and three in the VL (L1, L2, L3). A number of hypervariable region delineations are in use and are encompassed herein. The Kabat Complementarity Determining Regions (CDRs) are based on sequence variability and are the most commonly used (see, e.g., Kabat et al., supra). Chothia refers instead to the location of the structural loops (see, e.g., Chothia and Lesk, 1987, J. Mol. Biol. 196:901-17). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., *Antibody Engineering* Vol. 2 (Kontermann and Dithel eds., 2d ed. 2010)). The "contact" hypervariable regions are based on an analysis of the available complex crystal structures. The residues from each of these hypervariable regions or CDRs are noted below.

Recently, a universal numbering system has been developed and widely adopted, ImMunoGeneTics (IMGT) Information System® (Lafranc et al., 2003, Dev. Comp. Immunol. 27(1):55-77). IMGT is an integrated information system specializing in immunoglobulins (IG), T cell receptors (TCR), and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. This information can be used in grafting and replacement of CDR residues from immunoglobulins of one species into an acceptor framework from, typically, a human antibody. An additional numbering system (AHon) has been developed by Honegger and Plückthun, 2001, J. Mol. Biol. 309: 657-70. Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra). In some embodiments, the CDRs are as defined by the IMGT numbering system. In other embodiments, the CDRs are as defined by the Kabat numbering system. In certain embodiments, the CDRs are as defined by the AbM numbering system. In other embodiments, the CDRs are as defined by the Chothia system. In yet other embodiments, the CDRs are as defined by the Contact numbering system.

|  | IMGT | Kabat | AbM | Chothia | Contact |
| --- | --- | --- | --- | --- | --- |
| $V_H$ CDR1 | 27-38 | 31-35 | 26-35 | 26-32 | 30-35 |
| $V_H$ CDR2 | 56-65 | 50-65 | 50-58 | 53-55 | 47-58 |
| $V_H$ CDR3 | 105-117 | 95-102 | 95-102 | 96-101 | 93-101 |
| $V_L$ CDR1 | 27-38 | 24-34 | 24-34 | 26-32 | 30-36 |
| $V_L$ CDR2 | 56-65 | 50-56 | 50-56 | 50-52 | 46-55 |
| $V_L$ CDR3 | 105-117 | 89-97 | 89-97 | 91-96 | 89-96 |

Hypervariable regions may comprise "extended hypervariable regions" as follows: 24-36 or 24-34 (L1), 46-56 or 50-56 (L2), and 89-97 or 89-96 (L3) in the VL, and 26-35 or 26-35A (H1), 50-65 or 49-65 (H2), and 93-102, 94-102, or 95-102 (H3) in the VH. As used herein, the terms "HVR" and "CDR" are used interchangeably.

The term "constant region" or "constant domain" refers to a carboxy terminal portion of the light and heavy chain which is not directly involved in binding of the antibody to antigen but exhibits various effector function, such as interaction with the Fc receptor. The term refers to the portion of an immunoglobulin molecule having a more conserved amino acid sequence relative to the other portion of the immunoglobulin, the variable region, which contains the antigen binding site. The constant region may contain the CH1, CH2, and CH3 regions of the heavy chain and the CL region of the light chain.

The term "framework" or "FR" refers to those variable region residues flanking the CDRs. FR residues are present, for example, in chimeric, humanized, human, domain antibodies, diabodies, linear antibodies, and bispecific antibodies. FR residues are those variable domain residues other than the hypervariable region residues or CDR residues.

An "affinity matured" antibody is one with one or more alterations (e.g., amino acid sequence variations, including changes, additions, and/or deletions) in one or more HVRs thereof which result in an improvement in the affinity of the antibody for antigen, compared to a parent antibody which does not possess those alteration(s). Affinity matured antibodies can have nanomolar or even picomolar affinities for the target antigen. Affinity matured antibodies are produced by procedures known in the art. For review, see Hudson and Souriau, 2003, Nature Medicine 9:129-34; Hoogenboom, 2005, Nature Biotechnol. 23:1105-16; Quiroz and Sinclair, 2010, Revista Ingeniera Biomedia 4:39-51.

A "blocking" antibody or an "antagonist" antibody is one which inhibits or reduces biological activity of the antigen it binds. For example, blocking antibodies or antagonist antibodies may substantially or completely inhibit the biological activity of the antigen.

An "agonist" antibody is an antibody that triggers a response, e.g., one that mimics at least one of the functional activities of a polypeptide of interest (e.g., PD-L1). An agonist antibody includes an antibody that is a ligand mimetic, for example, wherein a ligand binds to a cell surface receptor and the binding induces cell signaling or activities via an intercellular cell signaling pathway and wherein the antibody induces a similar cell signaling or activation. An "agonist" of PD-1 refers to a molecule that is capable of activating or otherwise increasing one or more of the biological activities of PD-1, such as in a cell expressing PD-1. In some embodiments, an agonist of PD-1 (e.g., an agonistic antibody as described herein) may, for example, act by activating or otherwise increasing the activation and/or cell signaling pathways of a cell expressing a PD-1 protein, thereby increasing a PD-1-mediated biological activity of the cell relative to the PD-1-mediated biological activity in the absence of agonist. In some embodiments the antibodies provided herein are agonistic anti-PD-1 antibodies, including antibodies that induce PD-1 signaling.

"Binding affinity" generally refers to the strength of the sum total of noncovalent interactions between a single binding site of a molecule (e.g., a binding protein such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a binding molecule X for its binding partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. Specific illustrative embodiments include the following. In one embodiment, the "$K_D$" or "$K_D$ value" may be measured by assays known in the art, for example by a binding assay. The $K_D$ may be measured in a RIA, for example, performed with the Fab version of an antibody of interest and its antigen (Chen et al., 1999, J. Mol Biol 293:865-81). The $K_D$ or $K_D$ value may also be measured by using surface plasmon resonance assays by Biacore®, using, for example, a Biacore® TM-2000 or a Biacore® TM-3000, or by biolayer interferometry using, for example, the Octet® QK384 system. An "on-rate" or "rate of association" or "association rate" or "$k_{on}$" may also be determined with the same surface plasmon resonance or biolayer interferometry techniques described above using, for example, a Biacore® TM-2000 or a Biacore® TM-3000, or the Octet® QK384 system.

The phrase "substantially similar" or "substantially the same" denotes a sufficiently high degree of similarity between two numeric values (e.g., one associated with an antibody of the present disclosure and the other associated with a reference antibody) such that one of skill in the art would consider the difference between the two values to be of little or no biological and/or statistical significance within the context of the biological characteristic measured by the values (e.g., $K_D$ values). For example, the difference between the two values may be less than about 50%, less than about 40%, less than about 30%, less than about 20%, less than about 10%, or less than about 5%, as a function of the value for the reference antibody.

The phrase "substantially increased," "substantially reduced," or "substantially different," as used herein, denotes a sufficiently high degree of difference between two numeric values (e.g., one associated with an antibody of the present disclosure and the other associated with a reference antibody) such that one of skill in the art would consider the difference between the two values to be of statistical significance within the context of the biological characteristic measured by the values. For example, the difference between said two values can be greater than about 10%, greater than about 20%, greater than about 30%, greater than about 40%, or greater than about 50%, as a function of the value for the reference antibody.

The term "inhibition" or "inhibit," when used herein, refers to partial (such as, 1%, 2%, 5%, 10%, 20%, 25%, 50%, 75%, 90%, 95%, 99%) or complete (i.e., 100%) inhibition.

"Antibody effector functions" refer to the biological activities attributable to the Fc region (e.g., a native sequence Fc region or amino acid sequence variant Fc region) of an antibody, and vary with the antibody isotype. Examples of antibody effector functions include but are not limited to: C1q binding; CDC; Fc receptor binding; ADCC; phagocytosis; downregulation of cell surface receptors (e.g., B cell receptor); and B cell activation.

"T cell effector functions" refer to the biological activities attributable to various types of T cells, including but not limited to cytotoxic T cells, T helper cells, regulatory T cells, and memory T cells. Examples of T cell effector functions include: increasing T cell proliferation, secreting cytokines, releasing cytotoxins, expressing membrane-associated molecules, killing target cells, activating macrophages, and activating B cells.

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; CDC; Fc receptor binding; ADCC; phagocytosis; downregulation of cell surface receptors (e.g., B cell receptor), etc. Such effector functions generally require the Fc region to be combined with a binding region or binding domain (e.g., an antibody variable region or domain) and can be assessed using various assays as disclosed.

A "native sequence Fc region" comprises an amino acid sequence identical to the amino acid sequence of an Fc region found in nature, and not manipulated, modified, and/or changed (e.g., isolated, purified, selected, including or combining with other sequences such as variable region sequences) by a human. Native sequence human IgG1 Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof. For example, a native human IgG1 Fc region amino acid sequence is provided below:

(SEQ ID NO: 36, K322 emphasized)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKC<u>K</u>VSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

An exemplary native human IgG4 Fc region sequence is provided below:

(SEQ ID NO: 38, S228 and L235 emphasized)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCP<u>S</u>CPAPEF<u>L</u>GGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSPGK.

A "variant Fc region" comprises an amino acid sequence which differs from that of a native sequence Fc region by virtue of at least one amino acid modification (e.g., substituting, addition, or deletion). In certain embodiments, the variant Fc region has at least one amino acid substitution compared to a native sequence Fc region or to the Fc region of a parent polypeptide, for example, from about one to about ten amino acid substitutions, or from about one to about five amino acid substitutions in a native sequence Fc region or in the Fc region of a parent polypeptide. The variant Fc region herein can possess at least about 80% homology with a native sequence Fc region and/or with an Fc region of a parent polypeptide, or at least about 90% homology therewith, for example, at least about 95% homology therewith. For example, a variant with one amino acid K change to A at 322 position in the human IgG1 Fc amino acid sequence, IgG1-K322A Fc region, is provided below:

(SEQ ID NO: 37, K322A substitution emphasized)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKC<u>A</u>VSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

An exemplary variant with one amino acid S change to P at 228 position in the human IgG4 Fc amino acid sequence, IgG4P Fc region, is provided below:

(SEQ ID NO: 39, S228P substitution emphasized)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCP<u>P</u>CPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSPGK.

An exemplary variant with two amino acid changes at 228 and 235 positions in the human IgG4 Fc amino acid sequence, IgG4PE Fc region, is provided below:

(SEQ ID NO: 40, S228P and L235E substitutions emphasized)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCP<u>P</u>CPAPEF<u>E</u>GGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSPGK.

The term "variant" when used in relation to PD-1 or to an anti-PD-1 antibody may refer to a peptide or polypeptide comprising one or more (such as, for example, about 1 to about 25, about 1 to about 20, about 1 to about 15, about 1 to about 10, or about 1 to about 5) amino acid sequence substitutions, deletions, and/or additions as compared to a native or unmodified sequence. For example, a PD-1 variant may result from one or more (such as, for example, about 1 to about 25, about 1 to about 20, about 1 to about 15, about 1 to about 10, or about 1 to about 5) changes to an amino acid sequence of a native PD-1. Also by way of example, a variant of an anti-PD-1 antibody may result from one or more (such as, for example, about 1 to about 25, about 1 to about 20, about 1 to about 15, about 1 to about 10, or about 1 to about 5) changes to an amino acid sequence of a native or previously unmodified anti-PD-1 antibody. Variants may be naturally occurring, such as allelic or splice variants, or may be artificially constructed. Polypeptide variants may be prepared from the corresponding nucleic acid molecules encoding the variants. In specific embodiments, the PD-1 variant or anti-PD-1 antibody variant at least retains PD-1 or anti-PD-1 antibody functional activity, respectively. In specific embodiments, an anti-PD-1 antibody variant binds PD-1 and/or is antagonistic to PD-1 activity. In specific embodiments, an anti-PD-1 antibody variant binds PD-1 and/or is agonistic to PD-1 activity. In certain embodiments, the variant is encoded by a single nucleotide polymorphism (SNP) variant of a nucleic acid molecule that encodes PD-1 or anti-PD-1 antibody VH or VL regions or subregions, such as one or more CDRs.

The term "vector" refers to a substance that is used to carry or include a nucleic acid sequence, including for example, a nucleic acid sequence encoding an anti-PD-1 antibody as described herein, in order to introduce a nucleic acid sequence into a host cell. Vectors applicable for use include, for example, expression vectors, plasmids, phage vectors, viral vectors, episomes, and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like, which are well known in the art. When two or more nucleic acid molecules are to be co-expressed (e.g., both an antibody heavy and light chain or an antibody VH and VL), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product (e.g., an anti-PD-1 antibody as described herein), and it is further understood that expression levels can be optimized to obtain sufficient expression using methods well known in the art.

"Antibody-dependent cell-mediated cytotoxicity" or "ADCC" refers to a form of cytotoxicity in which secreted immunoglobulin bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. NK cells, the primary cells for mediating ADCC, express FcγRIII only, whereas monocytes express FcγRI, FcγRII, and FcγRIII FcR expression on hematopoietic cells is known (see, e.g., Ravetch and Kinet, 1991, Annu. Rev. Immunol. 9:457-92). To assess ADCC activity of a molecule of interest, an in vitro ADCC assay (see, e.g., U.S. Pat. Nos. 5,500,362 and 5,821,337) can be performed. Useful effector cells for such assays include peripheral blood mononuclear cells (PBMC) and Natural Killer (NK) cells. Alternatively or additionally, ADCC activity of the molecule of interest may be assessed in vivo, for example, in an animal model (see, e.g., Clynes et al., 1998, Proc. Natl. Acad. Sci. USA 95:652-56). Antibodies with little or no ADCC activity may be selected for use.

"Antibody-dependent cellular phagocytosis" or "ADCP" refers to the destruction of target cells via monocyte or macrophage-mediated phagocytosis when immunoglobulin bound onto Fc receptors (FcRs) present on certain phagocytic cells (e.g., neutrophils, monocytes, and macrophages) enable these phagocytotic cells to bind specifically to an antigen-bearing target cell and subsequently kill the target cell. To assess ADCP activity of a molecule of interest, an in vitro ADCP assay (see, e.g., Bracher et al., 2007, J. Immunol. Methods 323:160-71) can be performed. Useful phagocytotic cells for such assays include peripheral blood mononuclear cells (PBMC), purified monocytes from PBMC, or U937 cells differentiated to the mononuclear type. Alternatively or additionally, ADCP activity of the molecule of interest may be assessed in vivo, for example, in an animal model (see, e.g., Wallace et al., 2001, J. Immunol. Methods 248:167-82). Antibodies with little or no ADCP activity may be selected for use.

"Fc receptor" or "FcR" describes a receptor that binds to the Fc region of an antibody. An exemplary FcR is a native sequence human FcR. Moreover, an exemplary FcR is one that binds an IgG antibody (e.g., a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof (see, e.g., Daëron, 1997, Annu. Rev. Immunol. 15:203-34). Various FcRs are known (see, e.g., Ravetch and Kinet, 1991, Annu. Rev. Immunol. 9:457-92; Capel et al., 1994, Immunomethods 4:25-34; and de Haas et al., 1995, J. Lab. Clin. Med. 126:330-41). Other FcRs, including those to be identified in the future, are encompassed by the term "FcR" herein. The term also includes the neonatal receptor, FcRn, which is responsible for the transfer of maternal IgGs to the fetus (see, e.g., Guyer et al., 1976, J. Immunol. 117:587-93; and Kim et al., 1994, Eu. J. Immunol. 24:2429-34). Antibody variants with improved or diminished binding to FcRs have been described (see, e.g., WO 2000/42072; U.S. Pat. Nos. 7,183,387; 7,332,581; and 7,335,742; Shields et al. 2001, J. Biol. Chem. 9(2):6591-604).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay (see, e.g., Gazzano-Santoro et al., 1996, J. Immunol. Methods 202:163) may be performed. Polypeptide variants with altered Fc region amino acid sequences (polypeptides with a variant Fc region) and increased or decreased C1q binding capability have been described (see, e.g., U.S. Pat. No. 6,194,551; WO 1999/51642; Idusogie et al., 2000, J. Immunol. 164: 4178-84). Antibodies with little or no CDC activity may be selected for use.

A PD-1 polypeptide "extracellular domain" or "ECD" refers to a form of the PD-1 polypeptide that is essentially free of the transmembrane and cytoplasmic domains. For example, a PD-1 polypeptide ECD may have less than 1% of such transmembrane and/or cytoplasmic domains and can have less than 0.5% of such domains.

The term "identity" refers to a relationship between the sequences of two or more polypeptide molecules or two or more nucleic acid molecules, as determined by aligning and comparing the sequences. "Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or MEGALIGN (DNAStar, Inc.) software. Those skilled in the art can determine appropriate parameters for aligning sequences, including any algorithms needed to achieve maximal alignment over the full length of the sequences being compared.

A "modification" of an amino acid residue/position refers to a change of a primary amino acid sequence as compared to a starting amino acid sequence, wherein the change results from a sequence alteration involving said amino acid residue/position. For example, typical modifications include substitution of the residue with another amino acid (e.g., a conservative or non-conservative substitution), insertion of one or more (e.g., generally fewer than 5, 4, or 3) amino acids adjacent to said residue/position, and/or deletion of said residue/position.

An "epitope" is the site on the surface of an antigen molecule to which a single antibody molecule binds, such as a localized region on the surface of an antigen, such as a PD-1 polypeptide, a PD-1 polypeptide fragment, that is capable of being bound to one or more antigen binding regions of an antibody, and that has antigenic or immunogenic activity in an animal, such as a mammal (e.g., a human), that is capable of eliciting an immune response. An epitope having immunogenic activity is a portion of a polypeptide that elicits an antibody response in an animal. An epitope having antigenic activity is a portion of a polypeptide to which an antibody binds as determined by any method well known in the art, including, for example, by an immunoassay. Antigenic epitopes need not necessarily be immunogenic. Epitopes often consist of chemically active surface groupings of molecules such as amino acids or sugar side chains and have specific three dimensional structural characteristics as well as specific charge characteristics. Antibody epitopes may be linear epitopes or conformational epitopes. Linear epitopes are formed by a continuous sequence of amino acids in a protein. Conformational epitopes are formed of amino acids that are discontinuous in the protein sequence, but which are brought together upon folding of the protein into its three-dimensional structure. Induced epitopes are formed when the three dimensional structure of the protein is in an altered conformation, such as following activation or binding of another protein or ligand. In certain embodiments, a PD-1 epitope is a three-dimensional surface feature of a PD-1 polypeptide. In other embodiments, a PD-1 epitope is linear feature of a PD-1 polypeptide. Generally an antigen has several or many different epitopes and may react with many different antibodies.

An antibody binds "an epitope," "essentially the same epitope," or "the same epitope" as a reference antibody, when the two antibodies recognize identical, overlapping, or adjacent epitopes in a three-dimensional space. The most widely used and rapid methods for determining whether two antibodies bind to identical, overlapping, or adjacent epitopes in a three-dimensional space are competition assays, which can be configured in a number of different formats, for example, using either labeled antigen or labeled antibody. In some assays, the antigen is immobilized on a 96-well plate, or expressed on a cell surface, and the ability of unlabeled antibodies to block the binding of labeled antibodies is measured using radioactive, fluorescent, or enzyme labels.

"Epitope mapping" is the process of identifying the binding sites, or epitopes, of antibodies on their target antigens. "Epitope binning" is the process of grouping antibodies based on the epitopes they recognize. More particularly, epitope binning comprises methods and systems for discriminating the epitope recognition properties of different antibodies, using competition assays combined with computational processes for clustering antibodies based on their epitope recognition properties and identifying antibodies having distinct binding specificities.

An "effective amount" is generally an amount sufficient to reduce the severity and/or frequency of symptoms, eliminate the symptoms and/or underlying cause, prevent the occurrence of symptoms and/or their underlying cause, and/or improve or remediate the damage that results from or is associated with a disease, disorder, or condition, including, for example, vitiligo. In some embodiments, the effective amount is a therapeutically effective amount or a prophylactically effective amount.

The term "therapeutically effective amount" as used herein refers to the amount of an agent (e.g., an antibody provided herein or any other agent described herein) that is sufficient to reduce and/or ameliorate the severity and/or duration of a given disease, disorder, or condition, and/or a symptom related thereto (e.g., vitiligo). A "therapeutically effective amount" of a substance/molecule/agent of the present disclosure (e.g., an anti-PD-1 antibody) may vary according to factors such as the disease state, age, sex, and weight of the individual, and the ability of the substance/molecule/agent to elicit a desired response in the individual. A therapeutically effective amount encompasses an amount in which any toxic or detrimental effects of the substance/molecule/agent are outweighed by the therapeutically beneficial effects. In certain embodiments, the term "therapeutically effective amount" refers to an amount of an antibody or other agent (e.g., drug) effective to "treat" a disease, disorder, or condition, in a subject or mammal.

A "prophylactically effective amount" is an amount of a pharmaceutical composition that, when administered to a subject, will have the intended prophylactic effect, e.g., preventing, delaying, or reducing the likelihood of the onset (or reoccurrence) of a disease, disorder, condition, or associated symptom(s) (e.g., vitiligo). Typically, but not necessarily, since a prophylactic dose is used in subjects prior to or at an earlier stage of a disease, disorder, or condition, a prophylactically effective amount may be less than a therapeutically effective amount. The full therapeutic or prophylactic effect does not necessarily occur by administration of one dose, and may occur only after administration of a series of doses. Thus, a therapeutically or prophylactically effective amount may be administered in one or more administrations.

"Chronic" administration refers to administration of the agent(s) in a continuous mode (e.g., for a period of time such as days, weeks, months, or years) as opposed to an acute mode, so as to maintain the initial therapeutic effect (activity) for an extended period of time. "Intermittent" administration is treatment that is not consecutively done without interruption, but rather is cyclic in nature.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers, such as phosphate, citrate, and other organic acids; antioxidants, including ascorbic acid; low molecular weight (e.g., fewer than about 10 amino acid residues) polypeptide; proteins, such as serum albumin, gelatin, or immunoglobulins; hydrophilic polymers, such as polyvinylpyrrolidone; amino acids, such as glycine, glutamine, asparagine, arginine, or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN™, polyethylene glycol (PEG), and PLURONICS™. The term "carrier" can also refer to a diluent, adjuvant (e.g., Freund's adjuvant (complete or incomplete)), excipient, or vehicle. Such carriers, including pharmaceutical carriers, can be sterile liquids, such as water and oils, including those of petroleum, animal, vegetable, or synthetic origin, such as peanut oil, soybean oil, mineral oil, sesame oil, and the like. Water is an exemplary carrier when a composition (e.g., a pharmaceutical composition) is administered intravenously. Saline solutions and aqueous dextrose and glycerol solutions can also be employed as liquid carriers, particularly for injectable solutions. Suitable excipients (e.g., pharmaceutical excipients) include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. Compositions can take the form of solutions, suspensions, emulsion, tablets, pills, capsules, powders, sustained-release formulations, and the like. Oral compositions, including formulations, can include standard carriers such as pharmaceutical grades of mannitol, lactose, starch, magnesium stearate, sodium saccharine, cellulose, magnesium carbonate, etc. Examples of suitable pharmaceutical carriers are described in Remington and Gennaro, *Remington's Pharmaceutical Sciences* (18th ed. 1990). Compositions, including pharmaceutical compounds, may contain an anti-PD-1 antibody, for example, in isolated or purified form, together with a suitable amount of carriers.

The term "pharmaceutically acceptable" as used herein means being approved by a regulatory agency of the Federal or a state government, or listed in *United States Pharmacopeia, European Pharmacopeia*, or other generally recognized Pharmacopeia for use in animals, and more particularly in humans.

"Polyclonal antibodies" as used herein refer to an antibody population generated in an immunogenic response to a protein having many epitopes and thus includes a variety of different antibodies directed to the same or different epitopes within the protein. Methods for producing polyclonal antibodies are known in the art (See, e.g., *Short Protocols in Molecular Biology* (Ausubel et al. eds., 5th ed. 2002)).

An "isolated nucleic acid" is a nucleic acid, for example, an RNA, DNA, or a mixed nucleic acids, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, one or more nucleic acid molecules encoding an antibody as described herein are isolated or purified. The term embraces nucleic acid sequences that have been removed from their naturally occurring environment, and includes recombinant or cloned DNA isolates and chemically synthesized analogues or analogues biologically synthesized by heterologous systems. A substantially pure molecule may include isolated forms of the molecule.

"Polynucleotide" or "nucleic acid," as used interchangeably herein, refers to polymers of nucleotides of any length and includes DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. "Oligonucleotide," as used herein, refers to short, generally single-stranded, synthetic polynucleotides that are generally, but not necessarily, fewer than about 200 nucleotides in length. The terms "oligonucleotide" and "polynucleotide" are not mutually exclusive. The description above for polynucleotides is equally and fully applicable to oligonucleotides. A cell that produces an anti-PD-1 antibody of the present disclosure may include a parent hybridoma cell, as well as bacterial and eukaryotic host cells into which nucleic acids encoding the antibodies have been introduced. Suitable host cells are disclosed below.

Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences."

The terms "prevent," "preventing," and "prevention" refer to reducing the likelihood of the onset (or recurrence) of a disease, disorder, condition, or associated symptom(s) (e.g., vitiligo).

The term "prophylactic agent" refers to any agent that can totally or partially inhibit the development, recurrence, onset, or spread of a disease (e.g., vitiligo) and/or symptom related thereto in a subject. In certain embodiments, the term "prophylactic agent" refers to an anti-PD-1 antibody as described herein.

As used herein, a "prophylactically effective serum titer" is the serum titer of a PD-1 antibody, e.g., a PD-1 antibody as described herein, in a subject (e.g., a human), that totally or partially inhibits the development, recurrence, onset, or spread of a disease (e.g., vitiligo), disorder, or condition, and/or symptom related thereto in the subject.

In certain embodiments, a "therapeutically effective serum titer" is the serum titer of a PD-1 antibody, e.g., a PD-1 antibody as described herein, in a subject (e.g., a human), that reduces the severity, the duration, and/or the symptoms associated with a PD-1-mediated disease, disorder, or condition, in the subject.

The term "recombinant antibody" refers to an antibody that is prepared, expressed, created, or isolated by recombinant means. Recombinant antibodies can be antibodies expressed using a recombinant expression vector transfected into a host cell, antibodies isolated from a recombinant, combinatorial antibody library, antibodies isolated from an animal (e.g., a mouse or cow) that is transgenic and/or transchromosomal for human immunoglobulin genes (see, e.g., Taylor et al., 1992, Nucl. Acids Res. 20:6287-95), or antibodies prepared, expressed, created, or isolated by any other means that involves splicing of immunoglobulin gene sequences to other DNA sequences. Such recombinant antibodies can have variable and constant regions, including those derived from human germline immunoglobulin sequences (See Kabat et al., supra). In certain embodiments, however, such recombinant antibodies may be subjected to in vitro mutagenesis (or, when an animal transgenic for human Ig sequences is used, in vivo somatic mutagenesis), thus the amino acid sequences of the VH and VL regions of the recombinant antibodies are sequences that, while derived from and related to human germline VH and VL sequences, may not naturally exist within the human antibody germline repertoire in vivo.

The term "serum titer" refers to an average serum titer in a subject from multiple samples (e.g., at multiple time points) or in a population of at least 10, at least 20, at least 40 subjects, up to about 100, 1000, or more.

The term "side effects" encompasses unwanted and/or adverse effects of a therapy (e.g., a prophylactic or therapeutic agent). Unwanted effects are not necessarily adverse. An adverse effect from a therapy (e.g., a prophylactic or therapeutic agent) might be harmful, uncomfortable, or risky. Examples of side effects include, diarrhea, cough, gastroenteritis, wheezing, nausea, vomiting, anorexia, abdominal cramping, fever, pain, loss of body weight, dehydration, alopecia, dyspnea, insomnia, dizziness, mucositis, nerve and muscle effects, fatigue, dry mouth, loss of appetite, rashes or swellings at the site of administration, flu-like symptoms such as fever, chills, and fatigue, digestive tract problems, and allergic reactions. Additional undesired effects experienced by patients are numerous and known in the art. Many are described in *Physician's Desk Reference* (68th ed. 2014).

The terms "subject" and "patient" may be used interchangeably. As used herein, in certain embodiments, a subject is a mammal, such as a non-primate (e.g., cow, pig, horse, cat, dog, rat, etc.) or a primate (e.g., monkey and human). In specific embodiments, the subject is a human. In one embodiment, the subject is a mammal (e.g., a human) having a disease, disorder, or condition (e.g., vitiligo). In another embodiment, the subject is a mammal (e.g., a human) at risk of developing a disease, disorder, or condition (e.g., vitiligo).

"Substantially all" refers to at least about 60%, at least about 65%, at least about 70%, at least about 75%, at least about 80%, at least about 85%, at least about 90%, at least about 95%, at least about 98%, at least about 99%, or about 100%.

The term "therapeutic agent" refers to any agent that can be used in treating, preventing, or alleviating a disease, disorder, or condition, including in the treatment, prevention, or alleviation of one or more symptoms of a disease, disorder, or condition (e.g., vitiligo) and/or a symptom related thereto. In certain embodiments, a therapeutic agent refers to an anti-PD-1 antibody as described herein.

The term "therapy" refers to any protocol, method, and/or agent that can be used in the prevention, management, treatment, and/or amelioration of a disease, disorder, or condition (e.g., vitiligo). In certain embodiments, the terms "therapies" and "therapy" refer to a biological therapy, supportive therapy, and/or other therapies useful in the prevention, management, treatment, and/or amelioration of a disease, disorder, or condition (e.g., vitiligo), known to one of skill in the art such as medical personnel.

The term "detectable probe" refers to a composition that provides a detectable signal. The term includes, without limitation, any fluorophore, chromophore, radiolabel, enzyme, antibody or antibody fragment, and the like, that provide a detectable signal via its activity.

The term "detectable agent" refers to a substance that can be used to ascertain the existence or presence of a desired molecule, such as an anti-PD-1 antibody as described herein, in a sample or subject. A detectable agent can be a substance that is capable of being visualized or a substance that is otherwise able to be determined and/or measured (e.g., by quantitation).

The term "diagnostic agent" refers to a substance administered to a subject that aids in the diagnosis of a disease, disorder, or condition. Such substances can be used to reveal, pinpoint, and/or define the localization of a disease causing process. In certain embodiments, a diagnostic agent includes a substance that is conjugated to an anti-PD-1 antibody as described herein, that when administered to a subject or contacted with a sample from a subject aids in the diagnosis of a disease (e.g., vitiligo).

The term "encoding nucleic acid" or grammatical equivalents thereof as it is used in reference to nucleic acid molecule refers to a nucleic acid molecule in its native state or when manipulated by methods well known to those skilled in the art that can be transcribed to produce mRNA, which is then translated into a polypeptide and/or a fragment thereof. The antisense strand is the complement of such a nucleic acid molecule, and the encoding sequence can be deduced therefrom.

The term "excipient" refers to an inert substance which is commonly used as a diluent, vehicle, preservative, binder, or stabilizing agent, and includes, but is not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.), and polyols (e.g., mannitol, sorbitol, etc.). See, also, Remington and Gennaro, *Remington's Pharmaceutical Sciences* (18th ed. 1990), which is hereby incorporated by reference in its entirety.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, PD-1 fragments or anti-PD-1 antibody fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, at least 250, at least 300, at least 350, at least 400, at least 450, at least 500, at least 550, at least 600, at least 650, at least 700, at least 750, at least 800, at least 850, at least 900, or at least 950 contiguous amino acid residues of the amino acid sequence of a PD-1 polypeptide or an anti-PD-1 antibody. In a specific embodiment, a fragment of a PD-1 polypeptide or an anti-PD-1 antibody retains at least 1, at least 2, at least 3, or more functions of the polypeptide or antibody.

The terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., prophylactic or therapeutic agents, such as an antibody provided herein) to "manage" a disease (e.g., vitiligo), one or more symptoms thereof, so as to prevent the progression or worsening of the disease.

The terms "about" and "approximately" mean within 20%, within 15%, within 10%, within 9%, within 8%, within 7%, within 6%, within 5%, within 4%, within 3%, within 2%, within 1%, or less of a given value or range.

"Administer" or "administration" refers to the act of injecting or otherwise physically delivering a substance as it exists outside the body (e.g., an anti-PD-1 antibody as described herein) into a patient, such as by mucosal, intradermal, intravenous, intramuscular delivery, and/or any other method of physical delivery described herein or known in the art. When a disease, disorder, condition, or a symptom thereof, is being treated, administration of the substance typically occurs after the onset of the disease, disorder, condition, or symptoms thereof. When a disease, disorder, condition, or symptoms thereof, are being prevented, administration of the substance typically occurs before the onset of the disease, disorder, condition, or symptoms thereof.

In the context of a polypeptide, the term "analog" as used herein refers to a polypeptide that possesses a similar or identical function as a PD-1 polypeptide, a fragment of a PD-1 polypeptide, or an anti-PD-1 antibody but does not necessarily comprise a similar or identical amino acid sequence of a PD-1 polypeptide, a fragment of a PD-1 polypeptide, or an anti-PD-1 antibody, or possess a similar or identical structure of a PD-1 polypeptide, a fragment of a PD-1 polypeptide, or an anti-PD-1 antibody. A polypeptide that has a similar amino acid sequence refers to a polypeptide that satisfies at least one of the followings: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a PD-1 polypeptide, a fragment of a PD-1 polypeptide, or an anti-PD-1 antibody provided herein; (b) a polypeptide encoded by a nucleotide sequence that hybridizes under stringent conditions to a nucleotide sequence encoding a PD-1 polypeptide, a fragment of a PD-1 polypeptide, or an anti-PD-1 antibody (or VH or VL region thereof) described herein at least 5 amino acid residues, at least 10 amino acid residues, at least 15 amino acid residues, at least 20 amino acid residues, at least 25 amino acid residues, at least 30 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues (see, e.g., Sambrook et al., *Molecular Cloning: A Laboratory Manual* (2001); and Maniatis et al., *Molecular Cloning: A Laboratory Manual* (1982)); or (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the nucleotide sequence encoding a PD-1 polypeptide, a fragment of a PD-1 polypeptide, or an anti-PD-1 antibody (or VH or VL region thereof) described herein. A polypeptide with similar structure to a PD-1 polypeptide, a fragment of a PD-1 polypeptide, or an anti-PD-1 antibody provided herein refers to a polypeptide that has a similar secondary, tertiary, or quaternary structure of a PD-1 polypeptide, a fragment of a PD-1 polypeptide, or an anti-PD-1 antibody provided herein. The structure of a polypeptide can be determined by methods known to those skilled in the art, including but not limited to, X-ray crystallography, nuclear magnetic resonance, and crystallographic electron microscopy.

In the context of a polypeptide, the term "derivative" as used herein refers to a polypeptide that comprises an amino acid sequence of a PD-1 polypeptide, a fragment of a PD-1 polypeptide, or an antibody that binds to a PD-1 polypeptide which has been altered by the introduction of amino acid residue substitutions, deletions, or additions. The term "derivative" as used herein also refers to a PD-1 polypeptide, a fragment of a PD-1 polypeptide, or an antibody that binds to a PD-1 polypeptide which has been chemically modified, e.g., by the covalent attachment of any type of molecule to the polypeptide. For example, but not by way of limitation, a PD-1 polypeptide, a fragment of a PD-1 polypeptide, or an anti-PD-1 antibody may be chemically modified, e.g., by glycosylation, acetylation, pegylation, phosphorylation, amidation, derivatization by known protecting/blocking groups, proteolytic cleavage, chemical cleavage, formulation, metabolic synthesis of tunicamycin, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. Further, a derivative of a PD-1 polypeptide, a fragment of a PD-1 polypeptide, or an anti-PD-1 antibody may contain one or more non-classical amino acids. A polypeptide derivative possesses a similar or identical function as a PD-1 polypeptide, a fragment of a PD-1 polypeptide, or an anti-PD-1 antibody provided herein.

The term "composition" is intended to encompass a product containing the specified ingredients (e.g., an antibody provided herein) in, optionally, the specified amounts.

4.3 Compositions and Methods of Making the Same

Provided herein are methods of managing, preventing, or treating vitiligo in a subject, comprising administering to a subject a therapeutically effective amount of an antibody that binds to a PD-1 polypeptide, a PD-1 polypeptide fragment, a PD-1 peptide, or a PD-1 epitope.

In certain embodiments of the methods, the antibodies provided herein bind to human and/or cyno PD-1. In one embodiment, the PD-1 antibodies bind to human PD-1. In one embodiment, the PD-1 antibodies bind to cyno PD-1. In one embodiment, the PD-1 antibodies bind to both human PD-1 and cyno PD-1. In other embodiments, the antibodies provided herein do not bind to rodent PD-1.

In some embodiments of the methods, the anti-PD-1 antibodies bind to the extracellular domain (ECD) of PD-1. In certain embodiments, the anti-PD-1 antibodies bind to an epitope in the ECD of PD-1, which is distinct from the PD-L1 binding site. In certain embodiments, the anti-PD-1 antibodies bind to an epitope in the ECD of PD-1, which is distinct from the PD-L2 biding site. In certain embodiments, the anti-PD-1 antibodies bind to an epitope in the ECD of PD-1, which is distinct from both the PD-L1 and PD-L2-binding site.

In still other embodiments of the methods, the antibodies competitively block an anti-PD-1 antibody provided herein from binding to a PD-1 polypeptide.

In another embodiment of the methods, the antibodies compete for binding to a PD-1 polypeptide with an anti-PD-1 antibody provided herein.

In some embodiments, the anti-PD-1 antibodies do not block the binding of PD-L1 to a PD-1 polypeptide. In some embodiments, the anti-PD-1 antibodies do not block the binding of PD-L2 to a PD-1 polypeptide. In some embodiments, the anti-PD-1 antibodies do not block the binding of PD-L1 or PD-L2 to a PD-1 polypeptide.

In some embodiments, the anti-PD-1 antibodies do not compete with PD-L1 for binding to a PD-1 polypeptide. In some embodiments, the anti-PD-1 antibodies do not compete with PD-L2 for binding to a PD-1 polypeptide. In some embodiments, the anti-PD-1 antibodies do not compete with PD-L1 or PD-L2 for binding to a PD-1 polypeptide.

In certain embodiments, binding of PD-L1 to PD-1 is not inhibited by the antibody. In other embodiments, binding of PD-L2 to PD-1 is not inhibited by the antibody. In specific embodiments, neither binding of PD-L1 to PD-1 nor binding of PD-L2 to PD-1 is inhibited by the antibody.

The anti-PD-1 antibodies provided herein can also be conjugated or recombinantly fused, e.g., to a diagnostic agent or detectable agent. Further provided are compositions comprising an anti-PD-1 antibody.

4.3.1 Anti-PD-1 Antibodies

In one embodiment, the present disclosure provides anti-PD-1 antibodies that may find use herein as therapeutic agents. In another embodiment, the present disclosure provides anti-PD-1 antibodies that may find use herein as diagnostic agents. Exemplary antibodies include polyclonal, monoclonal, humanized, human, bispecific, and heteroconjugate antibodies, as well as variants thereof having improved affinity or other properties.

In some embodiments, described herein are antibodies that bind to PD-1, including a PD-1 polypeptide, a PD-1 polypeptide fragment, a PD-1 peptide, or a PD-1 epitope. In certain embodiments, the antibodies provided herein bind to human and/or cyno PD-1. In other embodiments, the antibodies provided herein do not bind to rodent PD-1 (e.g., a mouse PD-1). In one embodiment, an antibody provided herein binds to human PD-1. In another embodiment, an antibody provided herein binds to cyno PD-1. In another embodiment, an antibody provided herein binds to human PD-1 and cyno PD-1. In some embodiments, an antibody provided herein binds to human PD-1 and does not bind to a rodent PD-1 (e.g., a mouse PD-1). In some embodiments, an antibody provided herein binds to cyno PD-1 and does not bind to a rodent PD-1 (e.g., a mouse PD-1). In some embodiments, an antibody provided herein binds to human PD-1, binds to a cyno PD-1, and does not bind to a rodent PD-1 (e.g., a mouse PD-1). In some embodiments, the anti-PD-1 antibodies do not block the binding of PD-L1 to a PD-1 polypeptide. In some embodiments, the anti-PD-1 antibodies do not block the binding of PD-L2 to a PD-1 polypeptide. In some embodiments, the anti-PD-1 antibodies do not block the binding of PD-L1 or PD-L2 to a PD-1 polypeptide. In other embodiments, the anti-PD-1 antibodies are humanized antibodies (e.g., comprising human constant regions) that bind PD-1, including a PD-1 polypeptide, a PD-1 polypeptide fragment, a PD-1 peptide, or a PD-1 epitope.

In certain embodiments, the anti-PD-1 antibody comprises a VH CDR1, VH CDR2, VH CDR3, VL CDR1, VL CDR2, and/or VL CDR3 of any one of the murine monoclonal antibodies provided herein. In some embodiments, the VH CDR1, VH CDR2, VH CDR3, VL CDR1, VL CDR2, and/or VL CDR3 is as defined by the IMGT numbering system. In other embodiments, the VH CDR1, VH CDR2, VH CDR3, VL CDR1, VL CDR2, and/or VL CDR3 is as defined by the Kabat numbering system. In certain embodiments, the VH CDR1, VH CDR2, VH CDR3, VL CDR1, VL CDR2, and/or VL CDR3 is as defined by the AbM numbering system. In other embodiments, the VH CDR1, VH CDR2, VH CDR3, VL CDR1, VL CDR2, and/or VL CDR3 is as defined by the Chothia system. In yet other embodiments, the VH CDR1, VH CDR2, VH CDR3, VL CDR1, VL CDR2, and/or VL CDR3 is as defined by the Contact numbering system. Accordingly, in some embodiments, the isolated antibody or functional fragment thereof provided herein comprises one, two, and/or three heavy chain CDRs and/or one, two, and/or three light chain CDRs from: (a) the antibody PD1AB-1, (b) the antibody PD1AB-2, (c) the antibody PD1AB-3, (d) the antibody PD1AB-4, (e) the antibody PD1AB-5, or (f) the antibody PD1AB-6, as shown in Tables 1-2.

TABLE 1

VL CDR Amino Acid Sequences

| Antibody | VL CDR1 (SEQ ID NO:) | VL CDR2 (SEQ ID NO:) | VL CDR3 (SEQ ID NO:) |
|---|---|---|---|
| PD1AB-1 | KSGQSVLYSSNQKNFLA (SEQ ID NO: 1) | WASTRES (SEQ ID NO: 2) | HQYLYSWT (SEQ ID NO: 3) |
| PD1AB-2 | KSSQSVLYSSNNKNYLA (SEQ ID NO: 7) | WASTRES (SEQ ID NO: 2) | HQYLYSWT (SEQ ID NO: 3) |
| PD1AB-3 | KSGQSVLYSSNQKNFLA (SEQ ID NO: 1) | WASTRES (SEQ ID NO: 2) | HQYLYSWT (SEQ ID NO: 3) |
| PD1AB-4 | KSSQSVLYSSNNKNYLA (SEQ ID NO: 7) | WASTRES (SEQ ID NO: 2) | HQYLYSWT (SEQ ID NO: 3) |
| PD1AB-5 | KSSQSVLYSSNNKNYLA (SEQ ID NO: 7) | WASTRES SEQ ID NO: 2) | HQYLYSWT (SEQ ID NO: 3) |
| PD1AB-6 | KSGQSVLYSSNQKNFLA (SEQ ID NO: 1) | WASTRES (SEQ ID NO: 2) | HQYLYSWT (SEQ ID NO: 3) |

TABLE 2

VH CDR Amino Acid Sequences

| Antibody | VH CDR1 (SEQ ID NO:) | VH CDR2 (SEQ ID NO:) | VH CDR3 (SEQ ID NO:) |
|---|---|---|---|
| PD1AB-1 | GENIKDIYMH (SEQ ID NO: 4) | RIDPANGDRK (SEQ ID NO: 5) | SGPVYYYGSSYVMDY (SEQ ID NO: 6) |
| PD1AB-2 | GENIKDIYMH (SEQ ID NO: 4) | RIDPANGDRK (SEQ ID NO: 5) | SGPVYYYGSSYVMDY (SEQ ID NO: 6) |
| PD1AB-3 | GENIKDIYMH (SEQ ID NO: 4) | RIDPANGDRK (SEQ ID NO: 5) | SGPVYYYGSSYVMDY (SEQ ID NO: 6) |
| PD1A13-4 | GFNIKDTYMH (SEQ ID NO: 4) | RIDPANGDRK (SEQ ID NO: 5) | SGPVYYYGSSYVMDY (SEQ ID NO: 6) |
| PD1A13-5 | GFNIKDTYMH (SEQ ID NO: 4) | RIDPANGDRK (SEQ ID NO: 5) | SGPVYYYGSSYVMDY (SEQ ID NO: 6) |
| PD1A13-6 | GFNIKDTYMH (SEQ ID NO: 4) | RIDPANGDRK (SEQ ID NO: 5) | SGPVYYYGSSYVMDY (SEQ ID NO: 6) |

In some embodiments, an antibody provided herein comprises or consists of six CDRs, for example, VH CDR1, VH CDR2, VH CDR3, VL CDR1, VL CDR2, and/or VL CDR3 identified in Tables 1-2. In some embodiments, an antibody provided herein can comprise fewer than six CDRs. In some embodiments, the antibody comprises or consists of one, two, three, four, or five CDRs selected from the group consisting of VH CDR1, VH CDR2, VH CDR3, VL CDR1, VL CDR2, and/or VL CDR3 identified in Tables 1-2. In some embodiments, the antibody comprises or consists of one, two, three, four, or five CDRs selected from the group consisting of VH CDR1, VH CDR2, VH CDR3, VL CDR1, VL CDR2, and/or VL CDR3 of the monoclonal antibody selected from the group consisting of: (a) the antibody PD1AB-1, (b) the antibody PD1AB-2, (c) the antibody PD1AB-3, (d) the antibody PD1AB-4, (e) the antibody PD1AB-5, and (f) the antibody PD1AB-6, described herein. Accordingly, in some embodiments, the antibody comprises or consists of one, two, three, four, or five CDRs of anyone of the VH CDR1, VH CDR2, VH CDR3, VL CDR1, VL CDR2, and/or VL CDR3 identified in Tables 1-2.

In some embodiments, the antibodies provided herein comprise one or more (e.g., one, two, or three) VH CDRs listed in Table 2. In other embodiments, the antibodies provided herein comprise one or more (e.g., one, two, or three) VL CDRs listed in Table 1. In yet other embodiments, the antibodies provided herein comprise one or more (e.g., one, two, or three) VH CDRs listed in Table 2 and one or more VL CDRs listed in Table 1. Accordingly, in some embodiments, the antibodies comprise a VH CDR1 having an amino acid sequence of SEQ ID NO:4. In some embodiments, the antibodies comprise a VH CDR2 having an amino acid sequence of SEQ ID NO:5. In some embodiments, the antibodies comprise a VH CDR3 having an amino acid sequence of SEQ ID NO:6. In some embodiments, the antibodies comprise a VH CDR1 and/or a VH CDR2 and/or a VH CDR3 independently selected from any one of the VH CDR1, VH CDR2, VH CDR3 amino acid sequence(s) as depicted in Table 2. In some embodiments, the antibodies comprise a VL CDR1 having an amino acid sequence of any one of SEQ ID NOS:1 and 7. In another embodiment, the antibodies comprise a VL CDR2 having an amino acid sequence of SEQ ID NO:2. In some embodiments, the antibodies comprise a VL CDR3 having an amino acid sequence of SEQ ID NO:3. In some embodiments, the antibodies comprise a VL CDR1 and/or a VL CDR2 and/or a VL CDR3 independently selected from any one of the VL CDR1, VL CDR2, VL CDR3 amino acid sequences as depicted in Table 1.

In certain embodiments, the antibodies provided herein comprise a VH region comprising: (1) a VH CDR1 having an amino acid sequence of SEQ ID NO:4; (2) a VH CDR2 having an amino acid sequence of SEQ ID NO:5; and (3) a VH CDR3 having an amino acid sequence of SEQ ID NO:6; and a VL region comprising: (1) a VL CDR1 having an amino acid sequence of SEQ ID NO:1; (2) a VL CDR2 having an amino acid sequence of SEQ ID NO:2; and (3) a VL CDR3 having an amino acid sequence of SEQ ID NO:3.

In certain embodiments, the antibodies provided herein comprise a VH region comprising: (1) a VH CDR1 having an amino acid sequence of SEQ ID NO:4; (2) a VH CDR2 having an amino acid sequence of SEQ ID NO:5; and (3) a VH CDR3 having an amino acid sequence of SEQ ID NO:6; and a VL region comprising: (1) a VL CDR1 having an amino acid of SEQ ID NOS:7; (2) a VL CDR2 having an amino acid sequence of SEQ ID NO:2; and (3) a VL CDR3 having an amino acid sequence of SEQ ID NO:3.

In some embodiments, the antibodies provided herein comprise a VH region comprising: (1) a VH CDR1 having an amino acid sequence of SEQ ID NO:4; (2) a VH CDR2 having an amino acid sequence of SEQ ID NO:5; and (3) a VH CDR3 having an amino acid sequence of SEQ ID NO:6.

In other embodiments, the antibodies provided herein comprise a VL region comprising: (1) a VL CDR1 having an amino acid sequence of SEQ ID NO:1; (2) a VL CDR2 having an amino acid sequence of SEQ ID NO:2; and (3) a VL CDR3 having an amino acid sequence of SEQ ID NO:3.

In some embodiments, the antibodies provided herein comprise a VL region comprising: (1) a VL CDR1 having an amino acid sequence of SEQ ID NOS: 7; (2) a VL CDR2 having an amino acid sequence of SEQ ID NO:2; and (3) a VL CDR3 having an amino acid sequence of SEQ ID NO:3.

Also described herein are antibodies comprising one or more (e.g., one, two, or three) VH CDRs and one or more (e.g., one, two, or three) VL CDRs listed in Tables 1-2. In particular, provided herein is an antibody comprising a VH CDR1 (SEQ ID NO:4) and a VL CDR1 (SEQ ID NOS:1 or 7). In one embodiment, the antibody comprises a VH CDR1 (SEQ ID NO:4) and a VL CDR2 (SEQ ID NO:2). In other embodiments, the antibody comprises a VH CDR1 (SEQ ID NO:4) and a VL CDR3 (SEQ ID NO:3). In another embodiment, the antibody comprises a VH CDR2 (SEQ ID NO:5) and a VL CDR1 (SEQ ID NOS:1 or 7). In some embodiments, the antibody comprises a VH CDR2 (SEQ ID NO:5) and a VL CDR2 (SEQ ID NO:2). In one embodiment, the antibody comprises a VH CDR2 (SEQ ID NO:5) and a VL CDR3 (SEQ ID NO:3). In another embodiment, the antibody comprises a VH CDR3 (SEQ ID NO:6) and a VL CDR1 (SEQ ID NOS:1 or 7). In other embodiments, the antibody comprises a VH CDR3 (SEQ ID NO:6) and a VL CDR2 (SEQ ID NO:2). In some embodiments, the antibody comprises a VH CDR3 (SEQ ID NO:6) and a VL CDR3 (SEQ ID NO:3). In another embodiment, the antibody comprises a VH CDR1 (SEQ ID NO:4), a VH CDR2 (SEQ ID NO:5), and a VL CDR1 (SEQ ID NOS:1 or 7). In one embodiment, the antibody comprises a VH CDR1 (SEQ ID NO:4), a VH CDR2 (SEQ ID NO:5), and a VL CDR2 (SEQ ID NO:2). In other embodiments, the antibody comprises a VH CDR1 (SEQ ID NO:4), a VH CDR2 (SEQ ID NO:5), and a VL CDR3 (SEQ ID NOS:3). In another embodiment, the antibody comprises a VH CDR2 (SEQ ID NO:5), a VH CDR3 (SEQ ID NO:6), and a VL CDR1 (SEQ ID NOS:1 or 7). In some embodiments, the antibody comprises a VH CDR2 (SEQ ID NO:5), a VH CDR3 (SEQ ID NO:6), and a VL CDR2 (SEQ ID NO:2). In one embodiment, the antibody comprises a VH CDR2 (SEQ ID NO:5), a VH CDR3 (SEQ ID NO:6), and a VL CDR3 (SEQ ID NO:3). In another embodiment, the antibody comprises a VH CDR1 (SEQ ID NO:4), a VH CDR3 (SEQ ID NO:6), and a VL CDR1 (SEQ ID NOS:1 or 7). In other embodiments, the antibody comprises a VH CDR1 (SEQ ID NO:4), a VH CDR3 (SEQ ID NO:6), and a VL CDR2 (SEQ ID NO:2). In some embodiments, the antibody comprises a VH CDR1 (SEQ ID NO:4), a VH CDR3 (SEQ ID NO:6), and a VL CDR3 (SEQ ID NO:3). In another embodiment, the antibody comprises a VH CDR1 (SEQ ID NO:4), a VL CDR1 (SEQ ID NOS:1 or 7), and a VL CDR2 (SEQ ID NO:2). In one embodiment, the antibody comprises a VH CDR1 (SEQ ID NO:4), a VL CDR1 (SEQ ID NOS:1 or 7), and a VL CDR3 (SEQ ID NO:3). In other embodiments, the antibody comprises a VH CDR1 (SEQ ID NO:4), a VL CDR2 (SEQ ID NO:2), and a VL CDR3 (SEQ ID NO:3). In another embodiment, the antibody comprises a VH CDR2 (SEQ ID NO:5), a VL CDR1 (SEQ ID NOS:1 or 7), and a VL CDR2 (SEQ ID NO:2). In some embodiments, the antibody comprises a VH CDR2 (SEQ ID NO:5), a VL CDR1 (SEQ ID NOS:1 or 7), and a VL CDR3 (SEQ ID NO:3). In one embodiment, the antibody comprises a VH CDR2 (SEQ ID NO:5), a VL CDR2 (SEQ ID NO:2), and a VL CDR3 (SEQ ID NO:3). In another embodiment, the antibody comprises a VH CDR3 (SEQ ID NO:6), a VL CDR1 (SEQ ID NOS:1 or 7), and a VL CDR2 (SEQ ID NO:2). In other embodiments, the antibody comprises a VH CDR3 (SEQ ID NO:6), a VL CDR1 (SEQ ID NOS:1 or 7), and a VL CDR3 (SEQ ID NO:3). In some embodiments, the antibody comprises a VH CDR3 (SEQ ID NO:6), a VL CDR2 (SEQ ID NO:2), and a VL CDR3 (SEQ ID NO:3). In another embodiment, the antibody comprises a VH CDR2 (SEQ ID NO:5), a VH CDR3 (SEQ ID NO:6), a VL CDR1 (SEQ ID NOS:1 or 7), and a VL CDR2 (SEQ ID NO:2). In one embodiment, the antibody comprises a VH CDR2 (SEQ ID NO:5), a VH CDR3 (SEQ ID NO:6), a VL CDR1 (SEQ ID NOS:1 or 7), and a VL CDR3 (SEQ ID NO:3). In other embodiments, the antibody comprises a VH CDR2 (SEQ ID NO:5), a VH CDR3 (SEQ ID NO:6), a VL CDR2 (SEQ ID NO:2), and a VL CDR3 (SEQ ID NO:3). In another embodiment, the antibody comprises a VH CDR1 (SEQ ID NO:4), a VH CDR2 (SEQ ID NO:5), a VH CDR3 (SEQ ID NO:6), a VL CDR1 (SEQ ID NOS:1 or 7), and a VL CDR2 (SEQ ID NO:2). In some embodiments, the antibody comprises a VH CDR1 (SEQ ID NO:4), a VH CDR2 (SEQ ID NO:5), a VH CDR3 (SEQ ID NO:6), a VL CDR1 (SEQ ID NOS:1 or 7), and a VL CDR3 (SEQ ID NO:3). In one embodiment, the antibody comprises a VH CDR1 (SEQ ID NO:4), a VH CDR2 (SEQ ID NO:5), a VH CDR3 (SEQ ID NO:6), a VL CDR2 (SEQ ID NO:2), and a VL CDR3 (SEQ ID NO:3). In another embodiment, the antibody comprises a VH CDR1 (SEQ ID NO:4), a VH CDR2 (SEQ ID NO:5), a VL CDR1 (SEQ ID NOS:1 or 7), a VL CDR2 (SEQ ID NO:2), and a VL CDR3 (SEQ ID NO:3). In other embodiments, the antibody comprises a VH CDR1 (SEQ ID NO:4), a VH CDR3 (SEQ ID NO:6), a VL CDR1 (SEQ ID NOS:1 or 7), a VL CDR2 (SEQ ID NO:2), and a VL CDR3 (SEQ ID NO:3). In some embodiments, the antibody comprises a VH CDR2 (SEQ ID NO:5), a VH CDR3 (SEQ ID NO:6), a VL CDR1 (SEQ ID NOS:1 or 7), a VL CDR2 (SEQ ID NO:2), and a VL CDR3 (SEQ ID NO:3). In another embodiment, the antibody comprises a VH CDR1 (SEQ ID NO:4), a VL CDR1 (SEQ ID NOS:1 or 7), a VL CDR2 (SEQ ID NO:2), and a VL CDR3 (SEQ ID NO:3). In one embodiment, the antibody comprises a VH CDR2 (SEQ ID NO:5), a VL CDR1 (SEQ ID NOS:1 or 7), a VL CDR2 (SEQ ID NO:2), and a VL CDR3 (SEQ ID NO:3). In other embodiments, the antibody comprises a VH CDR3 (SEQ ID NO:6), a VL CDR1 (SEQ ID NOS:1 or 7), a VL CDR2 (SEQ ID NO:2), and a VL CDR3 (SEQ ID NO:3). In another embodiment, the antibody comprises any combination thereof of the VH CDRs and VL CDRs listed in Tables 1-2.

In yet another aspect, the CDRs disclosed herein include consensus sequences derived from groups of related antibodies (see, e.g., Tables 1-2). As described herein, a "consensus sequence" refers to amino acid sequences having conserved amino acids common among a number of sequences and variable amino acids that vary within a given amino acid sequences.

In some embodiments, the isolated antibody or functional fragment thereof provided herein further comprises one, two, three, and/or four heavy chain FRs and/or one, two, three, and/or four light chain FRs from: (a) the antibody PD1AB-1, (b) the antibody PD1AB-2, (c) the antibody PD1AB-3, (d) the antibody PD1AB-4, (e) the antibody PD1AB-5, or (f) the antibody PD1AB-6, as shown in Tables 3-4.

TABLE 3

VL FR Amino Acid Sequences

| Antibody | VL FR1 (SEQ ID NO:) | VL FR2 (SEQ ID NO:) | VL FR3 (SEQ ID NO:) | VL FR4 (SEQ ID NO:) |
|---|---|---|---|---|
| PD1AB-1 | DIVMTQSPDSLA VSLGERATINC (SEQ ID NO: 14) | WYQQKPGQ PPKLLIY (SEQ ID NO: 15) | GVPDRFSGSGSGT DFTLTISSLQAED VAVYYC (SEQ ID NO: 16) | FGQGTKL EIKR (SEQ ID NO: 17) |
| PD1AB-2 | DIVMTQSPDSLA VSLGERATINC (SEQ ID NO: 14) | WYQQKPGQ PPKLLIY (SEQ ID NO: 15) | GVPDRFSGSGSGT DFTLTISSLQAED VAVYYC (SEQ ID NO: 16) | FGQGTKL EIKR (SEQ ID NO: 17) |

TABLE 3 -continued

VL FR Amino Acid Sequences

| Antibody | VL FR1 (SEQ ID NO:) | VL FR2 (SEQ ID NO:) | VL FR3 (SEQ ID NO:) | VL FR4 (SEQ ID NO:) |
|---|---|---|---|---|
| PD1AB-3 | DIVMTQSPDSLA VSLGERATINC (SEQ ID NO: 14) | WYQQKPGQ PPKLLIY (SEQ ID NO: 15) | GVPDRFSGSGSGT DFTLTISNLQAED VAVYYC (SEQ ID NO: 18) | FGQGTKL EIKR (SEQ ID NO: 17) |
| PD1AB-4 | DIVMTQSPDSLA VSLGERATINC (SEQ ID NO: 14) | WYQQKPGQ PPKLLIY (SEQ ID NO: 15) | GVPDRFSGSGSGT DFTLTISSLQAED VAVYYC (SEQ ID NO: 16) | FGQGTKL EIKR (SEQ ID NO: 17) |
| PD1AB-5 | DIVMTQSPDSLA VSLGERATINC (SEQ ID NO: 14) | WYQQKPGQ PPKLLIY (SEQ ID NO: 15) | GVPDRFSGSGSGT DFTLTISSLQAE DVAVYYC (SEQ ID NO: 16) | FGQGTKL EIKR (SEQ ID NO: 17) |
| PD1AB-6 | DIVMTQSPDSLA VSLGERATINC (SEQ ID NO: 14) | WYQQKPGQ PPKLLIY (SEQ ID NO: 15) | GVPDRFSGSGSGT DFTLTISSLQAED VAVYYC (SEQ ID NO: 16) | FGQGTKL EIKR (SEQ ID NO: 17) |

TABLE 4

VH FR Amino Acid Sequences

| Antibody | VH FR1 (SEQ ID NO:) | VH FR2 (SEQ ID NO:) | VH FR3 (SEQ ID NO:) | VH FR4 (SEQ ID NO:) |
|---|---|---|---|---|
| PD1AB-1 | EVQLVQS GAEVKKP GATVKIS CKVS (SEQ ID NO: 19) | WVQQAPGK GLEWMG (SEQ ID NO: 20) | YDPKFQGRVTIT ADTSTDTAYME LSSLRSEDT AVYYCAR (SEQ ID NO: 21) | WGQGTTVTV SS (SEQ ID NO: 22) |
| PD1AB-2 | EVQLVQS GAEVKKP GATVKIS CKVS (SEQ ID NO: 19) | WVQQAPGK GLEWMG (SEQ ID NO: 20) | YDPKFQGRVTIT ADTSTDTAYME LSSLRSEDT AVYYCAR (SEQ ID NO: 21) | WGQGTTVTV SS (SEQ ID NO: 22) |
| PD1A13-3 | EVQLVQS GAEVKKP GATVKIS CKVS (SEQ ID NO: 19) | WVQQAPGK GLEWMG (SEQ ID NO: 20) | YDPKFQGRVTIT ADTSTNTAYME LSSLRSEDT AVYYCAR (SEQ ID NO: 23) | WGQGTTVTV SS (SEQ ID NO: 22) |
| PD1AB-4 | EVQLVQS KGAEVKP GATVKIS CKVS (SEQ ID NO: 19) | WVQQAPGK GLEWMG (SEQ ID NO: 20) | YDPKFQGRVTIT ADTSTNTAYME LSSLRSEDT AVYYCAR (SEQ ID NO: 23) | WGQGTTVTV SS (SEQ ID NO: 22) |
| PD1A13-5 | EVQLVQS GAEVKKP GATVKIS CKAS (SEQ ID NO: 24) | WVQQAPGK GLEWMG (SEQ ID NO: 20) | YDPKFQGRVTIT ADTSTDTAYME LSSLRSEDT AVYYCAR (SEQ ID NO: 21) | WGQGTTVTV SS (SEQ ID NO: 22) |
| PD1AB-6 | EVQLVQS GAEVKKP GATVKIS CKAS (SEQ ID NO: 24) | WVQQAPGK GLEWMG (SEQ ID NO: 20) | YDPKFQGRVTIT ADTSTDTAYME LSSLRSEDT AVYYCAR (SEQ ID NO: 21) | WGQGTTVTV SS (SEQ ID NO: 22) |

In certain embodiments, the isolated antibody or functional fragment thereof provided herein further comprises one, two, three, and/or four heavy chain FRs from: (a) the antibody PD1AB-1, (b) the antibody PD1AB-2, (c) the antibody PD1AB-3, (d) the antibody PD1AB-4, (e) the antibody PD1AB-5, or (f) the antibody PD1AB-6, as shown in Table 4. In some embodiments, the antibody heavy chain FR(s) is from the antibody PD1AB-1. In some embodiments, the antibody heavy chain FR(s) is from the antibody PD1AB-2. In other embodiments, the antibody heavy chain FR(s) is from the antibody PD1AB-3. In certain embodiments, the antibody heavy chain FR(s) is from the antibody PD1AB-4. In other embodiments, the antibody heavy chain FR(s) is from the antibody PD1AB-5. In another embodiment, the antibody heavy chain FR(s) is from the antibody PD1AB-6.

In some embodiments, the isolated antibody or functional fragment thereof provided herein further comprises one, two, three, and/or four light chain FRs from: (a) the antibody PD1AB-1, (b) the antibody PD1AB-2, (c) the antibody PD1AB-3, (d) the antibody PD1AB-4, (e) the antibody PD1AB-5, or (f) the antibody PD1AB-6, as shown in Table 3. In some embodiments, the antibody light chain FR(s) is from the antibody PD1AB-1. In some embodiments, the antibody light chain FR(s) is from the antibody PD1AB-2. In other embodiments, the antibody light chain FR(s) is from the antibody PD1AB-3. In certain embodiments, the antibody light chain FR(s) is from the antibody PD1AB-4. In other embodiments, the antibody light chain FR(s) is from the antibody PD1AB-5. In another embodiment, the antibody light chain FR(s) is from the antibody PD1AB-6.

In certain embodiments, an antibody of fragment thereof described herein comprises a VH region that comprises: (1) a VH FR1 having an amino acid sequence selected from the group consisting of SEQ ID NOS:19 and 24; (2) a VH FR2 having an amino acid sequence of SEQ ID NO:20; (3) a VH FR3 having an amino acid sequence selected from the group consisting of SEQ ID NOS:21 and 23; and/or (4) a VH FR4 having an amino acid sequence of SEQ ID NO:22. In certain embodiments, an antibody of fragment thereof described herein comprises a VH region that comprises: (1) a VH FR1 having an amino acid of SEQ ID NO:19; (2) a VH FR2 having an amino acid sequence of SEQ ID NO:20; (3) a VH FR3 having an amino acid sequence of SEQ ID NO:21; and/or (4) a VH FR4 having an amino acid sequence of SEQ ID NO:22. In certain embodiments, an antibody of fragment thereof described herein comprises a VH region that comprises: (1) a VH FR1 having an amino acid sequence of SEQ ID NO:19; (2) a VH FR2 having an amino acid sequence of SEQ ID NO:20; (3) a VH FR3 having an amino acid sequence of SEQ ID NO: 23; and/or (4) a VH FR4 having an amino acid sequence of SEQ ID NO:22. In certain embodiments, an antibody of fragment thereof described herein comprises a VH region that comprises: (1) a VH FR1 having an amino acid sequence of SEQ ID NO: 24; (2) a VH FR2 having an amino acid sequence of SEQ ID NO:20; (3) a VH FR3 having an amino acid sequence of SEQ ID NO:21; and/or (4) a VH FR4 having an amino acid sequence of SEQ ID NO:22. In certain embodiments, an antibody of fragment thereof described herein comprises a VH region that comprises: (1) a VH FR1 having an amino acid sequence of SEQ ID NO:24; (2) a VH FR2 having an amino acid sequence of SEQ ID NO:20; (3) a VH FR3 having an amino acid sequence of SEQ ID NO: 23; and/or (4) a VH FR4 having an amino acid sequence of SEQ ID NO:22. In specific embodiments, the antibody comprises a VH region comprising all four of the above-referenced VH FR1, VH FR2, VH FR3, and VH FR4.

Accordingly, in some embodiments, the humanized antibody comprises a VH region that includes a VH FR1 having an amino acid sequence selected from the group consisting of SEQ ID NOS:19 and 24. In one embodiment, the humanized antibody comprises a VH region that includes a VH FR1 having an amino acid sequence of SEQ ID NO:19. In one embodiment, the humanized antibody comprises a VH region that includes a VH FR1 having an amino acid sequence of SEQ ID NO:24. In some embodiments, the humanized antibody comprises a VH region that includes a VH FR2 having an amino acid sequence of SEQ ID NO: 20. In some embodiments, the humanized antibody comprises a VH region that includes a VH FR3 having an amino acid sequence selected from the group consisting of SEQ ID NOS:21 and 23. In one embodiment, the humanized antibody comprises a VH region that includes a VH FR3 having an amino acid sequence of SEQ ID NO:21. In one embodiment, the humanized antibody comprises a VH region that includes a VH FR3 having an amino acid sequence of SEQ ID NO:23. In other embodiments, the humanized antibody comprises a VH region that includes a VH FR4 having an amino acid sequence of SEQ ID NO:22.

In certain embodiments, an antibody of fragment thereof described herein comprises a VL region that comprises: (1) a VL FR1 having an amino acid sequence of SEQ ID NO:14; (2) a VL FR2 having an amino acid sequence of SEQ ID NO:15; (3) a VL FR3 having an amino acid sequence selected from the group consisting of SEQ ID NOS:16 and 18; and/or (4) a VL FR4 having an amino acid sequence of SEQ ID NO:17. In some embodiments, the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NOS:16; and/or (4) a VL FR4 having an amino acid sequence of SEQ ID NO:17. In other embodiments, the VL region that comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO: 18; and/or (4) a VL FR4 having an amino acid sequence of SEQ ID NO:17.

Accordingly, in some embodiments, the humanized antibody comprises a VL region that includes a VL FR1 having an amino acid sequence of SEQ ID NO:14. In certain embodiments, the humanized antibody comprises a VL region that includes a VL FR2 having an amino acid sequence of SEQ ID NO:15. In other embodiments, the humanized antibody comprises a VL region that includes a VL FR3 having an amino acid sequence selected from the group consisting of SEQ ID NOS:16 and 18. In one embodiment, the humanized antibody comprises a VL region that includes a VL FR3 having an amino acid sequence of SEQ ID NOS:16. In other embodiments, the humanized antibody comprises a VL region that includes a VL FR3 having an amino acid sequence of SEQ ID NO: 18. In yet other embodiments, the humanized antibody comprises a VL region that includes a VL FR4 having an amino acid sequence of SEQ ID NO:17.

In certain embodiments, an antibody of fragment thereof described herein comprises a VH region and a VL region, wherein the VH region comprises: (1) a VH FR1 having an amino acid sequence selected from the group consisting of SEQ ID NOS:19 and 24; (2) a VH FR2 having an amino acid sequence of SEQ ID NO:20; (3) a VH FR3 having an amino acid sequence selected from the group consisting of SEQ ID NOS:21 and 23; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence selected from the group consisting of SEQ ID NOS:16 and 18; and/or (4) a VL FR4 having an amino acid sequence of SEQ ID NO:17. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

In some embodiments, an antibody of fragment thereof comprises a VH region and a VL region, wherein the VH region comprises: (1) a VH FR1 having an amino acid sequence of SEQ ID NO:19; (2) a VH FR2 having an amino acid sequence of SEQ ID NO:20; (3) a VH FR3 having an amino acid sequence of SEQ ID NO:21; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO:16; and/or (4) a VL FR4 having an amino acid sequence of SEQ ID NO:17. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

In some embodiments, an antibody of fragment thereof comprises a VH region and a VL region, wherein the VH region comprises: (1) a VH FR1 having an amino acid sequence of SEQ ID NO:19; (2) a VH FR2 having an amino acid sequence of SEQ ID NO:20; (3) a VH FR3 having an amino acid sequence of SEQ ID NO:21; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO:18; and/or (4) a VL FR4 having an amino acid sequence of SEQ ID NO:17. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

In some embodiments, an antibody of fragment thereof comprises a VH region and a VL region, wherein the VH region comprises: (1) a VH FR1 having an amino acid sequence of SEQ ID NO:19; (2) a VH FR2 having an amino acid sequence of SEQ ID NO:20; (3) a VH FR3 having an amino acid sequence of SEQ ID NO:23; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO:16; and/or (4) a VL FR4 having an amino acid sequence of SEQ ID NO:17. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

In some embodiments, an antibody of fragment thereof comprises a VH region and a VL region, wherein the VH region comprises: (1) a VH FR1 having an amino acid sequence of SEQ ID NO:19; (2) a VH FR2 having an amino acid sequence of SEQ ID NO:20; (3) a VH FR3 having an amino acid sequence of SEQ ID NO:23; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO:18; and/or (4) a VL FR4 having an amino acid sequence of SEQ ID NO:17. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

In some embodiments, an antibody of fragment thereof comprises a VH region and a VL region, wherein the VH region comprises: (1) a VH FR1 having an amino acid sequence of SEQ ID NO:24; (2) a VH FR2 having an amino acid sequence of SEQ ID NO:20; (3) a VH FR3 having an amino acid sequence of SEQ ID NO:21; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO:16; and/or (4) a VL FR4 having an amino acid sequence of SEQ ID NO:17. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

In some embodiments, an antibody of fragment thereof comprises a VH region and a VL region, wherein the VH region comprises: (1) a VH FR1 having an amino acid sequence of SEQ ID NO:24; (2) a VH FR2 having an amino acid sequence of SEQ ID NO:20; (3) a VH FR3 having an amino acid sequence of SEQ ID NO:21; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO:18; and/or (4) a VL FR4 having an amino acid sequence of SEQ ID NO:17. In some embodiments, the antibody comprises a VH region comprising all four of the above-referenced VH FR1, VH FR2, VH FR3 and VH FR4. In other embodiments, the antibody comprises a VL region comprising all four of the above-referenced VL FR1, VL FR2, VL FR3 and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

In some embodiments, an antibody of fragment thereof comprises a VH region and a VL region, wherein the VH region comprises: (1) a VH FR1 having an amino acid sequence of SEQ ID NO:24; (2) a VH FR2 having an amino acid sequence of SEQ ID NO:20; (3) a VH FR3 having an amino acid sequence of SEQ ID NO:23; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO:16; and/or (4) a VL FR4 having an amino acid sequence of SEQ ID NO:17. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

In some embodiments, an antibody of fragment thereof comprises a VH region and a VL region, wherein the VH region comprises: (1) a VH FR1 having an amino acid sequence of SEQ ID NO:24; (2) a VH FR2 having an amino acid sequence of SEQ ID NO:20; (3) a VH FR3 having an amino acid sequence of SEQ ID NO:23; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO:18; and/or (4) a VL FR4 having an amino acid sequence of SEQ ID NO:17. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

Also described herein are antibodies comprising one or more (e.g., one, two, three, or four) VH FRs and one or more (e.g., one, two, three, or four) VL FRs listed in Tables 3-4. In particular, provided herein is an antibody comprising a VH FR1 (SEQ ID NOS:19 or 24) and a VL FR1 (SEQ ID NO:14). In one embodiment, the antibody comprises a VH FR1 (SEQ ID NOS:19 or 24) and a VL FR2 (SEQ ID NO:15). In some embodiments, the antibody comprises a VH FR1 (SEQ ID NOS:19 or 24) and a VL FR3 (SEQ ID NOS:16 or 18). In another embodiment, the antibody comprises a VH FR1 (SEQ ID NOS:19 or 24) and a VL FR4 (SEQ ID NO:17). In other embodiments, the antibody comprises a VH FR2 (SEQ ID NO:20) and a VL FR1 (SEQ ID NO:14). In one embodiment, the antibody comprises a VH FR2 (SEQ ID NO:20) and a VL FR2 (SEQ ID NO:15). In some embodiments, the antibody comprises a VH FR2 (SEQ ID NO:20) and a VL FR3 (SEQ ID NOS:16 or 18). In another embodiment, the antibody comprises a VH FR2 (SEQ ID NO:20) and a VL FR4 (SEQ ID NO:17). In one embodiment, the antibody comprises a VH FR3 (SEQ ID NO:21) and a VL FR1 (SEQ ID NO:14). In other embodiments, the antibody comprises a VH FR3 (SEQ ID NO:21) and a VL FR2 (SEQ ID NO:15). In another embodiment, the antibody comprises a VH FR3 (SEQ ID NO:21) and a VL FR3 (SEQ ID NOS:16 or 18). In some embodiments, the antibody comprises a VH FR3 (SEQ ID NO:21) and a VL FR4 (SEQ ID NO:17). In one embodiment, the antibody comprises a VH FR4 (SEQ ID NO:22) and a VL FR1 (SEQ ID NO:14). In another embodiment, the antibody comprises a VH FR4 (SEQ ID NO:22) and a VL FR2 (SEQ ID NO:15). In one embodiment, the antibody comprises a VH FR4 (SEQ ID NO:22) and a VL FR3 (SEQ ID NOS:16 or 18). In some embodiments, the antibody comprises a VH FR4 (SEQ ID NO:22) and a VL FR4 (SEQ ID NO:17). In another embodiment, the antibody comprises a VH FR1 (SEQ ID NOS:19 or 24), a VH FR2 (SEQ ID NO:20), and a VL FR1 (SEQ ID NO:14). In other embodiments, the antibody comprises a VH FR1 (SEQ ID NOS:19 or 24), a VH FR2 (SEQ ID NO:20), and a VL FR2 (SEQ ID NO:15). In one embodiment, the antibody comprises a VH FR1 (SEQ ID NOS:19 or 24), a VH FR2 (SEQ ID NO:20), and a VL FR3 (SEQ ID NOS:16 or 18). In another embodiment, the antibody comprises a VH FR1 (SEQ ID NOS:19 or 24), a VH FR2 (SEQ ID NO:20), and a VL FR4 (SEQ ID NO:17). In some embodiments, the antibody comprises a VH FR2 (SEQ ID NO:20), a VH FR3 (SEQ ID NOS:21 or 23), and a VL FR1 (SEQ ID NO:14). In one embodiment, the antibody comprises a VH FR2 (SEQ ID NO:20), a VH FR3 (SEQ ID NOS:21 or 23), and a VL FR2 (SEQ ID NO:15). In another embodiment, the antibody comprises a VH FR2 (SEQ ID NO:20), a VH FR3 (SEQ ID NOS:21 or 23), and a VL FR3 (SEQ ID NOS:16 or 18). In other embodiments, the antibody comprises a VH FR2 (SEQ ID NO:20), a VH FR3 (SEQ ID NOS:21 or 23), and a VL FR4 (SEQ ID NO:17). In some embodiments, the antibody comprises a VH FR1 (SEQ ID NOS:19 or 24), a VL FR1 (SEQ ID NO:14), and a VL FR2 (SEQ ID NO:15). In another embodiment, the antibody comprises a VH FR1 (SEQ ID NOS:19 or 24), a VL FR1 (SEQ ID NO:14), and a VL FR3 (SEQ ID NOS:16 or 18). In one embodiment, the antibody comprises a VH FR1 (SEQ ID NOS:19 or 24), a VL FR1 (SEQ ID NO:14), and a VL FR4 (SEQ ID NO:17). In one embodiment, the antibody comprises a VH FR1 (SEQ ID NOS:19 or 24), a VL FR2 (SEQ ID NO:15) and a VL FR3 (SEQ ID NOS:16 or 18). In another embodiment, the antibody comprises a VH FR1 (SEQ ID NOS:19 or 24), a VL FR2 (SEQ ID NO:15) and a VL FR4 (SEQ ID NO:17). In some embodiments, the antibody comprises a VH FR1 (SEQ ID NO:19 or 24), a VL FR3 (SEQ ID NOS:16 or 18), and a VL FR4 (SEQ ID NO:17). In other embodiments, the antibody comprises a VH FR2 (SEQ ID NO:20), a VL FR1 (SEQ ID NO:14), and a VL FR2 (SEQ ID NO:15). In another embodiment, the antibody comprises a VH FR2 (SEQ ID NO:20), a VL FR1 (SEQ ID NO:14), and a VL FR3 (SEQ ID NOS:16 or 18). In one embodiment, the antibody comprises a VH FR2 (SEQ ID NO:20), a VL FR1 (SEQ ID NO:14), and a VL FR4 (SEQ ID NO:17). In some embodiments, the antibody comprises a VH FR2 (SEQ ID NO:20), a VL FR2 (SEQ ID NO:15) and a VL FR3 (SEQ ID NOS:16 or 18). In another embodiment, the antibody comprises a VH FR2 (SEQ ID NO:20), a VL FR2 (SEQ ID NO:15) and a VL FR4 (SEQ ID NO:17). In one embodiment, the antibody comprises a VH FR2 (SEQ ID NO:20), a VL FR3 (SEQ ID NOS:16 or 18), and a VL FR4 (SEQ ID NO:17). In another embodiment, the antibody comprises a VH FR3 (SEQ ID NOS:21 or 23), a VL FR1 (SEQ ID NO:14), and a VL FR2 (SEQ ID NO:15). In other embodiments, the antibody comprises a VH FR3 (SEQ ID NOS:21 or 23), a VL FR1 (SEQ ID NO:14), and a VL FR3 (SEQ ID NOS:16 or 18). In some embodiments, the antibody comprises a VH FR3 (SEQ ID NOS:21 or 23), a VL FR1 (SEQ ID NO:14), and a VL FR4 (SEQ ID NO:17). In another embodiment, the antibody comprises a VH FR3 (SEQ ID NOS:21 or 23), a VL FR2 (SEQ ID NO:15) and a VL FR3 (SEQ ID NOS:16 or 18). In one embodiment, the antibody comprises a VH FR3 (SEQ ID NOS:21 or 23), a VL FR2 (SEQ ID NO:15) and a VL FR4 (SEQ ID NO:17). In one embodiment, the antibody comprises a VH FR3 (SEQ ID NOS:21 or 23), a VL FR3 (SEQ ID NOS:16 or 18), and a VL FR4 (SEQ ID NO:17). In another embodiment, the antibody comprises a VH FR4 (SEQ ID NO:22), a VL FR1 (SEQ ID NO:14), and a VL FR2 (SEQ ID NO:15). In some embodiments, the antibody comprises a VH FR4 (SEQ ID NO:22), a VL FR1 (SEQ ID NO:14), and a VL FR3 (SEQ ID NOS:16 or 18). In other embodiments, the antibody comprises a VH FR4 (SEQ ID NO:22), a VL FR1 (SEQ ID NO:14), and a VL FR4 (SEQ ID NO:17). In another embodiment, the antibody comprises a VH FR4 (SEQ ID NO:22), a VL FR2 (SEQ ID NO:15) and a VL FR3 (SEQ ID NOS:16 or 18). In one embodiment, the antibody comprises a VH FR4 (SEQ ID NO:22), a VL FR2 (SEQ ID NO:15) and a VL FR4 (SEQ ID NO:17). In some embodiments, the antibody comprises a VH FR4 (SEQ ID NO:22), a VL FR3 (SEQ ID NOS:16 or 18), and a VL FR4 (SEQ ID NO:17). In another embodiment, the antibody comprises a VH FR1 (SEQ ID NOS:19 or 24), a VH FR2 (SEQ ID NO:20), a VH FR3 (SEQ ID NO:21), and a VL FR1 (SEQ ID NO:14). In one embodiment, the antibody comprises a VH FR1 (SEQ ID NOS:19 or 24), a VH FR2 (SEQ ID NO:20), a VH FR3 (SEQ ID NO:21), and a VL FR2 (SEQ ID NO:15). In other embodiments, the antibody comprises a VH FR1 (SEQ ID NOS:19 or 24), a VH FR2 (SEQ ID NO:20), a VH FR3 (SEQ ID NO:21), and a VL FR3 (SEQ ID NOS:16 or 18). In another embodiment, the antibody comprises a VH FR1 (SEQ ID NOS:19 or 24), a VH FR2 (SEQ ID NO:20), a VH FR3 (SEQ ID NO:21), and a VL FR4 (SEQ ID NO:17). In some embodiments, the antibody comprises a VH FR1 (SEQ ID NOS:19 or 24), a VH FR2 (SEQ ID NO:20), a VH FR4 (SEQ ID NO:22), and a VL FR1 (SEQ ID NO:14). In one embodiment, the antibody comprises a VH FR1 (SEQ ID NOS:19 or 24), a VH FR2 (SEQ ID NO:20), a VH FR4 (SEQ ID NO:22), and a VL FR2 (SEQ ID NO:15). In another embodiment, the antibody comprises a VH FR1 (SEQ ID NOS:19 or 24), a VH FR2 (SEQ ID NO:20), a VH FR4 (SEQ ID NO:22), and a VL FR3 (SEQ ID NOS:16 or 18). In one embodiment, the antibody comprises a VH FR1 (SEQ ID NOS:19 or 24), a VH FR2 (SEQ ID NO:20), a VH FR4 (SEQ ID NO:22), and a VL FR4 (SEQ ID NO:17). In some embodiments, the antibody comprises a VH FR1 (SEQ ID NOS:19 or 24), a VH FR3 (SEQ ID NOS:21 or 23), a VH FR4 (SEQ ID NO:22), and a VL FR1 (SEQ ID NO:14). In another embodiment, the antibody comprises a VH FR1 (SEQ ID NOS:19 or 24), a VH FR3 (SEQ ID NOS:21 or 23), a VH FR4 (SEQ ID NO:22), and a VL FR2 (SEQ ID NO:15). In other embodiments, the antibody comprises a VH FR1 (SEQ ID NOS:19 or 24), VH FR3 (SEQ ID NOS:21 or 23), a VH FR4 (SEQ ID NO:22), and a VL FR3 (SEQ ID NOS:16 or 18). In one embodiment, the antibody comprises a VH FR1 (SEQ ID NOS:19 or 24), a VH FR3 (SEQ ID NOS:21 or 23), a VH FR4 (SEQ ID NO:22), and a VL FR4 (SEQ ID NO:17). In another embodiment, the antibody comprises a VH FR2 (SEQ ID NO:20), a VH FR3 (SEQ ID NOS:21 or 23), a VH FR4 (SEQ ID NO:22), and a VL FR1 (SEQ ID NO:14). In some embodiments, the antibody comprises a VH FR2 (SEQ ID NO:20), a VH FR3 (SEQ ID NOS:21 or 23), a VH FR4 (SEQ ID NO:22), and a VL FR2 (SEQ ID NO:15). In one embodiment, the antibody comprises a VH FR2 (SEQ ID NO:20), VH FR3 (SEQ ID NOS:21 or 23), a VH FR4 (SEQ ID NO:22), and a VL FR3 (SEQ ID NOS:16 or 18). In another embodiment, the antibody comprises a VH FR2 (SEQ ID NO:20), a VH FR3 (SEQ ID NOS:21 or 23), a VH FR4 (SEQ ID NO:22), and a VL FR4 (SEQ ID NO:17). In other embodiments, the antibody comprises a VH FR1 (SEQ ID NOS:19 or 24), a VH FR2 (SEQ ID NO:20), a VL FR1 (SEQ ID NO:14), and a VL FR2 (SEQ ID NO:15). In some embodiments, the antibody comprises a VH FR1 (SEQ ID NOS:19 or 24), a VH FR2 (SEQ ID NO:20), a VL FR1 (SEQ ID NO:14), and a VL FR3 (SEQ ID NOS:16 or 18). In another embodiment, the antibody comprises a VH FR1 (SEQ ID NOS:19 or 24), a VH FR2 (SEQ ID NO:20), a VL FR1 (SEQ ID NO:14), and a VL FR4 (SEQ ID NO:17). In one embodiment, the antibody comprises a VH FR1 (SEQ ID NOS:19 or 24), a VH FR2 (SEQ ID NO:20), a VL FR2 (SEQ ID NO:15), and a VL FR3 (SEQ ID NOS: 16 or 18). In one embodiment, the antibody comprises a VH FR1 (SEQ ID NOS:19 or 24), a VH FR2 (SEQ ID NO:20), a VL FR2 (SEQ ID NO:15), and a VL FR4 (SEQ ID NO:17). In another embodiment, the antibody comprises a VH FR1 (SEQ ID NOS:19 or 24), a VH FR2 (SEQ ID NO:20), a VL FR3 (SEQ ID NOS:16 or 18), and a VL FR4 (SEQ ID NO:17). In some embodiments, the antibody comprises a VH FR1 (SEQ ID NOS:19 or 24), a VH FR3 (SEQ ID NO:21), a VL FR1 (SEQ ID NO:14), and a VL FR2 (SEQ ID NO:15). In other embodiments, the antibody comprises a VH FR1 (SEQ ID NOS:19 or 24), a VH FR3 (SEQ ID NO:21), a VL FR1 (SEQ ID NO:14), and a VL FR3 (SEQ ID NOS:16 or 18). In another embodiment, the antibody comprises a VH FR1 (SEQ ID NOS:19 or 24), a VH FR3 (SEQ ID NO:21), a VL FR1 (SEQ ID NO:14), and a VL FR4 (SEQ ID NO:17). In one embodiment, the antibody comprises a VH FR1 (SEQ ID NOS:19 or 24), a VH FR3 (SEQ ID NO:21), a VL FR2 (SEQ ID NO:15), and a VL FR3 (SEQ ID NOS:16 or 18). In some embodiments, the antibody comprises a VH FR1 (SEQ ID NOS:19 or 24), a VH FR3 (SEQ ID NO:21), a VL FR2 (SEQ ID NO:15), and a VL FR4 (SEQ ID NO:17). In another embodiment, the antibody comprises a VH FR1 (SEQ ID NOS:19 or 24), a VH FR3 (SEQ ID NO:21), a VL FR3 (SEQ ID NOS:16 or 18), and a VL FR4 (SEQ ID NO:17). In one embodiment, the antibody comprises a VH FR1 (SEQ ID NOS:19 or 24), a VH FR4 (SEQ ID NO:22), a VL FR1 (SEQ ID NO:14), and a VL FR2 (SEQ ID NO:15). In other embodiments, the antibody comprises a VH FR1 (SEQ ID NOS:19 or 24), a VH FR4 (SEQ ID NO:22), a VL FR1 (SEQ ID NO:14), and a VL FR3 (SEQ ID NOS:16 or 18). In another embodiment, the antibody comprises a VH FR1 (SEQ ID NOS:19 or 24), a VH FR4 (SEQ ID NO:22), a VL FR1 (SEQ ID NO:14), and a VL FR4 (SEQ ID NO:17). In some embodiments, the antibody comprises a VH FR1 (SEQ ID NOS:19 or 24), a VH FR4 (SEQ ID NO:22), a VL FR2 (SEQ ID NO:15), and a VL FR3 (SEQ ID NOS:16 or 18). In one embodiment, the antibody comprises a VH FR1 (SEQ ID NOS:19 or 24), a VH FR4 (SEQ ID NO:22), a VL FR2 (SEQ ID NO:15), and a VL FR4 (SEQ ID NO:17). In another embodiment, the antibody comprises a VH FR1 (SEQ ID NOS:19 or 24), a VH FR4 (SEQ ID NO:22), a VL FR3 (SEQ ID NOS:16 or 18), and a VL FR4 (SEQ ID NO:17). In one embodiment, the antibody comprises a VH FR2 (SEQ ID NO:20), a VH FR3

(SEQ ID NO:21), a VL FR1 (SEQ ID NO:14), and a VL FR2 (SEQ ID NO:15). In some embodiments, the antibody comprises a VH FR2 (SEQ ID NO:20), a VH FR3 (SEQ ID NO:21), a VL FR1 (SEQ ID NO:14), and a VL FR3 (SEQ ID NOS:16 or 18). In another embodiment, the antibody comprises a VH FR2 (SEQ ID NO:20), a VH FR3 (SEQ ID NO:21), a VL FR1 (SEQ ID NO:14), and a VL FR4 (SEQ ID NO:17). In other embodiments, the antibody comprises a VH FR2 (SEQ ID NO:20), a VH FR3 (SEQ ID NO:21), a VL FR2 (SEQ ID NO:15), and a VL FR3 (SEQ ID NOS:16 or 18). In one embodiment, the antibody comprises a VH FR2 (SEQ ID NO:20), a VH FR3 (SEQ ID NO:21), a VL FR2 (SEQ ID NO:15), and a VL FR4 (SEQ ID NO:17). In another embodiment, the antibody comprises a VH FR2 (SEQ ID NO:20), a VH FR3 (SEQ ID NO:21), a VL FR3 (SEQ ID NOS:16 or 18), and a VL FR4 (SEQ ID NO:17). In some embodiments, the antibody comprises a VH FR2 (SEQ ID NO:20), a VH FR4 (SEQ ID NO:22), a VL FR1 (SEQ ID NO:14), and a VL FR2 (SEQ ID NO:15). In one embodiment, the antibody comprises a VH FR2 (SEQ ID NO:20), a VH FR4 (SEQ ID NO:22), a VL FR1 (SEQ ID NO:14), and a VL FR3 (SEQ ID NOS:16 or 18). In another embodiment, the antibody comprises a VH FR2 (SEQ ID NO:20), a VH FR4 (SEQ ID NO:22), a VL FR1 (SEQ ID NO:14), and a VL FR4 (SEQ ID NO:17). In other embodiments, the antibody comprises a VH FR2 (SEQ ID NO:20), a VH FR4 (SEQ ID NO:22), a VL FR2 (SEQ ID NO:15), and a VL FR3 (SEQ ID NOS:16 or 18). In some embodiments, the antibody comprises a VH FR2 (SEQ ID NO:20), a VH FR4 (SEQ ID NO:22), a VL FR2 (SEQ ID NO:15), and a VL FR4 (SEQ ID NO:17). In another embodiment, the antibody comprises a VH FR2 (SEQ ID NO:20), a VH FR4 (SEQ ID NO:22), a VL FR3 (SEQ ID NOS:16 or 18), and a VL FR4 (SEQ ID NO:17). In one embodiment, the antibody comprises a VH FR3 (SEQ ID NOS:21 or 23), a VH FR4 (SEQ ID NO:22), a VL FR1 (SEQ ID NO:14), and a VL FR2 (SEQ ID NO:15). In one embodiment, the antibody comprises a VH FR3 (SEQ ID NOS:21 or 23), a VH FR4 (SEQ ID NO:22), a VL FR1 (SEQ ID NO:14), and a VL FR3 (SEQ ID NOS:16 or 18). In another embodiment, the antibody comprises a VH FR3 (SEQ ID NOS:21 or 23), a VH FR4 (SEQ ID NO:22), a VL FR1 (SEQ ID NO:14), and a VL FR4 (SEQ ID NO:17). In some embodiments, the antibody comprises a VH FR3 (SEQ ID NOS:21 or 23), a VH FR4 (SEQ ID NO:22), a VL FR2 (SEQ ID NO:15), and a VL FR3 (SEQ ID NOS:16 or 18). In other embodiments, the antibody comprises a VH FR3 (SEQ ID NOS:21 or 23), a VH FR4 (SEQ ID NO:22), a VL FR2 (SEQ ID NO:15), and a VL FR4 (SEQ ID NO:17). In another embodiment, the antibody comprises a VH FR3 (SEQ ID NOS:21 or 23), a VH FR4 (SEQ ID NO:22), a VL FR3 (SEQ ID NOS:16 or 18), and a VL FR4 (SEQ ID NO:17). In one embodiment, the antibody comprises a VH FR1 (SEQ ID NOS:19 or 24), a VL FR1 (SEQ ID NO:14), a VL FR2 (SEQ ID NO:15), and a VL FR3 (SEQ ID NOS:16 or 18). In some embodiments, the antibody comprises a VH FR1 (SEQ ID NOS:19 or 24), a VL FR1 (SEQ ID NO:14), a VL FR2 (SEQ ID NO:15), and a VL FR4 (SEQ ID NO:17). In another embodiment, the antibody comprises a VH FR1 (SEQ ID NOS:19 or 24), a VL FR1 (SEQ ID NO:14), a VL FR3 (SEQ ID NOS:16 or 18), and a VL FR4 (SEQ ID NO:17). In one embodiment, the antibody comprises a VH FR1 (SEQ ID NOS:19 or 24), a VL FR2 (SEQ ID NO:15), a VL FR3 (SEQ ID NOS:16 or 18), and a VL FR4 (SEQ ID NO:17). In other embodiments, the antibody comprises a VH FR2 (SEQ ID NO:20), a VL FR1 (SEQ ID NO:14), a VL FR2 (SEQ ID NO:15), and a VL FR3 (SEQ ID NOS:16 or 18). In another embodiment, the antibody comprises a VH FR2 (SEQ ID NO:20), a VL FR1 (SEQ ID NO:14), a VL FR2 (SEQ ID NO:15), and a VL FR4 (SEQ ID NO:17). In some embodiments, the antibody comprises a VH FR2 (SEQ ID NO:20), a VL FR1 (SEQ ID NO:14), a VL FR3 (SEQ ID NOS:16 or 18), and a VL FR4 (SEQ ID NO:17). In one embodiment, the antibody comprises a VH FR2 (SEQ ID NO:20), a VL FR2 (SEQ ID NO:15), a VL FR3 (SEQ ID NOS:16 or 18), and a VL FR4 (SEQ ID NO:17). In another embodiment, the antibody comprises a VH FR3 (SEQ ID NOS:21 or 23), a VL FR1 (SEQ ID NO:14), a VL FR2 (SEQ ID NO:15), and a VL FR3 (SEQ ID NOS:16 or 18). In one embodiment, the antibody comprises a VH FR3 (SEQ ID NOS:21 or 23), a VL FR1 (SEQ ID NO:14), a VL FR2 (SEQ ID NO:15), and a VL FR4 (SEQ ID NO:17). In some embodiments, the antibody comprises a VH FR3 (SEQ ID NOS:21 or 23), a VL FR1 (SEQ ID NO:14), a VL FR3 (SEQ ID NOS:16 or 18), and a VL FR4 (SEQ ID NO:17). In another embodiment, the antibody comprises a VH FR3 (SEQ ID NOS:21 or 23), a VL FR2 (SEQ ID NO:15), a VL FR3 (SEQ ID NOS:16 or 18), and a VL FR4 (SEQ ID NO:17). In other embodiments, the antibody comprises a VH FR4 (SEQ ID NO:22), a VL FR1 (SEQ ID NO:14), a VL FR2 (SEQ ID NO:15), and a VL FR3 (SEQ ID NOS:16 or 18). In one embodiment, the antibody comprises a VH FR4 (SEQ ID NO:22), a VL FR1 (SEQ ID NO:14), a VL FR2 (SEQ ID NO:15), and a VL FR4 (SEQ ID NO:17). In another embodiment, the antibody comprises a VH FR4 (SEQ ID NO:22), a VL FR1 (SEQ ID NO:14), a VL FR3 (SEQ ID NOS:16 or 18), and a VL FR4 (SEQ ID NO:17). In some embodiments, the antibody comprises a VH FR4 (SEQ ID NO:22), a VL FR2 (SEQ ID NO:15), a VL FR3 (SEQ ID NOS:16 or 18), and a VL FR4 (SEQ ID NO:17). In one embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), and a VL FR1 (SEQ ID NO:14). In another embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), and a VL FR2 (SEQ ID NO:15). In other embodiments, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), and a VL FR3 (SEQ ID NOS:16 or 18). In some embodiments, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), and a VL FR4 (SEQ ID NO:17). In another embodiment, the antibody comprises a VH FR1 (SEQ ID NOS:19 or 24), a VH FR2 (SEQ ID NO:20), a VH FR3 (SEQ ID NOS:21 or 23), a VL FR1 (SEQ ID NO:14), and a VL FR2 (SEQ ID NO:15). In one embodiment, the antibody comprises a VH FR1 (SEQ ID NOS:19 or 24), a VH FR2 (SEQ ID NO:20), a VH FR3 (SEQ ID NOS:21 or 23), a VL FR1 (SEQ ID NO:14), and a VL FR3 (SEQ ID NOS:16 or 18). In one embodiment, the antibody comprises a VH FR1 (SEQ ID NOS:19 or 24), a VH FR2 (SEQ ID NO:20), a VH FR3 (SEQ ID NOS:21 or 23), a VL FR1 (SEQ ID NO:14), and a VL FR4 (SEQ ID NO:17). In another embodiment, the antibody comprises a VH FR1 (SEQ ID NOS:19 or 24), a VH FR2 (SEQ ID NO:20), a VH FR3 (SEQ ID NOS:21 or 23), a VL FR2 (SEQ ID NO:15), and a VL FR3 (SEQ ID NOS:16 or 18). In some embodiments, the antibody comprises a VH FR1 (SEQ ID NOS:19 or 24), a VH FR2 (SEQ ID NO:20), a VH FR3 (SEQ ID NOS:21 or 23), a VL FR2 (SEQ ID NO:15), and a VL FR4 (SEQ ID NO:17). In other embodiments, the antibody comprises a VH FR1 (SEQ ID NOS:19 or 24), a VH FR2 (SEQ ID NO:20), a VH FR3 (SEQ ID NOS:21 or 23), a VL FR3 (SEQ ID NOS:16 or 18), and a VL FR4 (SEQ ID NO:17). In another embodiment, the antibody comprises a VH FR1 (SEQ ID NOS:19 or 24), a VH FR2 (SEQ ID NO:20), a VH FR4 (SEQ ID NO:22), a VL FR1 (SEQ ID NO:14), and a VL FR2 (SEQ ID NO:15). In one embodiment, the antibody comprises a VH FR1 (SEQ ID NOS:19 or 24), a VH FR2 (SEQ ID NO:20), a VH FR4 (SEQ ID NO:22), a VL FR1 (SEQ ID NO:14), and a VL FR3 (SEQ ID NOS:16 or 18). In some embodiments, the antibody comprises a VH FR1 (SEQ ID NOS:19 or 24), a VH FR2 (SEQ ID NO:20), a VH FR4 (SEQ ID NO:22), a VL FR1 (SEQ ID NO:14), and a VL FR4 (SEQ ID NO:17). In another embodiment, the antibody comprises a VH FR1 (SEQ ID NOS:19 or 24), a VH FR2 (SEQ ID NO:20), a VH FR4 (SEQ ID NO:22), a VL FR2 (SEQ ID NO:15), and a VL FR3 (SEQ ID NOS:16 or 18). In one embodiment, the antibody comprises a VH FR1 (SEQ ID NOS:19 or 24), a VH FR2 (SEQ ID NO:20), a VH FR4 (SEQ ID NO:22), a VL FR2 (SEQ ID NO:15), and a VL FR4 (SEQ ID NO:17). In other embodiments, the antibody comprises a VH FR1 (SEQ ID NOS:19 or 24), a VH FR2 (SEQ ID NO:20), a VH FR4 (SEQ ID NO:22), a VL FR3 (SEQ ID NOS:16 or 18), and a VL FR4 (SEQ ID NO:17). In another embodiment, the antibody comprises a VH FR1 (SEQ ID NOS:19 or 24), a VH FR3 (SEQ ID NOS:21 or 23), a VH FR4 (SEQ ID NO:22), a VL FR1 (SEQ ID NO:14), and a VL FR2 (SEQ ID NO:15). In some embodiments, the antibody comprises a VH FR1 (SEQ ID NOS:19 or 24), a VH FR3 (SEQ ID NOS:21 or 23), a VH FR4 (SEQ ID NO:22), a VL FR1 (SEQ ID NO:14), and a VL FR3 (SEQ ID NOS:16 or 18). In one embodiment, the antibody comprises a VH FR1 (SEQ ID NOS:19 or 24), a VH FR3 (SEQ ID NOS:21 or 23), a VH FR4 (SEQ ID NO:22), a VL FR1 (SEQ ID NO:14), and a VL FR4 (SEQ ID NO:17). In another embodiment, the antibody comprises a VH FR1 (SEQ ID NOS:19 or 24), a VH FR3 (SEQ ID NOS:21 or 23), a VH FR4 (SEQ ID NO:22), a VL FR2 (SEQ ID NO:15), and a VL FR3 (SEQ ID NOS:16 or 18). In one embodiment, the antibody comprises a VH FR1 (SEQ ID NOS:19 or 24), a VH FR3 (SEQ ID NOS:21 or 23), a VH FR4 (SEQ ID NO:22), a VL FR2 (SEQ ID NO:15), and a VL FR4 (SEQ ID NO:17). In some embodiments, the antibody comprises a VH FR1 (SEQ ID NOS:19 or 24), a VH FR3 (SEQ ID NOS:21 or 23), a VH FR4 (SEQ ID NO:22), a VL FR3 (SEQ ID NOS:16 or 18), and a VL FR4 (SEQ ID NO:17). In another embodiment, the antibody comprises a VH FR2 (SEQ ID NO:20), a VH FR3 (SEQ ID NOS:21 or 23), a VH FR4 (SEQ ID NO:22), a VL FR1 (SEQ ID NO:14), and a VL FR2 (SEQ ID NO:15). In other embodiments, the antibody comprises a VH FR2 (SEQ ID NO:20), a VH FR3 (SEQ ID NOS:21 or 23), a VH FR4 (SEQ ID NO:22), a VL FR1 (SEQ ID NO:14), and a VL FR3 (SEQ ID NOS:16 or 18). In one embodiment, the antibody comprises a VH FR2 (SEQ ID NO:20), a VH FR3 (SEQ ID NOS:21 or 23), a VH FR4 (SEQ ID NO:22), a VL FR1 (SEQ ID NO:14), and a VL FR4 (SEQ ID NO:17). In another embodiment, the antibody comprises a VH FR2 (SEQ ID NO:20), a VH FR3 (SEQ ID NOS:21 or 23), a VH FR4 (SEQ ID NO:22), a VL FR2 (SEQ ID NO:15), and a VL FR3 (SEQ ID NOS:16 or 18). In some embodiments, the antibody comprises a VH FR2 (SEQ ID NO:20), a VH FR3 (SEQ ID NOS:21 or 23), a VH FR4 (SEQ ID NO:22), a VL FR2 (SEQ ID NO:15), and a VL FR4 (SEQ ID NO:17). In another embodiment, the antibody comprises a VH FR1 (SEQ ID NOS:19 or 24), a VH FR2 (SEQ ID NO:20), a VL FR1 (SEQ ID NO:14), a VL FR2 (SEQ ID NO:15), and a VL FR3 (SEQ ID NOS:16 or 18). In other embodiments, the antibody comprises a VH FR1 (SEQ ID NOS:19 or 24), a VH FR2 (SEQ ID NO:20), a VL FR1 (SEQ ID NO:14), a VL FR2 (SEQ ID NO:15), and a VL FR4 (SEQ ID NO:17). In some embodiments, the antibody comprises a VH FR1 (SEQ ID NOS:19 or 24), a VH FR2 (SEQ ID NO:20), a VL FR1 (SEQ ID NO:14), a VL FR3 (SEQ ID NOS:16 or 18), and a VL FR4 (SEQ ID NO:17). In another embodiment, the antibody comprises a VH FR1 (SEQ ID NOS:19 or 24), a VH FR2 (SEQ ID NO:20), a VL FR2 (SEQ ID NO:15), a VL FR3 (SEQ ID NOS:16 or 18), and a VL FR4 (SEQ ID NO:17). In one embodiment, the antibody comprises a VH FR1 (SEQ ID NOS:19 or 24), a VH FR3 (SEQ ID NOS:21 or 23), a VL FR1 (SEQ ID NO:14), a VL FR2 (SEQ ID NO:15), and a VL FR3 (SEQ ID NOS:16 or 18). In one embodiment, the antibody comprises a VH FR1 (SEQ ID NOS:19 or 24), a VH FR3 (SEQ ID NOS:21 or 23), a VL FR1 (SEQ ID NO:14), a VL FR2 (SEQ ID NO:15), and a VL FR4 (SEQ ID NO:17). In another embodiment, the antibody comprises a VH FR1 (SEQ ID NOS:19 or 24), a VH FR3 (SEQ ID NOS:21 or 23), a VL FR1 (SEQ ID NO:14), a VL FR3 (SEQ ID NOS:16 or 18), and a VL FR4 (SEQ ID NO:17). In some embodiments, the antibody comprises a VH FR1 (SEQ ID NOS:19 or 24), a VH FR3 (SEQ ID NOS:21 or 23), a VL FR2 (SEQ ID NO:15), a VL FR3 (SEQ ID NOS:16 or 18), and a VL FR4 (SEQ ID NO:17). In other embodiments, the antibody comprises a VH FR1 (SEQ ID NOS:19 or 24), a VH FR4 (SEQ ID NO:22), a VL FR1 (SEQ ID NO:14), a VL FR2 (SEQ ID NO:15), and a VL FR3 (SEQ ID NOS:16 or 18). In another embodiment, the antibody comprises a VH FR1 (SEQ ID NOS:19 or 24), a VH FR4 (SEQ ID NO:22), a VL FR1 (SEQ ID NO:14), a VL FR2 (SEQ ID NO:15), and a VL FR4 (SEQ ID NO:17). In one embodiment, the antibody comprises a VH FR1 (SEQ ID NOS:19 or 24), a VH FR4 (SEQ ID NO:22), a VL FR1 (SEQ ID NO:14), a VL FR3 (SEQ ID NOS:16 or 18), and a VL FR4 (SEQ ID NO:17). In some embodiments, the antibody comprises a VH FR1 (SEQ ID NOS:19 or 24), a VH FR4 (SEQ ID NO:22), a VL FR2 (SEQ ID NO:15), a VL FR3 (SEQ ID NOS:16 or 18), and a VL FR4 (SEQ ID NO:17). In another embodiment, the antibody comprises a VH FR2 (SEQ ID NO:20), a VH FR3 (SEQ ID NOS:21 or 23), a VL FR1 (SEQ ID NO:14), a VL FR2 (SEQ ID NO:15), and a VL FR3 (SEQ ID NOS:16 or 18). In one embodiment, the antibody comprises a VH FR2 (SEQ ID NO:20), a VH FR3 (SEQ ID NOS:21 or 23), a VL FR1 (SEQ ID NO:14), a VL FR2 (SEQ ID NO:15), and a VL FR4 (SEQ ID NO:17). In other embodiments, the antibody comprises a VH FR2 (SEQ ID NO:20), a VH FR3 (SEQ ID NOS:21 or 23), a VL FR1 (SEQ ID NO:14), a VL FR3 (SEQ ID NOS:16 or 18), and a VL FR4 (SEQ ID NO:17). In another embodiment, the antibody comprises a VH FR2 (SEQ ID NO:20), a VH FR3 (SEQ ID NOS:21 or 23), a VL FR2 (SEQ ID NO:15), a VL FR3 (SEQ ID NOS:16 or 18), and a VL FR4 (SEQ ID NO:17). In some embodiments, the antibody comprises a VH FR2 (SEQ ID NO:20), a VH FR4 (SEQ ID NO:22), a VL FR1 (SEQ ID NO:14), a VL FR2 (SEQ ID NO:15), and a VL FR3 (SEQ ID NOS:16 or 18). In one embodiment, the antibody comprises a VH FR2 (SEQ ID NO:20), a VH FR4 (SEQ ID NO:22), a VL FR1 (SEQ ID NO:14), a VL FR2 (SEQ ID NO:15), and a VL FR4 (SEQ ID NO:17). In another embodiment, the antibody comprises a VH FR2 (SEQ ID NO:20), a VH FR4 (SEQ ID NO:22), a VL FR1 (SEQ ID NO:14), a VL FR3 (SEQ ID NOS:16 or 18), and a VL FR4 (SEQ ID NO:17). In one embodiment, the antibody comprises a VH FR2 (SEQ ID NO:20), a VH FR4 (SEQ ID NO:22), a VL FR2 (SEQ ID NO:15), a VL FR3 (SEQ ID NOS:16 or 18), and a VL FR4 (SEQ ID NO:17). In some embodiments, the antibody comprises a VH FR3 (SEQ ID NOS:21 or 23), a VH FR4 (SEQ ID NO:22), a VL FR1 (SEQ ID NO:14), a VL FR2 (SEQ ID NO:15), and a VL FR3 (SEQ ID NOS:16 or 18). In another embodiment, the antibody comprises a VH FR3 (SEQ ID NOS:21 or 23), a VH FR4 (SEQ ID NO:22), a VL FR1 (SEQ ID NO:14), a VL FR2 (SEQ ID NO:15), and a VL FR4 (SEQ ID NO:17). In other embodiments, the antibody comprises a VH FR3 (SEQ ID NOS:21 or 23), a VH FR4 (SEQ ID NO:22), a VL FR1 (SEQ ID NO:14), a VL FR3 (SEQ ID NOS:16 or 18), and a VL FR4 (SEQ ID NO:17). In one embodiment, the antibody comprises a VH FR3 (SEQ ID NOS:21 or 23), a VH FR4 (SEQ ID NO:22), a VL FR2 (SEQ ID NO:15), a VL FR3 (SEQ ID NOS:16 or 18), and a VL FR4 (SEQ ID NO:17). In another embodiment, the antibody comprises a VH FR1 (SEQ ID NOS:19 or 24), a VL FR1 (SEQ ID NO:14), a VL FR2 (SEQ ID NO:15), a VL FR3 (SEQ ID NOS:16 or 18), and a VL FR4 (SEQ ID NO:17). In some embodiments, the antibody comprises a VH FR2 (SEQ ID NO:20), a VL FR1 (SEQ ID NO:14), a VL FR2 (SEQ ID NO:15), a VL FR3 (SEQ ID NOS:16 or 18), and a VL FR4 (SEQ ID NO:17). In one embodiment, the antibody comprises a VH FR3 (SEQ ID NOS:21 or 23), a VL FR1 (SEQ ID NO:14), a VL FR2 (SEQ ID NO:15), a VL FR3 (SEQ ID NOS:16 or 18), and a VL FR4 (SEQ ID NO:17). In another embodiment, the antibody comprises a VH FR4 (SEQ ID NO:22), a VL FR1 (SEQ ID NO:14), a VL FR2 (SEQ ID NO:15), a VL FR3 (SEQ ID NOS:16 or 18), and a VL FR4 (SEQ ID NO:17). In other embodiments, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR1 (SEQ ID NO:14), and a VL FR2 (SEQ ID NO:15). In some embodiments, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR1 (SEQ ID NO:14), and a VL FR3 (SEQ ID NOS:16 or 18). In another embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR1 (SEQ ID NO:14), and a VL FR4 (SEQ ID NO:17). In one embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR2 (SEQ ID NO:15), and a VL FR3 (SEQ ID NOS:16 or 18). In one embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR2 (SEQ ID NO:15), and a VL FR4 (SEQ ID NO:17). In another embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR3 (SEQ ID NOS:16 or 18), and a VL FR4 (SEQ ID NO:17). In some embodiments, the antibody comprises a VH FR1 (SEQ ID NOS:19 or 24), a VH FR2 (SEQ ID NO:20), a VH FR3 (SEQ ID NOS:21 or 23), a VL FR1 (SEQ ID NO:14), a VL FR2 (SEQ ID NO:15), and a VL FR3 (SEQ ID NOS:16 or 18). In other embodiments, the antibody comprises a VH FR1 (SEQ ID NOS:19 or 24), a VH FR2 (SEQ ID NO:20), a VH FR3 (SEQ ID NOS:21 or 23), a VL FR1 (SEQ ID NO:14), a VL FR2 (SEQ ID NO:15), and a VL FR4 (SEQ ID NO:17). In another embodiment, the antibody comprises a VH FR1 (SEQ ID NOS:19 or 24), a VH FR2 (SEQ ID NO:20), a VH FR3 (SEQ ID NOS:21 or 23), a VL FR1 (SEQ ID NO:14), a VL FR3 (SEQ ID NOS:16 or 18), and a VL FR4 (SEQ ID NO:17). In one embodiment, the antibody comprises a VH FR1 (SEQ ID NOS:19 or 24), a VH FR2 (SEQ ID NO:20), a VH FR3 (SEQ ID NOS:21 or 23), a VL FR2 (SEQ ID NO:15), a VL FR3 (SEQ ID NOS:16 or 18), and a VL FR4 (SEQ ID NO:17). In some embodiments, the antibody comprises a VH FR1 (SEQ ID NOS:19 or 24), a VH FR2 (SEQ ID NO:20), a VH FR4 (SEQ ID NO:22), a VL FR1 (SEQ ID NO:14), a VL FR2 (SEQ ID NO:15), and a VL FR3 (SEQ ID NOS:16 or 18). In another embodiment, the antibody comprises a VH FR1 (SEQ ID NOS:19 or 24), a VH FR2 (SEQ ID NO:20), a VH FR4 (SEQ ID NO:22), a VL FR1 (SEQ ID NO:14), a VL FR2 (SEQ ID NO:15), and a VL FR4 (SEQ ID NO:17). In one embodiment, the antibody comprises a VH FR1 (SEQ ID NOS:19 or 24), a VH FR2 (SEQ ID NO:20), a VH FR4 (SEQ ID NO:22), a VL FR1 (SEQ ID NO:14), a VL FR3 (SEQ ID NOS:16 or 18), and a VL FR4 (SEQ ID NO:17). In other embodiments, the antibody comprises a VH FR1 (SEQ ID NOS:19 or 24), a VH FR2 (SEQ ID NO:20), a VH FR4 (SEQ ID NO:22), a VL FR2 (SEQ ID NO:15), a VL FR3 (SEQ ID NOS:16 or 18), and a VL FR4 (SEQ ID NO:17). In another embodiment, the antibody comprises a VH FR1 (SEQ ID NOS:19 or 24), a VH FR3 (SEQ ID NOS:21 or 23), a VH FR4 (SEQ ID NO:22), a VL FR1 (SEQ ID NO:14), a VL FR2 (SEQ ID NO:15), and a VL FR3 (SEQ ID NOS:16 or 18). In some embodiments, the antibody comprises a VH FR1 (SEQ ID NOS:19 or 24), a VH FR3 (SEQ ID NOS:21 or 23), a VH FR4 (SEQ ID NO:22), a VL FR1 (SEQ ID NO:14), a VL FR2 (SEQ ID NO:15), and a VL FR4 (SEQ ID NO:17). In one embodiment, the antibody comprises a VH FR1 (SEQ ID NOS:19 or 24), a VH FR3 (SEQ ID NOS:21 or 23), a VH FR4 (SEQ ID NO:22), a VL FR1 (SEQ ID NO:14), a VL FR3 (SEQ ID NOS:16 or 18), and a VL FR4 (SEQ ID NO:17). In another embodiment, the antibody comprises a VH FR1 (SEQ ID NOS:19 or 24), a VH FR3 (SEQ ID NOS:21 or 23), a VH FR4 (SEQ ID NO:22), a VL FR2 (SEQ ID NO:15), a VL FR3 (SEQ ID NOS:16 or 18), and a VL FR4 (SEQ ID NO:17). In one embodiment, the antibody comprises a VH FR2 (SEQ ID NO:20), a VH FR3 (SEQ ID NOS:21 or 23), a VH FR4 (SEQ ID NO:22), a VL FR1 (SEQ ID NO:14), a VL FR2 (SEQ ID NO:15), and a VL FR3 (SEQ ID NOS:16 or 18). In some embodiments, the antibody comprises a VH FR2 (SEQ ID NO:20), a VH FR3 (SEQ ID NOS:21 or 23), a VH FR4 (SEQ ID NO:22), a VL FR1 (SEQ ID NO:14), a VL FR2 (SEQ ID NO:15), and a VL FR4 (SEQ ID NO:17). In another embodiment, the antibody comprises a VH FR2 (SEQ ID NO:20), a VH FR3 (SEQ ID NOS:21 or 23), a VH FR4 (SEQ ID NO:22), a VL FR1 (SEQ ID NO:14), a VL FR3 (SEQ ID NOS:16 or 18), and a VL FR4 (SEQ ID NO:17). In other embodiments, the antibody comprises a VH FR2 (SEQ ID NO:20), a VH FR3 (SEQ ID NOS:21 or 23), a VH FR4 (SEQ ID NO:22), a VL FR2 (SEQ ID NO:15), a VL FR3 (SEQ ID NOS:16 or 18), and a VL FR4 (SEQ ID NO:17). In one embodiment, the antibody comprises a VH FR1 (SEQ ID NOS:19 or 24), a VH FR2 (SEQ ID NO:20), a VL FR1 (SEQ ID NO:14), a VL FR2 (SEQ ID NO:15), a VL FR3 (SEQ ID NOS:16 or 18), and a VL FR4 (SEQ ID NO:17). In another embodiment, the antibody comprises a VH FR1 (SEQ ID NOS:19 or 24), a VH FR3 (SEQ ID NOS:21 or 23), a VL FR1 (SEQ ID NO:14), a VL FR2 (SEQ ID NO:15), a VL FR3 (SEQ ID NOS:16 or 18), and a VL FR4 (SEQ ID NO:17). In some embodiments, the antibody comprises a VH FR1 (SEQ ID NOS:19 or 24), a VH FR4 (SEQ ID NO:22), a VL FR1 (SEQ ID NO:14), a VL FR2 (SEQ ID NO:15), a VL FR3 (SEQ ID NOS:16 or 18), and a VL FR4 (SEQ ID NO:17). In one embodiment, the antibody comprises a VH FR2 (SEQ ID NO:20), a VH FR3 (SEQ ID NOS:21 or 23), a VL FR1 (SEQ ID NO:14), a VL FR2 (SEQ ID NO:15), a VL FR3 (SEQ ID NOS:16 or 18), and a VL FR4 (SEQ ID NO:17). In another embodiment, the antibody comprises a VH FR2 (SEQ ID NO:20), a VH FR4 (SEQ ID NO:22), a VL FR1 (SEQ ID NO:14), a VL FR2 (SEQ ID NO:15), a VL FR3 (SEQ ID NOS:16 or 18), and a VL FR4 (SEQ ID NO:17). In other embodiments, the antibody comprises a VH FR3 (SEQ ID NOS:21 or 23), a VH FR4 (SEQ ID NO:22), a VL FR1 (SEQ ID NO:14), a VL FR2 (SEQ ID NO:15), a VL FR3 (SEQ ID NOS:16 or 18), and a VL FR4 (SEQ ID NO:17). In some embodiments, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR1 (SEQ ID NO:14), a VL FR2 (SEQ ID NO:15), and a VL FR3 (SEQ ID NOS:16 or 18). In another embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR1 (SEQ ID NO:14), a VL FR2 (SEQ ID NO:15), and a VL FR4 (SEQ ID NO:17). In one embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR1 (SEQ ID NO:14), a VL FR3 (SEQ ID NOS:16 or 18), and a VL FR4 (SEQ ID NO:17). In one embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR2 (SEQ ID NO:15), a VL FR3 (SEQ ID NOS:16 or 18), and a VL FR4 (SEQ ID NO:17). In another embodiment, the antibody comprises a VH FR1 (SEQ ID NOS:19 or 24), a VH FR2 (SEQ ID NO:20), a VH FR3 (SEQ ID NOS:21 or 23), a VL FR1 (SEQ ID NO:14), a VL FR2 (SEQ ID NO:15), a VL FR3 (SEQ ID NOS:16 or 18), and a VL FR4 (SEQ ID NO:17). In some embodiments, the antibody comprises a VH FR1 (SEQ ID NOS:19 or 24), a VH FR2 (SEQ ID NO:20), a VH FR4 (SEQ ID NO:22), a VL FR1 (SEQ ID NO:14), a VL FR2 (SEQ ID NO:15), a VL FR3 (SEQ ID NOS:16 or 18), and a VL FR4 (SEQ ID NO:17). In other embodiments, the antibody comprises a VH FR1 (SEQ ID NOS:19 or 24), a VH FR3 (SEQ ID NOS:21 or 23), a VH FR4 (SEQ ID NO:22), a VL FR1 (SEQ ID NO:14), a VL FR2 (SEQ ID NO:15), a VL FR3 (SEQ ID NOS:16 or 18), and a VL FR4 (SEQ ID NO:17). In one embodiment, the antibody comprises a VH FR2 (SEQ ID NO:20), a VH FR3 (SEQ ID NOS:21 or 23), a VH FR4 (SEQ ID NO:22), a VL FR1 (SEQ ID NO:14), a VL FR2 (SEQ ID NO:15), a VL FR3 (SEQ ID NOS:16 or 18), and a VL FR4 (SEQ ID NO:17). In some embodiments, the antibody comprises any combination thereof of the VH FRs (SEQ ID NOS:19-24) and the VL FRs (SEQ ID NOS:14-18) listed in Tables 3-4.

In some embodiments, the antibodies provided herein comprise a VH region or VH domain. In other embodiments, the antibodies provided herein comprise a VL region or VL domain. In certain embodiments, the antibodies provided herein have a combination of (i) a VH domain or VH region; and/or (ii) a VL domain or VL region. In yet other embodiments, the antibodies provided herein have a combination of (i) a VH domain or VH region; and/or (ii) a VL domain or VL region selected from the group consisting of SEQ ID NOS: 8-13 as set forth in Tables 5-6. In still other embodiments, the antibodies provided herein have a combination of (i) a VH domain or VH region; and/or (ii) a VL domain or VL region of any one of antibodies PD1AB-1, PD1AB-2, PD1AB-3, PD1AB-4, PD1AB-5, or PD1AB-6, as set forth in Tables 5-6.

In certain embodiments, the antibodies provided herein comprise a VH region comprising: (1) a VH CDR1 having an amino acid sequence of SEQ ID NO:4; (2) a VH CDR2 having an amino acid sequence of SEQ ID NO:5; and (3) a VH CDR3 having an amino acid sequence of SEQ ID NO:6; and a VL region selected from the group consisting of SEQ ID NOS:8-10 as set forth in Table 5. In some embodiments, the VL region has an amino acid sequence of SEQ ID NO:8. In other embodiments, the VL region has an amino acid sequence of SEQ ID NO:9. In some embodiments, the VL region has an amino acid sequence of SEQ ID NO:10.

In other embodiments, the antibodies provided herein comprise a VH region selected from the group consisting of SEQ ID NOS:11-13 as set forth in Table 6; and a VL region comprising: (1) a VL CDR1 having an amino acid sequence selected from the group consisting of SEQ ID NOS:1 and 7; (2) a VL CDR2 having an amino acid sequence of SEQ ID NO:2; and (3) a VL CDR3 having an amino acid sequence of SEQ ID NO:3. In yet some embodiments, the antibodies provided herein comprise a VH region selected from the group consisting of SEQ ID NOS:11-13 as set forth in Table 6; and a VL region comprising: (1) a VL CDR1 having an amino acid sequence of SEQ ID NO:1; (2) a VL CDR2 having an amino acid sequence of SEQ ID NO:2; and (3) a VL CDR3 having an amino acid sequence of SEQ ID NO:3. In still other embodiments, the antibodies provided herein comprise a VH region selected from the group consisting of SEQ ID NOS:11-13 as set forth in Table 6; and a VL region comprising: (1) a VL CDR1 having an amino acid sequence of SEQ ID NO:7; (2) a VL CDR2 having an amino acid sequence of SEQ ID NO:2; and (3) a VL CDR3 having an amino acid sequence of SEQ ID NO:3. In some embodiments, the VH region has an amino acid sequence of SEQ ID NO:11. In some embodiments, the VH region has an amino acid sequence of SEQ ID NO:12. In some embodiments, the VH region has an amino acid sequence of SEQ ID NO:13.

TABLE 5

VL Domain Amino Acid Sequences

| Antibody | VL (SEQ ID NO:) |
|---|---|
| PD1AB-1 | DIVMTQSPDSLAVSLGERATINCKSGQSVLYSSNQKNFLAW YQQKPGQPPKLLIYWASTRESGVPDRFSGSGSGTDFTLTIS SLQAEDVAVYYCHQYLYSWTFGQGTKLEIKR (SEQ ID NO: 8) |
| PD1AB-2 | DIVMTQSPDSLAVSLGERATINCKSSQSVLYSSNNKNYLAW YQQKPGQPPKLLIYWASTRESGVPDRFSGSGSGTDFTLTIS SLQAEDVAVYYCHQYLYSWTFGQGTKLEIKR (SEQ ID NO: 9) |
| PD1AB-3 | DIVMTQSPDSLAVSLGERATINCKSGQSVLYSSNQKNFLAW YQQKPGQPPKLLIYWASTRESGVPDRFSGSGSGTDFTLTIS NLQAEDVAVYYCHQYLYSWTFGQGTKLEIKR (SEQ ID NO: 10) |
| PD1AB-4 | DIVMTQSPDSLAVSLGERATINCKSSQSVLYSSNNKNYLAW YQQKPGQPPKLLIYWASTRESGVPDRFSGSGSGTDFTLTIS SLQAEDVAVYYCHQYLYSWTFGQGTKLEIKR (SEQ ID NO: 9) |
| PD1AB-5 | DIVMTQSPDSLAVSLGERATINCKSSQSVLYSSNNKNYLAW YQQKPGQPPKLLIYWASTRESGVPDRFSGSGSGTDFTLTIS SLQAEDVAVYYCHQYLYSWTFGQGTKLEIKR (SEQ ID NO: 9) |

TABLE 5 -continued

VL Domain Amino Acid Sequences

| Antibody | VL (SEQ ID NO:) |
|---|---|
| PD1AB-6 | DIVMTQSPDSLAVSLGERATINCKSGQSVLYSSNQKNFLAW YQQKPGQPPKLLIYWASTRESGVPDRFSGSGSGTDFTLTIS SLQAEDVAVYYCHQYLYSWTFGQGTKLEIKR (SEQ ID NO: 8) |

TABLE 6

VH Domain Amino Acid Sequences

| Antibody | VH (SEQ ID NO:) |
|---|---|
| PD1AB-1 | EVQLVQSGAEVKKPGATVKISCKVSGFNIKDTYMHWVQQAP GKGLEWMGRIDPANGDRKYDPKFQGRVTITADTSTDTAYME LSSLRSEDTAVYYCARSGPVYYYGSSYVMDYWGQGTTVTVS S (SEQ ID NO: 11) |
| PD1AB-2 | EVQLVQSGAEVKKPGATVKISCKVSGFNIKDTYMHWVQQAP GKGLEWMGRIDPANGDRKYDPKFQGRVTITADTSTDTAYME LSSLRSEDTAVYYCARSGPVYYYGSSYVMDYWGQGTTVTVS S (SEQ ID NO: 11) |
| PD1AB-3 | EVQLVQSGAEVKKPGATVKISCKVSGFNIKDTYMHWVQQAP GKGLEWMGRIDPANGDRKYDPKFQGRVTITADTSTNTAYME LSSLRSEDTAVYYCARSGPVYYYGSSYVMDYWGQGTTVTVS S (SEQ ID NO: 12) |
| PD1AB-4 | EVQLVQSGAEVKKPGATVKISCKVSGFNIKDTYMHWVQQAP GKGLEWMGRIDPANGDRKYDPKFQGRVTITADTSTNTAYME LSSLRSEDTAVYYCARSGPVYYYGSSYVMDYWGQGTTVTVS S (SEQ ID NO: 12) |
| PD1AB-5 | EVQLVQSGAEVKKPGATVKISCKASGENIKDTYMHWVQQAP GKGLEWMGRIDPANGDRKYDPKFQGRVTITADTSTDTAYME LSSLRSEDTAVYYCARSGPVYYYGSSYVMDYWGQGTTVTVS S (SEQ ID NO: 13) |
| PD1AB-6 | EVQLVQSGAEVKKPGATVKISCKASGENIKDTYMHWVQQAP GKGLEWMGRIDPANGDRKYDPKFQGRVTITADTSTDTAYME LSSLRSEDTAVYYCARSGPVYYYGSSYVMDYWGQGTTVTVS S (SEQ ID NO: 13) |

Also provided herein are isolated nucleic acid molecules encoding an immunoglobulin heavy chain, light chain, VH region, VL region, VH CDR1, VH CDR2, VH CDR3, VL CDR1, VL CDR2, and/or VL CDR3 of anti-PD-1 antibodies that bind to a PD-1 polypeptide, a PD-1 polypeptide fragment, a PD-1 peptide, or a PD-1 epitope. The exemplary nucleic acid sequences for the VL region and the VH region of any one of antibodies PD1AB-1, PD1AB-2, PD1AB-3, PD1AB-4, PD1AB-5, and PD1AB-6 are shown in Tables 7-8.

TABLE 7

VL Nucleic Acid Sequences

| Antibody | Nucleotide sequences |
|---|---|
| PD1AB-1 | GACATCGTGATGACCCAGTCTCCAGACTCCCTGGCTGTGTCTCTGGGCGAGAGGGCCACCATCAA CTGCAAGTCCGGTCAAAGTGTTTTATACAGTTCAAATCAGAAGAACTTCTTGGCCTGGTACCAGC AGAAACCAGGACAGCCTCCTAAGCTGCTCATTTACTGGGCATCCACTAGGGAATCTGGGGTCCCT GACCGATTCAGTGGCAGCGGGTCTGGGACAGATTTCACTCTCACCATCAGCAGCCTGCAAGCTGA AGATGTGGCAGTTTATTACTGTCATCAATACCTCTACTCGTGGACGTTTGGCCAGGGGACCAAGC TGGAGATCAAACGGAC (SEQ ID NO: 25 ) |
| PD1AB-2 | GACATCGTGATGACCCAGTCTCCAGACTCCCTGGCTGTGTCTCTGGGCGAGAGGGCCACCATCAA CTGCAAGTCCAGCCAGAGTGTTTTATACAGCTCCAACAATAAGAACTACTTAGCTTGGTACCAGC AGAAACCAGGACAGCCTCCTAAGCTGCTCATTTACTGGGCATCTACCCGGGAATCCGGGGTCCCT GACCGATTCAGTGGCAGCGGGTCTGGGACAGATTTCACTCTCACCATCAGCAGCCTGCAAGCTGA AGATGTGGCAGTTTATTACTGTCATCAATACCTCTACTCGTGGACGTTTGGCCAGGGGACCAAGC TGGAGATCAAACGGAC (SEQ ID NO: 26) |
| PD1AB-3 | GACATCGTGATGACCCAGTCTCCAGACTCCCTGGCTGTGTCTCTGGGCGAGAGGGCCACCATCAA CTGCAAGTCCGGTCAAAGTGTTTTATACAGTTCAAATCAGAAGAACTTCTTGGCCTGGTACCAGC AGAAACCAGGACAGCCTCCTAAGCTGCTCATTTACTGGGCATCCACTAGGGAATCTGGGGTCCCT GACCGATTCAGTGGCAGCGGGTCTGGGACAGATTTCACTCTCACCATCAGCAACCTGCAAGCTGA AGATGTGGCAGTTTATTACTGTCATCAATACCTCTACTCGTGGACGTTTGGCCAGGGGACCAAGC TGGAGATCAAACGGAC (SEQ ID NO: 27) |
| PD1AB-4 | GACATCGTGATGACCCAGTCTCCAGACTCCCTGGCTGTGTCTCTGGGCGAGAGGGCCACCATCAA CTGCAAGTCCAGCCAGAGTGTTTTATACAGCTCCAACAATAAGAACTACTTAGCTTGGTACCAGC AGAAACCAGGACAGCCTCCTAAGCTGCTCATTTACTGGGCATCTACCCGGGAATCCGGGGTCCCT GACCGATTCAGTGGCAGCGGGTCTGGGACAGATTTCACTCTCACCATCAGCAGCCTGCAAGCTGA AGATGTGGCAGTTTATTACTGTCATCAATACCTCTACTCGTGGACGTTTGGCCAGGGGACCAAGC TGGAGATCAAACGGAC (SEQ ID NO: 26) |
| PD1AB-5 | GACATCGTGATGACCCAGTCTCCAGACTCCCTGGCTGTGTCTCTGGGCGAGAGGGCCACCATCAA CTGCAAGTCCAGCCAGAGTGTTTTATACAGCTCCAACAATAAGAACTACTTAGCTTGGTACCAGC AGAAACCAGGACAGCCTCCTAAGCTGCTCATTTACTGGGCATCTACCCGGGAATCCGGGGTCCCT GACCGATTCAGTGGCAGCGGGTCTGGGACAGATTTCACTCTCACCATCAGCAGCCTGCAAGCTGA AGATGTGGCAGTTTATTACTGTCATCAATACCTCTACTCGTGGACGTTTGGCCAGGGGACCAAGC TGGAGATCAAACGGAC (SEQ ID NO: 26) |

TABLE 7 -continued

VL Nucleic Acid Sequences

Antibody Nucleotide sequences

PD1AB-6  GACATCGTGATGACCCAGTCTCCAGACTCCCTGGCTGTGTCTCTGGGCGAGAGGGCCACCATCAA
CTGCAAGTCCGGTCAAAGTGTTTTATACAGTTCAAATCAGAAGAACTTCTTGGCCTGGTACCAGC
AGAAACCAGGACAGCCTCCTAAGCTGCTCATTTACTGGGCATCCACTAGGGAATCTGGGGTCCCT
GACCGATTCAGTGGCAGCGGGTCTGGGACAGATTTCACTCTCACCATCAGCAGCCTGCAAGCTGA
AGATGTGGCAGTTTATTACTGTCATCAATACCTCTACTCGTGGACGTTTGGCCAGGGGACCAAGC
TGGAGATCAAACGGAC
(SEQ ID NO: 25)

TABLE 8

VH Nucleic Acid Sequences

Antibody Nucleotide sequences

PD1AB-1  GAGGTCCAGCTGGTACAGTCTGGGGCTGAGGTGAAGAAGCCTGGGGCTACAGTGAAAATCTCCTG
CAAGGTTTCTGGATTCAACATTAAAGACACGTATATGCACTGGGTGCAACAGGCCCCTGGAAAAG
GGCTTGAGTGGATGGGAAGGATTGATCCTGCGAATGGTGATAGGAAATATGACCCGAAGTTCCAG
GGCAGAGTCACCATAACCGCGGACACGTCTACAGACACAGCCTACATGGAGCTGAGCAGCCTGAG
ATCTGAGGACACGGCCGTGTATTACTGTGCTAGATCAGGCCCTGTTTATTACTACGGTAGTAGCT
ACGTTATGGACTACTGGGGTCAAGGAACCACAGTCACCGTCTCCTCA
(SEQ ID NO: 28)

PD1AB-2  GAGGTCCAGCTGGTACAGTCTGGGGCTGAGGTGAAGAAGCCTGGGGCTACAGTGAAAATCTCCTG
CAAGGTTTCTGGATTCAACATTAAAGACACGTATATGCACTGGGTGCAACAGGCCCCTGGAAAAG
GGCTTGAGTGGATGGGAAGGATTGATCCTGCGAATGGTGATAGGAAATATGACCCGAAGTTCCAG
GGCAGAGTCACCATAACCGCGGACACGTCTACAGACACAGCCTACATGGAGCTGAGCAGCCTGAG
ATCTGAGGACACGGCCGTGTATTACTGTGCTAGATCAGGCCCTGTTTATTACTACGGTAGTAGCT
ACGTTATGGACTACTGGGGTCAAGGAACCACAGTCACCGTCTCCTCA
(SEQ ID NO: 28)

PD1AB-3  GAGGTCCAGCTGGTACAGTCTGGGGCTGAGGTGAAGAAGCCTGGGGCTACAGTGAAAATCTCCTG
CAAGGTTTCTGGATTCAACATTAAAGACACGTATATGCACTGGGTGCAACAGGCCCCTGGAAAAG
GGCTTGAGTGGATGGGAAGGATTGATCCTGCGAATGGTGATAGGAAATATGACCCGAAGTTCCAG
GGCAGAGTCACCATAACCGCGGACACGTCTACAAACACAGCCTACATGGAGCTGAGCAGCCTGAG
ATCTGAGGACACGGCCGTGTATTACTGTGCTAGATCAGGCCCTGTTTATTACTACGGTAGTAGCT
ACGTTATGGACTACTGGGGTCAAGGAACCACAGTCACCGTCTCCTCA
(SEQ ID NO: 29)

PD1AB-4  GAGGTCCAGCTGGTACAGTCTGGGGCTGAGGTGAAGAAGCCTGGGGCTACAGTGAAAATCTCCTG
CAAGGTTTCTGGATTCAACATTAAAGACACGTATATGCACTGGGTGCAACAGGCCCCTGGAAAAG
GGCTTGAGTGGATGGGAAGGATTGATCCTGCGAATGGTGATAGGAAATATGACCCGAAGTTCCAG
GGCAGAGTCACCATAACCGCGGACACGTCTACAAACACAGCCTACATGGAGCTGAGCAGCCTGAG
ATCTGAGGACACGGCCGTGTATTACTGTGCTAGATCAGGCCCTGTTTATTACTACGGTAGTAGCT
ACGTTATGGACTACTGGGGTCAAGGAACCACAGTCACCGTCTCCTCA
(SEQ ID NO: 29)

PD1AB-5  GAGGTCCAGCTGGTACAGTCTGGGGCTGAGGTGAAGAAGCCTGGGGCTACAGTGAAAATCTCCTG
CAAGGCTTCTGGATTCAACATTAAAGACACGTATATGCACTGGGTGCAACAGGCCCCTGGAAAAG
GGCTTGAGTGGATGGGAAGGATTGATCCTGCGAATGGTGATAGGAAATATGACCCGAAGTTCCAG
GGCAGAGTCACCATAACCGCGGACACGTCTACAGACACAGCCTACATGGAGCTGAGCAGCCTGAG
ATCTGAGGACACGGCCGTGTATTACTGTGCTAGATCAGGCCCTGTTTATTACTACGGTAGTAGCT
ACGTTATGGACTACTGGGGTCAAGGAACCACAGTCACCGTCTCCTCA
(SEQ ID NO: 30)

PD1AB-6  GAGGTCCAGCTGGTACAGTCTGGGGCTGAGGTGAAGAAGCCTGGGGCTACAGTGAAAATCTCCTG
CAAGGCTTCTGGATTCAACATTAAAGACACGTATATGCACTGGGTGCAACAGGCCCCTGGAAAAG
GGCTTGAGTGGATGGGAAGGATTGATCCTGCGAATGGTGATAGGAAATATGACCCGAAGTTCCAG
GGCAGAGTCACCATAACCGCGGACACGTCTACAGACACAGCCTACATGGAGCTGAGCAGCCTGAG
ATCTGAGGACACGGCCGTGTATTACTGTGCTAGATCAGGCCCTGTTTATTACTACGGTAGTAGCT
ACGTTATGGACTACTGGGGTCAAGGAACCACAGTCACCGTCTCCTCA
(SEQ ID NO: 30)

In some embodiments, an antibody provided herein has a VH and a VL amino acid sequence of PD1AB-1. In some embodiments, an antibody comprises a VH amino acid sequence of SEQ ID NO:11, and a VL amino acid sequence of SEQ ID NO:8.

In other embodiments, an antibody provided herein has a VH and a VL amino acid sequence of PD1AB-2. In some embodiments, an antibody comprises a VH amino acid sequence of SEQ ID NO:11, and a VL amino acid sequence of SEQ ID NO:9.

In some embodiments, an antibody provided herein has a VH and a VL amino acid sequence of PD1AB-3. In some embodiments, an antibody comprises a VH amino acid sequence of SEQ ID NO:12, and a VL amino acid sequence of SEQ ID NO:10.

In other embodiments, an antibody provided herein has a VH and a VL amino acid sequence of PD1AB-4. In some embodiments, an antibody comprises a VH amino acid sequence of SEQ ID NO:12, and a VL amino acid sequence of SEQ ID NO:9.

In some embodiments, an antibody provided herein has a VH and a VL amino acid sequence of PD1AB-5. In some embodiments, an antibody comprises a VH amino acid sequence of SEQ ID NO:13, and a VL amino acid sequence of SEQ ID NO:9.

In other embodiments, an antibody provided herein has a VH and a VL amino acid sequence of PD1AB-6. In some embodiments, an antibody comprises a VH amino acid sequence of SEQ ID NO:13, and a VL amino acid sequence of SEQ ID NO:8.

In certain embodiments, an antibody or antigen-binding fragment thereof described herein, which specifically binds to a PD-1 polypeptide (e.g., an ECD of PD-1, for example human PD-1), comprises a light chain and a heavy chain, wherein the light chain comprises a constant region having an amino acid sequence of:

(SEQ ID NO: 41)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.

In other embodiments, an antibody or antigen-binding fragment thereof described herein, which specifically binds to a PD-1 polypeptide (e.g., an ECD of PD-1, for example human PD-1), comprises a light chain and a heavy chain, wherein the heavy chain comprises a human IgG1 Fc region having an amino acid sequence of:

(SEQ ID NO: 36, K322 emphasized)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In some embodiments, an antibody or antigen-binding fragment thereof described herein, which specifically binds to a PD-1 polypeptide (e.g., an ECD of PD-1, for example human PD-1), comprises a light chain and a heavy chain, wherein the heavy chain does not comprise a human IgG1 Fc region having an amino acid sequence of SEQ ID NO:36.

In certain embodiments, an antibody or antigen-binding fragment thereof described herein, which specifically binds to a PD-1 polypeptide (e.g., an ECD of PD-1, for example human PD-1), comprises a light chain and a heavy chain, wherein the heavy chain comprises a human IgG1-K322A Fc region having an amino acid sequence of:

(SEQ ID NO: 37, K322A substitution emphasized)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCAVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In some embodiments, an antibody or antigen-binding fragment thereof described herein, which specifically binds to a PD-1 polypeptide (e.g., an ECD of PD-1, for example human PD-1), comprises a light chain and a heavy chain, wherein the heavy chain comprises a human IgG4 Fc region having an amino acid sequence of:

(SEQ ID NO: 38, S228 and L235 emphasized)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSPGK.

In another embodiment, an antibody or antigen-binding fragment thereof described herein, which specifically binds to a PD-1 polypeptide (e.g., an ECD of PD-1, for example human PD-1), comprises a light chain and a heavy chain, wherein the heavy chain comprises a human IgG4P Fc region having an amino acid sequence of:

(SEQ ID NO: 39, S228P substitution emphasized)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSPGK.

In yet another embodiment, an antibody or antigen-binding fragment thereof described herein, which specifically binds to a PD-1 polypeptide (e.g., an ECD of PD-1, for example human PD-1), comprises a light chain and a heavy chain, wherein the heavy chain comprises a human IgG4PE Fc region having an amino acid sequence of:

(SEQ ID NO: 40, S228P and L235E substitutions emphasized)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFEGGPSVFLFPPKPKDTLMISRTPEVTCVVVDVSQED

PEVQFNWYVDGVEVHNAKTKPREEQFNSTYRVVSVLTVLHQDWLNGKEYK

-continued
CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSPGK.

In some embodiments, an antibody or antigen-binding fragment thereof described herein, which specifically binds to a PD-1 polypeptide (e.g., an ECD of PD-1, for example human PD-1), comprises a light chain and a heavy chain, wherein the heavy chain does not comprise a human IgG4PE Fc region having an amino acid sequence of SEQ ID NO:40.

In still another embodiment, an antibody or antigen-binding fragment thereof described herein, which specifically binds to a PD-1 polypeptide (e.g., an ECD of PD-1, for example human PD-1), comprises a light chain and a heavy chain, wherein the light chain comprises a constant region having an amino acid sequence of SEQ ID NO:41; and the heavy chain comprises an Fc region having an amino acid sequence selected from the group consisting of SEQ ID NOS:36-40.

In certain embodiments, an antibody provided herein, which specifically binds to a PD-1 polypeptide (e.g., an ECD of PD-1, for example human PD-1), comprises a light chain and a heavy chain, wherein the light chain comprises an amino acid sequence as follows:

```
                    (SEQ ID NO: 31, LC_PD1AB-6-IgG1)
DIVMTQSPDSLAVSLGERATINCKSGQSVLYSSNQKNFLAWYQQKPGQPP

KLLIYWASTRESGVPDRFSGSGSGTDFTLTISSLQAEDVAVYYCHQYLYS

WTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.
```

In some embodiments, an antibody provided herein, which specifically binds to a PD-1 polypeptide (e.g., an ECD of PD-1, for example human PD-1), comprises a light chain and a heavy chain, wherein the heavy chain comprises an amino acid sequence as follows:

```
  (SEQ ID NO: 32, HC_PD1AB-6-IgG1, K322 emphasized)
EVQLVQSGAEVKKPGATVKISCKASGFNIKDTYMHWVQQAPGKGLEWMGR

IDPANGDRKYDPKFQGRVTITADTSTDTAYMELSSLRSEDTAVYYCARSG

PVYYYGSSYVMDYWGQGTTVIVSSASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSL

SPGK.
```

In other embodiments, an antibody provided herein, which specifically binds to a PD-1 polypeptide (e.g., an ECD of PD-1, for example human PD-1), comprises a light chain and a heavy chain, wherein the heavy chain comprises an amino acid sequence as follows:

```
          (SEQ ID NO: 33, HC_PD1AB-6-IgG1-K322A, K322A
                                substitution emphasized)
EVQLVQSGAEVKKPGATVKISCKASGFNIKDTYMHWVQQAPGKGLEWMGR

IDPANGDRKYDPKFQGRVTITADTSTDTAYMELSSLRSEDTAVYYCARSG

PVYYYGSSYVMDYWGQGTTVIVSSASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPRE

EQYNSTYRVVSVLTVLHQDWLNGKEYKCAVSNKALPAPIEKTISKAKGQP

REPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSL

SPGK.
```

In another embodiment, an antibody provided herein, which specifically binds to a PD-1 polypeptide (e.g., an ECD of PD-1, for example human PD-1), comprises a light chain and a heavy chain, wherein the heavy chain comprises an amino acid sequence as follows:

```
       (SEQ ID NO: 34, HC_PD1AB-6-IgG4P, IgG4P Fc backbone
                                italicized and underlined)
EVQLVQSGAEVKKPGATVKISCKASGFNIKDTYMHWVQQAPGKGLEWMGRIDPANGDRKYDPKF

QGRVTITADTSTDTAYMELSSLRSEDTAVYYCARSGPVYYYGSSYVMDYWGQGTTVTVSSASTK

GPSVFPLAPCSRSTSESTAALGCLVKDYFPEPVTVSWNSGALTSGVHTFPAVLQSSGLYSLSSV

VTVPSSSLGTKTYTCNVDHKPSNTKVDKRVESKYGPPCPPCPAPEFLGGPSVFLFPPKPKDTLM

VTVPSSSLGTKTYTCNVDHKPSNTKVDKRVESKYGPPCPPCPAPEFLGGPSVFLFPPKPKDTLM

ISRTPEVTCVVVDVSQEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSLTCLVKGFYPSDIAVE

WESNGQPENNYKTTPPVLDSDGSFFLYSRLTVDKSRWQEGNVFSCSVMHEALHNHYTQKSLSLS

PGK.
```

In yet another embodiment, an antibody provided herein, which specifically binds to a PD-1 polypeptide (e.g., an ECD of PD-1, for example human PD-1), comprises a light chain and a heavy chain, wherein the heavy chain comprises an amino acid sequence as follows:

(SEQ ID NO: 35, HC_PD1AB-6-IgG4PE, IgG4PE Fc backbone italicized and underlined)
EVQLVQSGAEVKKPGATVKISCKASGFNIKDTYMHWVQQAPGKGLEWMGRIDPANGDRKYDPKF

QGRVTITADTSTDTAYMELSSLRSEDTAVYYCARSGPVYYYGSSYVMDYWGQGTTVTVSS*ASTK*

*GPSVFPLAPCSRSTSESTAALGCLVKDYFPEPVTVSWNSGALTSGVHTFPAVLQSSGLYSLSSV*

*VTVPSSSLGTKTYTCNVDHKPSNTKVDKRVESKYGPPCPPCPAPEFEGGPSVFLFPPKPKDTLM*

*ISRTPEVTCVVVDVSQEDPEVQFNWYVDGVEVHNAKTKPREEQFNSTYRVVSVLTVLHQDWLNG*

*KEYKCKVSNKGLPSSIEKTISKAKGQPREPQVYTLPPSQEEMTKNQVSLTCLVKGFYPSDIAVE*

*WESNGQPENNYKTTPPVLDSDGSFFLYSRLTVDKSRWQEGNVFSCSVMHEALHNHYTQKSLSLS*

*PGK*.

In one particular embodiment, an antibody provided herein, which specifically binds to a PD-1 polypeptide (e.g., an ECD of PD-1, for example human PD-1), comprises a light chain and a heavy chain, wherein (i) the light chain comprises an amino acid sequence of SEQ ID NO:31; and (ii) the heavy chain comprises an amino acid sequence of SEQ ID NO:32.

In another particular embodiment, an antibody provided herein, which specifically binds to a PD-1 polypeptide (e.g., an ECD of PD-1, for example human PD-1), comprises a light chain and a heavy chain, wherein (i) the light chain comprises an amino acid sequence of SEQ ID NO:31; and (ii) the heavy chain comprises an amino acid sequence of SEQ ID NO:33.

In yet another particular embodiment, an antibody provided herein, which specifically binds to a PD-1 polypeptide (e.g., an ECD of PD-1, for example human PD-1), comprises a light chain and a heavy chain, wherein (i) the light chain comprises an amino acid sequence of SEQ ID NO:31; and (ii) the heavy chain comprises an amino acid sequence of SEQ ID NO:34.

In still another particular embodiment, an antibody provided herein, which specifically binds to a PD-1 polypeptide (e.g., an ECD of PD-1, for example human PD-1), comprises a light chain and a heavy chain, wherein (i) the light chain comprises an amino acid sequence of SEQ ID NO:31; and (ii) the heavy chain comprises an amino acid sequence of SEQ ID NO:35.

In yet another aspect, antibodies are provided that compete with one of the exemplified antibodies or functional fragments for binding to PD-1. Such antibodies may also bind to the same epitope as one of the herein exemplified antibodies, or an overlapping epitope. Antibodies and fragments that compete with or bind to the same epitope as the exemplified antibodies are expected to show similar functional properties. The exemplified antigen-binding proteins and fragments include those with the VH and VL regions, and CDRs provided herein, including those in Tables 1-6. Thus, as a specific example, the antibodies that are provided include those that compete with an antibody comprising: (a) 1, 2, 3, 4, 5, or all 6 of the CDRs listed for an antibody listed in Tables 1-2; (b) a VH and a VL selected from the VH and the VL regions listed for an antibody listed in Tables 5-6; or (c) two light chains and two heavy chains comprising a VH and a VL as specified for an antibody listed in Tables 5-6. In some embodiments, the antibody is PD1AB-1. In some embodiments, the antibody is PD1AB-2. In some embodiments, the antibody is PD1AB-3. In some embodiments, the antibody is PD1AB-4. In some embodiments, the antibody is PD1AB-5. In some embodiments, the antibody is PD1AB-6.

In another aspect, antibodies or antigen-binding fragments thereof provided herein bind to a region, including an epitope, of human PD-1 or cyno PD-1. For example, in some embodiments, an antibody provided herein binds to a region of human PD-1 (SEQ ID NO:42) comprising amino acid residues 33 to 109 of human PD-1. In still another aspect, antibodies provided herein bind to a specific epitope of human PD-1.

In certain embodiments, the antibody or antigen-binding fragment thereof, when bound to PD-1, binds to at least one of residues 100-109 (SEQ ID NO:43) within an amino acid sequence of SEQ ID NO:42. In some embodiments, the antibody or antigen-binding fragment thereof, when bound to PD-1, binds to at least one of residues 100-105 (SEQ ID NO:44) within an amino acid sequence of SEQ ID NO:42.

In particular embodiments, the antibody or antigen-binding fragment thereof, when bound to PD-1, binds to at least one residue selected from the group consisting of N33, T51, S57, L100, N102, G103, R104, D105, H107, and S109 within an amino acid sequence of SEQ ID NO:42. In some embodiments, the antibody or antigen-binding fragment thereof, when bound to PD-1, binds to at least one residue selected from the group consisting of L100, N102, G103, R104, D105, H107, and S109 within an amino acid sequence of SEQ ID NO:42.

In some embodiments, the antibody or antigen-binding fragment thereof, when bound to PD-1, binds to two or more residues selected from the group consisting of N33, T51, S57, L100, N102, G103, R104, D105, H107, and S109 within an amino acid sequence of SEQ ID NO:42.

In other embodiments, the antibody or antigen-binding fragment thereof, when bound to PD-1, binds to three or more residues selected from the group consisting of N33, T51, S57, L100, N102, G103, R104, D105, H107, and S109 within an amino acid sequence of SEQ ID NO:42.

In certain embodiments, the antibody or antigen-binding fragment thereof, when bound to PD-1, binds to four or more residues selected from the group consisting of N33, T51, S57, L100, N102, G103, R104, D105, H107, and S109 within an amino acid sequence of SEQ ID NO:42.

In one embodiment, the antibody or antigen-binding fragment thereof, when bound to PD-1, binds to five or more residues selected from the group consisting of N33, T51, S57, L100, N102, G103, R104, D105, H107, and S109 within an amino acid sequence of SEQ ID NO:42.

In another embodiment, the antibody or antigen-binding fragment thereof, when bound to PD-1, binds to six or more residues selected from the group consisting of N33, T51, S57, L100, N102, G103, R104, D105, H107, and S109 within an amino acid sequence of SEQ ID NO:42.

In yet another embodiment, the antibody or antigen-binding fragment thereof, when bound to PD-1, binds to seven or more residues selected from the group consisting of N33, T51, S57, L100, N102, G103, R104, D105, H107, and S109 within an amino acid sequence of SEQ ID NO:42.

In still another embodiment, the antibody or antigen-binding fragment thereof, when bound to PD-1, binds to eight or more residues selected from the group consisting of N33, T51, S57, L100, N102, G103, R104, D105, H107, and S109 within an amino acid sequence of SEQ ID NO:42.

In certain embodiments, the antibody or antigen-binding fragment thereof, when bound to PD-1, binds to nine or more residues selected from the group consisting of N33, T51, S57, L100, N102, G103, R104, D105, H107, and S109 within an amino acid sequence of SEQ ID NO:42.

In other embodiments, the antibody or antigen-binding fragment thereof, when bound to PD-1, binds to all ten residues from the group consisting of N33, T51, S57, L100, N102, G103, R104, D105, H107, and S109 within an amino acid sequence of SEQ ID NO:42.

In another embodiment, the antibody or antigen-binding fragment thereof, when bound to PD-1, binds to N33 within an amino acid sequence of SEQ ID NO:42. In another embodiment, the antibody or antigen-binding fragment thereof, when bound to PD-1, binds to T51 within an amino acid sequence of SEQ ID NO:42. In a particular embodiment, the antibody or antigen-binding fragment thereof, when bound to PD-1, binds to S57 within an amino acid sequence of SEQ ID NO:42. In one specific embodiment, the antibody or antigen-binding fragment thereof, when bound to PD-1, binds to L100 within an amino acid sequence of SEQ ID NO:42. In some embodiments, the antibody or antigen-binding fragment thereof, when bound to PD-1, binds to N102 within an amino acid sequence of SEQ ID NO:42. In other embodiments, the antibody or antigen-binding fragment thereof, when bound to PD-1, binds to G103 within an amino acid sequence of SEQ ID NO:42. In another embodiment, the antibody or antigen-binding fragment thereof, when bound to PD-1, binds to R104 within an amino acid sequence of SEQ ID NO:42. In yet another embodiment, the antibody or antigen-binding fragment thereof, when bound to PD-1, binds to G103 and R104 within an amino acid sequence of SEQ ID NO:42. In still another embodiment, the antibody or antigen-binding fragment thereof, when bound to PD-1, binds to D105 within an amino acid sequence of SEQ ID NO:42. In some embodiments, the antibody or antigen-binding fragment thereof, when bound to PD-1, binds to H107 within an amino acid sequence of SEQ ID NO:42. In certain embodiments, the antibody or antigen-binding fragment thereof, when bound to PD-1, binds to S109 within an amino acid sequence of SEQ ID NO:42. Any combination of two, three, four, five, six, seven, eight, nine, ten or more of the above-referenced amino acid PD-1 binding sites is also contemplated.

In one aspect, described herein are antibodies that specifically bind to PD-1 and can modulate PD-1 activity and/or expression (e.g., activate PD-1 signaling and/or inhibit PD-1 expression). In certain embodiments, a PD-1 agonist is provided herein that is an antibody provided herein that specifically binds to an ECD of human PD-1, and activates (e.g., partially activates) at least one PD-1 activity (e.g., inhibiting cytokine production). In certain embodiments, a PD-1 agonist provided herein is an antibody provided herein that specifically binds to an ECD of human PD-1, and downregulates PD-1 expression. In certain embodiments, described herein are antibodies that specifically bind to PD-1 and that (a) attenuate T cell activity, e.g., as determined by inhibition of cytokine production; and/or (b) downregulate PD-1 expression in a cell. In certain embodiments, described herein are antibodies that specifically bind to PD-1 and that (a) attenuate T cell activity, e.g., as determined by inhibition of cytokine production; (b) downregulate PD-1 expression in a cell; and/or (c) do not inhibit PD-L1 and/or PD-L2 binding to PD-1. In certain embodiments, the antibodies that specifically bind to PD-1 bind to an ECD of human PD-1, or an epitope of an ECD of human PD-1 thereof. In certain embodiments, the antibodies specifically bind to an epitope of an ECD of human PD-1 that is distinct from the PD-L1 binding site. In certain embodiments, the antibodies specifically bind to an epitope of an ECD of human PD-1 that is distinct from the PD-L2 binding site. In certain embodiments, the antibodies specifically bind to an epitope of an ECD of human PD-1 that is distinct from both the PD-L1 and PD-L2 binding sites. In certain embodiments, binding of PD-L1 to PD-1 is not inhibited by the antibody. In other embodiments, binding of PD-L2 to PD-1 is not inhibited by the antibody. In specific embodiments, neither binding of PD-L1 to PD-1 nor binding of PD-L2 to PD-1 is inhibited by the antibody.

PD-1 activity can relate to any activity of PD-1 such as those known or described in the art. PD-1 activity and PD-1 signaling are used interchangeably herein. In certain aspects, PD-1 activity is induced by PD-1 ligand (e.g., PD-L1) binding to PD-1. Expression levels of PD-1 can be assessed by methods described herein or known to one of skill in the art (e.g., Western blotting, ELISA, immunohistochemistry, or flow cytometry). In certain embodiments, described herein are antibodies that specifically bind to PD-1 and decrease PD-1 expression. In certain embodiments, described herein are antibodies that specifically bind to PD-1 and attenuate T cell activity. In certain embodiments, described herein are antibodies that specifically bind to PD-1 and inhibit cytokine production. In certain embodiments, described herein are antibodies that specifically bind to PD-1 and activate (e.g., partially activate) PD-1 signaling. In certain embodiments, the antibodies that specifically bind to PD-1 bind to an ECD of human PD-1, or an epitope of an ECD of human PD-1 thereof. In certain embodiments, the antibodies specifically bind to an epitope of an ECD of human PD-1 that is distinct from the PD-L1 binding site. In certain embodiments, the antibodies specifically bind to an epitope of an ECD of human PD-1 that is distinct from the PD-L2 binding site. In certain embodiments, the antibodies specifically bind to an epitope of an ECD of human PD-1 that is distinct from both the PD-L1 and PD-L2 binding sites. In certain embodiments, binding of PD-L1 to PD-1 is not inhibited by the antibody. In other embodiments, binding of PD-L2 to PD-1 is not inhibited by the antibody. In specific embodiments, neither binding of PD-L1 to PD-1 nor binding of PD-L2 to PD-1 is inhibited by the antibody.

In certain embodiments, an anti-PD-1 antibody provided herein attenuates (e.g., partially attenuate) T cell activity. In some embodiments, an anti-PD-1 antibody provided herein attenuates T cell activity by at least about 10%. In some embodiments, an anti-PD-1 antibody provided herein attenuates T cell activity by at least about 15%. In some embodiments, an anti-PD-1 antibody provided herein attenuates T cell activity by at least about 20%. In some embodiments, an anti-PD-1 antibody provided herein attenuates T cell activity by at least about 25%. In some embodiments, an anti-PD-1 antibody provided herein attenuates T cell activity by at least about 30%. In some embodiments, an anti-PD-1 antibody provided herein attenuates T cell activity by at least about 35%. In some embodiments, an anti-PD-1 antibody provided herein attenuates T cell activity by at least about 40%. In some embodiments, an anti-PD-1 antibody provided herein attenuates T cell activity by at least about 45%. In some embodiments, an anti-PD-1 antibody provided herein attenuates T cell activity by at least about 50%. In some embodiments, an anti-PD-1 antibody provided herein attenuates T cell activity by at least about 55%. In some embodiments, an anti-PD-1 antibody provided herein attenuates T cell activity by at least about 60%. In some embodiments, an anti-PD-1 antibody provided herein attenuates T cell activity by at least about 65%. In some embodiments, an anti-PD-1 antibody provided herein attenuates T cell activity by at least about 70%. In some embodiments, an anti-PD-1 antibody provided herein attenuates T cell activity by at least about 75%. In some embodiments, an anti-PD-1 antibody provided herein attenuates T cell activity by at least about 80%. In some embodiments, an anti-PD-1 antibody provided herein attenuates T cell activity by at least about 85%. In some embodiments, an anti-PD-1 antibody provided herein attenuates T cell activity by at least about 90%. In some embodiments, an anti-PD-1 antibody provided herein attenuates T cell activity by at least about 95%. In some embodiments, an anti-PD-1 antibody provided herein attenuates T cell activity by at least about 98%. In some embodiments, an anti-PD-1 antibody provided herein attenuates T cell activity by at least about 99%. In some embodiments, an anti-PD-1 antibody provided herein attenuates T cell activity by at least about 100%. In certain embodiments, an anti-PD-1 antibody provided herein can attenuate (e.g., partially attenuate) T cell activity by at least about 25% to about 65%. In specific embodiments, the T cell activity attenuation is assessed by methods described herein. In some embodiments, the T cell activity attenuation is assessed by methods known to one of skill in the art. In certain embodiments, the T cell activity attenuation is relative to T cell activity in the presence of stimulation without any anti-PD-1 antibody. In certain embodiments, the T cell activity attenuation is relative to T cell activity in the presence of stimulation with an unrelated antibody (e.g., an antibody that does not specifically bind to PD-1).

In one embodiment, attenuation of T cell activity is indicated by inhibition of T cell proliferation. In specific embodiments, the T cell proliferation is CD4+ T cell proliferation. In certain embodiments, the T cell proliferation is CD8+ T cell proliferation. In some embodiments, an anti-PD-1 antibody provided herein inhibits T cell proliferation by at least about 10%. In some embodiments, an anti-PD-1 antibody provided herein inhibits T cell proliferation by at least about 15%. In some embodiments, an anti-PD-1 antibody provided herein inhibits T cell proliferation by at least about 20%. In some embodiments, an anti-PD-1 antibody provided herein inhibits T cell proliferation by at least about 25%. In some embodiments, an anti-PD-1 antibody provided herein inhibits T cell proliferation by at least about 30%. In some embodiments, an anti-PD-1 antibody provided herein inhibits T cell proliferation by at least about 35%. In some embodiments, an anti-PD-1 antibody provided herein inhibits T cell proliferation by at least about 40%. In some embodiments, an anti-PD-1 antibody provided herein inhibits T cell proliferation by at least about 45%. In some embodiments, an anti-PD-1 antibody provided herein inhibits T cell proliferation by at least about 50%. In some embodiments, an anti-PD-1 antibody provided herein inhibits T cell proliferation by at least about 55%. In some embodiments, an anti-PD-1 antibody provided herein inhibits T cell proliferation by at least about 60%. In some embodiments, an anti-PD-1 antibody provided herein inhibits T cell proliferation by at least about 65%. In some embodiments, an anti-PD-1 antibody provided herein inhibits T cell proliferation by at least about 70%. In some embodiments, an anti-PD-1 antibody provided herein inhibits T cell proliferation by at least about 75%. In some embodiments, an anti-PD-1 antibody provided herein inhibits T cell proliferation by at least about 80%. In some embodiments, an anti-PD-1 antibody provided herein inhibits T cell proliferation by at least about 85%. In some embodiments, an anti-PD-1 antibody provided herein inhibits T cell proliferation by at least about 90%. In some embodiments, an anti-PD-1 antibody provided herein inhibits T cell proliferation by at least about 95%. In some embodiments, an anti-PD-1 antibody provided herein inhibits T cell proliferation by at least about 98%. In some embodiments, an anti-PD-1 antibody provided herein inhibits T cell proliferation by at least about 99%. In some embodiments, an anti-PD-1 antibody provided herein inhibits T cell proliferation by at least about 100%. In certain embodiments, an anti-PD-1 antibody provided herein can inhibit (e.g., partially inhibit) T cell proliferation by at least about 25% to about 65%. In specific embodiments, the T cell proliferation is assessed by methods described herein. In some embodiments, the T cell proliferation is assessed by methods known to one of skill in the art. In certain embodiments, the T cell proliferation is relative to T cell proliferation in the presence of stimulation without any anti-PD-1 antibody. In certain embodiments, the T cell proliferation is relative to T cell proliferation in the presence of stimulation with an unrelated antibody (e.g., an antibody that does not specifically bind to PD-1).

In certain embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and inhibit CD4+ T cell proliferation. In one embodiment, an antibody provided herein specifically binds to PD-1 and inhibits CD4+ T cell proliferation by at least about 5%. In one embodiment, an antibody provided herein specifically binds to PD-1 and inhibits CD4+ T cell proliferation by at least about 10%. In another embodiment, an antibody provided herein specifically binds to PD-1 and inhibits CD4+ T cell proliferation by at least about 15%. In some embodiments, an antibody provided herein specifically binds to PD-1 and inhibits CD4+ T cell proliferation by at least about 20%. In other embodiments, an antibody provided herein specifically binds to PD-1 and inhibits CD4+ T cell proliferation by at least about 25%. In another embodiment, an antibody provided herein specifically binds to PD-1 and inhibits CD4+ T cell proliferation by at least about 30%. In one embodiment, an antibody provided herein specifically binds to PD-1 and inhibits CD4+ T cell proliferation by at least about 35%. In some embodiments, an antibody provided herein specifically binds to PD-1 and inhibits CD4+ T cell proliferation by at least about 40%. In another embodiment, an antibody provided herein specifically binds to PD-1 and inhibits CD4+ T cell proliferation by at least about 45%. In one embodiment, an antibody provided herein specifically binds to PD-1 and inhibits CD4+ T cell proliferation by at least about 50%. In other embodiments, an antibody provided herein specifically binds to PD-1 and inhibits CD4+ T cell proliferation by at least about 55%. In another embodiment, an antibody provided herein specifically binds to PD-1 and inhibits CD4+ T cell proliferation by at least about 60%. In some embodiments, an antibody provided herein specifically binds to PD-1 and inhibits CD4+ T cell proliferation by at least about 65%. In one embodiment, an antibody provided herein specifically binds to PD-1 and inhibits CD4+ T cell proliferation by at least about 70%. In another embodiment, an antibody provided herein specifically binds to PD-1 and inhibits CD4+ T cell proliferation by at least about 75%. In one embodiment, an antibody provided herein specifically binds to PD-1 and inhibits CD4+ T cell proliferation by at least about 80%. In some embodiments, an antibody provided herein specifically binds to PD-1 and inhibits CD4+ T cell proliferation by at least about 85%. In another embodiment, an antibody provided herein specifically binds to PD-1 and inhibits CD4+ T cell proliferation by at least about 90%. In other embodiments, an antibody provided herein specifically binds to PD-1 and inhibits CD4+ T cell proliferation by at least about 95%. In one embodiment, an antibody provided herein specifically binds to PD-1 and inhibits CD4+ T cell proliferation by at least about 98%. In another embodiment, an antibody provided herein specifically binds to PD-1 and inhibits CD4+ T cell proliferation by at least about 99%. In specific embodiments, antibodies provided herein specifically bind to PD-1 and inhibits CD4+ T cell proliferation by at least about 25% or 35%, optionally to about 75%. In some embodiments, the inhibition of CD4+ T cell proliferation is assessed by methods described herein. In other embodiments, the inhibition of CD4+ T cell proliferation is assessed by methods known to one of skill in the art (e.g., thymidine incorporation assay, MTT assay, or cell proliferation biomarker assay). In a specific embodiment, the inhibition of CD4+ T cell proliferation is assessed by thymidine incorporation assay. In another embodiment, the inhibition of CD4+ T cell proliferation is assessed by MTT assay. In yet another embodiment, the inhibition of CD4+ T cell proliferation is assessed by cell proliferation biomarker assay. In a specific embodiment, CD4+ T cell proliferation is inhibited relative to CD4+ T cell proliferation in the presence of stimulation without any anti-PD-1 antibody. In other embodiments, the CD4+ T cell proliferation is inhibited relative to CD4+ T cell proliferation in the presence of stimulation with an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) inhibits CD4+ T cell proliferation. In one embodiment, an anti-PD-1 antibody provided herein inhibits CD4+ T cell proliferation with an $EC_{50}$ of at most about 50 nM. In other embodiments, an anti-PD-1 antibody provided herein inhibits CD4+ T cell proliferation with an $EC_{50}$ of at most about 40 nM. In another embodiment, an anti-PD-1 antibody provided herein inhibits CD4+ T cell proliferation with an $EC_{50}$ of at most about 30 nM. In some embodiments, an anti-PD-1 antibody provided herein inhibits CD4+ T cell proliferation with an $EC_{50}$ of at most about 20 nM. In one embodiment, an anti-PD-1 antibody provided herein inhibits CD4+ T cell proliferation with an $EC_{50}$ of at most about 10 nM. In another embodiment, an anti-PD-1 antibody provided herein inhibits CD4+ T cell proliferation with an $EC_{50}$ of at most about 5 nM. In one embodiment, an anti-PD-1 antibody provided herein inhibits CD4+ T cell proliferation with an $EC_{50}$ of at most about 1 nM. In some embodiments, an anti-PD-1 antibody provided herein inhibits CD4+ T cell proliferation with an $EC_{50}$ of at most about 0.75 nM. In another embodiment, an anti-PD-1 antibody provided herein inhibits CD4+ T cell proliferation with an $EC_{50}$ of at most about 0.5 nM. In other embodiments, an anti-PD-1 antibody provided herein inhibits CD4+ T cell proliferation with an $EC_{50}$ of at most about 0.1 nM. In one embodiment, an anti-PD-1 antibody provided herein inhibits CD4+ T cell proliferation with an $EC_{50}$ of at most about 0.05 nM. In another embodiment, an anti-PD-1 antibody provided herein inhibits CD4+ T cell proliferation with an $EC_{50}$ of at most about 0.01 nM. In some embodiments, an anti-PD-1 antibody provided herein inhibits CD4+ T cell proliferation with an $EC_{50}$ of at most about 0.005 nM. In one embodiment, an anti-PD-1 antibody provided herein inhibits CD4+ T cell proliferation with an $EC_{50}$ of at most about 0.001 nM. In another embodiment, an anti-PD-1 antibody provided herein inhibits CD4+ T cell proliferation with an $EC_{50}$ of at least about 50 nM. In other embodiments, an anti-PD-1 antibody provided herein inhibits CD4+ T cell proliferation with an $EC_{50}$ of at least about 40 nM. In some embodiments, an anti-PD-1 antibody provided herein inhibits CD4+ T cell proliferation with an $EC_{50}$ of at least about 30 nM. In another embodiment, an anti-PD-1 antibody provided herein inhibits CD4+ T cell proliferation with an $EC_{50}$ of at least about 20 nM. In one embodiment, an anti-PD-1 antibody provided herein inhibits CD4+ T cell proliferation with an $EC_{50}$ of at least about 10 nM. In one embodiment, an anti-PD-1 antibody provided herein inhibits CD4+ T cell proliferation with an $EC_{50}$ of at least about 5 nM. In another embodiment, an anti-PD-1 antibody provided herein inhibits CD4+ T cell proliferation with an $EC_{50}$ of at least about 1 nM. In some embodiments, an anti-PD-1 antibody provided herein inhibits CD4+ T cell proliferation with an $EC_{50}$ of at least about 0.75 nM. In other embodiments, an anti-PD-1 antibody provided herein inhibits CD4+ T cell proliferation with an $EC_{50}$ of at least about 0.5 nM. In another embodiment, an anti-PD-1 antibody provided herein inhibits CD4+ T cell proliferation with an $EC_{50}$ of at least about 0.1 nM. In one embodiment, an anti-PD-1 antibody provided herein inhibits CD4+ T cell proliferation with an $EC_{50}$ of at least about 0.05 nM. In some embodiments, an anti-PD-1 antibody provided herein inhibits CD4+ T cell proliferation with an $EC_{50}$ of at least about 0.01 nM. In another embodiment, an anti-PD-1 antibody provided herein inhibits CD4+ T cell proliferation with an $EC_{50}$ of at least about 0.005 nM. In one embodiment, an anti-PD-1 antibody provided herein inhibits CD4+ T cell proliferation with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., thymidine incorporation assay, MTT assay, or cell proliferation biomarker assay). In a specific embodiment, the $EC_{50}$ is assessed by thymidine incorporation assay. In another embodiment, the $EC_{50}$ is assessed by MTT assay. In yet another embodiment, the $EC_{50}$ is assessed by cell proliferation biomarker assay.

In certain embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and inhibit CD8+ T cell proliferation. In one embodiment, an antibody provided herein specifically binds to PD-1 and inhibits CD8+ T cell proliferation by at least about 5%. In one embodiment, an antibody provided herein specifically binds to PD-1 and inhibits CD8+ T cell proliferation by at least about 10%. In another embodiment, an antibody provided herein specifically binds to PD-1 and inhibits CD8+ T cell proliferation by at least about 15%. In some embodiments, an antibody provided herein specifically binds to PD-1 and inhibits CD8+ T cell proliferation by at least about 20%. In other embodiments, an antibody provided herein specifically binds to PD-1 and inhibits CD8+ T cell proliferation by at least about 25%. In another embodiment, an antibody provided herein specifically binds to PD-1 and inhibits CD8+ T cell proliferation by at least about 30%. In one embodiment, an antibody provided herein specifically binds to PD-1 and inhibits CD8+ T cell proliferation by at least about 35%. In some embodiments, an antibody provided herein specifically binds to PD-1 and inhibits CD8+ T cell proliferation by at least about 40%. In another embodiment, an antibody provided herein specifically binds to PD-1 and inhibits CD8+ T cell proliferation by at least about 45%. In one embodiment, an antibody provided herein specifically binds to PD-1 and inhibits CD8+ T cell proliferation by at least about 50%. In other embodiments, an antibody provided herein specifically binds to PD-1 and inhibits CD8+ T cell proliferation by at least about 55%. In another embodiment, an antibody provided herein specifically binds to PD-1 and inhibits CD8+ T cell proliferation by at least about 60%. In some embodiments, an antibody provided herein specifically binds to PD-1 and inhibits CD8+ T cell proliferation by at least about 65%. In one embodiment, an antibody provided herein specifically binds to PD-1 and inhibits CD8+ T cell proliferation by at least about 70%. In another embodiment, an antibody provided herein specifically binds to PD-1 and inhibits CD8+ T cell proliferation by at least about 75%. In one embodiment, an antibody provided herein specifically binds to PD-1 and inhibits CD8+ T cell proliferation by at least about 80%. In some embodiments, an antibody provided herein specifically binds to PD-1 and inhibits CD8+ T cell proliferation by at least about 85%. In another embodiment, an antibody provided herein specifically binds to PD-1 and inhibits CD8+ T cell proliferation by at least about 90%. In other embodiments, an antibody provided herein specifically binds to PD-1 and inhibits CD8+ T cell proliferation by at least about 95%. In one embodiment, an antibody provided herein specifically binds to PD-1 and inhibits CD8+ T cell proliferation by at least about 98%. In another embodiment, an antibody provided herein specifically binds to PD-1 and inhibits CD8+ T cell proliferation by at least about 99%. In specific embodiments, antibodies provided herein specifically bind to PD-1 and inhibits CD8+ T cell proliferation by at least about 25% or 35%, optionally to about 75%. In some embodiments, the inhibition of CD8+ T cell proliferation is assessed by methods described herein. In other embodiments, the inhibition of CD8+ T cell proliferation is assessed by methods known to one of skill in the art (e.g., thymidine incorporation assay, MTT assay, or cell proliferation biomarker assay). In a specific embodiment, the inhibition of CD8+ T cell proliferation is assessed by thymidine incorporation assay. In another embodiment, the inhibition of CD8+ T cell proliferation is assessed by MTT assay. In yet another embodiment, the inhibition of CD8+ T cell proliferation is assessed by cell proliferation biomarker assay. In a specific embodiment, CD8+ T cell proliferation is inhibited relative to CD8+ T cell proliferation in the presence of stimulation without any anti-PD-1 antibody. In other embodiments, the CD8+ T cell proliferation is inhibited relative to CD8+ T cell proliferation in the presence of stimulation with an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) inhibits CD8+ T cell proliferation. In one embodiment, an anti-PD-1 antibody provided herein inhibits CD8+ T cell proliferation with an $EC_{50}$ of at most about 50 nM. In other embodiments, an anti-PD-1 antibody provided herein inhibits CD8+ T cell proliferation with an $EC_{50}$ of at most about 40 nM. In another embodiment, an anti-PD-1 antibody provided herein inhibits CD8+ T cell proliferation with an $EC_{50}$ of at most about 30 nM. In some embodiments, an anti-PD-1 antibody provided herein inhibits CD8+ T cell proliferation with an $EC_{50}$ of at most about 20 nM. In one embodiment, an anti-PD-1 antibody provided herein inhibits CD8+ T cell proliferation with an $EC_{50}$ of at most about 10 nM. In another embodiment, an anti-PD-1 antibody provided herein inhibits CD8+ T cell proliferation with an $EC_{50}$ of at most about 5 nM. In one embodiment, an anti-PD-1 antibody provided herein inhibits CD8+ T cell proliferation with an $EC_{50}$ of at most about 1 nM. In some embodiments, an anti-PD-1 antibody provided herein inhibits CD8+ T cell proliferation with an $EC_{50}$ of at most about 0.75 nM. In another embodiment, an anti-PD-1 antibody provided herein inhibits CD8+ T cell proliferation with an $EC_{50}$ of at most about 0.5 nM. In other embodiments, an anti-PD-1 antibody provided herein inhibits CD8+ T cell proliferation with an $EC_{50}$ of at most about 0.1 nM. In one embodiment, an anti-PD-1 antibody provided herein inhibits CD8+ T cell proliferation with an $EC_{50}$ of at most about 0.05 nM. In another embodiment, an anti-PD-1 antibody provided herein inhibits CD8+ T cell proliferation with an $EC_{50}$ of at most about 0.01 nM. In some embodiments, an anti-PD-1 antibody provided herein inhibits CD8+ T cell proliferation with an $EC_{50}$ of at most about 0.005 nM. In one embodiment, an anti-PD-1 antibody provided herein inhibits CD8+ T cell proliferation with an $EC_{50}$ of at most about 0.001 nM. In another embodiment, an anti-PD-1 antibody provided herein inhibits CD8+ T cell proliferation with an $EC_{50}$ of at least about 50 nM. In other embodiments, an anti-PD-1 antibody provided herein inhibits CD8+ T cell proliferation with an $EC_{50}$ of at least about 40 nM. In some embodiments, an anti-PD-1 antibody provided herein inhibits CD8+ T cell proliferation with an $EC_{50}$ of at least about 30 nM. In another embodiment, an anti-PD-1 antibody provided herein inhibits CD8+ T cell proliferation with an $EC_{50}$ of at least about 20 nM. In one embodiment, an anti-PD-1 antibody provided herein inhibits CD8+ T cell proliferation with an $EC_{50}$ of at least about 10 nM. In one embodiment, an anti-PD-1 antibody provided herein inhibits CD8+ T cell proliferation with an $EC_{50}$ of at least about 5 nM. In another embodiment, an anti-PD-1 antibody provided herein inhibits CD8+ T cell proliferation with an $EC_{50}$ of at least about 1 nM. In some embodiments, an anti-PD-1 antibody provided herein inhibits CD8+ T cell proliferation with an $EC_{50}$ of at least about 0.75 nM. In other embodiments, an anti-PD-1 antibody provided herein inhibits CD8+ T cell proliferation with an $EC_{50}$ of at least about 0.5 nM. In another embodiment, an anti-PD-1 antibody provided herein inhibits CD8+ T cell proliferation with an $EC_{50}$ of at least about 0.1 nM. In one embodiment, an anti-PD-1 antibody provided herein inhibits CD8+ T cell proliferation with an $EC_{50}$ of at least about 0.05 nM. In some embodiments, an anti-PD-1 antibody provided herein inhibits CD8+ T cell proliferation with an $EC_{50}$ of at least about 0.01 nM. In another embodiment, an anti-PD-1 antibody provided herein inhibits CD8+ T cell proliferation with an $EC_{50}$ of at least about 0.005 nM. In one embodiment, an anti-PD-1 antibody provided herein inhibits CD8+ T cell proliferation with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., thymidine incorporation assay, MTT assay, or cell proliferation biomarker assay). In a specific embodiment, the $EC_{50}$ is assessed by thymidine incorporation assay. In another embodiment, the $EC_{50}$ is assessed by MTT assay. In yet another embodiment, the $EC_{50}$ is assessed by cell proliferation biomarker assay.

In some embodiments, attenuation of T cell activity is indicated by downregulation of T cell activation biomarkers. In one embodiment, the T cell activation biomarker is CD25. In another embodiment, the T cell activation biomarker is CD69.

In certain embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and downregulate the expression of CD25. In one embodiment, an antibody provided herein specifically binds to PD-1 and downregulates CD25 expression by at least about 5%. In one embodiment, an antibody provided herein specifically binds to PD-1 and downregulates CD25 expression by at least about 10%. In another embodiment, an antibody provided herein specifically binds to PD-1 and downregulates CD25 expression by at least about 15%. In some embodiments, an antibody provided herein specifically binds to PD-1 and downregulates CD25 expression by at least about 20%. In other embodiments, an antibody provided herein specifically binds to PD-1 and downregulates CD25 expression by at least about 25%. In another embodiment, an antibody provided herein specifically binds to PD-1 and downregulates CD25 expression by at least about 30%. In one embodiment, an antibody provided herein specifically binds to PD-1 and downregulates CD25 expression by at least about 35%. In some embodiments, an antibody provided herein specifically binds to PD-1 and downregulates CD25 expression by at least about 40%. In another embodiment, an antibody provided herein specifically binds to PD-1 and downregulates CD25 expression by at least about 45%. In one embodiment, an antibody provided herein specifically binds to PD-1 and downregulates CD25 expression by at least about 50%. In other embodiments, an antibody provided herein specifically binds to PD-1 and downregulates CD25 expression by at least about 55%. In another embodiment, an antibody provided herein specifically binds to PD-1 and downregulates CD25 expression by at least about 60%. In some embodiments, an antibody provided herein specifically binds to PD-1 and downregulates CD25 expression by at least about 65%. In one embodiment, an antibody provided herein specifically binds to PD-1 and downregulates CD25 expression by at least about 70%. In another embodiment, an antibody provided herein specifically binds to PD-1 and downregulates CD25 expression by at least about 75%. In one embodiment, an antibody provided herein specifically binds to PD-1 and downregulates CD25 expression by at least about 80%. In some embodiments, an antibody provided herein specifically binds to PD-1 and downregulates CD25 expression by at least about 85%. In another embodiment, an antibody provided herein specifically binds to PD-1 and downregulates CD25 expression by at least about 90%. In other embodiments, an antibody provided herein specifically binds to PD-1 and downregulates CD25 expression by at least about 95%. In one embodiment, an antibody provided herein specifically binds to PD-1 and downregulates CD25 expression by at least about 98%. In another embodiment, an antibody provided herein specifically binds to PD-1 and downregulates CD25 expression by at least about 99%. In specific embodiments, antibodies provided herein specifically bind to PD-1 and downregulate CD25 expression by at least about 25% or 35%, optionally to about 75%. In some embodiments, the downregulation of CD25 expression is assessed by methods described herein. In other embodiments, the downregulation of CD25 expression is assessed by methods known to one of skill in the art (e.g., flow cytometry, Western blotting, Northern blotting, or RT-PCR). In a specific embodiment, the downregulation of CD25 expression is assessed by flow cytometry. In another embodiment, the downregulation of CD25 expression is assessed by Western blotting. In yet another embodiment, the downregulation of CD25 expression is assessed by Northern blotting. In still another embodiment, the downregulation of CD25 expression is assessed by RT-PCR. In a specific embodiment, CD25 expression is downregulated relative to CD25 expression in the presence of stimulation without any anti-PD-1 antibody. In other embodiments, the CD25 expression is downregulated relative to CD25 expression in the presence of stimulation with an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) downregulates CD25 expression. In one embodiment, an anti-PD-1 antibody provided herein downregulates CD25 expression with an $EC_{50}$ of at most about 50 nM. In other embodiments, an anti-PD-1 antibody provided herein downregulates CD25 expression with an $EC_{50}$ of at most about 40 nM. In another embodiment, an anti-PD-1 antibody provided herein downregulates CD25 expression with an $EC_{50}$ of at most about 30 nM. In some embodiments, an anti-PD-1 antibody provided herein downregulates CD25 expression with an $EC_{50}$ of at most about 20 nM. In one embodiment, an anti-PD-1 antibody provided herein downregulates CD25 expression with an $EC_{50}$ of at most about 10 nM. In another embodiment, an anti-PD-1 antibody provided herein downregulates CD25 expression with an $EC_{50}$ of at most about 5 nM. In one embodiment, an anti-PD-1 antibody provided herein downregulates CD25 expression with an $EC_{50}$ of at most about 1 nM. In some embodiments, an anti-PD-1 antibody provided herein downregulates CD25 expression with an $EC_{50}$ of at most about 0.75 nM. In another embodiment, an anti-PD-1 antibody provided herein downregulates CD25 expression with an $EC_{50}$ of at most about 0.5 nM. In other embodiments, an anti-PD-1 antibody provided herein downregulates CD25 expression with an $EC_{50}$ of at most about 0.1 nM. In one embodiment, an anti-PD-1 antibody provided herein downregulates CD25 expression with an $EC_{50}$ of at most about 0.05 nM. In another embodiment, an anti-PD-1 antibody provided herein downregulates CD25 expression with an $EC_{50}$ of at most about 0.01 nM. In some embodiments, an anti-PD-1 antibody provided herein downregulates CD25 expression with an $EC_{50}$ of at most about 0.005 nM. In one embodiment, an anti-PD-1 antibody provided herein downregulates CD25 expression with an $EC_{50}$ of at most about 0.001 nM. In another embodiment, an anti-PD-1 antibody provided herein downregulates CD25 expression with an $EC_{50}$ of at least about 50 nM. In other embodiments, an anti-PD-1 antibody provided herein downregulates CD25 expression with an $EC_{50}$ of at least about 40 nM. In some embodiments, an anti-PD-1 antibody provided herein downregulates CD25 expression with an $EC_{50}$ of at least about 30 nM. In another embodiment, an anti-PD-1 antibody provided herein downregulates CD25 expression with an $EC_{50}$ of at least about 20 nM. In one embodiment, an anti-PD-1 antibody provided herein downregulates CD25 expression with an $EC_{50}$ of at least about 10 nM. In one embodiment, an anti-PD-1 antibody provided herein downregulates CD25 expression with an $EC_{50}$ of at least about 5 nM. In another embodiment, an anti-PD-1 antibody provided herein downregulates CD25 expression with an $EC_{50}$ of at least about 1 nM. In some embodiments, an anti-PD-1 antibody provided herein downregulates CD25 expression with an $EC_{50}$ of at least about 0.75 nM. In other embodiments, an anti-PD-1 antibody provided herein downregulates CD25 expression with an $EC_{50}$ of at least about 0.5 nM. In another embodiment, an anti-PD-1 antibody provided herein downregulates CD25 expression with an $EC_{50}$ of at least about 0.1 nM. In one embodiment, an anti-PD-1 antibody provided herein downregulates CD25 expression with an $EC_{50}$ of at least about 0.05 nM. In some embodiments, an anti-PD-1 antibody provided herein downregulates CD25 expression with an $EC_{50}$ of at least about 0.01 nM. In another embodiment, an anti-PD-1 antibody provided herein downregulates CD25 expression with an $EC_{50}$ of at least about 0.005 nM. In one embodiment, an anti-PD-1 antibody provided herein downregulates CD25 expression with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., flow cytometry, Western blotting, Northern blotting, or RT-PCR). In a specific embodiment, the $EC_{50}$ is assessed by flow cytometry. In another embodiment, the $EC_{50}$ is assessed by Western blotting. In yet another embodiment, the $EC_{50}$ is assessed by Northern blotting. In still another embodiment, the $EC_{50}$ is assessed by RT-PCR.

In certain embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and downregulate the expression of CD69. In one embodiment, an antibody provided herein specifically binds to PD-1 and downregulates CD69 expression by at least about 5%. In one embodiment, an antibody provided herein specifically binds to PD-1 and downregulates CD69 expression by at least about 10%. In another embodiment, an antibody provided herein specifically binds to PD-1 and downregulates CD69 expression by at least about 15%. In some embodiments, an antibody provided herein specifically binds to PD-1 and downregulates CD69 expression by at least about 20%. In other embodiments, an antibody provided herein specifically binds to PD-1 and downregulates CD69 expression by at least about 25%. In another embodiment, an antibody provided herein specifically binds to PD-1 and downregulates CD69 expression by at least about 30%. In one embodiment, an antibody provided herein specifically binds to PD-1 and downregulates CD69 expression by at least about 35%. In some embodiments, an antibody provided herein specifically binds to PD-1 and downregulates CD69 expression by at least about 40%. In another embodiment, an antibody provided herein specifically binds to PD-1 and downregulates CD69 expression by at least about 45%. In one embodiment, an antibody provided herein specifically binds to PD-1 and downregulates CD69 expression by at least about 50%. In other embodiments, an antibody provided herein specifically binds to PD-1 and downregulates CD69 expression by at least about 55%. In another embodiment, an antibody provided herein specifically binds to PD-1 and downregulates CD69 expression by at least about 60%. In some embodiments, an antibody provided herein specifically binds to PD-1 and downregulates CD69 expression by at least about 65%. In one embodiment, an antibody provided herein specifically binds to PD-1 and downregulates CD69 expression by at least about 70%. In another embodiment, an antibody provided herein specifically binds to PD-1 and downregulates CD69 expression by at least about 75%. In one embodiment, an antibody provided herein specifically binds to PD-1 and downregulates CD69 expression by at least about 80%. In some embodiments, an antibody provided herein specifically binds to PD-1 and downregulates CD69 expression by at least about 85%. In another embodiment, an antibody provided herein specifically binds to PD-1 and downregulates CD69 expression by at least about 90%. In other embodiments, an antibody provided herein specifically binds to PD-1 and downregulates CD69 expression by at least about 95%. In one embodiment, an antibody provided herein specifically binds to PD-1 and downregulates CD69 expression by at least about 98%. In another embodiment, an antibody provided herein specifically binds to PD-1 and downregulates CD69 expression by at least about 99%. In specific embodiments, antibodies provided herein specifically bind to PD-1 and downregulate CD69 expression by at least about 25% or 35%, optionally to about 75%. In some embodiments, the downregulation of CD69 expression is assessed by methods described herein. In other embodiments, the downregulation of CD69 expression is assessed by methods known to one of skill in the art (e.g., flow cytometry, Western blotting, Northern blotting, or RT-PCR). In a specific embodiment, the downregulation of CD69 expression is assessed by flow cytometry. In another embodiment, the downregulation of CD69 expression is assessed by Western blotting. In yet another embodiment, the downregulation of CD69 expression is assessed by Northern blotting. In still another embodiment, the downregulation of CD69 expression is assessed by RT-PCR. In a specific embodiment, CD69 expression is downregulated relative to CD69 expression in the presence of stimulation without any anti-PD-1 antibody. In other embodiments, the CD69 expression is downregulated relative to CD69 expression in the presence of stimulation with an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) downregulates CD69 expression. In one embodiment, an anti-PD-1 antibody provided herein downregulates CD69 expression with an $EC_{50}$ of at most about 50 nM. In other embodiments, an anti-PD-1 antibody provided herein downregulates CD69 expression with an $EC_{50}$ of at most about 40 nM. In another embodiment, an anti-PD-1 antibody provided herein downregulates CD69 expression with an $EC_{50}$ of at most about 30 nM. In some embodiments, an anti-PD-1 antibody provided herein downregulates CD69 expression with an $EC_{50}$ of at most about 20 nM. In one embodiment, an anti-PD-1 antibody provided herein downregulates CD69 expression with an $EC_{50}$ of at most about 10 nM. In another embodiment, an anti-PD-1 antibody provided herein downregulates CD69 expression with an $EC_{50}$ of at most about 5 nM. In one embodiment, an anti-PD-1 antibody provided herein downregulates CD69 expression with an $EC_{50}$ of at most about 1 nM. In some embodiments, an anti-PD-1 antibody provided herein downregulates CD69 expression with an $EC_{50}$ of at most about 0.75 nM. In another embodiment, an anti-PD-1 antibody provided herein downregulates CD69 expression with an $EC_{50}$ of at most about 0.5 nM. In other embodiments, an anti-PD-1 antibody provided herein downregulates CD69 expression with an $EC_{50}$ of at most about 0.1 nM. In one embodiment, an anti-PD-1 antibody provided herein downregulates CD69 expression with an $EC_{50}$ of at most about 0.05 nM. In another embodiment, an anti-PD-1 antibody provided herein downregulates CD69 expression with an $EC_{50}$ of at most about 0.01 nM. In some embodiments, an anti-PD-1 antibody provided herein downregulates CD69 expression with an $EC_{50}$ of at most about 0.005 nM. In one embodiment, an anti-PD-1 antibody provided herein downregulates CD69 expression with an $EC_{50}$ of at most about 0.001 nM. In another embodiment, an anti-PD-1 antibody provided herein downregulates CD69 expression with an $EC_{50}$ of at least about 50 nM. In other embodiments, an anti-PD-1 antibody provided herein downregulates CD69 expression with an $EC_{50}$ of at least about 40 nM. In some embodiments, an anti-PD-1 antibody provided herein downregulates CD69 expression with an $EC_{50}$ of at least about 30 nM. In another embodiment, an anti-PD-1 antibody provided herein downregulates CD69 expression with an $EC_{50}$ of at least about 20 nM. In one embodiment, an anti-PD-1 antibody provided herein downregulates CD69 expression with an $EC_{50}$ of at least about 10 nM. In one embodiment, an anti-PD-1 antibody provided herein downregulates CD69 expression with an $EC_{50}$ of at least about 5 nM. In another embodiment, an anti-PD-1 antibody provided herein downregulates CD69 expression with an $EC_{50}$ of at least about 1 nM. In some embodiments, an anti-PD-1 antibody provided herein downregulates CD69 expression with an $EC_{50}$ of at least about 0.75 nM. In other embodiments, an anti-PD-1 antibody provided herein downregulates CD69 expression with an $EC_{50}$ of at least about 0.5 nM. In another embodiment, an anti-PD-1 antibody provided herein downregulates CD69 expression with an $EC_{50}$ of at least about 0.1 nM. In one embodiment, an anti-PD-1 antibody provided herein downregulates CD69 expression with an $EC_{50}$ of at least about 0.05 nM. In some embodiments, an anti-PD-1 antibody provided herein downregulates CD69 expression with an $EC_{50}$ of at least about 0.01 nM. In another embodiment, an anti-PD-1 antibody provided herein downregulates CD69 expression with an $EC_{50}$ of at least about 0.005 nM. In one embodiment, an anti-PD-1 antibody provided herein downregulates CD69 expression with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., flow cytometry, Western blotting, Northern blotting, or RT-PCR). In a specific embodiment, the $EC_{50}$ is assessed by flow cytometry. In another embodiment, the $EC_{50}$ is assessed by Western blotting. In yet another embodiment, the $EC_{50}$ is assessed by Northern blotting. In still another embodiment, the $EC_{50}$ is assessed by RT-PCR.

In some embodiments, attenuation of T cell activity is indicated by upregulation of regulatory T cell biomarkers. In one embodiment, the regulatory T cell biomarker is Foxp3.

In certain embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and upregulate the expression of Foxp3. In one embodiment, an antibody provided herein specifically binds to PD-1 and upregulates Foxp3 expression by at least about 5%. In one embodiment, an antibody provided herein specifically binds to PD-1 and upregulates Foxp3 expression by at least about 10%. In another embodiment, an antibody provided herein specifically binds to PD-1 and upregulates Foxp3 expression by at least about 15%. In some embodiments, an antibody provided herein specifically binds to PD-1 and upregulates Foxp3 expression by at least about 20%. In other embodiments, an antibody provided herein specifically binds to PD-1 and upregulates Foxp3 expression by at least about 25%. In another embodiment, an antibody provided herein specifically binds to PD-1 and upregulates Foxp3 expression by at least about 30%. In one embodiment, an antibody provided herein specifically binds to PD-1 and upregulates Foxp3 expression by at least about 35%. In some embodiments, an antibody provided herein specifically binds to PD-1 and upregulates Foxp3 expression by at least about 40%. In another embodiment, an antibody provided herein specifically binds to PD-1 and upregulates Foxp3 expression by at least about 45%. In one embodiment, an antibody provided herein specifically binds to PD-1 and upregulates Foxp3 expression by at least about 50%. In other embodiments, an antibody provided herein specifically binds to PD-1 and upregulates Foxp3 expression by at least about 55%. In another embodiment, an antibody provided herein specifically binds to PD-1 and upregulates Foxp3 expression by at least about 60%. In some embodiments, an antibody provided herein specifically binds to PD-1 and upregulates Foxp3 expression by at least about 65%. In one embodiment, an antibody provided herein specifically binds to PD-1 and upregulates Foxp3 expression by at least about 70%. In another embodiment, an antibody provided herein specifically binds to PD-1 and upregulates Foxp3 expression by at least about 75%. In one embodiment, an antibody provided herein specifically binds to PD-1 and upregulates Foxp3 expression by at least about 80%. In some embodiments, an antibody provided herein specifically binds to PD-1 and upregulates Foxp3 expression by at least about 85%. In another embodiment, an antibody provided herein specifically binds to PD-1 and upregulates Foxp3 expression by at least about 90%. In other embodiments, an antibody provided herein specifically binds to PD-1 and upregulates Foxp3 expression by at least about 95%. In one embodiment, an antibody provided herein specifically binds to PD-1 and upregulates Foxp3 expression by at least about 98%. In another embodiment, an antibody provided herein specifically binds to PD-1 and upregulates Foxp3 expression by at least about 99%. In specific embodiments, antibodies provided herein specifically bind to PD-1 and upregulate Foxp3 expression by at least about 25% or 35%, optionally to about 75%. In some embodiments, the upregulation of Foxp3 expression is assessed by methods described herein. In other embodiments, the upregulation of Foxp3 expression is assessed by methods known to one of skill in the art (e.g., flow cytometry, Western blotting, Northern blotting, or RT-PCR). In a specific embodiment, the upregulation of Foxp3 expression is assessed by flow cytometry. In another embodiment, the upregulation of Foxp3 expression is assessed by Western blotting. In yet another embodiment, the upregulation of Foxp3 expression is assessed by Northern blotting. In still another embodiment, the upregulation of Foxp3 expression is assessed by RT-PCR. In a specific embodiment, Foxp3 expression is upregulated relative to Foxp3 expression in the presence of stimulation without any anti-PD-1 antibody. In other embodiments, the Foxp3 expression is upregulated relative to FOXP3 expression in the presence of stimulation with an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) upregulates Foxp3 expression. In one embodiment, an anti-PD-1 antibody provided herein upregulates Foxp3 expression with an $EC_{50}$ of at most about 50 nM. In other embodiments, an anti-PD-1 antibody provided herein upregulates Foxp3 expression with an $EC_{50}$ of at most about 40 nM. In another embodiment, an anti-PD-1 antibody provided herein upregulates Foxp3 expression with an $EC_{50}$ of at most about 30 nM. In some embodiments, an anti-PD-1 antibody provided herein upregulates Foxp3 expression with an $EC_{50}$ of at most about 20 nM. In one embodiment, an anti-PD-1 antibody provided herein upregulates Foxp3 expression with an $EC_{50}$ of at most about 10 nM. In another embodiment, an anti-PD-1 antibody provided herein upregulates Foxp3 expression with an $EC_{50}$ of at most about 5 nM. In one embodiment, an anti-PD-1 antibody provided herein upregulates Foxp3 expression with an $EC_{50}$ of at most about 1 nM. In some embodiments, an anti-PD-1 antibody provided herein upregulates Foxp3 expression with an $EC_{50}$ of at most about 0.75 nM. In another embodiment, an anti-PD-1 antibody provided herein upregulates Foxp3 expression with an $EC_{50}$ of at most about 0.5 nM. In other embodiments, an anti-PD-1 antibody provided herein upregulates Foxp3 expression with an $EC_{50}$ of at most about 0.1 nM. In one embodiment, an anti-PD-1 antibody provided herein upregulates Foxp3 expression with an $EC_{50}$ of at most about 0.05 nM. In another embodiment, an anti-PD-1 antibody provided herein upregulates Foxp3 expression with an $EC_{50}$ of at most about 0.01 nM. In some embodiments, an anti-PD-1 antibody provided herein upregulates Foxp3 expression with an $EC_{50}$ of at most about 0.005 nM. In one embodiment, an anti-PD-1 antibody provided herein upregulates Foxp3 expression with an $EC_{50}$ of at most about 0.001 nM. In another embodiment, an anti-PD-1 antibody provided herein upregulates Foxp3 expression with an $EC_{50}$ of at least about 50 nM. In other embodiments, an anti-PD-1 antibody provided herein upregulates Foxp3 expression with an $EC_{50}$ of at least about 40 nM. In some embodiments, an anti-PD-1 antibody provided herein upregulates Foxp3 expression with an $EC_{50}$ of at least about 30 nM. In another embodiment, an anti-PD-1 antibody provided herein upregulates Foxp3 expression with an $EC_{50}$ of at least about 20 nM. In one embodiment, an anti-PD-1 antibody provided herein upregulates Foxp3 expression with an $EC_{50}$ of at least about 10 nM. In one embodiment, an anti-PD-1 antibody provided herein upregulates Foxp3 expression with an $EC_{50}$ of at least about 5 nM. In another embodiment, an anti-PD-1 antibody provided herein upregulates Foxp3 expression with an $EC_{50}$ of at least about 1 nM. In some embodiments, an anti-PD-1 antibody provided herein upregulates Foxp3 expression with an $EC_{50}$ of at least about 0.75 nM. In other embodiments, an anti-PD-1 antibody provided herein upregulates Foxp3 expression with an $EC_{50}$ of at least about 0.5 nM. In another embodiment, an anti-PD-1 antibody provided herein upregulates Foxp3 expression with an $EC_{50}$ of at least about 0.1 nM. In one embodiment, an anti-PD-1 antibody provided herein upregulates Foxp3 expression with an $EC_{50}$ of at least about 0.05 nM. In some embodiments, an anti-PD-1 antibody provided herein upregulates Foxp3 expression with an $EC_{50}$ of at least about 0.01 nM. In another embodiment, an anti-PD-1 antibody provided herein upregulates Foxp3 expression with an $EC_{50}$ of at least about 0.005 nM. In one embodiment, an anti-PD-1 antibody provided herein upregulates Foxp3 expression with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., flow cytometry, Western blotting, Northern blotting, or RT-PCR). In a specific embodiment, the $EC_{50}$ is assessed by flow cytometry. In another embodiment, the $EC_{50}$ is assessed by Western blotting. In yet another embodiment, the $EC_{50}$ is assessed by Northern blotting. In still another embodiment, the $EC_{50}$ is assessed by RT-PCR.

In one embodiment, attenuation of T cell activity is indicated by increase of regulatory T cells. In some embodiments, attenuation of T cell activity is indicated by increase of Foxp3+ regulatory T cells. In certain embodiments, attenuation of T cell activity is indicated by increase of CD25+Foxp3+ regulatory T cells.

In certain embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and increase CD25+Foxp3+ regulatory T cells. In one embodiment, an antibody provided herein specifically binds to PD-1 and increases CD25+Foxp3+ regulatory T cells by at least about 5%. In one embodiment, an antibody provided herein specifically binds to PD-1 and increases CD25+Foxp3+ regulatory T cells by at least about 10%. In another embodiment, an antibody provided herein specifically binds to PD-1 and increases CD25+Foxp3+ regulatory T cells by at least about 15%. In some embodiments, an antibody provided herein specifically binds to PD-1 and increases CD25+Foxp3+ regulatory T cells by at least about 20%. In other embodiments, an antibody provided herein specifically binds to PD-1 and increases CD25+Foxp3+ regulatory T cells by at least about 25%. In another embodiment, an antibody provided herein specifically binds to PD-1 and increases CD25+Foxp3+ regulatory T cells by at least about 30%. In one embodiment, an antibody provided herein specifically binds to PD-1 and increases CD25+Foxp3+ regulatory T cells by at least about 35%. In some embodiments, an antibody provided herein specifically binds to PD-1 and increases CD25+Foxp3+ regulatory T cells by at least about 40%. In another embodiment, an antibody provided herein specifically binds to PD-1 and increases CD25+Foxp3+ regulatory T cells by at least about 45%. In one embodiment, an antibody provided herein specifically binds to PD-1 and increases CD25+Foxp3+ regulatory T cells by at least about 50%. In other embodiments, an antibody provided herein specifically binds to PD-1 and increases CD25+Foxp3+ regulatory T cells by at least about 55%. In another embodiment, an antibody provided herein specifically binds to PD-1 and increases CD25+Foxp3+ regulatory T cells by at least about 60%. In some embodiments, an antibody provided herein specifically binds to PD-1 and increases CD25+Foxp3+ regulatory T cells by at least about 65%. In one embodiment, an antibody provided herein specifically binds to PD-1 and increases CD25+Foxp3+ regulatory T cells by at least about 70%. In another embodiment, an antibody provided herein specifically binds to PD-1 and increases CD25+Foxp3+ regulatory T cells by at least about 75%. In one embodiment, an antibody provided herein specifically binds to PD-1 and increases CD25+Foxp3+ regulatory T cells by at least about 80%. In some embodiments, an antibody provided herein specifically binds to PD-1 and increases CD25+Foxp3+ regulatory T cells by at least about 85%. In another embodiment, an antibody provided herein specifically binds to PD-1 and increases CD25+Foxp3+ regulatory T cells by at least about 90%. In other embodiments, an antibody provided herein specifically binds to PD-1 and increases CD25+Foxp3+ regulatory T cells by at least about 95%. In one embodiment, an antibody provided herein specifically binds to PD-1 and increases CD25+Foxp3+ regulatory T cells by at least about 98%. In another embodiment, an antibody provided herein specifically binds to PD-1 and increases CD25+Foxp3+ regulatory T cells by at least about 99%. In specific embodiments, antibodies provided herein specifically bind to PD-1 and increase CD25+Foxp3+ regulatory T cells by at least about 25% or 35%, optionally to about 75%. In some embodiments, the increase of CD25+Foxp3+ regulatory T cells is assessed by methods described herein. In other embodiments, the increase of CD25+Foxp3+ regulatory T cells is assessed by methods known to one of skill in the art (e.g., flow cytometry, Western blotting, Northern blotting, or RT-PCR). In a specific embodiment, the increase of CD25+Foxp3+ regulatory T cells is assessed by flow cytometry. In another embodiment, the increase of CD25+Foxp3+ regulatory T cells is assessed by Western blotting. In yet another embodiment, the increase of CD25+Foxp3+ regulatory T cells is assessed by Northern blotting. In still another embodiment, the increase of CD25+Foxp3+ regulatory T cells is assessed by RT-PCR. In a specific embodiment, CD25+Foxp3+ regulatory T cells are increased relative to CD25+Foxp3+ regulatory T cells in the presence of stimulation without any anti-PD-1 antibody. In other embodiments, CD25+Foxp3+ regulatory T cells are increased relative to CD25+Foxp3+ regulatory T cells in the presence of stimulation with an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) increases CD25+Foxp3+ regulatory T cells. In one embodiment, an anti-PD-1 antibody provided herein increases CD25+Foxp3+ regulatory T cells with an $EC_{50}$ of at most about 50 nM. In other embodiments, an anti-PD-1 antibody provided herein increases CD25+Foxp3+ regulatory T cells with an $EC_{50}$ of at most about 40 nM. In another embodiment, an anti-PD-1 antibody provided herein increases CD25+Foxp3+ regulatory T cells with an $EC_{50}$ of at most about 30 nM. In some embodiments, an anti-PD-1 antibody provided herein increases CD25+Foxp3+ regulatory T cells with an $EC_{50}$ of at most about 20 nM. In one embodiment, an anti-PD-1 antibody provided herein increases CD25+Foxp3+ regulatory T cells with an $EC_{50}$ of at most about 10 nM. In another embodiment, an anti-PD-1 antibody provided herein increases CD25+Foxp3+ regulatory T cells with an $EC_{50}$ of at most about 5 nM. In one embodiment, an anti-PD-1 antibody provided herein increases CD25+Foxp3+ regulatory T cells with an $EC_{50}$ of at most about 1 nM. In some embodiments, an anti-PD-1 antibody provided herein increases CD25+Foxp3+ regulatory T cells with an $EC_{50}$ of at most about 0.75 nM. In another embodiment, an anti-PD-1 antibody provided herein increases CD25+Foxp3+ regulatory T cells with an $EC_{50}$ of at most about 0.5 nM. In other embodiments, an anti-PD-1 antibody provided herein increases CD25+Foxp3+ regulatory T cells with an $EC_{50}$ of at most about 0.1 nM. In one embodiment, an anti-PD-1 antibody provided herein increases CD25+Foxp3+ regulatory T cells with an $EC_{50}$ of at most about 0.05 nM. In another embodiment, an anti-PD-1 antibody provided herein increases CD25+Foxp3+ regulatory T cells with an $EC_{50}$ of at most about 0.01 nM. In some embodiments, an anti-PD-1 antibody provided herein increases CD25+Foxp3+ regulatory T cells with an $EC_{50}$ of at most about 0.005 nM. In one embodiment, an anti-PD-1 antibody provided herein increases CD25+Foxp3+ regulatory T cells with an $EC_{50}$ of at most about 0.001 nM. In another embodiment, an anti-PD-1 antibody provided herein increases CD25+Foxp3+ regulatory T cells with an $EC_{50}$ of at least about 50 nM. In other embodiments, an anti-PD-1 antibody provided herein increases CD25+Foxp3+ regulatory T cells with an $EC_{50}$ of at least about 40 nM. In some embodiments, an anti-PD-1 antibody provided herein increases CD25+Foxp3+ regulatory T cells with an $EC_{50}$ of at least about 30 nM. In another embodiment, an anti-PD-1 antibody provided herein increases CD25+Foxp3+ regulatory T cells with an $EC_{50}$ of at least about 20 nM. In one embodiment, an anti-PD-1 antibody provided herein increases CD25+Foxp3+ regulatory T cells with an $EC_{50}$ of at least about 10 nM. In one embodiment, an anti-PD-1 antibody provided herein increases CD25+Foxp3+ regulatory T cells with an $EC_{50}$ of at least about 5 nM. In another embodiment, an anti-PD-1 antibody provided herein increases CD25+Foxp3+ regulatory T cells with an $EC_{50}$ of at least about 1 nM. In some embodiments, an anti-PD-1 antibody provided herein increases CD25+Foxp3+ regulatory T cells with an $EC_{50}$ of at least about 0.75 nM. In other embodiments, an anti-PD-1 antibody provided herein increases CD25+Foxp3+ regulatory T cells with an $EC_{50}$ of at least about 0.5 nM. In another embodiment, an anti-PD-1 antibody provided herein increases CD25+Foxp3+ regulatory T cells with an $EC_{50}$ of at least about 0.1 nM. In one embodiment, an anti-PD-1 antibody provided herein increases CD25+Foxp3+ regulatory T cells with an $EC_{50}$ of at least about 0.05 nM. In some embodiments, an anti-PD-1 antibody provided herein increases CD25+Foxp3+ regulatory T cells with an $EC_{50}$ of at least about 0.01 nM. In another embodiment, an anti-PD-1 antibody provided herein increases CD25+Foxp3+ regulatory T cells with an $EC_{50}$ of at least about 0.005 nM. In one embodiment, an anti-PD-1 antibody provided herein increases CD25+Foxp3+ regulatory T cells with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., flow cytometry, Western blotting, Northern blotting, or RT-PCR). In a specific embodiment, the $EC_{50}$ is assessed by flow cytometry. In another embodiment, the $EC_{50}$ is assessed by Western blotting. In yet another embodiment, the $EC_{50}$ is assessed by Northern blotting. In still another embodiment, the $EC_{50}$ is assessed by RT-PCR.

In one embodiment, attenuation of T cell activity is indicated by inhibition of a cytokine secretion. In some embodiments, the cytokine is selected from the group consisting of IL-2, IL-17, IFN-γ, or any combination thereof. In certain embodiments, the cytokine is selected from the group consisting of IL-1, IL-2, IL-6, IL-12, IL-17, IL-22, IL-23, GM-CSF, IFN-γ, and TNF-α. In certain embodiments, the cytokine is IL-1. In some embodiments, the cytokine is IL-2. In other embodiments, the cytokine is IL-6. In another embodiment, the cytokine is IL-12. In other embodiments, the cytokine is IL-17. In yet other embodiments, the cytokine is IL-22. In still other embodiments, the cytokine is IL-23. In some embodiments, the cytokine is GM-CSF. In other embodiments, the cytokine is IFN-γ. In yet other embodiments, the cytokine is TNF-α. In certain embodiments, the cytokine is IL-2 and IL-17. In some embodiments, the cytokine is IL-2 and IFN-γ. In yet other embodiments, the cytokine is IL-17 and IFN-γ. In still other embodiments, the cytokine is IL-2, IL-17, and IFN-γ.

In specific embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and inhibit IL-2 secretion (e.g., from a cell, for example, T cells). In one embodiment, an antibody provided herein specifically binds to PD-1 and inhibits IL-2 secretion by at least about 5%. In some embodiments, an antibody provided herein specifically binds to PD-1 and inhibits IL-2 secretion by at least about 10%. In another embodiment, an antibody provided herein specifically binds to PD-1 and inhibits IL-2 secretion by at least about 15%. In other embodiments, an antibody provided herein specifically binds to PD-1 and inhibits IL-2 secretion by at least about 20%. In one embodiment, an antibody provided herein specifically binds to PD-1 and inhibits IL-2 secretion by at least about 25%. In another embodiment, an antibody provided herein specifically binds to PD-1 and inhibits IL-2 secretion by at least about 30%. In some embodiments, an antibody provided herein specifically binds to PD-1 and inhibits IL-2 secretion by at least about 35%. In one embodiment, an antibody provided herein specifically binds to PD-1 and inhibits IL-2 secretion by at least about 40%. In another embodiment, an antibody provided herein specifically binds to PD-1 and inhibits IL-2 secretion by at least about 45%. In other embodiments, an antibody provided herein specifically binds to PD-1 and inhibits IL-2 secretion by at least about 50%. In some embodiments, an antibody provided herein specifically binds to PD-1 and inhibits IL-2 secretion by at least about 55%. In another embodiment, an antibody provided herein specifically binds to PD-1 and inhibits IL-2 secretion by at least about 60%. In one embodiment, an antibody provided herein specifically binds to PD-1 and inhibits IL-2 secretion by at least about 65%. In one embodiment, an antibody provided herein specifically binds to PD-1 and inhibits IL-2 secretion by at least about 70%. In another embodiment, an antibody provided herein specifically binds to PD-1 and inhibits IL-2 secretion by at least about 75%. In some embodiments, an antibody provided herein specifically binds to PD-1 and inhibits IL-2 secretion by at least about 80%. In other embodiments, an antibody provided herein specifically binds to PD-1 and inhibits IL-2 secretion by at least about 85%. In another embodiment, an antibody provided herein specifically binds to PD-1 and inhibits IL-2 secretion by at least about 90%. In one embodiment, an antibody provided herein specifically binds to PD-1 and inhibits IL-2 secretion by at least about 95%. In some embodiments, an antibody provided herein specifically binds to PD-1 and inhibits IL-2 secretion by at least about 98%. In another embodiment, an antibody provided herein specifically binds to PD-1 and inhibits IL-2 secretion by at least about 99%. In specific embodiments, antibodies provided herein specifically bind to PD-1 and inhibit IL-2 secretion by at least about 25% or 35%, optionally to about 75%. In some embodiments, the inhibition of IL-2 secretion is assessed by methods described herein. In other embodiments, the inhibition of IL-2 secretion is assessed by methods known to one of skill in the art (e.g., MesoScale™ Discovery (MSD) multiplex assay). In a specific embodiment, the IL-2 secretion is inhibited relative to IL-2 secretion in the absence of anti-PD-1 antibody. In other embodiments, the IL-2 secretion is inhibited relative to IL-2 secretion in the presence of an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) inhibits IL-2 secretion. In one embodiment, an anti-PD-1 antibody provided herein inhibits IL-2 secretion with an $EC_{50}$ of at most about 50 nM. In other embodiments, an anti-PD-1 antibody provided herein inhibits IL-2 secretion with an $EC_{50}$ of at most about 40 nM. In another embodiment, an anti-PD-1 antibody provided herein inhibits IL-2 secretion with an $EC_{50}$ of at most about 30 nM. In some embodiments, an anti-PD-1 antibody provided herein inhibits IL-2 secretion with an $EC_{50}$ of at most about 20 nM. In one embodiment, an anti-PD-1 antibody provided herein inhibits IL-2 secretion with an $EC_{50}$ of at most about 10 nM. In another embodiment, an anti-PD-1 antibody provided herein inhibits IL-2 secretion with an $EC_{50}$ of at most about 5 nM. In one embodiment, an anti-PD-1 antibody provided herein inhibits IL-2 secretion with an $EC_{50}$ of at most about 1 nM. In some embodiments, an anti-PD-1 antibody provided herein inhibits IL-2 secretion with an $EC_{50}$ of at most about 0.75 nM. In another embodiment, an anti-PD-1 antibody provided herein inhibits IL-2 secretion with an $EC_{50}$ of at most about 0.5 nM. In other embodiments, an anti-PD-1 antibody provided herein inhibits IL-2 secretion with an $EC_{50}$ of at most about 0.1 nM. In one embodiment, an anti-PD-1 antibody provided herein inhibits IL-2 secretion with an $EC_{50}$ of at most about 0.05 nM. In another embodiment, an anti-PD-1 antibody provided herein inhibits IL-2 secretion with an $EC_{50}$ of at most about 0.01 nM. In some embodiments, an anti-PD-1 antibody provided herein inhibits IL-2 secretion with an $EC_{50}$ of at most about 0.005 nM. In one embodiment, an anti-PD-1 antibody provided herein inhibits IL-2 secretion with an $EC_{50}$ of at most about 0.001 nM. In another embodiment, an anti-PD-1 antibody provided herein inhibits IL-2 secretion with an $EC_{50}$ of at least about 50 nM. In other embodiments, an anti-PD-1 antibody provided herein inhibits IL-2 secretion with an $EC_{50}$ of at least about 40 nM. In some embodiments, an anti-PD-1 antibody provided herein inhibits IL-2 secretion with an $EC_{50}$ of at least about 30 nM. In another embodiment, an anti-PD-1 antibody provided herein inhibits IL-2 secretion with an $EC_{50}$ of at least about 20 nM. In one embodiment, an anti-PD-1 antibody provided herein inhibits IL-2 secretion with an $EC_{50}$ of at least about 10 nM. In one embodiment, an anti-PD-1 antibody provided herein inhibits IL-2 secretion with an $EC_{50}$ of at least about 5 nM. In another embodiment, an anti-PD-1 antibody provided herein inhibits IL-2 secretion with an $EC_{50}$ of at least about 1 nM. In some embodiments, an anti-PD-1 antibody provided herein inhibits IL-2 secretion with an $EC_{50}$ of at least about 0.75 nM. In other embodiments, an anti-PD-1 antibody provided herein inhibits IL-2 secretion with an $EC_{50}$ of at least about 0.5 nM. In another embodiment, an anti-PD-1 antibody provided herein inhibits IL-2 secretion with an $EC_{50}$ of at least about 0.1 nM. In one embodiment, an anti-PD-1 antibody provided herein inhibits IL-2 secretion with an $EC_{50}$ of at least about 0.05 nM. In some embodiments, an anti-PD-1 antibody provided herein inhibits IL-2 secretion with an $EC_{50}$ of at least about 0.01 nM. In another embodiment, an anti-PD-1 antibody provided herein inhibits IL-2 secretion with an $EC_{50}$ of at least about 0.005 nM. In one embodiment, an anti-PD-1 antibody provided herein inhibits IL-2 secretion with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., MSD multiplex assay). In a specific embodiment, the $EC_{50}$ is assessed by MSD multiplex assay.

In specific embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and inhibit IL-17 secretion (e.g., from a cell, for example, T cells). In other embodiments, an antibody provided herein specifically binds to PD-1 and inhibits IL-17 secretion by at least about 5%. In another embodiment, an antibody provided herein specifically binds to PD-1 and inhibits IL-17 secretion by at least about 10%. In some embodiments, an antibody provided herein specifically binds to PD-1 and inhibits IL-17 secretion by at least about 15%. In one embodiment, an antibody provided herein specifically binds to PD-1 and inhibits IL-17 secretion by at least about 20%. In another embodiment, an antibody provided herein specifically binds to PD-1 and inhibits IL-17 secretion by at least about 25%. In one embodiment, an antibody provided herein specifically binds to PD-1 and inhibits IL-17 secretion by at least about 30%. In some embodiments, an antibody provided herein specifically binds to PD-1 and inhibits IL-17 secretion by at least about 35%. In another embodiment, an antibody provided herein specifically binds to PD-1 and inhibits IL-17 secretion by at least about 40%. In other embodiments, an antibody provided herein specifically binds to PD-1 and inhibits IL-17 secretion by at least about 45%. In one embodiment, an antibody provided herein specifically binds to PD-1 and inhibits IL-17 secretion by at least about 50%. In another embodiment, an antibody provided herein specifically binds to PD-1 and inhibits IL-17 secretion by at least about 55%. In some embodiments, an antibody provided herein specifically binds to PD-1 and inhibits IL-17 secretion by at least about 60%. In one embodiment, an antibody provided herein specifically binds to PD-1 and inhibits IL-17 secretion by at least about 65%. In another embodiment, an antibody provided herein specifically binds to PD-1 and inhibits IL-17 secretion by at least about 70%. In other embodiments, an antibody provided herein specifically binds to PD-1 and inhibits IL-17 secretion by at least about 75%. In some embodiments, an antibody provided herein specifically binds to PD-1 and inhibits IL-17 secretion by at least about 80%. In another embodiment, an antibody provided herein specifically binds to PD-1 and inhibits IL-17 secretion by at least about 85%. In one embodiment, an antibody provided herein specifically binds to PD-1 and inhibits IL-17 secretion by at least about 90%. In one embodiment, an antibody provided herein specifically binds to PD-1 and inhibits IL-17 secretion by at least about 95%. In another embodiment, an antibody provided herein specifically binds to PD-1 and inhibits IL-17 secretion by at least about 98%. In some embodiments, an antibody provided herein specifically binds to PD-1 and inhibits IL-17 secretion by at least about 99%. In specific embodiments, antibodies provided herein specifically bind to PD-1 and inhibit IL-17 secretion by at least about 25% or 35%, optionally to about 75%. In some embodiments, the inhibition of IL-17 secretion is assessed by methods described herein. In other embodiments, the inhibition of IL-17 secretion is assessed by methods known to one of skill in the art (e.g., MSD multiplex assay). In a specific embodiment, the IL-17 secretion is inhibited relative to IL-17 secretion in the absence of anti-PD-1 antibody. In other embodiments, the IL-17 secretion is inhibited relative to IL-17 secretion in the presence of an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) inhibits IL-17 secretion. In other embodiments, an anti-PD-1 antibody provided herein inhibits IL-17 secretion with an $EC_{50}$ of at most about 50 nM. In another embodiment, an anti-PD-1 antibody provided herein inhibits IL-17 secretion with an $EC_{50}$ of at most about 40 nM. In one embodiment, an anti-PD-1 antibody provided herein inhibits IL-17 secretion with an $EC_{50}$ of at most about 30 nM. In some embodiments, an anti-PD-1 antibody provided herein inhibits IL-17 secretion with an $EC_{50}$ of at most about 20 nM. In another embodiment, an anti-PD-1 antibody provided herein inhibits IL-17 secretion with an $EC_{50}$ of at most about 10 nM. In one embodiment, an anti-PD-1 antibody provided herein inhibits IL-17 secretion with an $EC_{50}$ of at most about 5 nM. In other embodiments, an anti-PD-1 antibody provided herein inhibits IL-17 secretion with an $EC_{50}$ of at most about 1 nM. In another embodiment, an anti-PD-1 antibody provided herein inhibits IL-17 secretion with an $EC_{50}$ of at most about 0.75 nM. In some embodiments, an anti-PD-1 antibody provided herein inhibits IL-17 secretion with an $EC_{50}$ of at most about 0.5 nM. In one embodiment, an anti-PD-1 antibody provided herein inhibits IL-17 secretion with an $EC_{50}$ of at most about 0.1 nM. In another embodiment, an anti-PD-1 antibody provided herein inhibits IL-17 secretion with an $EC_{50}$ of at most about 0.05 nM. In one embodiment, an anti-PD-1 antibody provided herein inhibits IL-17 secretion with an $EC_{50}$ of at most about 0.01 nM. In some embodiments, an anti-PD-1 antibody provided herein inhibits IL-17 secretion with an $EC_{50}$ of at most about 0.005 nM. In another embodiment, an anti-PD-1 antibody provided herein inhibits IL-17 secretion with an $EC_{50}$ of at most about 0.001 nM. In other embodiments, an anti-PD-1 antibody provided herein inhibits IL-17 secretion with an $EC_{50}$ of at least about 50 nM. In one embodiment, an anti-PD-1 antibody provided herein inhibits IL-17 secretion with an $EC_{50}$ of at least about 40 nM. In another embodiment, an anti-PD-1 antibody provided herein inhibits IL-17 secretion with an $EC_{50}$ of at least about 30 nM. In some embodiments, an anti-PD-1 antibody provided herein inhibits IL-17 secretion with an $EC_{50}$ of at least about 20 nM. In one embodiment, an anti-PD-1 antibody provided herein inhibits IL-17 secretion with an $EC_{50}$ of at least about 10 nM. In another embodiment, an anti-PD-1 antibody provided herein inhibits IL-17 secretion with an $EC_{50}$ of at least about 5 nM. In other embodiments, an anti-PD-1 antibody provided herein inhibits IL-17 secretion with an $EC_{50}$ of at least about 1 nM. In some embodiments, an anti-PD-1 antibody provided herein inhibits IL-17 secretion with an $EC_{50}$ of at least about 0.75 nM. In another embodiment, an anti-PD-1 antibody provided herein inhibits IL-17 secretion with an $EC_{50}$ of at least about 0.5 nM. In one embodiment, an anti-PD-1 antibody provided herein inhibits IL-17 secretion with an $EC_{50}$ of at least about 0.1 nM. In one embodiment, an anti-PD-1 antibody provided herein inhibits IL-17 secretion with an $EC_{50}$ of at least about 0.05 nM. In another embodiment, an anti-PD-1 antibody provided herein inhibits IL-17 secretion with an $EC_{50}$ of at least about 0.01 nM. In some embodiments, an anti-PD-1 antibody provided herein inhibits IL-17 secretion with an $EC_{50}$ of at least about 0.005 nM. In other embodiments, an anti-PD-1 antibody provided herein inhibits IL-17 secretion with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., MSD multiplex assay). In a specific embodiment, the $EC_{50}$ is assessed by MSD multiplex assay.

In specific embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and inhibit IFN-γ secretion (e.g., from a cell, for example, T cells). In another embodiment, an antibody provided herein specifically binds to PD-1 and inhibits IFN-γ secretion by at least about 5%. In one embodiment, an antibody provided herein specifically binds to PD-1 and inhibits IFN-γ secretion by at least about 10%. In some embodiments, an antibody provided herein specifically binds to PD-1 and inhibits IFN-γ secretion by at least about 15%. In another embodiment, an antibody provided herein specifically binds to PD-1 and inhibits IFN-γ secretion by at least about 20%. In one embodiment, an antibody provided herein specifically binds to PD-1 and inhibits IFN-γ secretion by at least about 25%. In other embodiments, an antibody provided herein specifically binds to PD-1 and inhibits IFN-γ secretion by at least about 30%. In another embodiment, an antibody provided herein specifically binds to PD-1 and inhibits IFN-γ secretion by at least about 35%. In some embodiments, an antibody provided herein specifically binds to PD-1 and inhibits IFN-γ secretion by at least about 40%. In one embodiment, an antibody provided herein specifically binds to PD-1 and inhibits IFN-γ secretion by at least about 45%. In another embodiment, an antibody provided herein specifically binds to PD-1 and inhibits IFN-γ secretion by at least about 50%. In one embodiment, an antibody provided herein specifically binds to PD-1 and inhibits IFN-γ secretion by at least about 55%. In some embodiments, an antibody provided herein specifically binds to PD-1 and inhibits IFN-γ secretion by at least about 60%. In another embodiment, an antibody provided herein specifically binds to PD-1 and inhibits IFN-γ secretion by at least about 65%. In other embodiments, an antibody provided herein specifically binds to PD-1 and inhibits IFN-γ secretion by at least about 70%. In one embodiment, an antibody provided herein specifically binds to PD-1 and inhibits IFN-γ secretion by at least about 75%. In another embodiment, an antibody provided herein specifically binds to PD-1 and inhibits IFN-γ secretion by at least about 80%. In some embodiments, an antibody provided herein specifically binds to PD-1 and inhibits IFN-γ secretion by at least about 85%. In one embodiment, an antibody provided herein specifically binds to PD-1 and inhibits IFN-γ secretion by at least about 90%. In another embodiment, an antibody provided herein specifically binds to PD-1 and inhibits IFN-γ secretion by at least about 95%. In other embodiments, an antibody provided herein specifically binds to PD-1 and inhibits IFN-γ secretion by at least about 98%. In some embodiments, an antibody provided herein specifically binds to PD-1 and inhibits IFN-γ secretion by at least about 99%. In specific embodiments, antibodies provided herein specifically bind to PD-1 and inhibit IFN-γ secretion by at least about 25% or 35%, optionally to about 75%. In some embodiments, the inhibition of IFN-γ secretion is assessed by methods described herein. In other embodiments, the inhibition of IFN-γ secretion is assessed by methods known to one of skill in the art (e.g., MSD multiplex assay). In a specific embodiment, the IFN-γ secretion is inhibited relative to IFN-γ secretion in the absence of anti-PD-1 antibody. In other embodiments, the IFN-γ secretion is inhibited relative to IFN-γ secretion in the presence of an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) inhibits IFN-γ secretion. In another embodiment, an anti-PD-1 antibody provided herein inhibits IFN-γ secretion with an $EC_{50}$ of at most about 50 nM. In one embodiment, an anti-PD-1 antibody provided herein inhibits IFN-γ secretion with an $EC_{50}$ of at most about 40 nM. In one embodiment, an anti-PD-1 antibody provided herein inhibits IFN-γ secretion with an $EC_{50}$ of at most about 30 nM. In another embodiment, an anti-PD-1 antibody provided herein inhibits IFN-γ secretion with an $EC_{50}$ of at most about 20 nM. In some embodiments, an anti-PD-1 antibody provided herein inhibits IFN-γ secretion with an $EC_{50}$ of at most about 10 nM. In other embodiments, an anti-PD-1 antibody provided herein inhibits IFN-γ secretion with an $EC_{50}$ of at most about 5 nM. In another embodiment, an anti-PD-1 antibody provided herein inhibits IFN-γ secretion with an $EC_{50}$ of at most about 1 nM. In one embodiment, an anti-PD-1 antibody provided herein inhibits IFN-γ secretion with an $EC_{50}$ of at most about 0.75 nM. In some embodiments, an anti-PD-1 antibody provided herein inhibits IFN-γ secretion with an $EC_{50}$ of at most about 0.5 nM. In another embodiment, an anti-PD-1 antibody provided herein inhibits IFN-γ secretion with an $EC_{50}$ of at most about 0.1 nM. In one embodiment, an anti-PD-1 antibody provided herein inhibits IFN-γ secretion with an $EC_{50}$ of at most about 0.05 nM. In other embodiments, an anti-PD-1 antibody provided herein inhibits IFN-γ secretion with an $EC_{50}$ of at most about 0.01 nM. In another embodiment, an anti-PD-1 antibody provided herein inhibits IFN-γ secretion with an $EC_{50}$ of at most about 0.005 nM. In some embodiments, an anti-PD-1 antibody provided herein inhibits IFN-γ secretion with an $EC_{50}$ of at most about 0.001 nM. In one embodiment, an anti-PD-1 antibody provided herein inhibits IFN-γ secretion with an $EC_{50}$ of at least about 50 nM. In another embodiment, an anti-PD-1 antibody provided herein inhibits IFN-γ secretion with an $EC_{50}$ of at least about 40 nM. In one embodiment, an anti-PD-1 antibody provided herein inhibits IFN-γ secretion with an $EC_{50}$ of at least about 30 nM. In some embodiments, an anti-PD-1 antibody provided herein inhibits IFN-γ secretion with an $EC_{50}$ of at least about 20 nM. In another embodiment, an anti-PD-1 antibody provided herein inhibits IFN-γ secretion with an $EC_{50}$ of at least about 10 nM. In other embodiments, an anti-PD-1 antibody provided herein inhibits IFN-γ secretion with an $EC_{50}$ of at least about 5 nM. In one embodiment, an anti-PD-1 antibody provided herein inhibits IFN-γ secretion with an $EC_{50}$ of at least about 1 nM. In another embodiment, an anti-PD-1 antibody provided herein inhibits IFN-γ secretion with an $EC_{50}$ of at least about 0.75 nM. In some embodiments, an anti-PD-1 antibody provided herein inhibits IFN-γ secretion with an $EC_{50}$ of at least about 0.5 nM. In one embodiment, an anti-PD-1 antibody provided herein inhibits IFN-γ secretion with an $EC_{50}$ of at least about 0.1 nM. In another embodiment, an anti-PD-1 antibody provided herein inhibits IFN-γ secretion with an $EC_{50}$ of at least about 0.05 nM. In other embodiments, an anti-PD-1 antibody provided herein inhibits IFN-γ secretion with an $EC_{50}$ of at least about 0.01 nM. In some embodiments, an anti-PD-1 antibody provided herein inhibits IFN-γ secretion with an $EC_{50}$ of at least about 0.005 nM. In another embodiment, an anti-PD-1 antibody provided herein inhibits IFN-γ secretion with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., MSD multiplex assay). In a specific embodiment, the $EC_{50}$ is assessed by MSD multiplex assay.

In specific embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and inhibit IL-1 secretion (e.g., from a cell, for example, T cells). In one embodiment, an antibody provided herein specifically binds to PD-1 and inhibits IL-1 secretion by at least about 5%. In some embodiments, an antibody provided herein specifically binds to PD-1 and inhibits IL-1 secretion by at least about 10%. In another embodiment, an antibody provided herein specifically binds to PD-1 and inhibits IL-1 secretion by at least about 15%. In other embodiments, an antibody provided herein specifically binds to PD-1 and inhibits IL-1 secretion by at least about 20%. In one embodiment, an antibody provided herein specifically binds to PD-1 and inhibits IL-1 secretion by at least about 25%. In another embodiment, an antibody provided herein specifically binds to PD-1 and inhibits IL-1 secretion by at least about 30%. In some embodiments, an antibody provided herein specifically binds to PD-1 and inhibits IL-1 secretion by at least about 35%. In one embodiment, an antibody provided herein specifically binds to PD-1 and inhibits IL-1 secretion by at least about 40%. In another embodiment, an antibody provided herein specifically binds to PD-1 and inhibits IL-1 secretion by at least about 45%. In other embodiments, an antibody provided herein specifically binds to PD-1 and inhibits IL-1 secretion by at least about 50%. In some embodiments, an antibody provided herein specifically binds to PD-1 and inhibits IL-1 secretion by at least about 55%. In another embodiment, an antibody provided herein specifically binds to PD-1 and inhibits IL-1 secretion by at least about 60%. In one embodiment, an antibody provided herein specifically binds to PD-1 and inhibits IL-1 secretion by at least about 65%. In one embodiment, an antibody provided herein specifically binds to PD-1 and inhibits IL-1 secretion by at least about 70%. In another embodiment, an antibody provided herein specifically binds to PD-1 and inhibits IL-1 secretion by at least about 75%. In some embodiments, an antibody provided herein specifically binds to PD-1 and inhibits IL-1 secretion by at least about 80%. In other embodiments, an antibody provided herein specifically binds to PD-1 and inhibits IL-1 secretion by at least about 85%. In another embodiment, an antibody provided herein specifically binds to PD-1 and inhibits IL-1 secretion by at least about 90%. In one embodiment, an antibody provided herein specifically binds to PD-1 and inhibits IL-1 secretion by at least about 95%. In some embodiments, an antibody provided herein specifically binds to PD-1 and inhibits IL-1 secretion by at least about 98%. In another embodiment, an antibody provided herein specifically binds to PD-1 and inhibits IL-1 secretion by at least about 99%. In specific embodiments, antibodies provided herein specifically bind to PD-1 and inhibit IL-1 secretion by at least about 25% or 35%, optionally to about 75%. In some embodiments, the inhibition of IL-1 secretion is assessed by methods described herein. In other embodiments, the inhibition of IL-1 secretion is assessed by methods known to one of skill in the art (e.g., MSD multiplex assay). In a specific embodiment, the IL-1 secretion is inhibited relative to IL-1 secretion in the absence of anti-PD-1 antibody. In other embodiments, the IL-1 secretion is inhibited relative to IL-1 secretion in the presence of an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) inhibits IL-1 secretion. In one embodiment, an anti-PD-1 antibody provided herein inhibits IL-1 secretion with an $EC_{50}$ of at most about 50 nM. In other embodiments, an anti-PD-1 antibody provided herein inhibits IL-1 secretion with an $EC_{50}$ of at most about 40 nM. In another embodiment, an anti-PD-1 antibody provided herein inhibits IL-1 secretion with an $EC_{50}$ of at most about 30 nM. In some embodiments, an anti-PD-1 antibody provided herein inhibits IL-1 secretion with an $EC_{50}$ of at most about 20 nM. In one embodiment, an anti-PD-1 antibody provided herein inhibits IL-1 secretion with an $EC_{50}$ of at most about 10 nM. In another embodiment, an anti-PD-1 antibody provided herein inhibits IL-1 secretion with an $EC_{50}$ of at most about 5 nM. In one embodiment, an anti-PD-1 antibody provided herein inhibits IL-1 secretion with an $EC_{50}$ of at most about 1 nM. In some embodiments, an anti-PD-1 antibody provided herein inhibits IL-1 secretion with an $EC_{50}$ of at most about 0.75 nM. In another embodiment, an anti-PD-1 antibody provided herein inhibits IL-1 secretion with an $EC_{50}$ of at most about 0.5 nM. In other embodiments, an anti-PD-1 antibody provided herein inhibits IL-1 secretion with an $EC_{50}$ of at most about 0.1 nM. In one embodiment, an anti-PD-1 antibody provided herein inhibits IL-1 secretion with an $EC_{50}$ of at most about 0.05 nM. In another embodiment, an anti-PD-1 antibody provided herein inhibits IL-1 secretion with an $EC_{50}$ of at most about 0.01 nM. In some embodiments, an anti-PD-1 antibody provided herein inhibits IL-1 secretion with an $EC_{50}$ of at most about 0.005 nM. In one embodiment, an anti-PD-1 antibody provided herein inhibits IL-1 secretion with an $EC_{50}$ of at most about 0.001 nM. In another embodiment, an anti-PD-1 antibody provided herein inhibits IL-1 secretion with an $EC_{50}$ of at least about 50 nM. In other embodiments, an anti-PD-1 antibody provided herein inhibits IL-1 secretion with an $EC_{50}$ of at least about 40 nM. In some embodiments, an anti-PD-1 antibody provided herein inhibits IL-1 secretion with an $EC_{50}$ of at least about 30 nM. In another embodiment, an anti-PD-1 antibody provided herein inhibits IL-1 secretion with an $EC_{50}$ of at least about 20 nM. In one embodiment, an anti-PD-1 antibody provided herein inhibits IL-1 secretion with an $EC_{50}$ of at least about 10 nM. In one embodiment, an anti-PD-1 antibody provided herein inhibits IL-1 secretion with an $EC_{50}$ of at least about 5 nM. In another embodiment, an anti-PD-1 antibody provided herein inhibits IL-1 secretion with an $EC_{50}$ of at least about 1 nM. In some embodiments, an anti-PD-1 antibody provided herein inhibits IL-1 secretion with an $EC_{50}$ of at least about 0.75 nM. In other embodiments, an anti-PD-1 antibody provided herein inhibits IL-1 secretion with an $EC_{50}$ of at least about 0.5 nM. In another embodiment, an anti-PD-1 antibody provided herein inhibits IL-1 secretion with an $EC_{50}$ of at least about 0.1 nM. In one embodiment, an anti-PD-1 antibody provided herein inhibits IL-1 secretion with an $EC_{50}$ of at least about 0.05 nM. In some embodiments, an anti-PD-1 antibody provided herein inhibits IL-1 secretion with an $EC_{50}$ of at least about 0.01 nM. In another embodiment, an anti-PD-1 antibody provided herein inhibits IL-1 secretion with an $EC_{50}$ of at least about 0.005 nM. In one embodiment, an anti-PD-1 antibody provided herein inhibits IL-1 secretion with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., MSD multiplex assay). In a specific embodiment, the $EC_{50}$ is assessed by MSD multiplex assay.

In specific embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and inhibit IL-6 secretion (e.g., from a cell, for example, T cells). In one embodiment, an antibody provided herein specifically binds to PD-1 and inhibits IL-6 secretion by at least about 5%. In some embodiments, an antibody provided herein specifically binds to PD-1 and inhibits IL-6 secretion by at least about 10%. In another embodiment, an antibody provided herein specifically binds to PD-1 and inhibits IL-6 secretion by at least about 15%. In other embodiments, an antibody provided herein specifically binds to PD-1 and inhibits IL-6 secretion by at least about 20%. In one embodiment, an antibody provided herein specifically binds to PD-1 and inhibits IL-6 secretion by at least about 25%. In another embodiment, an antibody provided herein specifically binds to PD-1 and inhibits IL-6 secretion by at least about 30%. In some embodiments, an antibody provided herein specifically binds to PD-1 and inhibits IL-6 secretion by at least about 35%. In one embodiment, an antibody provided herein specifically binds to PD-1 and inhibits IL-6 secretion by at least about 40%. In another embodiment, an antibody provided herein specifically binds to PD-1 and inhibits IL-6 secretion by at least about 45%. In other embodiments, an antibody provided herein specifically binds to PD-1 and inhibits IL-6 secretion by at least about 50%. In some embodiments, an antibody provided herein specifically binds to PD-1 and inhibits IL-6 secretion by at least about 55%. In another embodiment, an antibody provided herein specifically binds to PD-1 and inhibits IL-6 secretion by at least about 60%. In one embodiment, an antibody provided herein specifically binds to PD-1 and inhibits IL-6 secretion by at least about 65%. In one embodiment, an antibody provided herein specifically binds to PD-1 and inhibits IL-6 secretion by at least about 70%. In another embodiment, an antibody provided herein specifically binds to PD-1 and inhibits IL-6 secretion by at least about 75%. In some embodiments, an antibody provided herein specifically binds to PD-1 and inhibits IL-6 secretion by at least about 80%. In other embodiments, an antibody provided herein specifically binds to PD-1 and inhibits IL-6 secretion by at least about 85%. In another embodiment, an antibody provided herein specifically binds to PD-1 and inhibits IL-6 secretion by at least about 90%. In one embodiment, an antibody provided herein specifically binds to PD-1 and inhibits IL-6 secretion by at least about 95%. In some embodiments, an antibody provided herein specifically binds to PD-1 and inhibits IL-6 secretion by at least about 98%. In another embodiment, an antibody provided herein specifically binds to PD-1 and inhibits IL-6 secretion by at least about 99%. In specific embodiments, antibodies provided herein specifically bind to PD-1 and inhibit IL-6 secretion by at least about 25% or 35%, optionally to about 75%. In some embodiments, the inhibition of IL-6 secretion is assessed by methods described herein. In other embodiments, the inhibition of IL-6 secretion is assessed by methods known to one of skill in the art (e.g., MSD multiplex assay). In a specific embodiment, the IL-6 secretion is inhibited relative to IL-6 secretion in the absence of anti-PD-1 antibody. In other embodiments, the IL-6 secretion is inhibited relative to IL-6 secretion in the presence of an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) inhibits IL-6 secretion. In one embodiment, an anti-PD-1 antibody provided herein inhibits IL-6 secretion with an $EC_{50}$ of at most about 50 nM. In other embodiments, an anti-PD-1 antibody provided herein inhibits IL-6 secretion with an $EC_{50}$ of at most about 40 nM. In another embodiment, an anti-PD-1 antibody provided herein inhibits IL-6 secretion with an $EC_{50}$ of at most about 30 nM. In some embodiments, an anti-PD-1 antibody provided herein inhibits IL-6 secretion with an $EC_{50}$ of at most about 20 nM. In one embodiment, an anti-PD-1 antibody provided herein inhibits IL-6 secretion with an $EC_{50}$ of at most about 10 nM. In another embodiment, an anti-PD-1 antibody provided herein inhibits IL-6 secretion with an $EC_{50}$ of at most about 5 nM. In one embodiment, an anti-PD-1 antibody provided herein inhibits IL-6 secretion with an $EC_{50}$ of at most about 1 nM. In some embodiments, an anti-PD-1 antibody provided herein inhibits IL-6 secretion with an $EC_{50}$ of at most about 0.75 nM. In another embodiment, an anti-PD-1 antibody provided herein inhibits IL-6 secretion with an $EC_{50}$ of at most about 0.5 nM. In other embodiments, an anti-PD-1 antibody provided herein inhibits IL-6 secretion with an $EC_{50}$ of at most about 0.1 nM. In one embodiment, an anti-PD-1 antibody provided herein inhibits IL-6 secretion with an $EC_{50}$ of at most about 0.05 nM. In another embodiment, an anti-PD-1 antibody provided herein inhibits IL-6 secretion with an $EC_{50}$ of at most about 0.01 nM. In some embodiments, an anti-PD-1 antibody provided herein inhibits IL-6 secretion with an $EC_{50}$ of at most about 0.005 nM. In one embodiment, an anti-PD-1 antibody provided herein inhibits IL-6 secretion with an $EC_{50}$ of at most about 0.001 nM. In another embodiment, an anti-PD-1 antibody provided herein inhibits IL-6 secretion with an $EC_{50}$ of at least about 50 nM. In other embodiments, an anti-PD-1 antibody provided herein inhibits IL-6 secretion with an $EC_{50}$ of at least about 40 nM. In some embodiments, an anti-PD-1 antibody provided herein inhibits IL-6 secretion with an $EC_{50}$ of at least about 30 nM. In another embodiment, an anti-PD-1 antibody provided herein inhibits IL-6 secretion with an $EC_{50}$ of at least about 20 nM. In one embodiment, an anti-PD-1 antibody provided herein inhibits IL-6 secretion with an $EC_{50}$ of at least about 10 nM. In one embodiment, an anti-PD-1 antibody provided herein inhibits IL-6 secretion with an $EC_{50}$ of at least about 5 nM. In another embodiment, an anti-PD-1 antibody provided herein inhibits IL-6 secretion with an $EC_{50}$ of at least about 1 nM. In some embodiments, an anti-PD-1 antibody provided herein inhibits IL-6 secretion with an $EC_{50}$ of at least about 0.75 nM. In other embodiments, an anti-PD-1 antibody provided herein inhibits IL-6 secretion with an $EC_{50}$ of at least about 0.5 nM. In another embodiment, an anti-PD-1 antibody provided herein inhibits IL-6 secretion with an $EC_{50}$ of at least about 0.1 nM. In one embodiment, an anti-PD-1 antibody provided herein inhibits IL-6 secretion with an $EC_{50}$ of at least about 0.05 nM. In some embodiments, an anti-PD-1 antibody provided herein inhibits IL-6 secretion with an $EC_{50}$ of at least about 0.01 nM. In another embodiment, an anti-PD-1 antibody provided herein inhibits IL-6 secretion with an $EC_{50}$ of at least about 0.005 nM. In one embodiment, an anti-PD-1 antibody provided herein inhibits IL-6 secretion with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., MSD multiplex assay). In a specific embodiment, the $EC_{50}$ is assessed by MSD multiplex assay.

In specific embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and inhibit IL-12 secretion (e.g., from a cell, for example, T cells). In one embodiment, an antibody provided herein specifically binds to PD-1 and inhibits IL-12 secretion by at least about 5%. In some embodiments, an antibody provided herein specifically binds to PD-1 and inhibits IL-12 secretion by at least about 10%. In another embodiment, an antibody provided herein specifically binds to PD-1 and inhibits IL-12 secretion by at least about 15%. In other embodiments, an antibody provided herein specifically binds to PD-1 and inhibits IL-12 secretion by at least about 20%. In one embodiment, an antibody provided herein specifically binds to PD-1 and inhibits IL-12 secretion by at least about 25%. In another embodiment, an antibody provided herein specifically binds to PD-1 and inhibits IL-12 secretion by at least about 30%. In some embodiments, an antibody provided herein specifically binds to PD-1 and inhibits IL-12 secretion by at least about 35%. In one embodiment, an antibody provided herein specifically binds to PD-1 and inhibits IL-12 secretion by at least about 40%. In another embodiment, an antibody provided herein specifically binds to PD-1 and inhibits IL-12 secretion by at least about 45%. In other embodiments, an antibody provided herein specifically binds to PD-1 and inhibits IL-12 secretion by at least about 50%. In some embodiments, an antibody provided herein specifically binds to PD-1 and inhibits IL-12 secretion by at least about 55%. In another embodiment, an antibody provided herein specifically binds to PD-1 and inhibits IL-12 secretion by at least about 60%. In one embodiment, an antibody provided herein specifically binds to PD-1 and inhibits IL-12 secretion by at least about 65%. In one embodiment, an antibody provided herein specifically binds to PD-1 and inhibits IL-12 secretion by at least about 70%. In another embodiment, an antibody provided herein specifically binds to PD-1 and inhibits IL-12 secretion by at least about 75%. In some embodiments, an antibody provided herein specifically binds to PD-1 and inhibits IL-12 secretion by at least about 80%. In other embodiments, an antibody provided herein specifically binds to PD-1 and inhibits IL-12 secretion by at least about 85%. In another embodiment, an antibody provided herein specifically binds to PD-1 and inhibits IL-12 secretion by at least about 90%. In one embodiment, an antibody provided herein specifically binds to PD-1 and inhibits IL-12 secretion by at least about 95%. In some embodiments, an antibody provided herein specifically binds to PD-1 and inhibits IL-12 secretion by at least about 98%. In another embodiment, an antibody provided herein specifically binds to PD-1 and inhibits IL-12 secretion by at least about 99%. In specific embodiments, antibodies provided herein specifically bind to PD-1 and inhibit IL-12 secretion by at least about 25% or 35%, optionally to about 75%. In some embodiments, the inhibition of IL-12 secretion is assessed by methods described herein. In other embodiments, the inhibition of IL-12 secretion is assessed by methods known to one of skill in the art (e.g., MSD multiplex assay). In a specific embodiment, the IL-12 secretion is inhibited relative to IL-12 secretion in the absence of anti-PD-1 antibody. In other embodiments, the IL-12 secretion is inhibited relative to IL-12 secretion in the presence of an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) inhibits IL-12 secretion. In one embodiment, an anti-PD-1 antibody provided herein inhibits IL-12 secretion with an $EC_{50}$ of at most about 50 nM. In other embodiments, an anti-PD-1 antibody provided herein inhibits IL-12 secretion with an $EC_{50}$ of at most about 40 nM. In another embodiment, an anti-PD-1 antibody provided herein inhibits IL-12 secretion with an $EC_{50}$ of at most about 30 nM. In some embodiments, an anti-PD-1 antibody provided herein inhibits IL-12 secretion with an $EC_{50}$ of at most about 20 nM. In one embodiment, an anti-PD-1 antibody provided herein inhibits IL-12 secretion with an $EC_{50}$ of at most about 10 nM. In another embodiment, an anti-PD-1 antibody provided herein inhibits IL-12 secretion with an $EC_{50}$ of at most about 5 nM. In one embodiment, an anti-PD-1 antibody provided herein inhibits IL-12 secretion with an $EC_{50}$ of at most about 1 nM. In some embodiments, an anti-PD-1 antibody provided herein inhibits IL-12 secretion with an $EC_{50}$ of at most about 0.75 nM. In another embodiment, an anti-PD-1 antibody provided herein inhibits IL-12 secretion with an $EC_{50}$ of at most about 0.5 nM. In other embodiments, an anti-PD-1 antibody provided herein inhibits IL-12 secretion with an $EC_{50}$ of at most about 0.1 nM. In one embodiment, an anti-PD-1 antibody provided herein inhibits IL-12 secretion with an $EC_{50}$ of at most about 0.05 nM. In another embodiment, an anti-PD-1 antibody provided herein inhibits IL-12 secretion with an $EC_{50}$ of at most about 0.01 nM. In some embodiments, an anti-PD-1 antibody provided herein inhibits IL-12 secretion with an $EC_{50}$ of at most about 0.005 nM. In one embodiment, an anti-PD-1 antibody provided herein inhibits IL-12 secretion with an $EC_{50}$ of at most about 0.001 nM. In another embodiment, an anti-PD-1 antibody provided herein inhibits IL-12 secretion with an $EC_{50}$ of at least about 50 nM. In other embodiments, an anti-PD-1 antibody provided herein inhibits IL-12 secretion with an $EC_{50}$ of at least about 40 nM. In some embodiments, an anti-PD-1 antibody provided herein inhibits IL-12 secretion with an $EC_{50}$ of at least about 30 nM. In another embodiment, an anti-PD-1 antibody provided herein inhibits IL-12 secretion with an $EC_{50}$ of at least about 20 nM. In one embodiment, an anti-PD-1 antibody provided herein inhibits IL-12 secretion with an $EC_{50}$ of at least about 10 nM. In one embodiment, an anti-PD-1 antibody provided herein inhibits IL-12 secretion with an $EC_{50}$ of at least about 5 nM. In another embodiment, an anti-PD-1 antibody provided herein inhibits IL-12 secretion with an $EC_{50}$ of at least about 1 nM. In some embodiments, an anti-PD-1 antibody provided herein inhibits IL-12 secretion with an $EC_{50}$ of at least about 0.75 nM. In other embodiments, an anti-PD-1 antibody provided herein inhibits IL-12 secretion with an $EC_{50}$ of at least about 0.5 nM. In another embodiment, an anti-PD-1 antibody provided herein inhibits IL-12 secretion with an $EC_{50}$ of at least about 0.1 nM. In one embodiment, an anti-PD-1 antibody provided herein inhibits IL-12 secretion with an $EC_{50}$ of at least about 0.05 nM. In some embodiments, an anti-PD-1 antibody provided herein inhibits IL-12 secretion with an $EC_{50}$ of at least about 0.01 nM. In another embodiment, an anti-PD-1 antibody provided herein inhibits IL-12 secretion with an $EC_{50}$ of at least about 0.005 nM. In one embodiment, an anti-PD-1 antibody provided herein inhibits IL-12 secretion with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., MSD multiplex assay). In a specific embodiment, the $EC_{50}$ is assessed by MSD multiplex assay.

In specific embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and inhibit IL-22 secretion (e.g., from a cell, for example, a T cell). In one embodiment, an antibody provided herein specifically binds to PD-1 and inhibits IL-22 secretion by at least about 5%. In some embodiments, an antibody provided herein specifically binds to PD-1 and inhibits IL-22 secretion by at least about 10%. In another embodiment, an antibody provided herein specifically binds to PD-1 and inhibits IL-22 secretion by at least about 15%. In other embodiments, an antibody provided herein specifically binds to PD-1 and inhibits IL-22 secretion by at least about 20%. In one embodiment, an antibody provided herein specifically binds to PD-1 and inhibits IL-22 secretion by at least about 25%. In another embodiment, an antibody provided herein specifically binds to PD-1 and inhibits IL-22 secretion by at least about 30%. In some embodiments, an antibody provided herein specifically binds to PD-1 and inhibits IL-22 secretion by at least about 35%. In one embodiment, an antibody provided herein specifically binds to PD-1 and inhibits IL-22 secretion by at least about 40%. In another embodiment, an antibody provided herein specifically binds to PD-1 and inhibits IL-22 secretion by at least about 45%. In other embodiments, an antibody provided herein specifically binds to PD-1 and inhibits IL-22 secretion by at least about 50%. In some embodiments, an antibody provided herein specifically binds to PD-1 and inhibits IL-22 secretion by at least about 55%. In another embodiment, an antibody provided herein specifically binds to PD-1 and inhibits IL-22 secretion by at least about 60%. In one embodiment, an antibody provided herein specifically binds to PD-1 and inhibits IL-22 secretion by at least about 65%. In one embodiment, an antibody provided herein specifically binds to PD-1 and inhibits IL-22 secretion by at least about 70%. In another embodiment, an antibody provided herein specifically binds to PD-1 and inhibits IL-22 secretion by at least about 75%. In some embodiments, an antibody provided herein specifically binds to PD-1 and inhibits IL-22 secretion by at least about 80%. In other embodiments, an antibody provided herein specifically binds to PD-1 and inhibits IL-22 secretion by at least about 85%. In another embodiment, an antibody provided herein specifically binds to PD-1 and inhibits IL-22 secretion by at least about 90%. In one embodiment, an antibody provided herein specifically binds to PD-1 and inhibits IL-22 secretion by at least about 95%. In some embodiments, an antibody provided herein specifically binds to PD-1 and inhibits IL-22 secretion by at least about 98%. In another embodiment, an antibody provided herein specifically binds to PD-1 and inhibits IL-22 secretion by at least about 99%. In specific embodiments, antibodies provided herein specifically bind to PD-1 and inhibit IL-22 secretion by at least about 25% or 35%, optionally to about 75%. In some embodiments, the inhibition of IL-22 secretion is assessed by methods described herein. In other embodiments, the inhibition of IL-22 secretion is assessed by methods known to one of skill in the art (e.g., MSD multiplex assay). In a specific embodiment, the IL-22 secretion is inhibited relative to IL-22 secretion in the absence of anti-PD-1 antibody. In other embodiments, the IL-22 secretion is inhibited relative to IL-22 secretion in the presence of an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) inhibits IL-22 secretion. In one embodiment, an anti-PD-1 antibody provided herein inhibits IL-22 secretion with an $EC_{50}$ of at most about 50 nM. In other embodiments, an anti-PD-1 antibody provided herein inhibits IL-22 secretion with an $EC_{50}$ of at most about 40 nM. In another embodiment, an anti-PD-1 antibody provided herein inhibits IL-22 secretion with an $EC_{50}$ of at most about 30 nM. In some embodiments, an anti-PD-1 antibody provided herein inhibits IL-22 secretion with an $EC_{50}$ of at most about 20 nM. In one embodiment, an anti-PD-1 antibody provided herein inhibits IL-22 secretion with an $EC_{50}$ of at most about 10 nM. In another embodiment, an anti-PD-1 antibody provided herein inhibits IL-22 secretion with an $EC_{50}$ of at most about 5 nM. In one embodiment, an anti-PD-1 antibody provided herein inhibits IL-22 secretion with an $EC_{50}$ of at most about 1 nM. In some embodiments, an anti-PD-1 antibody provided herein inhibits IL-22 secretion with an $EC_{50}$ of at most about 0.75 nM. In another embodiment, an anti-PD-1 antibody provided herein inhibits IL-22 secretion with an $EC_{50}$ of at most about 0.5 nM. In other embodiments, an anti-PD-1 antibody provided herein inhibits IL-22 secretion with an $EC_{50}$ of at most about 0.1 nM. In one embodiment, an anti-PD-1 antibody provided herein inhibits IL-22 secretion with an $EC_{50}$ of at most about 0.05 nM. In another embodiment, an anti-PD-1 antibody provided herein inhibits IL-22 secretion with an $EC_{50}$ of at most about 0.01 nM. In some embodiments, an anti-PD-1 antibody provided herein inhibits IL-22 secretion with an $EC_{50}$ of at most about 0.005 nM. In one embodiment, an anti-PD-1 antibody provided herein inhibits IL-22 secretion with an $EC_{50}$ of at most about 0.001 nM. In another embodiment, an anti-PD-1 antibody provided herein inhibits IL-22 secretion with an $EC_{50}$ of at least about 50 nM. In other embodiments, an anti-PD-1 antibody provided herein inhibits IL-22 secretion with an $EC_{50}$ of at least about 40 nM. In some embodiments, an anti-PD-1 antibody provided herein inhibits IL-22 secretion with an $EC_{50}$ of at least about 30 nM. In another embodiment, an anti-PD-1 antibody provided herein inhibits IL-22 secretion with an $EC_{50}$ of at least about 20 nM. In one embodiment, an anti-PD-1 antibody provided herein inhibits IL-22 secretion with an $EC_{50}$ of at least about 10 nM. In one embodiment, an anti-PD-1 antibody provided herein inhibits IL-22 secretion with an $EC_{50}$ of at least about 5 nM. In another embodiment, an anti-PD-1 antibody provided herein inhibits IL-22 secretion with an $EC_{50}$ of at least about 1 nM. In some embodiments, an anti-PD-1 antibody provided herein inhibits IL-22 secretion with an $EC_{50}$ of at least about 0.75 nM. In other embodiments, an anti-PD-1 antibody provided herein inhibits IL-22 secretion with an $EC_{50}$ of at least about 0.5 nM. In another embodiment, an anti-PD-1 antibody provided herein inhibits IL-22 secretion with an $EC_{50}$ of at least about 0.1 nM. In one embodiment, an anti-PD-1 antibody provided herein inhibits IL-22 secretion with an $EC_{50}$ of at least about 0.05 nM. In some embodiments, an anti-PD-1 antibody provided herein inhibits IL-22 secretion with an $EC_{50}$ of at least about 0.01 nM. In another embodiment, an anti-PD-1 antibody provided herein inhibits IL-22 secretion with an $EC_{50}$ of at least about 0.005 nM. In one embodiment, an anti-PD-1 antibody provided herein inhibits IL-22 secretion with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., MSD multiplex assay). In a specific embodiment, the $EC_{50}$ is assessed by MSD multiplex assay.

In specific embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and inhibit IL-23 secretion (e.g., from a cell, for example, a T cell). In one embodiment, an antibody provided herein specifically binds to PD-1 and inhibits IL-23 secretion by at least about 5%. In some embodiments, an antibody provided herein specifically binds to PD-1 and inhibits IL-23 secretion by at least about 10%. In another embodiment, an antibody provided herein specifically binds to PD-1 and inhibits IL-23 secretion by at least about 15%. In other embodiments, an antibody provided herein specifically binds to PD-1 and inhibits IL-23 secretion by at least about 20%. In one embodiment, an antibody provided herein specifically binds to PD-1 and inhibits IL-23 secretion by at least about 25%. In another embodiment, an antibody provided herein specifically binds to PD-1 and inhibits IL-23 secretion by at least about 30%. In some embodiments, an antibody provided herein specifically binds to PD-1 and inhibits IL-23 secretion by at least about 35%. In one embodiment, an antibody provided herein specifically binds to PD-1 and inhibits IL-23 secretion by at least about 40%. In another embodiment, an antibody provided herein specifically binds to PD-1 and inhibits IL-23 secretion by at least about 45%. In other embodiments, an antibody provided herein specifically binds to PD-1 and inhibits IL-23 secretion by at least about 50%. In some embodiments, an antibody provided herein specifically binds to PD-1 and inhibits IL-23 secretion by at least about 55%. In another embodiment, an antibody provided herein specifically binds to PD-1 and inhibits IL-23 secretion by at least about 60%. In one embodiment, an antibody provided herein specifically binds to PD-1 and inhibits IL-23 secretion by at least about 65%. In one embodiment, an antibody provided herein specifically binds to PD-1 and inhibits IL-23 secretion by at least about 70%. In another embodiment, an antibody provided herein specifically binds to PD-1 and inhibits IL-23 secretion by at least about 75%. In some embodiments, an antibody provided herein specifically binds to PD-1 and inhibits IL-23 secretion by at least about 80%. In other embodiments, an antibody provided herein specifically binds to PD-1 and inhibits IL-23 secretion by at least about 85%. In another embodiment, an antibody provided herein specifically binds to PD-1 and inhibits IL-23 secretion by at least about 90%. In one embodiment, an antibody provided herein specifically binds to PD-1 and inhibits IL-23 secretion by at least about 95%. In some embodiments, an antibody provided herein specifically binds to PD-1 and inhibits IL-23 secretion by at least about 98%. In another embodiment, an antibody provided herein specifically binds to PD-1 and inhibits IL-23 secretion by at least about 99%. In specific embodiments, antibodies provided herein specifically bind to PD-1 and inhibit IL-23 secretion by at least about 25% or 35%, optionally to about 75%. In some embodiments, the inhibition of IL-23 secretion is assessed by methods described herein. In other embodiments, the inhibition of IL-23 secretion is assessed by methods known to one of skill in the art (e.g., MSD multiplex assay). In a specific embodiment, the IL-23 secretion is inhibited relative to IL-23 secretion in the absence of anti-PD-1 antibody. In other embodiments, the IL-23 secretion is inhibited relative to IL-23 secretion in the presence of an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) inhibits IL-23 secretion. In one embodiment, an anti-PD-1 antibody provided herein inhibits IL-23 secretion with an $EC_{50}$ of at most about 50 nM. In other embodiments, an anti-PD-1 antibody provided herein inhibits IL-23 secretion with an $EC_{50}$ of at most about 40 nM. In another embodiment, an anti-PD-1 antibody provided herein inhibits IL-23 secretion with an $EC_{50}$ of at most about 30 nM. In some embodiments, an anti-PD-1 antibody provided herein inhibits IL-23 secretion with an $EC_{50}$ of at most about 20 nM. In one embodiment, an anti-PD-1 antibody provided herein inhibits IL-23 secretion with an $EC_{50}$ of at most about 10 nM. In another embodiment, an anti-PD-1 antibody provided herein inhibits IL-23 secretion with an $EC_{50}$ of at most about 5 nM. In one embodiment, an anti-PD-1 antibody provided herein inhibits IL-23 secretion with an $EC_{50}$ of at most about 1 nM. In some embodiments, an anti-PD-1 antibody provided herein inhibits IL-23 secretion with an $EC_{50}$ of at most about 0.75 nM. In another embodiment, an anti-PD-1 antibody provided herein inhibits IL-23 secretion with an $EC_{50}$ of at most about 0.5 nM. In other embodiments, an anti-PD-1 antibody provided herein inhibits IL-23 secretion with an $EC_{50}$ of at most about 0.1 nM. In one embodiment, an anti-PD-1 antibody provided herein inhibits IL-23 secretion with an $EC_{50}$ of at most about 0.05 nM. In another embodiment, an anti-PD-1 antibody provided herein inhibits IL-23 secretion with an $EC_{50}$ of at most about 0.01 nM. In some embodiments, an anti-PD-1 antibody provided herein inhibits IL-23 secretion with an $EC_{50}$ of at most about 0.005 nM. In one embodiment, an anti-PD-1 antibody provided herein inhibits IL-23 secretion with an $EC_{50}$ of at most about 0.001 nM. In another embodiment, an anti-PD-1 antibody provided herein inhibits IL-23 secretion with an $EC_{50}$ of at least about 50 nM. In other embodiments, an anti-PD-1 antibody provided herein inhibits IL-23 secretion with an $EC_{50}$ of at least about 40 nM. In some embodiments, an anti-PD-1 antibody provided herein inhibits IL-23 secretion with an $EC_{50}$ of at least about 30 nM. In another embodiment, an anti-PD-1 antibody provided herein inhibits IL-23 secretion with an $EC_{50}$ of at least about 20 nM. In one embodiment, an anti-PD-1 antibody provided herein inhibits IL-23 secretion with an $EC_{50}$ of at least about 10 nM. In one embodiment, an anti-PD-1 antibody provided herein inhibits IL-23 secretion with an $EC_{50}$ of at least about 5 nM. In another embodiment, an anti-PD-1 antibody provided herein inhibits IL-23 secretion with an $EC_{50}$ of at least about 1 nM. In some embodiments, an anti-PD-1 antibody provided herein inhibits IL-23 secretion with an $EC_{50}$ of at least about 0.75 nM. In other embodiments, an anti-PD-1 antibody provided herein inhibits IL-23 secretion with an $EC_{50}$ of at least about 0.5 nM. In another embodiment, an anti-PD-1 antibody provided herein inhibits IL-23 secretion with an $EC_{50}$ of at least about 0.1 nM. In one embodiment, an anti-PD-1 antibody provided herein inhibits IL-23 secretion with an $EC_{50}$ of at least about 0.05 nM. In some embodiments, an anti-PD-1 antibody provided herein inhibits IL-23 secretion with an $EC_{50}$ of at least about 0.01 nM. In another embodiment, an anti-PD-1 antibody provided herein inhibits IL-23 secretion with an $EC_{50}$ of at least about 0.005 nM. In one embodiment, an anti-PD-1 antibody provided herein inhibits IL-23 secretion with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., MSD multiplex assay). In a specific embodiment, the $EC_{50}$ is assessed by MSD multiplex assay.

In specific embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and inhibit GM-CSF secretion (e.g., from a cell, for example, T cells). In one embodiment, an antibody provided herein specifically binds to PD-1 and inhibits GM-CSF secretion by at least about 5%. In some embodiments, an antibody provided herein specifically binds to PD-1 and inhibits GM-CSF secretion by at least about 10%. In another embodiment, an antibody provided herein specifically binds to PD-1 and inhibits GM-CSF secretion by at least about 15%. In other embodiments, an antibody provided herein specifically binds to PD-1 and inhibits GM-CSF secretion by at least about 20%. In one embodiment, an antibody provided herein specifically binds to PD-1 and inhibits GM-CSF secretion by at least about 25%. In another embodiment, an antibody provided herein specifically binds to PD-1 and inhibits GM-CSF secretion by at least about 30%. In some embodiments, an antibody provided herein specifically binds to PD-1 and inhibits GM-CSF secretion by at least about 35%. In one embodiment, an antibody provided herein specifically binds to PD-1 and inhibits GM-CSF secretion by at least about 40%. In another embodiment, an antibody provided herein specifically binds to PD-1 and inhibits GM-CSF secretion by at least about 45%. In other embodiments, an antibody provided herein specifically binds to PD-1 and inhibits GM-CSF secretion by at least about 50%. In some embodiments, an antibody provided herein specifically binds to PD-1 and inhibits GM-CSF secretion by at least about 55%. In another embodiment, an antibody provided herein specifically binds to PD-1 and inhibits GM-CSF secretion by at least about 60%. In one embodiment, an antibody provided herein specifically binds to PD-1 and inhibits GM-CSF secretion by at least about 65%. In one embodiment, an antibody provided herein specifically binds to PD-1 and inhibits GM-CSF secretion by at least about 70%. In another embodiment, an antibody provided herein specifically binds to PD-1 and inhibits GM-CSF secretion by at least about 75%. In some embodiments, an antibody provided herein specifically binds to PD-1 and inhibits GM-CSF secretion by at least about 80%. In other embodiments, an antibody provided herein specifically binds to PD-1 and inhibits GM-CSF secretion by at least about 85%. In another embodiment, an antibody provided herein specifically binds to PD-1 and inhibits GM-CSF secretion by at least about 90%. In one embodiment, an antibody provided herein specifically binds to PD-1 and inhibits GM-CSF secretion by at least about 95%. In some embodiments, an antibody provided herein specifically binds to PD-1 and inhibits GM-CSF secretion by at least about 98%. In another embodiment, an antibody provided herein specifically binds to PD-1 and inhibits GM-CSF secretion by at least about 99%. In specific embodiments, antibodies provided herein specifically bind to PD-1 and inhibit GM-CSF secretion by at least about 25% or 35%, optionally to about 75%. In some embodiments, the inhibition of GM-CSF secretion is assessed by methods described herein. In other embodiments, the inhibition of GM-CSF secretion is assessed by methods known to one of skill in the art (e.g., MSD multiplex assay). In a specific embodiment, the GM-CSF secretion is inhibited relative to GM-CSF secretion in the absence of anti-PD-1 antibody. In other embodiments, the GM-CSF secretion is inhibited relative to GM-CSF secretion in the presence of an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) inhibits GM-CSF secretion. In one embodiment, an anti-PD-1 antibody provided herein inhibits GM-CSF secretion with an $EC_{50}$ of at most about 50 nM. In other embodiments, an anti-PD-1 antibody provided herein inhibits GM-CSF secretion with an $EC_{50}$ of at most about 40 nM. In another embodiment, an anti-PD-1 antibody provided herein inhibits GM-CSF secretion with an $EC_{50}$ of at most about 30 nM. In some embodiments, an anti-PD-1 antibody provided herein inhibits GM-CSF secretion with an $EC_{50}$ of at most about 20 nM. In one embodiment, an anti-PD-1 antibody provided herein inhibits GM-CSF secretion with an $EC_{50}$ of at most about 10 nM. In another embodiment, an anti-PD-1 antibody provided herein inhibits GM-CSF secretion with an $EC_{50}$ of at most about 5 nM. In one embodiment, an anti-PD-1 antibody provided herein inhibits GM-CSF secretion with an $EC_{50}$ of at most about 1 nM. In some embodiments, an anti-PD-1 antibody provided herein inhibits GM-CSF secretion with an $EC_{50}$ of at most about 0.75 nM. In another embodiment, an anti-PD-1 antibody provided herein inhibits GM-CSF secretion with an $EC_{50}$ of at most about 0.5 nM. In other embodiments, an anti-PD-1 antibody provided herein inhibits GM-CSF secretion with an $EC_{50}$ of at most about 0.1 nM. In one embodiment, an anti-PD-1 antibody provided herein inhibits GM-CSF secretion with an $EC_{50}$ of at most about 0.05 nM. In another embodiment, an anti-PD-1 antibody provided herein inhibits GM-CSF secretion with an $EC_{50}$ of at most about 0.01 nM. In some embodiments, an anti-PD-1 antibody provided herein inhibits GM-CSF secretion with an $EC_{50}$ of at most about 0.005 nM. In one embodiment, an anti-PD-1 antibody provided herein inhibits GM-CSF secretion with an $EC_{50}$ of at most about 0.001 nM. In another embodiment, an anti-PD-1 antibody provided herein inhibits GM-CSF secretion with an $EC_{50}$ of at least about 50 nM. In other embodiments, an anti-PD-1 antibody provided herein inhibits GM-CSF secretion with an $EC_{50}$ of at least about 40 nM. In some embodiments, an anti-PD-1 antibody provided herein inhibits GM-CSF secretion with an $EC_{50}$ of at least about 30 nM. In another embodiment, an anti-PD-1 antibody provided herein inhibits GM-CSF secretion with an $EC_{50}$ of at least about 20 nM. In one embodiment, an anti-PD-1 antibody provided herein inhibits GM-CSF secretion with an $EC_{50}$ of at least about 10 nM. In one embodiment, an anti-PD-1 antibody provided herein inhibits GM-CSF secretion with an $EC_{50}$ of at least about 5 nM. In another embodiment, an anti-PD-1 antibody provided herein inhibits GM-CSF secretion with an $EC_{50}$ of at least about 1 nM. In some embodiments, an anti-PD-1 antibody provided herein inhibits GM-CSF secretion with an $EC_{50}$ of at least about 0.75 nM. In other embodiments, an anti-PD-1 antibody provided herein inhibits GM-CSF secretion with an $EC_{50}$ of at least about 0.5 nM. In another embodiment, an anti-PD-1 antibody provided herein inhibits GM-CSF secretion with an $EC_{50}$ of at least about 0.1 nM. In one embodiment, an anti-PD-1 antibody provided herein inhibits GM-CSF secretion with an $EC_{50}$ of at least about 0.05 nM. In some embodiments, an anti-PD-1 antibody provided herein inhibits GM-CSF secretion with an $EC_{50}$ of at least about 0.01 nM. In another embodiment, an anti-PD-1 antibody provided herein inhibits GM-CSF secretion with an $EC_{50}$ of at least about 0.005 nM. In one embodiment, an anti-PD-1 antibody provided herein inhibits GM-CSF secretion with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., MSD multiplex assay). In a specific embodiment, the $EC_{50}$ is assessed by MSD multiplex assay.

In specific embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and inhibit TNF-α secretion (e.g., from a cell, for example, a T cell). In one embodiment, an antibody provided herein specifically binds to PD-1 and inhibits TNF-α secretion by at least about 5%. In some embodiments, an antibody provided herein specifically binds to PD-1 and inhibits TNF-α secretion by at least about 10%. In another embodiment, an antibody provided herein specifically binds to PD-1 and inhibits TNF-α secretion by at least about 15%. In other embodiments, an antibody provided herein specifically binds to PD-1 and inhibits TNF-α secretion by at least about 20%. In one embodiment, an antibody provided herein specifically binds to PD-1 and inhibits TNF-α secretion by at least about 25%. In another embodiment, an antibody provided herein specifically binds to PD-1 and inhibits TNF-α secretion by at least about 30%. In some embodiments, an antibody provided herein specifically binds to PD-1 and inhibits TNF-α secretion by at least about 35%. In one embodiment, an antibody provided herein specifically binds to PD-1 and inhibits TNF-α secretion by at least about 40%. In another embodiment, an antibody provided herein specifically binds to PD-1 and inhibits TNF-α secretion by at least about 45%. In other embodiments, an antibody provided herein specifically binds to PD-1 and inhibits TNF-α secretion by at least about 50%. In some embodiments, an antibody provided herein specifically binds to PD-1 and inhibits TNF-α secretion by at least about 55%. In another embodiment, an antibody provided herein specifically binds to PD-1 and inhibits TNF-α secretion by at least about 60%. In one embodiment, an antibody provided herein specifically binds to PD-1 and inhibits TNF-α secretion by at least about 65%. In one embodiment, an antibody provided herein specifically binds to PD-1 and inhibits TNF-α secretion by at least about 70%. In another embodiment, an antibody provided herein specifically binds to PD-1 and inhibits TNF-α secretion by at least about 75%. In some embodiments, an antibody provided herein specifically binds to PD-1 and inhibits TNF-α secretion by at least about 80%. In other embodiments, an antibody provided herein specifically binds to PD-1 and inhibits TNF-α secretion by at least about 85%. In another embodiment, an antibody provided herein specifically binds to PD-1 and inhibits TNF-α secretion by at least about 90%. In one embodiment, an antibody provided herein specifically binds to PD-1 and inhibits TNF-α secretion by at least about 95%. In some embodiments, an antibody provided herein specifically binds to PD-1 and inhibits TNF-α secretion by at least about 98%. In another embodiment, an antibody provided herein specifically binds to PD-1 and inhibits TNF-α secretion by at least about 99%. In specific embodiments, antibodies provided herein specifically bind to PD-1 and inhibit TNF-α secretion by at least about 25% or 35%, optionally to about 75%. In some embodiments, the inhibition of TNF-α secretion is assessed by methods described herein. In other embodiments, the inhibition of TNF-α secretion is assessed by methods known to one of skill in the art (e.g., MSD multiplex assay). In a specific embodiment, the TNF-α secretion is inhibited relative to TNF-α secretion in the absence of anti-PD-1 antibody. In other embodiments, the TNF-α secretion is inhibited relative to TNF-α secretion in the presence of an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) inhibits TNF-α secretion. In one embodiment, an anti-PD-1 antibody provided herein inhibits TNF-α secretion with an $EC_{50}$ of at most about 50 nM. In other embodiments, an anti-PD-1 antibody provided herein inhibits TNF-α secretion with an $EC_{50}$ of at most about 40 nM. In another embodiment, an anti-PD-1 antibody provided herein inhibits TNF-α secretion with an $EC_{50}$ of at most about 30 nM. In some embodiments, an anti-PD-1 antibody provided herein inhibits TNF-α secretion with an $EC_{50}$ of at most about 20 nM. In one embodiment, an anti-PD-1 antibody provided herein inhibits TNF-α secretion with an $EC_{50}$ of at most about 10 nM. In another embodiment, an anti-PD-1 antibody provided herein inhibits TNF-α secretion with an $EC_{50}$ of at most about 5 nM. In one embodiment, an anti-PD-1 antibody provided herein inhibits TNF-α secretion with an $EC_{50}$ of at most about 1 nM. In some embodiments, an anti-PD-1 antibody provided herein inhibits TNF-α secretion with an $EC_{50}$ of at most about 0.75 nM. In another embodiment, an anti-PD-1 antibody provided herein inhibits TNF-α secretion with an $EC_{50}$ of at most about 0.5 nM. In other embodiments, an anti-PD-1 antibody provided herein inhibits TNF-α secretion with an $EC_{50}$ of at most about 0.1 nM. In one embodiment, an anti-PD-1 antibody provided herein inhibits TNF-α secretion with an $EC_{50}$ of at most about 0.05 nM. In another embodiment, an anti-PD-1 antibody provided herein inhibits TNF-α secretion with an $EC_{50}$ of at most about 0.01 nM. In some embodiments, an anti-PD-1 antibody provided herein inhibits TNF-α secretion with an $EC_{50}$ of at most about 0.005 nM. In one embodiment, an anti-PD-1 antibody provided herein inhibits TNF-α secretion with an $EC_{50}$ of at most about 0.001 nM. In another embodiment, an anti-PD-1 antibody provided herein inhibits TNF-α secretion with an $EC_{50}$ of at least about 50 nM. In other embodiments, an anti-PD-1 antibody provided herein inhibits TNF-α secretion with an $EC_{50}$ of at least about 40 nM. In some embodiments, an anti-PD-1 antibody provided herein inhibits TNF-α secretion with an $EC_{50}$ of at least about 30 nM. In another embodiment, an anti-PD-1 antibody provided herein inhibits TNF-α secretion with an $EC_{50}$ of at least about 20 nM. In one embodiment, an anti-PD-1 antibody provided herein inhibits TNF-α secretion with an $EC_{50}$ of at least about 10 nM. In one embodiment, an anti-PD-1 antibody provided herein inhibits TNF-α secretion with an $EC_{50}$ of at least about 5 nM. In another embodiment, an anti-PD-1 antibody provided herein inhibits TNF-α secretion with an $EC_{50}$ of at least about 1 nM. In some embodiments, an anti-PD-1 antibody provided herein inhibits TNF-α secretion with an $EC_{50}$ of at least about 0.75 nM. In other embodiments, an anti-PD-1 antibody provided herein inhibits TNF-α secretion with an $EC_{50}$ of at least about 0.5 nM. In another embodiment, an anti-PD-1 antibody provided herein inhibits TNF-α secretion with an $EC_{50}$ of at least about 0.1 nM. In one embodiment, an anti-PD-1 antibody provided herein inhibits TNF-α secretion with an $EC_{50}$ of at least about 0.05 nM. In some embodiments, an anti-PD-1 antibody provided herein inhibits TNF-α secretion with an $EC_{50}$ of at least about 0.01 nM. In another embodiment, an anti-PD-1 antibody provided herein inhibits TNF-α secretion with an $EC_{50}$ of at least about 0.005 nM. In one embodiment, an anti-PD-1 antibody provided herein inhibits TNF-α secretion with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., MSD multiplex assay). In a specific embodiment, the $EC_{50}$ is assessed by MSD multiplex assay.

In specific embodiments, antibodies provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) specifically bind to PD-1 and downregulate PD-1 expression (e.g., in a cell, for example, T cells). In one embodiment, an antibody provided herein specifically binds to PD-1 and downregulates PD-1 expression by at least about 5%. In one embodiment, an antibody provided herein specifically binds to PD-1 and downregulates PD-1 expression by at least about 10%. In another embodiment, an antibody provided herein specifically binds to PD-1 and downregulates PD-1 expression by at least about 15%. In some embodiments, an antibody provided herein specifically binds to PD-1 and downregulates PD-1 expression by at least about 20%. In other embodiments, an antibody provided herein specifically binds to PD-1 and downregulates PD-1 expression by at least about 25%. In another embodiment, an antibody provided herein specifically binds to PD-1 and downregulates PD-1 expression by at least about 30%. In one embodiment, an antibody provided herein specifically binds to PD-1 and downregulates PD-1 expression by at least about 35%. In some embodiments, an antibody provided herein specifically binds to PD-1 and downregulates PD-1 expression by at least about 40%. In another embodiment, an antibody provided herein specifically binds to PD-1 and downregulates PD-1 expression by at least about 45%. In one embodiment, an antibody provided herein specifically binds to PD-1 and downregulates PD-1 expression by at least about 50%. In other embodiments, an antibody provided herein specifically binds to PD-1 and downregulates PD-1 expression by at least about 55%. In another embodiment, an antibody provided herein specifically binds to PD-1 and downregulates PD-1 expression by at least about 60%. In some embodiments, an antibody provided herein specifically binds to PD-1 and downregulates PD-1 expression by at least about 65%. In one embodiment, an antibody provided herein specifically binds to PD-1 and downregulates PD-1 expression by at least about 70%. In another embodiment, an antibody provided herein specifically binds to PD-1 and downregulates PD-1 expression by at least about 75%. In one embodiment, an antibody provided herein specifically binds to PD-1 and downregulates PD-1 expression by at least about 80%. In some embodiments, an antibody provided herein specifically binds to PD-1 and downregulates PD-1 expression by at least about 85%. In another embodiment, an antibody provided herein specifically binds to PD-1 and downregulates PD-1 expression by at least about 90%. In other embodiments, an antibody provided herein specifically binds to PD-1 and downregulates PD-1 expression by at least about 95%. In one embodiment, an antibody provided herein specifically binds to PD-1 and downregulates PD-1 expression by at least about 98%. In another embodiment, an antibody provided herein specifically binds to PD-1 and downregulates PD-1 expression by at least about 99%. In specific embodiments, antibodies provided herein specifically bind to PD-1 and downregulates PD-1 expression by at least about 25% or 35%, optionally to about 75%. In some embodiments, the downregulation of PD-1 expression is assessed by methods described herein. In other embodiments, the downregulation of PD-1 expression is assessed by methods known to one of skill in the art (e.g., flow cytometry, Western blotting, Northern blotting, or RT-PCR). In a specific embodiment, the downregulation of PD-1 expression is assessed by flow cytometry. In another embodiment, the downregulation of PD-1 expression is assessed by Western blotting. In yet another embodiment, the downregulation of PD-1 expression is assessed by Northern blotting. In still another embodiment, the downregulation of PD-1 expression is assessed by RT-PCR. In a specific embodiment, the PD-1 expression is downregulated relative to PD-1 expression downregulation in the absence of anti-PD-1 antibody. In other embodiments, the PD-1 expression is downregulated relative to PD-1 expression downregulation in the presence of an unrelated antibody (e.g., an antibody that does not specifically bind to PD-1).

In certain embodiments, an anti-PD-1 antibody provided herein (e.g., any one of antibodies PD1AB-1, PD1AB-2, PD1AB-3, PD1AB-4, PD1AB-5, or PD1AB-6 or an antigen-binding fragment thereof, or an antibody comprising CDRs of any one of antibodies PD1AB-1, PD1AB-2, PD1AB-3, PD1AB-4, PD1AB-5, or PD1AB-6) downregulates PD-1 expression. In one embodiment, an anti-PD-1 antibody provided herein downregulates PD-1 expression with an $EC_{50}$ of at most about 50 nM. In other embodiments, an anti-PD-1 antibody provided herein downregulates PD-1 expression with an $EC_{50}$ of at most about 40 nM. In another embodiment, an anti-PD-1 antibody provided herein downregulates PD-1 expression with an $EC_{50}$ of at most about 30 nM. In some embodiments, an anti-PD-1 antibody provided herein downregulates PD-1 expression with an $EC_{50}$ of at most about 20 nM. In one embodiment, an anti-PD-1 antibody provided herein downregulates PD-1 expression with an $EC_{50}$ of at most about 10 nM. In another embodiment, an anti-PD-1 antibody provided herein downregulates PD-1 expression with an $EC_{50}$ of at most about 5 nM. In one embodiment, an anti-PD-1 antibody provided herein downregulates PD-1 expression with an $EC_{50}$ of at most about 1 nM. In some embodiments, an anti-PD-1 antibody provided herein downregulates PD-1 expression with an $EC_{50}$ of at most about 0.75 nM. In another embodiment, an anti-PD-1 antibody provided herein downregulates PD-1 expression with an $EC_{50}$ of at most about 0.5 nM. In other embodiments, an anti-PD-1 antibody provided herein downregulates PD-1 expression with an $EC_{50}$ of at most about 0.1 nM. In one embodiment, an anti-PD-1 antibody provided herein downregulates PD-1 expression with an $EC_{50}$ of at most about 0.05 nM. In another embodiment, an anti-PD-1 antibody provided herein downregulates PD-1 expression with an $EC_{50}$ of at most about 0.01 nM. In some embodiments, an anti-PD-1 antibody provided herein downregulates PD-1 expression with an $EC_{50}$ of at most about 0.005 nM. In one embodiment, an anti-PD-1 antibody provided herein downregulates PD-1 expression with an $EC_{50}$ of at most about 0.001 nM. In another embodiment, an anti-PD-1 antibody provided herein downregulates PD-1 expression with an $EC_{50}$ of at least about 50 nM. In other embodiments, an anti-PD-1 antibody provided herein downregulates PD-1 expression with an $EC_{50}$ of at least about 40 nM. In some embodiments, an anti-PD-1 antibody provided herein downregulates PD-1 expression with an $EC_{50}$ of at least about 30 nM. In another embodiment, an anti-PD-1 antibody provided herein downregulates PD-1 expression with an $EC_{50}$ of at least about 20 nM. In one embodiment, an anti-PD-1 antibody provided herein downregulates PD-1 expression with an $EC_{50}$ of at least about 10 nM. In one embodiment, an anti-PD-1 antibody provided herein downregulates PD-1 expression with an $EC_{50}$ of at least about 5 nM. In another embodiment, an anti-PD-1 antibody provided herein downregulates PD-1 expression with an $EC_{50}$ of at least about 1 nM. In some embodiments, an anti-PD-1 antibody provided herein downregulates PD-1 expression with an $EC_{50}$ of at least about 0.75 nM. In other embodiments, an anti-PD-1 antibody provided herein downregulates PD-1 expression with an $EC_{50}$ of at least about 0.5 nM. In another embodiment, an anti-PD-1 antibody provided herein downregulates PD-1 expression with an $EC_{50}$ of at least about 0.1 nM. In one embodiment, an anti-PD-1 antibody provided herein downregulates PD-1 expression with an $EC_{50}$ of at least about 0.05 nM. In some embodiments, an anti-PD-1 antibody provided herein downregulates PD-1 expression with an $EC_{50}$ of at least about 0.01 nM. In another embodiment, an anti-PD-1 antibody provided herein downregulates PD-1 expression with an $EC_{50}$ of at least about 0.005 nM. In one embodiment, an anti-PD-1 antibody provided herein downregulates PD-1 expression with an $EC_{50}$ of at least about 0.001 nM. In specific embodiments, the $EC_{50}$ is assessed by methods described herein. In other embodiments, the $EC_{50}$ is assessed by other methods known to one of skill in the art (e.g., flow cytometry, Western blotting, Northern blotting, or RT-PCR). In a specific embodiment, the $EC_{50}$ is assessed by flow cytometry. In another embodiment, the $EC_{50}$ is assessed by Western blotting. In yet another embodiment, the $EC_{50}$ is assessed by Northern blotting. In still another embodiment, the $EC_{50}$ is assessed by RT-PCR.

In certain embodiments of the methods, the downregulation of PD-1 expression on the surface of T cells occurs as early as 4 hours after the contact with the antibody or antigen-binding fragment thereof. In another embodiment, the downregulation occurs as early as 6 hours after the contact. In yet another embodiment, the downregulation occurs as early as 8 hours after the contact. In still another embodiment, the downregulation occurs as early as 10 hours after the contact. In one embodiment, the downregulation occurs as early as 12 hours after the contact. In another embodiment, the downregulation occurs as early as 14 hours after the contact. In yet another embodiment, the downregulation occurs as early as 16 hours after the contact. In still another embodiment, the downregulation occurs as early as 18 hours after the contact. In one embodiment, the downregulation occurs as early as 20 hours after the contact. In another embodiment, the downregulation occurs as early as 22 hours after the contact. In yet another embodiment, the downregulation occurs as early as 24 hours after the contact. In some embodiments, the contact is with the antibody. In other embodiments, the contact is with an antigen-binding fragment thereof.

In some embodiments, the downregulation of PD-1 expression on the surface of T cells precedes cytokine inhibition. In one embodiment, the downregulation of PD-1 expression on the surface of T cells occurs as early as 4 hours after the contact with the antibody or antigen-binding fragment thereof, and precedes cytokine inhibition. In another embodiment, the downregulation occurs as early as 6 hours after the contact with the antibody or antigen-binding fragment thereof, and precedes cytokine inhibition. In yet another embodiment, the downregulation occurs as early as 8 hours after the contact with the antibody or antigen-binding fragment thereof, and precedes cytokine inhibition. In still another embodiment, the downregulation occurs as early as 10 hours after the contact with the antibody or antigen-binding fragment thereof, and precedes cytokine inhibition. In one embodiment, the downregulation occurs as early as 12 hours after the contact with the antibody or antigen-binding fragment thereof, and precedes cytokine inhibition. In another embodiment, the downregulation occurs as early as 14 hours after the contact with the antibody or antigen-binding fragment thereof, and precedes cytokine inhibition. In yet another embodiment, the downregulation occurs as early as 16 hours after the contact with the antibody or antigen-binding fragment thereof, and precedes cytokine inhibition. In still another embodiment, the downregulation occurs as early as 18 hours after the contact with the antibody or antigen-binding fragment thereof, and precedes cytokine inhibition. In one embodiment, the downregulation occurs as early as 20 hours after the contact with the antibody or antigen-binding fragment thereof, and precedes cytokine inhibition. In another embodiment, the downregulation occurs as early as 22 hours after the contact with the antibody or antigen-binding fragment thereof, and precedes cytokine inhibition. In yet another embodiment, the downregulation occurs as early as 24 hours after the contact with the antibody or antigen-binding fragment thereof, and precedes cytokine inhibition.

In other embodiments, the downregulation of PD-1 expression on the surface of T cells is concurrent with cytokine inhibition. In one embodiment, the downregulation of PD-1 expression on the surface of T cells occurs as early as 4 hours after the contact with the antibody or antigen-binding fragment thereof, and is concurrent with cytokine inhibition. In another embodiment, the downregulation occurs as early as 6 hours after the contact with the antibody or antigen-binding fragment thereof, and is concurrent with cytokine inhibition. In yet another embodiment, the downregulation occurs as early as 8 hours after the contact with the antibody or antigen-binding fragment thereof, and is concurrent with cytokine inhibition. In still another embodiment, the downregulation occurs as early as 10 hours after the contact with the antibody or antigen-binding fragment thereof, and is concurrent with cytokine inhibition. In one embodiment, the downregulation occurs as early as 12 hours after the contact with the antibody or antigen-binding fragment thereof, and is concurrent with cytokine inhibition. In another embodiment, the downregulation occurs as early as 14 hours after the contact with the antibody or antigen-binding fragment thereof, and is concurrent with cytokine inhibition. In yet another embodiment, the downregulation occurs as early as 16 hours after the contact with the antibody or antigen-binding fragment thereof, and is concurrent with cytokine inhibition. In still another embodiment, the downregulation occurs as early as 18 hours after the contact with the antibody or antigen-binding fragment thereof, and is concurrent with cytokine inhibition. In one embodiment, the downregulation occurs as early as 20 hours after the contact with the antibody or antigen-binding fragment thereof, and is concurrent with cytokine inhibition. In another embodiment, the downregulation occurs as early as 22 hours after the contact with the antibody or antigen-binding fragment thereof, and is concurrent with cytokine inhibition. In yet another embodiment, the downregulation occurs as early as 24 hours after the contact with the antibody or antigen-binding fragment thereof, and is concurrent with cytokine inhibition.

In yet other embodiments, the downregulation of PD-1 expression on the surface of T cells is after cytokine inhibition. In one embodiment, the downregulation of PD-1 expression on the surface of T cells occurs as early as 4 hours after the contact with the antibody or antigen-binding fragment thereof, and is after cytokine inhibition. In another embodiment, the downregulation occurs as early as 6 hours after the contact with the antibody or antigen-binding fragment thereof, and is after cytokine inhibition. In yet another embodiment, the downregulation occurs as early as 8 hours after the contact with the antibody or antigen-binding fragment thereof, and is after cytokine inhibition. In still another embodiment, the downregulation occurs as early as 10 hours after the contact with the antibody or antigen-binding fragment thereof, and is after cytokine inhibition. In one embodiment, the downregulation occurs as early as 12 hours after the contact with the antibody or antigen-binding fragment thereof, and is after cytokine inhibition. In another embodiment, the downregulation occurs as early as 14 hours after the contact with the antibody or antigen-binding fragment thereof, and is after cytokine inhibition. In yet another embodiment, the downregulation occurs as early as 16 hours after the contact with the antibody or antigen-binding fragment thereof, and is after cytokine inhibition. In still another embodiment, the downregulation occurs as early as 18 hours after the contact with the antibody or antigen-binding fragment thereof, and is after cytokine inhibition. In one embodiment, the downregulation occurs as early as 20 hours after the contact with the antibody or antigen-binding fragment thereof, and is after cytokine inhibition. In another embodiment, the downregulation occurs as early as 22 hours after the contact with the antibody or antigen-binding fragment thereof, and is after cytokine inhibition. In yet another embodiment, the downregulation occurs as early as 24 hours after the contact with the antibody or antigen-binding fragment thereof, and is after cytokine inhibition.

4.3.1.1 Polyclonal Antibodies

The antibodies of the present disclosure may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include a PD-1 polypeptide or a fusion protein thereof. It may be useful to conjugate the immunizing agent to a protein known to be immunogenic in the mammal being immunized or to immunize the mammal with the protein and one or more adjuvants. Examples of such immunogenic proteins include, but are not limited to, keyhole limpet hemocyanin, serum albumin, bovine thyroglobulin, and soybean trypsin inhibitor. Examples of adjuvants which may be employed include Ribi, CpG, Poly 1C, Freund's complete adjuvant, and MPL-TDM adjuvant (monophosphoryl Lipid A, synthetic trehalose dicorynomycolate). The immunization protocol may be selected by one skilled in the art without undue experimentation. The mammal can then be bled, and the serum assayed for PD-1 antibody titer. If desired, the mammal can be boosted until the antibody titer increases or plateaus. Additionally or alternatively, lymphocytes may be obtained from the immunized animal for fusion and preparation of monoclonal antibodies from hybridoma as described below.

4.3.1.2 Monoclonal Antibodies

The antibodies of the present disclosure may alternatively be monoclonal antibodies. Monoclonal antibodies may be made using the hybridoma method first described by Kohler et al., 1975, Nature 256:495-97, or may be made by recombinant DNA methods (see, e.g., U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice* 59-103 (1986)).

The hybridoma cells thus prepared are seeded and grown in a suitable culture medium which, in certain embodiments, contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which prevent the growth of HGPRT-deficient cells.

Exemplary fusion partner myeloma cells are those that fuse efficiently, support stable high-level production of antibody by the selected antibody-producing cells, and are sensitive to a selective medium that selects against the unfused parental cells. Exemplary myeloma cell lines are murine myeloma lines, such as SP-2 and derivatives, for example, X63-Ag8-653 cells available from the American Type Culture Collection (Manassas, Va.), and those derived from MOPC-21 and MPC-11 mouse tumors available from the Salk Institute Cell Distribution Center (San Diego, Calif.). Human myeloma and mouse-human heteromyeloma cell lines also have been described for the production of human monoclonal antibodies (Kozbor, 1984, Immunol. 133:3001-05; and Brodeur et al., *Monoclonal Antibody Production Techniques and Applications* 51-63 (1987)).

Culture medium in which hybridoma cells are growing is assayed for production of monoclonal antibodies directed against the antigen. The binding specificity of monoclonal antibodies produced by hybridoma cells is determined by immunoprecipitation or by an in vitro binding assay, such as RIA or ELISA. The binding affinity of the monoclonal antibody can, for example, be determined by the Scatchard analysis described in Munson et al., 1980, Anal. Biochem. 107:220-39.

Once hybridoma cells that produce antibodies of the desired specificity, affinity, and/or activity are identified, the clones may be subcloned by limiting dilution procedures and grown by standard methods (Goding, supra). Suitable culture media for this purpose include, for example, DMEM or RPMI-1640 medium. In addition, the hybridoma cells may be grown in vivo as ascites tumors in an animal, for example, by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells can serve as a source of such DNA. Once isolated, the DNA may be placed into expression vectors, which are then transfected into host cells, such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., 1993, Curr. Opinion in Immunol. 5:256-62 and Pluckthun, 1992, Immunol. Revs. 130:151-88.

In some embodiments, an antibody that binds a PD-1 epitope comprises an amino acid sequence of a VH domain and/or an amino acid sequence of a VL domain encoded by a nucleotide sequence that hybridizes to (1) the complement of a nucleotide sequence encoding any one of the VH and/or VL domain described herein under stringent conditions (e.g., hybridization to filter-bound DNA in 6× sodium chloride/sodium citrate (SSC) at about 45° C. followed by one or more washes in 0.2×SSC/0.1% SDS at about 50-65° C.), under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art. See, e.g., *Current Protocols in Molecular Biology* Vol. I, 6.3.1-6.3.6 and 2.10.3 (Ausubel et al. eds., 1989).

In some embodiments, an antibody that binds a PD-1 epitope comprises an amino acid sequence of a VH CDR or an amino acid sequence of a VL CDR encoded by a nucleotide sequence that hybridizes to the complement of a nucleotide sequence encoding any one of the VH CDRs and/or VL CDRs depicted in Tables 1-2 under stringent conditions (e.g., hybridization to filter-bound DNA in 6×SSC at about 45° C. followed by one or more washes in 0.2×SSC/0.1% SDS at about 50-65° C.), under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, e.g., Ausubel et al., supra).

In a further embodiment, monoclonal antibodies or antibody fragments can be isolated from antibody phage libraries generated using the techniques described in, for example, *Antibody Phage Display: Methods and Protocols* (O'Brien and Aitken eds., 2002). In principle, synthetic antibody clones are selected by screening phage libraries containing phages that display various fragments of antibody variable region (Fv) fused to phage coat protein. Such phage libraries are screened against the desired antigen. Clones expressing Fv fragments capable of binding to the desired antigen are adsorbed to the antigen and thus separated from the non-binding clones in the library. The binding clones are then eluted from the antigen and can be further enriched by additional cycles of antigen adsorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described, for example, in Winter et al., 1994, Ann. Rev. Immunol. 12:433-55.

Repertoires of VH and VL genes can be separately cloned by PCR and recombined randomly in phage libraries, which can then be searched for antigen-binding clones as described in Winter et al., supra. Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., 1993, EMBO J 12:725-34. Finally, naive libraries can also be made synthetically by cloning the unrearranged V-gene segments from stem cells, and using PCR primers containing random sequence to encode the highly variable CDR3 regions and to accomplish rearrangement in vitro as described, for example, by Hoogenboom and Winter, 1992, J. Mol. Biol. 227:381-88.

Screening of the libraries can be accomplished by various techniques known in the art. For example, PD-1 (e.g., a PD-1 polypeptide, fragment, or epitope) can be used to coat the wells of adsorption plates, expressed on host cells affixed to adsorption plates or used in cell sorting, conjugated to biotin for capture with streptavidin-coated beads, or used in any other method for panning display libraries. The selection of antibodies with slow dissociation kinetics (e.g., good binding affinities) can be promoted by use of long washes and monovalent phage display as described in Bass et al., 1990, Proteins 8:309-14 and WO 92/09690, and by use of a low coating density of antigen as described in Marks et al., 1992, Biotechnol. 10:779-83.

Anti-PD-1 antibodies can be obtained by designing a suitable antigen screening procedure to select for the phage clone of interest followed by construction of a full length anti-PD-1 antibody clone using VH and/or VL sequences (e.g., the Fv sequences), or various CDR sequences from VH and VL sequences, from the phage clone of interest and suitable constant region (e.g., Fc) sequences described in Kabat et al., supra.

In another embodiment, anti-PD-1 antibody is generated by using methods as described in Bowers et al., 2011, Proc Natl Acad Sci USA. 108:20455-60, e.g., the SHM-XHL™ platform (AnaptysBio, San Diego, Calif.). Briefly, in this approach, a fully human library of IgGs is constructed in a mammalian cell line (e.g., HEK293) as a starting library. Mammalian cells displaying immunoglobulin that binds to a target peptide or epitope are selected (e.g., by FACS sorting), then activation-induced cytidine deaminase (AID)-triggered somatic hypermutation is reproduced in vitro to expand diversity of the initially selected pool of antibodies. After several rounds of affinity maturation by coupling mammalian cell surface display with in vitro somatic hypermutation, high affinity, high specificity anti-PD-1 antibodies are generated. Further methods that can be used to generate antibody libraries and/or antibody affinity maturation are disclosed, e.g., in U.S. Pat. Nos. 8,685,897 and 8,603,930, and U.S. Publ. Nos. 2014/0170705, 2014/0094392, 2012/0028301, 2011/0183855, and 2009/0075378, each of which are incorporated herein by reference.

4.3.1.3 Antibody Fragments

The present disclosure provides antibodies and antibody fragments that bind to PD-1. In certain circumstances there are advantages of using antibody fragments, rather than whole antibodies. The smaller size of the fragments allows for rapid clearance, and may lead to improved access to cells, tissues, or organs. For a review of certain antibody fragments, see Hudson et al., 2003, Nature Med. 9:129-34.

Various techniques have been developed for the production of antibody fragments. Traditionally, these fragments were derived via proteolytic digestion of intact antibodies (see, e.g., Morimoto et al., 1992, J. Biochem. Biophys. Methods 24:107-17; and Brennan et al., 1985, Science 229:81-83). However, these fragments can now be produced directly by recombinant host cells. Fab, Fv, and scFv antibody fragments can all be expressed in and secreted from $E.$ $coli$ or yeast cells, thus allowing the facile production of large amounts of these fragments. Antibody fragments can be isolated from the antibody phage libraries discussed above. Alternatively, Fab'-SH fragments can be directly recovered from $E.$ $coli$ and chemically coupled to form $F(ab')_2$ fragments (Carter et al., 1992, Bio/Technology 10:163-67). According to another approach, $F(ab')_2$ fragments can be isolated directly from recombinant host cell culture. Fab and $F(ab')_2$ fragment with increased in vivo half-life comprising salvage receptor binding epitope residues are described in, for example, U.S. Pat. No. 5,869,046. Other techniques for the production of antibody fragments will be apparent to the skilled practitioner. In certain embodiments, an antibody is a single chain Fv fragment (scFv) (see, e.g., WO 93/16185; U.S. Pat. Nos. 5,571,894 and 5,587,458). Fv and scFv have intact combining sites that are devoid of constant regions; thus, they may be suitable for reduced nonspecific binding during in vivo use. scFv fusion proteins may be constructed to yield fusion of an effector protein at either the amino or the carboxy terminus of an scFv (See, e.g., Borrebaeck ed., supra). The antibody fragment may also be a "linear antibody," for example, as described in the references cited above. Such linear antibodies may be monospecific or multi-specific, such as bispecific.

Smaller antibody-derived binding structures are the separate variable domains (V domains) also termed single variable domain antibodies (sdAbs). Certain types of organisms, the camelids and cartilaginous fish, possess high affinity single V-like domains mounted on an Fc equivalent domain structure as part of their immune system. (Woolven et al., 1999, Immunogenetics 50: 98-101; and Streltsov et al., 2004, Proc Natl Acad Sci USA. 101:12444-49). The V-like domains (called VhH in camelids and V-NAR in sharks) typically display long surface loops, which allow penetration of cavities of target antigens. They also stabilize isolated VH domains by masking hydrophobic surface patches.

These VhH and V-NAR domains have been used to engineer sdAbs. Human V domain variants have been designed using selection from phage libraries and other approaches that have resulted in stable, high binding VL- and VH-derived domains.

Antibodies provided herein include, but are not limited to, immunoglobulin molecules and immunologically active portions of immunoglobulin molecules, for example, molecules that contain an antigen binding site that bind to a PD-1 epitope. The immunoglobulin molecules provided herein can be of any class (e.g., IgG, IgE, IgM, IgD, and IgA) or any subclass (e.g., IgG1, IgG2, IgG3, IgG4, IgA1, and IgA2) of immunoglobulin molecule.

Variants and derivatives of antibodies include antibody functional fragments that retain the ability to bind to a PD-1 epitope. Exemplary functional fragments include Fab fragments (e.g., an antibody fragment that contains the antigen-binding domain and comprises a light chain and part of a heavy chain bridged by a disulfide bond); Fab' (e.g., an antibody fragment containing a single antigen-binding domain comprising an Fab and an additional portion of the heavy chain through the hinge region); $F(ab')_2$ (e.g., two Fab' molecules joined by interchain disulfide bonds in the hinge regions of the heavy chains; the Fab' molecules may be directed toward the same or different epitopes); a bispecific Fab (e.g., a Fab molecule having two antigen binding domains, each of which may be directed to a different epitope); a single chain comprising a variable region, also known as, scFv (e.g., the variable, antigen-binding determinative region of a single light and heavy chain of an antibody linked together by a chain of 10-25 amino acids); a disulfide-linked Fv, or dsFv (e.g., the variable, antigen-binding determinative region of a single light and heavy chain of an antibody linked together by a disulfide bond); a camelized VH (e.g., the variable, antigen-binding determinative region of a single heavy chain of an antibody in which some amino acids at the VH interface are those found in the heavy chain of naturally occurring camel antibodies); a bispecific scFv (e.g., an scFv or a dsFv molecule having two antigen-binding domains, each of which may be directed to a different epitope); a diabody (e.g., a dimerized scFv formed when the VH domain of a first scFv assembles with the VL domain of a second scFv and the VL domain of the first scFv assembles with the VH domain of the second scFv; the two antigen-binding regions of the diabody may be directed towards the same or different epitopes); and a triabody (e.g., a trimerized scFv, formed in a manner similar to a diabody, but in which three antigen-binding domains are created in a single complex; the three antigen-binding domains may be directed towards the same or different epitopes).

4.3.1.4 Humanized Antibodies

In some embodiments, antibodies provided herein can be humanized antibodies that bind PD-1, including human and/or cyno PD-1. For example, humanized antibodies of the present disclosure may comprise one or more CDRs as shown in Tables 1-2. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanization may be performed, for example, following the method of Jones et al., 1986, Nature 321:522-25; Riechmann et al., 1988, Nature 332: 323-27; and Verhoeyen et al., 1988, Science 239:1534-36), by substituting hypervariable region sequences for the corresponding sequences of a human antibody.

In some cases, the humanized antibodies are constructed by CDR grafting, in which the amino acid sequences of the six CDRs of the parent non-human antibody (e.g., rodent) are grafted onto a human antibody framework. For example, Padlan et al. determined that only about one third of the residues in the CDRs actually contact the antigen, and termed these the "specificity determining residues," or SDRs (Padlan et al., 1995, FASEB J. 9:133-39). In the technique of SDR grafting, only the SDR residues are grafted onto the human antibody framework (see, e.g., Kashmiri et al., 2005, Methods 36:25-34).

The choice of human variable domains, both light and heavy, to be used in making the humanized antibodies can be important to reduce antigenicity. For example, according to the so-called "best-fit" method, the sequence of the variable domain of a non-human (e.g., rodent) antibody is screened against the entire library of known human variable-domain sequences. The human sequence that is closest to that of the rodent may be selected as the human framework for the humanized antibody (Sims et al., 1993, J. Immunol. 151:2296-308; and Chothia et al., 1987, J. Mol. Biol. 196:901-17). Another method uses a particular framework derived from the consensus sequence of all human antibodies of a particular subgroup of light or heavy chains. The same framework may be used for several different humanized antibodies (Carter et al., 1992, Proc. Natl. Acad. Sci. USA 89:4285-89; and Presta et al., 1993, J. Immunol. 151:2623-32). In some cases, the framework is derived from the consensus sequences of the most abundant human sub-classes, $V_L 6$ subgroup I ($V_L 6I$) and $V_H$ subgroup III ($V_H III$). In another method, human germline genes are used as the source of the framework regions.

In an alternative paradigm based on comparison of CDRs, called superhumanization, FR homology is irrelevant. The method consists of comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs (see, e.g., Tan et al., 2002, J. Immunol. 169:1119-25).

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, 2000, Protein Eng. 13:819-24), Modeller (Sali and Blundell, 1993, J. Mol. Biol. 234:779-815), and Swiss PDB Viewer (Guex and Peitsch, 1997, Electrophoresis 18:2714-23). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Another method for antibody humanization is based on a metric of antibody humanness termed Human String Content (HSC). This method compares the mouse sequence with the repertoire of human germline genes, and the differences are scored as HSC. The target sequence is then humanized by maximizing its HSC rather than using a global identity measure to generate multiple diverse humanized variants (Lazar et al., 2007, Mol. Immunol. 44:1986-98).

In addition to the methods described above, empirical methods may be used to generate and select humanized antibodies. These methods include those that are based upon the generation of large libraries of humanized variants and selection of the best clones using enrichment technologies or high throughput screening techniques. Antibody variants may be isolated from phage, ribosome, and yeast display libraries as well as by bacterial colony screening (see, e.g., Hoogenboom, 2005, Nat. Biotechnol. 23:1105-16; Dufner et al., 2006, Trends Biotechnol. 24:523-29; Feldhaus et al., 2003, Nat. Biotechnol. 21:163-70; and Schlapschy et al., 2004, Protein Eng. Des. Sel. 17:847-60).

In the FR library approach, a collection of residue variants are introduced at specific positions in the FR followed by screening of the library to select the FR that best supports the grafted CDR. The residues to be substituted may include some or all of the "Vernier" residues identified as potentially contributing to CDR structure (see, e.g., Foote and Winter, 1992, J. Mol. Biol. 224:487-99), or from the more limited set of target residues identified by Baca et al. (1997, J. Biol. Chem. 272:10678-84).

In FR shuffling, whole FRs are combined with the non-human CDRs instead of creating combinatorial libraries of selected residue variants (see, e.g., Dall'Acqua et al., 2005, Methods 36:43-60). The libraries may be screened for binding in a two-step process, first humanizing VL, followed by VH. Alternatively, a one-step FR shuffling process may be used. Such a process has been shown to be more efficient than the two-step screening, as the resulting antibodies exhibited improved biochemical and physicochemical properties including enhanced expression, increased affinity, and thermal stability (see, e.g., Damschroder et al., 2007, Mol. Immunol. 44:3049-60).

The "humaneering" method is based on experimental identification of essential minimum specificity determinants (MSDs) and is based on sequential replacement of non-human fragments into libraries of human FRs and assessment of binding. It begins with regions of the CDR3 of non-human VH and VL chains and progressively replaces other regions of the non-human antibody into the human FRs, including the CDR1 and CDR2 of both VH and VL. This methodology typically results in epitope retention and identification of antibodies from multiple subclasses with distinct human V-segment CDRs. Humaneering allows for isolation of antibodies that are 91-96% homologous to human germline gene antibodies (see, e.g., Alfenito, Cambridge Healthtech Institute's Third Annual PEGS, The Protein Engineering Summit, 2007).

The "human engineering" method involves altering a non-human antibody or antibody fragment, such as a mouse or chimeric antibody or antibody fragment, by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human (e.g., mouse) antibody as "low risk," "moderate risk," or "high risk" residues. The classification is performed using a global risk/reward calculation that evaluates the predicted benefits of making particular substitution (e.g., for immunogenicity in humans) against the risk that the substitution will affect the resulting antibody's folding. The particular human amino acid residue to be substituted at a given position (e.g., low or moderate risk) of a non-human (e.g., mouse) antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., 1994, Protein Engineering 7:805-14; U.S. Pat. Nos. 5,766,886; 5,770,196; 5,821,123; and 5,869,619; and PCT Publication WO 93/11794.

4.3.1.5 Human Antibodies

Human anti-PD-1 antibodies can be constructed by combining Fv clone variable domain sequence(s) selected from human-derived phage display libraries with known human constant domain sequences(s). Alternatively, human monoclonal anti-PD-1 antibodies of the present disclosure can be made by the hybridoma method. Human myeloma and mouse-human heteromyeloma cell lines for the production of human monoclonal antibodies have been described, for example, by Kozbor, 1984, J. Immunol. 133:3001-05; Brodeur et al., *Monoclonal Antibody Production Techniques and Applications* 51-63 (1987); and Boerner et al., 1991, J. Immunol. 147:86-95.

It is also possible to produce transgenic animals (e.g., mice) that are capable, upon immunization, of producing a full repertoire of human antibodies in the absence of endogenous immunoglobulin production. Transgenic mice that express human antibody repertoires have been used to generate high-affinity human sequence monoclonal antibodies against a wide variety of potential drug targets (see, e.g., Jakobovits, A., 1995, Curr. Opin. Biotechnol. 6(5):561-66; Bruggemann and Taussing, 1997, Curr. Opin. Biotechnol. 8(4):455-58; U.S. Pat. Nos. 6,075,181 and 6,150,584; and Lonberg et al., 2005, Nature Biotechnol. 23:1117-25).

Alternatively, the human antibody may be prepared via immortalization of human B lymphocytes producing an antibody directed against a target antigen (e.g., such B lymphocytes may be recovered from an individual or may have been immunized in vitro) (see, e.g., Cole et al., *Monoclonal Antibodies and Cancer Therapy* (1985); Boerner et al., 1991, J. Immunol. 147(1):86-95; and U.S. Pat. No. 5,750,373).

Gene shuffling can also be used to derive human antibodies from non-human, for example, rodent antibodies, where the human antibody has similar affinities and specificities to the starting non-human antibody. According to this method, which is also called "epitope imprinting" or "guided selection," either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone (e.g., the epitope guides (imprints) the choice of the human chain partner). When the process is repeated in order to replace the remaining non-human chain, a human antibody is obtained (see, e.g., PCT WO 93/06213; and Osbourn et al., 2005, Methods 36:61-68). Unlike traditional humanization of non-human antibodies by CDR grafting, this technique provides completely human antibodies, which have no FR or CDR residues of non-human origin. Examples of guided selection to humanize mouse antibodies towards cell surface antigens include the folate-binding protein present on ovarian cancer cells (see, e.g., Figini et al., 1998, Cancer Res. 58:991-96) and CD147, which is highly expressed on hepatocellular carcinoma (see, e.g., Bao et al., 2005, Cancer Biol. Ther. 4:1374-80).

A potential disadvantage of the guided selection approach is that shuffling of one antibody chain while keeping the other constant could result in epitope drift. In order to maintain the epitope recognized by the non-human antibody, CDR retention can be applied (see, e.g., Klimka et al., 2000, Br. J. Cancer. 83:252-60; and Beiboer et al., 2000, J. Mol. Biol. 296:833-49). In this method, the non-human VH CDR3 is commonly retained, as this CDR may be at the center of the antigen-binding site and may be the most important region of the antibody for antigen recognition. In some instances, however, VH CDR3 and VL CDR3, as well as VH CDR2, VL CDR2, and VL CDR1 of the non-human antibody may be retained.

4.3.1.6 Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for PD-1 and the other is for any other antigen. In some embodiments, one of the binding specificities is for PD-1, and the other is for another surface antigen expressed on cells expressing PD-1. In certain embodiments, bispecific antibodies may bind to two different epitopes of PD-1. Bispecific antibodies can be prepared as full length antibodies or antibody fragments (e.g., F(ab')$_2$ bispecific antibodies).

Methods for making bispecific antibodies are known in the art, such as, by co-expression of two immunoglobulin heavy chain-light chain pairs, where the two heavy chains have different specificities (see, e.g., Milstein and Cuello, 1983, Nature 305:537-40). For further details of generating bispecific antibodies, see, for example, *Bispecific Antibodies* (Kontermann ed., 2011).

4.3.1.7 Multivalent Antibodies

A multivalent antibody may be internalized (and/or catabolized) faster than a bivalent antibody by a cell expressing an antigen to which the antibodies bind. The antibodies of the present disclosure can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. In certain embodiments, the dimerization domain comprises (or consists of) an Fc region or a hinge region. In this scenario, the antibody will comprise an Fc region and three or more antigen binding sites amino-terminal to the Fc region. In certain embodiments, a multivalent antibody comprises (or consists of) three to about eight antigen binding sites. In one such embodiment, a multivalent antibody comprises (or consists of) four antigen binding sites. The multivalent antibody comprises at least one polypeptide chain (e.g., two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (e.g., four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

4.3.1.8 Fc Engineering

It may be desirable to modify an anti-PD-1 antibody provided herein by Fc engineering. In certain embodiments, the modification to the Fc region of the antibody results in the decrease or elimination of an effector function of the antibody. In certain embodiments, the effector function is ADCC, ADCP, and/or CDC. In some embodiments, the effector function is ADCC. In other embodiments, the effector function is ADCP. In other embodiments, the effector function is CDC. In one embodiment, the effector function is ADCC and ADCP. In one embodiment, the effector function is ADCC and CDC. In one embodiment, the effector function is ADCP and CDC. In one embodiment, the effector function is ADCC, ADCP and CDC. This may be achieved by introducing one or more amino acid substitutions in an Fc region of the antibody. For example, substitutions into human IgG1 using IgG2 residues at positions 233-236 and IgG4 residues at positions 327, 330, and 331 were shown to greatly reduce ADCC and CDC (see, e.g., Armour et al., 1999, Eur. J. Immunol. 29(8):2613-24; and Shields et al., 2001, J. Biol. Chem. 276(9): 6591-604). Other Fc variants are provided elsewhere herein.

To increase the serum half life of the antibody, one may incorporate a salvage receptor binding epitope into the antibody (especially an antibody fragment), for example, as described in U.S. Pat. No. 5,739,277. Term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

4.3.1.9 Alternative Binding Agents

The present disclosure encompasses non-immunoglobulin binding agents that specifically bind to the same epitope as an anti-PD-1 antibody disclosed herein. In some embodiments, a non-immunoglobulin binding agent is identified as an agent that displaces or is displaced by an anti-PD-1 antibody of the present disclosure in a competitive binding assay. These alternative binding agents may include, for example, any of the engineered protein scaffolds known in the art. Such scaffolds may comprise one or more CDRs as shown in Tables 1-2. Such scaffolds include, for example, anticalins, which are based upon the lipocalin scaffold, a protein structure characterized by a rigid beta-barrel that supports four hypervariable loops which form the ligand binding site. Novel binding specificities may be engineered by targeted random mutagenesis in the loop regions, in combination with functional display and guided selection (see, e.g., Skerra, 2008, FEBS J. 275:2677-83). Other suitable scaffolds may include, for example, adnectins, or monobodies, based on the tenth extracellular domain of human fibronectin III (see, e.g., Koide and Koide, 2007, Methods Mol. Biol. 352: 95-109); affibodies, based on the Z domain of staphylococcal protein A (see, e.g., Nygren et al., 2008, FEBS J. 275:2668-76); DARPins, based on ankyrin repeat proteins (see, e.g., Stumpp et al., 2008, Drug. Discov. Today 13:695-701); fynomers, based on the SH3 domain of the human Fyn protein kinase (see, e.g., Grabulovski et al., 2007, J. Biol. Chem. 282:3196-204); affitins, based on Sac7d from *Sulfolobus acidolarius* (see, e.g., Krehenbrink et al., 2008, J. Mol. Biol. 383:1058-68); affilins, based on human y-B-crystallin (see, e.g., Ebersbach et al., 2007, J. Mol. Biol. 372:172-85); avimers, based on the A domain of membrane receptor proteins (see, e.g., Silverman et al., 2005, Biotechnol. 23:1556-61); cysteine-rich knottin peptides (see, e.g., Kolmar, 2008, FEBS J. 275:2684-90); and engineered Kunitz-type inhibitors (see, e.g., Nixon and Wood, 2006, Curr. Opin. Drug. Discov. Dev. 9:261-68). For a review, see, for example, Gebauer and Skerra, 2009, Curr. Opin. Chem. Biol. 13:245-55.

4.3.2 Antibody Variants

In some embodiments, amino acid sequence modification(s) of the antibodies that bind to PD-1 or described herein are contemplated. For example, it may be desirable to improve the binding affinity and/or other biological properties of the antibody, including but not limited to specificity, thermostability, expression level, effector functions, glycosylation, reduced immunogenicity, or solubility. Thus, in addition to the anti-PD-1 antibodies provided herein, it is contemplated that anti-PD-1 antibody variants can be prepared. For example, anti-PD-1 antibody variants can be prepared by introducing appropriate nucleotide changes into the encoding DNA, and/or by synthesis of the desired antibody or polypeptide. Those skilled in the art who appreciate that amino acid changes may alter post-translational processes of the anti-PD-1 antibody, such as changing the number or position of glycosylation sites or altering the membrane anchoring characteristics.

In some embodiments, antibodies provided herein are chemically modified, for example, by the covalent attachment of any type of molecule to the antibody. The antibody derivatives may include antibodies that have been chemically modified, for example, by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formulation, metabolic synthesis of tunicamycin, etc. Additionally, the antibody may contain one or more non-classical amino acids.

Variations may be a substitution, deletion, or insertion of one or more codons encoding the antibody or polypeptide that results in a change in the amino acid sequence as compared with the native sequence antibody or polypeptide. Amino acid substitutions can be the result of replacing one amino acid with another amino acid having similar structural and/or chemical properties, such as the replacement of a leucine with a serine, e.g., conservative amino acid replacements. Insertions or deletions may optionally be in the range of about 1 to 5 amino acids. In certain embodiments, the substitution, deletion, or insertion includes fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, or fewer than 2 amino acid substitutions relative to the original molecule. In a specific embodiment, the substitution is a conservative amino acid substitution made at one or more predicted non-essential amino acid residues. The variation allowed may be determined by systematically making insertions, deletions, or substitutions of amino acids in the sequence and testing the resulting variants for activity exhibited by the full-length or mature native sequence.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for antibody-directed enzyme prodrug therapy) or a polypeptide which increases the serum half-life of the antibody.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Alternatively, conservative (e.g., within an amino acid group with similar properties and/or side chains) substitutions may be made, so as to maintain or not significantly change the properties. Amino acids may be grouped according to similarities in the properties of their side chains (see, e.g., Lehninger, *Biochemistry* 73-75 (2d ed. 1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); and (4) basic: Lys (K), Arg (R), His (H).

Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

Non-conservative substitutions entail exchanging a member of one of these classes for another class. Such substituted residues also may be introduced into the conservative substitution sites or, into the remaining (non-conserved) sites. Accordingly, in one embodiment, an antibody or fragment thereof that binds to a PD-1 epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a murine monoclonal antibody provided herein. In one embodiment, an antibody or fragment thereof that binds to a PD-1 epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence depicted in Tables 1-6. In yet another embodiment, an antibody or fragment thereof that binds to a PD-1 epitope comprises a VH CDR and/or a VL CDR amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to a VH CDR amino acid sequence depicted in Table 2 and/or a VL CDR amino acid sequence depicted in Table 1. The variations can be made using methods known in the art such as oligonucleotide-mediated (site-directed) mutagenesis, alanine scanning, and PCR mutagenesis. Site-directed mutagenesis (see, e.g., Carter, 1986, Biochem J. 237:1-7; and Zoller et al., 1982, Nucl. Acids Res. 10:6487-500), cassette mutagenesis (see, e.g., Wells et al., 1985, Gene 34:315-23), or other known techniques can be performed on the cloned DNA to produce the anti-PD-1 antibody variant DNA.

Any cysteine residue not involved in maintaining the proper conformation of the anti-PD-1 antibody also may be substituted, for example, with another amino acid, such as alanine or serine, to improve the oxidative stability of the molecule and to prevent aberrant crosslinking. Conversely, cysteine bond(s) may be added to the anti-PD-1 antibody to improve its stability (e.g., where the antibody is an antibody fragment such as an Fv fragment).

In some embodiments, an anti-PD-1 antibody molecule of the present disclosure is a "de-immunized" antibody. A "de-immunized" anti-PD-1 antibody is an antibody derived from a humanized or chimeric anti-PD-1 antibody, which has one or more alterations in its amino acid sequence resulting in a reduction of immunogenicity of the antibody, compared to the respective original non-de-immunized antibody. One of the procedures for generating such antibody mutants involves the identification and removal of T cell epitopes of the antibody molecule. In a first step, the immunogenicity of the antibody molecule can be determined by several methods, for example, by in vitro determination of T cell epitopes or in silico prediction of such epitopes, as known in the art. Once the critical residues for T cell epitope function have been identified, mutations can be made to remove immunogenicity and retain antibody activity. For review, see, for example, Jones et al., 2009, Methods in Molecular Biology 525:405-23.

4.3.2.1 In Vitro Affinity Maturation

In some embodiments, antibody variants having an improved property such as affinity, stability, or expression level as compared to a parent antibody may be prepared by in vitro affinity maturation. Like the natural prototype, in vitro affinity maturation is based on the principles of mutation and selection. Libraries of antibodies are displayed as Fab, scFv, or V domain fragments either on the surface of an organism (e.g., phage, bacteria, yeast, or mammalian cell) or in association (e.g., covalently or non-covalently) with their encoding mRNA or DNA. Affinity selection of the displayed antibodies allows isolation of organisms or complexes carrying the genetic information encoding the antibodies. Two or three rounds of mutation and selection using display methods such as phage display usually results in antibody fragments with affinities in the low nanomolar range. Affinity matured antibodies can have nanomolar or even picomolar affinities for the target antigen.

Phage display is a widespread method for display and selection of antibodies. The antibodies are displayed on the surface of Fd or M13 bacteriophages as fusions to the bacteriophage coat protein. Selection involves exposure to antigen to allow phage-displayed antibodies to bind their targets, a process referred to as "panning." Phage bound to antigen are recovered and used to infect bacteria to produce phage for further rounds of selection. For review, see, for example, Hoogenboom, 2002, Methods. Mol. Biol. 178:1-37; and Bradbury and Marks, 2004, J. Immunol. Methods 290:29-49.

In a yeast display system (see, e.g., Boder et al., 1997, Nat. Biotech. 15:553-57; and Chao et al., 2006, Nat. Protocols 1:755-68), the antibody may be displayed as single-chain variable fusions (scFv) in which the heavy and light chains are connected by a flexible linker. The scFv is fused to the adhesion subunit of the yeast agglutinin protein Aga2p, which attaches to the yeast cell wall through disulfide bonds to Aga1p. Display of a protein via Aga2p projects the protein away from the cell surface, minimizing potential interactions with other molecules on the yeast cell wall. Magnetic separation and flow cytometry are used to screen the library to select for antibodies with improved affinity or stability. Binding to a soluble antigen of interest is determined by labeling of yeast with biotinylated antigen and a secondary reagent such as streptavidin conjugated to a fluorophore. Variations in surface expression of the antibody can be measured through immunofluorescence labeling of either the hemagglutinin or c-Myc epitope tag flanking the scFv. Expression has been shown to correlate with the stability of the displayed protein, and thus antibodies can be selected for improved stability as well as affinity (see, e.g., Shusta et al., 1999, J. Mol. Biol. 292:949-56). An additional advantage of yeast display is that displayed proteins are folded in the endoplasmic reticulum of the eukaryotic yeast cells, taking advantage of endoplasmic reticulum chaperones and quality-control machinery. Once maturation is complete, antibody affinity can be conveniently "titrated" while displayed on the surface of the yeast, eliminating the need for expression and purification of each clone. A theoretical limitation of yeast surface display is the potentially smaller functional library size than that of other display methods; however, a recent approach uses the yeast cells' mating system to create combinatorial diversity estimated to be $10^{14}$ in size (see, e.g., U.S. Pat. Publication 2003/0186374; and Blaise et al., 2004, Gene 342:211-18).

In ribosome display, antibody-ribosome-mRNA (ARM) complexes are generated for selection in a cell-free system. The DNA library coding for a particular library of antibodies is genetically fused to a spacer sequence lacking a stop codon. This spacer sequence, when translated, is still attached to the peptidyl tRNA and occupies the ribosomal tunnel, and thus allows the protein of interest to protrude out of the ribosome and fold. The resulting complex of mRNA, ribosome, and protein can bind to surface-bound ligand, allowing simultaneous isolation of the antibody and its encoding mRNA through affinity capture with the ligand. The ribosome-bound mRNA is then reverse transcribed back into cDNA, which can then undergo mutagenesis and be used in the next round of selection (see, e.g., Fukuda et al., 2006, Nucleic Acids Res. 34:e127). In mRNA display, a covalent bond between antibody and mRNA is established using puromycin as an adaptor molecule (Wilson et al., 2001, Proc. Natl. Acad. Sci. USA 98:3750-55).

As these methods are performed entirely in vitro, they provide two main advantages over other selection technologies. First, the diversity of the library is not limited by the transformation efficiency of bacterial cells, but only by the number of ribosomes and different mRNA molecules present in the test tube. Second, random mutations can be introduced easily after each selection round, for example, by non-proofreading polymerases, as no library must be transformed after any diversification step.

In a mammalian cell display system (see, e.g., Bowers et al., 2011, Proc Natl Acad Sci USA. 108:20455-60), a fully human library of IgGs is constructed based on germline sequence V-gene segments joined to prerecombined D(J) regions. Full-length V regions for heavy chain and light chain are assembled with human heavy chain and light chain constant regions and transfected into a mammalian cell line (e.g., HEK293). The transfected library is expanded and subjected to several rounds of negative selection against streptavidin (SA)-coupled magnetic beads, followed by a round of positive selection against SA-coupled magnetic beads coated with biotinylated target protein, peptide fragment, or epitope. Positively selected cells are expanded, and then sorted by rounds of FACS to isolate single cell clones displaying antibodies that specifically bind to the target protein, peptide fragment, or epitope. Heavy and light chain pairs from these single cell clones are retransfected with AID for further maturation. Several rounds of mammalian cell display, coupled with AID-triggered somatic hypermutation, generate high specificity, high affinity antibodies.

Diversity may also be introduced into the CDRs or the whole V genes of the antibody libraries in a targeted manner or via random introduction. The former approach includes sequentially targeting all the CDRs of an antibody via a high or low level of mutagenesis or targeting isolated hot spots of somatic hypermutations (see, e.g., Ho et al., 2005, J. Biol. Chem. 280:607-17) or residues suspected of affecting affinity on experimental basis or structural reasons. In a specific embodiment, somatic hypermutation is performed by AID-triggered somatic hypermutation, e.g., using the SHM-XEL™ platform (AnaptysBio, San Diego, Calif.). Random mutations can be introduced throughout the whole V gene using E. coli mutator strains, error-prone replication with DNA polymerases (see, e.g., Hawkins et al., 1992, J. Mol. Biol. 226:889-96), or RNA replicases. Diversity may also be introduced by replacement of regions that are naturally diverse via DNA shuffling or similar techniques (see, e.g., Lu et al., 2003, J. Biol. Chem. 278:43496-507; U.S. Pat. Nos. 5,565,332 and 6,989,250). Alternative techniques target hypervariable loops extending into framework-region residues (see, e.g., Bond et al., 2005, J. Mol. Biol. 348:699-709) employ loop deletions and insertions in CDRs or use hybridization-based diversification (see, e.g., U.S. Pat. Publication No. 2004/0005709). Additional methods of generating diversity in CDRs are disclosed, for example, in U.S. Pat. No. 7,985,840. Further methods that can be used to generate antibody libraries and/or antibody affinity maturation are disclosed, e.g., in U.S. Pat. Nos. 8,685,897 and 8,603,930, and U.S. Publ. Nos. 2014/0170705, 2014/0094392, 2012/0028301, 2011/0183855, and 2009/0075378, each of which are incorporated herein by reference.

Screening of the libraries can be accomplished by various techniques known in the art. For example, PD-1 can be immobilized onto solid supports, columns, pins, or cellulose/poly(vinylidene fluoride) membranes/other filters, expressed on host cells affixed to adsorption plates or used in cell sorting, or conjugated to biotin for capture with streptavidin-coated beads or used in any other method for panning display libraries.

For review of in vitro affinity maturation methods, see, e.g., Hoogenboom, 2005, Nature Biotechnology 23:1105-16; Quiroz and Sinclair, 2010, Revista Ingeneria Biomedia 4:39-51; and references therein.

4.3.2.2 Modifications of Anti-PD-1 Antibodies

Covalent modifications of anti-PD-1 antibodies are included within the scope of the present disclosure. Covalent modifications include reacting targeted amino acid residues of an anti-PD-1 antibody with an organic derivatizing agent that is capable of reacting with selected side chains or the N- or C-terminal residues of the anti-PD-1 antibody. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (see, e.g., Creighton, *Proteins: Structure and Molecular Properties* 79-86 (1983)), acetylation of the N-terminal amine, and amidation of any C-terminal carboxyl group.

Other types of covalent modification of the anti-PD-1 antibody included within the scope of this present disclosure include altering the native glycosylation pattern of the antibody or polypeptide (see, e.g., Beck et al., 2008, Curr. Pharm. Biotechnol. 9:482-501; and Walsh, 2010, Drug Discov. Today 15:773-80), and linking the antibody to one of a variety of nonproteinaceous polymers, e.g., polyethylene glycol (PEG), polypropylene glycol, or polyoxyalkylenes, in the manner set forth, for example, in U.S. Pat. No. 4,640,835; 4,496,689; 4,301,144; 4,670,417; 4,791,192; or 4,179,337.

An anti-PD-1 antibody of the present disclosure may also be modified to form chimeric molecules comprising an anti-PD-1 antibody fused to another, heterologous polypeptide or amino acid sequence, for example, an epitope tag (see, e.g., Terpe, 2003, Appl. Microbiol. Biotechnol. 60:523-33) or the Fc region of an IgG molecule (see, e.g., Aruffo, *Antibody Fusion Proteins* 221-42 (Chamow and Ashkenazi eds., 1999)).

Also provided herein are fusion proteins comprising an antibody provided herein that binds to a PD-1 antigen and a heterologous polypeptide. In some embodiments, the heterologous polypeptide to which the antibody is fused is useful for targeting the antibody to cells having cell surface-expressed PD-1.

Also provided herein are panels of antibodies that bind to a PD-1 antigen. In specific embodiments, the panels of antibodies have different association rates, different dissociation rates, different affinities for a PD-1 antigen, and/or different specificities for a PD-1 antigen. In some embodiments, the panels comprise or consist of about 10, about 25, about 50, about 75, about 100, about 125, about 150, about 175, about 200, about 250, about 300, about 350, about 400, about 450, about 500, about 550, about 600, about 650, about 700, about 750, about 800, about 850, about 900, about 950, or about 1000 antibodies or more. Panels of antibodies can be used, for example, in 96-well or 384-well plates, for assays such as ELISAs.

4.3.3 Preparation of Anti-PD-1 Antibodies

Anti-PD-1 antibodies may be produced by culturing cells transformed or transfected with a vector containing anti-PD-1 antibody-encoding nucleic acids. Polynucleotide sequences encoding polypeptide components of the antibody of the present disclosure can be obtained using standard recombinant techniques. Desired polynucleotide sequences may be isolated and sequenced from antibody producing cells such as hybridomas cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in host cells. Many vectors that are available and known in the art can be used for the purpose of the present disclosure. Selection of an appropriate vector will depend mainly on the size of the nucleic acids to be inserted into the vector and the particular host cell to be transformed with the vector. Host cells suitable for expressing antibodies of the present disclosure include prokaryotes such as Archaebacteria and Eubacteria, including Gram-negative or Gram-positive organisms, eukaryotic microbes such as filamentous fungi or yeast, invertebrate cells such as insect or plant cells, and vertebrate cells such as mammalian host cell lines. Host cells are transformed with the above-described expression vectors and cultured in conventional nutrient media modified as appropriate for inducing promoters, selecting transformants, or amplifying the genes encoding the desired sequences. Antibodies produced by the host cells are purified using standard protein purification methods as known in the art.

Methods for antibody production including vector construction, expression, and purification are further described in Plückthun et al., *Antibody Engineering: Producing antibodies in Escherichia coli: From PCR to fermentation* 203-52 (McCafferty et al. eds., 1996); Kwong and Rader, *E. coli Expression and Purification of Fab Antibody Fragments, in Current Protocols in Protein Science* (2009); Tachibana and Takekoshi, Production of Antibody Fab Fragments in *Escherischia coli*, in *Antibody Expression and Production* (Al-Rubeai ed., 2011); and *Therapeutic Monoclonal Antibodies: From Bench to Clinic* (An ed., 2009).

It is, of course, contemplated that alternative methods, which are well known in the art, may be employed to prepare anti-PD-1 antibodies. For instance, the appropriate amino acid sequence, or portions thereof, may be produced by direct peptide synthesis using solid-phase techniques (see, e.g., Stewart et al., *Solid-Phase Peptide Synthesis* (1969); and Merrifield, 1963, J. Am. Chem. Soc. 85:2149-54). In vitro protein synthesis may be performed using manual techniques or by automation. Various portions of the anti-PD-1 antibody may be chemically synthesized separately and combined using chemical or enzymatic methods to produce the desired anti-PD-1 antibody. Alternatively, antibodies may be purified from cells or bodily fluids, such as milk, of a transgenic animal engineered to express the antibody, as disclosed, for example, in U.S. Pat. Nos. 5,545,807 and 5,827,690.

4.3.4 Immunoconjugates

The present disclosure also provides conjugates comprising any one of the anti-PD-1 antibodies of the present disclosure covalently bound by a synthetic linker to one or more non-antibody agents.

In some embodiments, antibodies provided herein are conjugated or recombinantly fused, e.g., to a diagnostic or detectable molecule. The conjugated or recombinantly fused antibodies can be useful, for example, for monitoring or prognosing the onset, development, progression, and/or severity of a PD-1-mediated disease.

Such diagnosis and detection can be accomplished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin or avidin/biotin; fluorescent materials, such as, but not limited to, umbelliferone, fluorescein, fluorescein isothiocynate, rhodamine, dichlorotriazinylamine fluorescein, dansyl chloride, or phycoerythrin; luminescent materials, such as, but not limited to, luminol; bioluminescent materials, such as, but not limited to, luciferase, luciferin, or aequorin; chemiluminescent material, such as, but not limited to, an acridinium based compound or a HALOTAG; radioactive materials, such as, but not limited to, iodine ($^{131}$I, $^{125}$I, $^{123}$I, and $^{121}$I,), carbon ($^{14}$C), sulfur ($^{35}$S), tritium ($^{3}$H), indium ($^{115}$In, $^{113}$In, $^{112}$In, and $^{111}$In), technetium ($^{99}$Tc), thallium ($^{201}$Ti), gallium ($^{68}$Ga and $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Rh, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, or $^{117}$Sn; positron emitting metals using various positron emission tomographies; and non-radioactive paramagnetic metal ions.

Also described herein are antibodies that are recombinantly fused or chemically conjugated (covalent or non-covalent conjugations) to a heterologous protein or polypeptide (or fragment thereof, for example, to a polypeptide of about 10, about 20, about 30, about 40, about 50, about 60, about 70, about 80, about 90, or about 100 amino acids) to generate fusion proteins, as well as uses thereof. In particular, provided herein are fusion proteins comprising an antigen-binding fragment of an antibody provided herein (e.g., a Fab fragment, Fc fragment, Fv fragment, F(ab)$_2$ fragment, a VH domain, a VH CDR, a VL domain, or a VL CDR) and a heterologous protein, polypeptide, or peptide. In one embodiment, the heterologous protein, polypeptide, or peptide that the antibody is fused to is useful for targeting the antibody to a particular cell type, such as a cell that expresses PD-1. For example, an antibody that binds to a cell surface receptor expressed by a particular cell type may be fused or conjugated to a modified antibody provided herein.

Moreover, antibodies provided herein can be fused to marker or "tag" sequences, such as a peptide, to facilitate purification. In specific embodiments, the marker or tag amino acid sequence is a hexa-histidine peptide, such as the tag provided in a pQE vector (see, e.g., QIAGEN, Inc.), among others, many of which are commercially available. For example, as described in Gentz et al., 1989, Proc. Natl. Acad. Sci. USA 86:821-24, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767-78), and the "FLAG" tag.

Methods for fusing or conjugating moieties (including polypeptides) to antibodies are known (see, e.g., Arnon et al., Monoclonal Antibodies for Immunotargeting of Drugs in Cancer Therapy, in Monoclonal Antibodies and Cancer Therapy 243-56 (Reisfeld et al. eds., 1985); Hellstrom et al., Antibodies for Drug Delivery, in Controlled Drug Delivery 623-53 (Robinson et al. eds., 2d ed. 1987); Thorpe, Antibody Carriers of Cytotoxic Agents in Cancer Therapy: A Review, in Monoclonal Antibodies: Biological and Clinical Applications 475-506 (Pinchera et al. eds., 1985); Analysis, Results, and Future Prospective of the Therapeutic Use of Radiolabeled Antibody in Cancer Therapy, in Monoclonal Antibodies for Cancer Detection and Therapy 303-16 (Baldwin et al. eds., 1985); Thorpe et al., 1982, Immunol. Rev. 62:119-58; U.S. Pat. Nos. 5,336,603; 5,622,929; 5,359,046; 5,349,053; 5,447,851; 5,723,125; 5,783,181; 5,908,626; 5,844,095; and 5,112,946; EP 307,434; EP 367,166; EP 394,827; PCT publications WO 91/06570, WO 96/04388, WO 96/22024, WO 97/34631, and WO 99/04813; Ashkenazi et al., 1991, Proc. Natl. Acad. Sci. USA, 88: 10535-39; Traunecker et al., 1988, Nature, 331:84-86; Zheng et al., 1995, J. Immunol. 154:5590-600; and Vil et al., 1992, Proc. Natl. Acad. Sci. USA 89:11337-41).

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of anti-PD-1 antibodies as provided herein, including, for example, antibodies with higher affinities and lower dissociation rates (see, e.g., U.S. Pat. Nos. 5,605,793; 5,811,238; 5,830,721; 5,834,252; and 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-13). Antibodies, or the encoded antibodies, may be altered by being subjected to random mutagenesis by error-prone PCR, random nucleotide insertion, or other methods prior to recombination. A polynucleotide encoding an antibody provided herein may be recombined with one or more components, motifs, sections, parts, domains, fragments, etc. of one or more heterologous molecules.

An antibody provided herein can also be conjugated to a second antibody to form an antibody heteroconjugate as described, for example, in U.S. Pat. No. 4,676,980.

Antibodies that bind to PD-1 as provided herein may also be attached to solid supports, which are particularly useful for immunoassays or purification of the target antigen. Such solid supports include, but are not limited to, glass, cellulose, polyacrylamide, nylon, polystyrene, polyvinyl chloride, or polypropylene.

The linker may be a "cleavable linker" facilitating release of the conjugated agent in the cell, but non-cleavable linkers are also contemplated herein. Linkers for use in the conjugates of the present disclosure include, without limitation, acid labile linkers (e.g., hydrazone linkers), disulfide-containing linkers, peptidase-sensitive linkers (e.g., peptide linkers comprising amino acids, for example, valine and/or citrulline such as citrulline-valine or phenylalanine-lysine), photolabile linkers, dimethyl linkers (see, e.g., Chari et al., 1992, Cancer Res. 52:127-31; and U.S. Pat. No. 5,208,020), thioether linkers, or hydrophilic linkers designed to evade multidrug transporter-mediated resistance (see, e.g., Kovtun et al., 2010, Cancer Res. 70:2528-37).

Conjugates of the antibody and agent may be made using a variety of bifunctional protein coupling agents such as BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, sulfo-SMPB, and SVSB (succinimidyl-(4-vinylsulfone)benzoate). The present disclosure further contemplates that conjugates of antibodies and agents may be prepared using any suitable methods as disclosed in the art (see, e.g., Bioconjugate Techniques (Hermanson ed., 2d ed. 2008)).

Conventional conjugation strategies for antibodies and agents have been based on random conjugation chemistries involving the c-amino group of Lys residues or the thiol group of Cys residues, which results in heterogenous conjugates. Recently developed techniques allow site-specific conjugation to antibodies, resulting in homogeneous loading and avoiding conjugate subpopulations with altered antigen-binding or pharmacokinetics. These include engineering of "thiomabs" comprising cysteine substitutions at positions on the heavy and light chains that provide reactive thiol groups and do not disrupt immunoglobulin folding and assembly or alter antigen binding (see, e.g., Junutula et al., 2008, J. Immunol. Meth. 332: 41-52; and Junutula et al., 2008, Nature Biotechnol. 26:925-32). In another method, selenocysteine is cotranslationally inserted into an antibody sequence by recoding the stop codon UGA from termination to selenocysteine insertion, allowing site specific covalent conjugation at the nucleophilic selenol group of selenocysteine in the presence of the other natural amino acids (see, e.g., Hofer et al., 2008, Proc. Natl. Acad. Sci. USA 105: 12451-56; and Hofer et al., 2009, Biochemistry 48(50): 12047-57).

4.4 Methods of Using the Antibodies and Compositions Thereof

Provided herein are methods of treating vitiligo in a subject. In certain embodiments, the method comprises administering a PD-1 binding protein provided herein to the subject in an amount effective for treating the vitiligo. Also provided herein are methods of managing vitiligo in a subject. In certain embodiments, the method comprises administering a PD-1 binding protein provided herein to the subject in an amount effective for managing the vitiligo. Also provided herein are methods of preventing vitiligo in a subject. In certain embodiments, the method comprises administering a PD-1 binding protein provided herein to the subject in an amount effective for preventing the vitiligo. In some embodiments, the subject has vitiligo In other embodiments, the subject is at risk of having vitiligo. In one embodiment, the subject is a subject in need thereof. In a specific embodiment, the PD-1 binding protein is a PD-1 antibody provided herein. In certain embodiments, the PD-1 binding protein is an antigen binding fragment of a PD-1 antibody provided herein.

In some embodiments, the various methods provided herein comprise administering an antibody that binds to PD-1, including a PD-1 polypeptide, a PD-1 polypeptide fragment, a PD-1 peptide, or a PD-1 epitope. In certain embodiments, the antibodies bind to human and/or cyno PD-1. In other embodiments, the antibodies do not bind to rodent PD-1 (e.g., a mouse PD-1). In one embodiment, an antibody binds to human PD-1. In another embodiment, an antibody binds to cyno PD-1. In another embodiment, the antibody binds to human PD-1 and cyno PD-1. In some embodiments, the antibody binds to human PD-1 and does not bind to a rodent PD-1 (e.g., a mouse PD-1). In some embodiments, the antibody binds to cyno PD-1 and does not bind to a rodent PD-1 (e.g., a mouse PD-1). In some embodiments, the antibody binds to human PD-1, binds to a cyno PD-1, and does not bind to a rodent PD-1 (e.g., a mouse PD-1). In some embodiments, the anti-PD-1 antibodies do not block the binding of PD-L1 to a PD-1 polypeptide. In some embodiments, the anti-PD-1 antibodies do not block the binding of PD-L2 to a PD-1 polypeptide. In some embodiments, the anti-PD-1 antibodies do not block the binding of PD-L1 or PD-L2 to a PD-1 polypeptide. In other embodiments, the anti-PD-1 antibodies are humanized antibodies (e.g., comprising human constant regions) that bind PD-1, including a PD-1 polypeptide, a PD-1 polypeptide fragment, a PD-1 peptide, or a PD-1 epitope. In certain embodiments, the anti-PD-1 antibody comprises a VH region, VL region, VH CDR1, VH CDR2, VH CDR3, VL CDR1, VL CDR2, and/or VL CDR3 of any one of the murine monoclonal antibodies provided herein, such as an amino acid sequence depicted in Tables 1-6. Accordingly, in some embodiments, the isolated antibody or functional fragment thereof provided herein comprises one, two, and/or three heavy chain CDRs and/or one, two, and/or three light chain CDRs from: (a) the antibody PD1AB-1, (b) the antibody PD1AB-2, (c) the antibody PD1AB-3, (d) the antibody PD1AB-4, (e) the antibody PD1AB-5, or (f) the antibody PD1AB-6, as shown in Tables 1-2.

In some embodiments, the various methods provided herein comprise administering an antibody that comprises or consists of six CDRs, for example, VH CDR1, VH CDR2, VH CDR3, VL CDR1, VL CDR2, and/or VL CDR3 identified in Tables 1-2. In some embodiments, the antibody can comprise fewer than six CDRs. In some embodiments, the antibody comprises or consists of one, two, three, four, or five CDRs selected from the group consisting of VH CDR1, VH CDR2, VH CDR3, VL CDR1, VL CDR2, and/or VL CDR3 identified in Tables 1-2. In some embodiments, the antibody comprises or consists of one, two, three, four, or five CDRs selected from the group consisting of VH CDR1, VH CDR2, VH CDR3, VL CDR1, VL CDR2, and/or VL CDR3 of the monoclonal antibody selected from the group consisting of: (a) the antibody PD1AB-1, (b) the antibody PD1AB-2, (c) the antibody PD1AB-3, (d) the antibody PD1AB-4, (e) the antibody PD1AB-5, and (f) the antibody PD1AB-6, described herein. Accordingly, in some embodiments, the various methods provided herein comprise administering an antibody comprises or consists of one, two, three, four, or five CDRs of anyone of the VH CDR1, VH CDR2, VH CDR3, VL CDR1, VL CDR2, and/or VL CDR3 identified in Tables 1-2.

In some embodiments, the various methods provided herein comprise administering an antibody comprising one or more (e.g., one, two, or three) VH CDRs listed in Table 2. In other embodiments, the antibodies comprise one or more (e.g., one, two, or three) VL CDRs listed in Table 1. In yet other embodiments, the antibodies comprise one or more (e.g., one, two, or three) VH CDRs listed in Table 2 and one or more VL CDRs listed in Table 1. Accordingly, in some embodiments, the antibodies comprise a VH CDR1 having an amino acid sequence of SEQ ID NO:4. In some embodiments, the antibodies comprise a VH CDR2 having an amino acid sequence of SEQ ID NO:5. In some embodiments, the antibodies comprise a VH CDR3 having an amino acid sequence of SEQ ID NO:6. In some embodiments, the antibodies comprise a VH CDR1 and/or a VH CDR2 and/or a VH CDR3 independently selected from any one of the VH CDR1, VH CDR2, VH CDR3 amino acid sequence(s) as depicted in Table 2. In some embodiments, the antibodies comprise a VL CDR1 having an amino acid sequence of any one of SEQ ID NOS:1 and 7. In another embodiment, the antibodies comprise a VL CDR2 having an amino acid sequence of SEQ ID NO:2. In some embodiments, the antibodies comprise a VL CDR3 having an amino acid sequence of SEQ ID NO:3. In some embodiments, the antibodies comprise a VL CDR1 and/or a VL CDR2 and/or a VL CDR3 independently selected from any one of the VL CDR1, VL CDR2, VL CDR3 amino acid sequences as depicted in Table 1.

In some embodiments, the various methods provided herein comprise administering an antibody comprising a VH region comprising: (1) a VH CDR1 having an amino acid sequence of SEQ ID NO:4; (2) a VH CDR2 having an amino acid sequence of SEQ ID NO:5; and (3) a VH CDR3 having an amino acid sequence of SEQ ID NO:6; and a VL region comprising: (1) a VL CDR1 having an amino acid sequence of SEQ ID NO:1; (2) a VL CDR2 having an amino acid sequence of SEQ ID NO:2; and (3) a VL CDR3 having an amino acid sequence of SEQ ID NO:3. In other embodiments, the antibody comprises a VH region comprising: (1)

a VH CDR1 having an amino acid sequence of SEQ ID NO:4; (2) a VH CDR2 having an amino acid sequence of SEQ ID NO:5; and (3) a VH CDR3 having an amino acid sequence of SEQ ID NO:6; and a VL region comprising: (1) a VL CDR1 having an amino acid of SEQ ID NOS:7; (2) a VL CDR2 having an amino acid sequence of SEQ ID NO:2; and (3) a VL CDR3 having an amino acid sequence of SEQ ID NO:3. In some embodiments, the antibody comprises a VH region comprising: (1) a VH CDR1 having an amino acid sequence of SEQ ID NO:4; (2) a VH CDR2 having an amino acid sequence of SEQ ID NO:5; and (3) a VH CDR3 having an amino acid sequence of SEQ ID NO:6. In other embodiments, the antibodies comprise a VL region comprising: (1) a VL CDR1 having an amino acid sequence of SEQ ID NO:1; (2) a VL CDR2 having an amino acid sequence of SEQ ID NO:2; and (3) a VL CDR3 having an amino acid sequence of SEQ ID NO:3. In some embodiments, the antibodies comprise a VL region comprising: (1) a VL CDR1 having an amino acid sequence of SEQ ID NOS: 7; (2) a VL CDR2 having an amino acid sequence of SEQ ID NO:2; and (3) a VL CDR3 having an amino acid sequence of SEQ ID NO:3.

In some embodiments, the various methods provided herein comprise administering an antibody comprising one or more (e.g., one, two, or three) VH CDRs and one or more (e.g., one, two, or three) VL CDRs listed in Tables 1-2. In particular embodiments, the antibody comprises a VH CDR1 (SEQ ID NO:4) and a VL CDR1 (SEQ ID NOS:1 or 7). In one embodiment, the antibody comprises a VH CDR1 (SEQ ID NO:4) and a VL CDR2 (SEQ ID NO:2). In other embodiments, the antibody comprises a VH CDR1 (SEQ ID NO:4) and a VL CDR3 (SEQ ID NO:3). In another embodiment, the antibody comprises a VH CDR2 (SEQ ID NO:5) and a VL CDR1 (SEQ ID NOS:1 or 7). In some embodiments, the antibody comprises a VH CDR2 (SEQ ID NO:5) and a VL CDR2 (SEQ ID NO:2). In one embodiment, the antibody comprises a VH CDR2 (SEQ ID NO:5) and a VL CDR3 (SEQ ID NO:3). In another embodiment, the antibody comprises a VH CDR3 (SEQ ID NO:6) and a VL CDR1 (SEQ ID NOS:1 or 7). In other embodiments, the antibody comprises a VH CDR3 (SEQ ID NO:6) and a VL CDR2 (SEQ ID NO:2). In some embodiments, the antibody comprises a VH CDR3 (SEQ ID NO:6) and a VL CDR3 (SEQ ID NO:3). In another embodiment, the antibody comprises a VH CDR1 (SEQ ID NO:4), a VH CDR2 (SEQ ID NO:5), and a VL CDR1 (SEQ ID NOS:1 or 7). In one embodiment, the antibody comprises a VH CDR1 (SEQ ID NO:4), a VH CDR2 (SEQ ID NO:5), and a VL CDR2 (SEQ ID NO:2). In other embodiments, the antibody comprises a VH CDR1 (SEQ ID NO:4), a VH CDR2 (SEQ ID NO:5), and a VL CDR3 (SEQ ID NOS:3). In another embodiment, the antibody comprises a VH CDR2 (SEQ ID NO:5), a VH CDR3 (SEQ ID NO:6), and a VL CDR1 (SEQ ID NOS:1 or 7). In some embodiments, the antibody comprises a VH CDR2 (SEQ ID NO:5), a VH CDR3 (SEQ ID NO:6), and a VL CDR2 (SEQ ID NO:2). In one embodiment, the antibody comprises a VH CDR2 (SEQ ID NO:5), a VH CDR3 (SEQ ID NO:6), and a VL CDR3 (SEQ ID NO:3). In another embodiment, the antibody comprises a VH CDR1 (SEQ ID NO:4), a VH CDR3 (SEQ ID NO:6), and a VL CDR1 (SEQ ID NOS:1 or 7). In other embodiments, the antibody comprises a VH CDR1 (SEQ ID NO:4), a VH CDR3 (SEQ ID NO:6), and a VL CDR2 (SEQ ID NO:2). In some embodiments, the antibody comprises a VH CDR1 (SEQ ID NO:4), a VH CDR3 (SEQ ID NO:6), and a VL CDR3 (SEQ ID NO:3). In another embodiment, the antibody comprises a VH CDR1 (SEQ ID NO:4), a VL CDR1 (SEQ ID NOS:1 or 7), and a VL CDR2 (SEQ ID NO:2). In one embodiment, the antibody comprises a VH CDR1 (SEQ ID NO:4), a VL CDR1 (SEQ ID NOS:1 or 7), and a VL CDR3 (SEQ ID NO:3). In other embodiments, the antibody comprises a VH CDR1 (SEQ ID NO:4), a VL CDR2 (SEQ ID NO:2), and a VL CDR3 (SEQ ID NO:3). In another embodiment, the antibody comprises a VH CDR2 (SEQ ID NO:5), a VL CDR1 (SEQ ID NOS:1 or 7), and a VL CDR2 (SEQ ID NO:2). In some embodiments, the antibody comprises a VH CDR2 (SEQ ID NO:5), a VL CDR1 (SEQ ID NOS:1 or 7), and a VL CDR3 (SEQ ID NO:3). In one embodiment, the antibody comprises a VH CDR2 (SEQ ID NO:5), a VL CDR2 (SEQ ID NO:2), and a VL CDR3 (SEQ ID NO:3). In another embodiment, the antibody comprises a VH CDR3 (SEQ ID NO:6), a VL CDR1 (SEQ ID NOS:1 or 7), and a VL CDR2 (SEQ ID NO:2). In other embodiments, the antibody comprises a VH CDR3 (SEQ ID NO:6), a VL CDR1 (SEQ ID NOS:1 or 7), and a VL CDR3 (SEQ ID NO:3). In some embodiments, the antibody comprises a VH CDR3 (SEQ ID NO:6), a VL CDR2 (SEQ ID NO:2), and a VL CDR3 (SEQ ID NO:3). In another embodiment, the antibody comprises a VH CDR2 (SEQ ID NO:5), a VH CDR3 (SEQ ID NO:6), a VL CDR1 (SEQ ID NOS:1 or 7), and a VL CDR2 (SEQ ID NO:2). In one embodiment, the antibody comprises a VH CDR2 (SEQ ID NO:5), a VH CDR3 (SEQ ID NO:6), a VL CDR1 (SEQ ID NOS:1 or 7), and a VL CDR3 (SEQ ID NO:3). In other embodiments, the antibody comprises a VH CDR2 (SEQ ID NO:5), a VH CDR3 (SEQ ID NO:6), a VL CDR2 (SEQ ID NO:2), and a VL CDR3 (SEQ ID NO:3). In another embodiment, the antibody comprises a VH CDR1 (SEQ ID NO:4), a VH CDR2 (SEQ ID NO:5), a VH CDR3 (SEQ ID NO:6), a VL CDR1 (SEQ ID NOS:1 or 7), and a VL CDR2 (SEQ ID NO:2). In some embodiments, the antibody comprises a VH CDR1 (SEQ ID NO:4), a VH CDR2 (SEQ ID NO:5), a VH CDR3 (SEQ ID NO:6), a VL CDR1 (SEQ ID NOS:1 or 7), and a VL CDR3 (SEQ ID NO:3). In one embodiment, the antibody comprises a VH CDR1 (SEQ ID NO:4), a VH CDR2 (SEQ ID NO:5), a VH CDR3 (SEQ ID NO:6), a VL CDR2 (SEQ ID NO:2), and a VL CDR3 (SEQ ID NO:3). In another embodiment, the antibody comprises a VH CDR1 (SEQ ID NO:4), a VH CDR2 (SEQ ID NO:5), a VL CDR1 (SEQ ID NOS:1 or 7), a VL CDR2 (SEQ ID NO:2), and a VL CDR3 (SEQ ID NO:3). In other embodiments, the antibody comprises a VH CDR1 (SEQ ID NO:4), a VH CDR3 (SEQ ID NO:6), a VL CDR1 (SEQ ID NOS:1 or 7), a VL CDR2 (SEQ ID NO:2), and a VL CDR3 (SEQ ID NO:3). In some embodiments, the antibody comprises a VH CDR2 (SEQ ID NO:5), a VH CDR3 (SEQ ID NO:6), a VL CDR1 (SEQ ID NOS:1 or 7), a VL CDR2 (SEQ ID NO:2), and a VL CDR3 (SEQ ID NO:3). In another embodiment, the antibody comprises a VH CDR1 (SEQ ID NO:4), a VL CDR1 (SEQ ID NOS:1 or 7), a VL CDR2 (SEQ ID NO:2), and a VL CDR3 (SEQ ID NO:3). In one embodiment, the antibody comprises a VH CDR2 (SEQ ID NO:5), a VL CDR1 (SEQ ID NOS:1 or 7), a VL CDR2 (SEQ ID NO:2), and a VL CDR3 (SEQ ID NO:3). In other embodiments, the antibody comprises a VH CDR3 (SEQ ID NO:6), a VL CDR1 (SEQ ID NOS:1 or 7), a VL CDR2 (SEQ ID NO:2), and a VL CDR3 (SEQ ID NO:3). In another embodiment, the antibody comprises any combination thereof of the VH CDRs and VL CDRs listed in Tables 1-2.

In some embodiments, the various methods provided herein comprise administering an antibody comprising CDRs disclosed herein that include consensus sequences derived from groups of related antibodies (see, e.g., Tables 1-2).

In other embodiments, the various methods provided herein comprise administering an antibody (or functional fragment thereof) that further comprises one, two, three, and/or four heavy chain FRs and/or one, two, three, and/or four light chain FRs from: (a) the antibody PD1AB-1, (b) the antibody PD1AB-2, (c) the antibody PD1AB-3, (d) the antibody PD1AB-4, (e) the antibody PD1AB-5, or (f) the antibody PD1AB-6, as shown in Tables 3-4.

In certain embodiments, the various methods provided herein comprise administering an antibody (or functional fragment thereof) that further comprises one, two, three, and/or four heavy chain FRs from: (a) the antibody PD1AB-1, (b) the antibody PD1AB-2, (c) the antibody PD1AB-3, (d) the antibody PD1AB-4, (e) the antibody PD1AB-5, or (f) the antibody PD1AB-6, as shown in Table 4. In some embodiments, the antibody heavy chain FR(s) is from the antibody PD1AB-1. In some embodiments, the antibody heavy chain FR(s) is from the antibody PD1AB-2. In other embodiments, the antibody heavy chain FR(s) is from the antibody PD1AB-3. In certain embodiments, the antibody heavy chain FR(s) is from the antibody PD1AB-4. In other embodiments, the antibody heavy chain FR(s) is from the antibody PD1AB-5. In another embodiment, the antibody heavy chain FR(s) is from the antibody PD1AB-6.

In other embodiments, the various methods provided herein comprise administering an antibody (or functional fragment thereof) that further comprises one, two, three, and/or four light chain FRs from: (a) the antibody PD1AB-1, (b) the antibody PD1AB-2, (c) the antibody PD1AB-3, (d) the antibody PD1AB-4, (e) the antibody PD1AB-5, or (f) the antibody PD1AB-6, as shown in Table 3. In some embodiments, the antibody light chain FR(s) is from the antibody PD1AB-1. In some embodiments, the antibody light chain FR(s) is from the antibody PD1AB-2. In other embodiments, the antibody light chain FR(s) is from the antibody PD1AB-3. In certain embodiments, the antibody light chain FR(s) is from the antibody PD1AB-4. In other embodiments, the antibody light chain FR(s) is from the antibody PD1AB-5. In another embodiment, the antibody light chain FR(s) is from the antibody PD1AB-6.

In some embodiments, the various methods provided herein comprise administering an antibody comprising a VH region that comprises, or further comprises: (1) a VH FR1 having an amino acid sequence selected from the group consisting of SEQ ID NOS:19 and 24; (2) a VH FR2 having an amino acid sequence of SEQ ID NO:20; (3) a VH FR3 having an amino acid sequence selected from the group consisting of SEQ ID NOS:21 and 23; and/or (4) a VH FR4 having an amino acid sequence of SEQ ID NO:22. In certain embodiments, the antibody comprises a VH region that comprises, or further comprises: (1) a VH FR1 having an amino acid of SEQ ID NO:19; (2) a VH FR2 having an amino acid sequence of SEQ ID NO:20; (3) a VH FR3 having an amino acid sequence of SEQ ID NO:21; and/or (4) a VH FR4 having an amino acid sequence of SEQ ID NO:22. In certain embodiments, the antibody comprises a VH region that comprises, or further comprises: (1) a VH FR1 having an amino acid sequence of SEQ ID NO:19; (2) a VH FR2 having an amino acid sequence of SEQ ID NO:20; (3) a VH FR3 having an amino acid sequence of SEQ ID NO: 23; and/or (4) a VH FR4 having an amino acid sequence of SEQ ID NO:22. In certain embodiments, the antibody comprises a VH region that comprises, or further comprises: (1) a VH FR1 having an amino acid sequence of SEQ ID NO: 24; (2) a VH FR2 having an amino acid sequence of SEQ ID NO:20; (3) a VH FR3 having an amino acid sequence of SEQ ID NO:21; and/or (4) a VH FR4 having an amino acid sequence of SEQ ID NO:22. In certain embodiments, the antibody comprises a VH region that comprises, or further comprises: (1) a VH FR1 having an amino acid sequence of SEQ ID NO:24; (2) a VH FR2 having an amino acid sequence of SEQ ID NO:20; (3) a VH FR3 having an amino acid sequence of SEQ ID NO: 23; and/or (4) a VH FR4 having an amino acid sequence of SEQ ID NO:22. In specific embodiments, the antibody comprises a VH region comprising all four of the above-referenced VH FR1, VH FR2, VH FR3, and VH FR4.

Accordingly, in some embodiments, the various methods provided herein comprise administering a humanized antibody comprising a VH region that includes a VH FR1 having an amino acid sequence selected from the group consisting of SEQ ID NOS:19 and 24. In one embodiment, the humanized antibody comprises a VH region that includes a VH FR1 having an amino acid sequence of SEQ ID NO:19. In one embodiment, the humanized antibody comprises a VH region that includes a VH FR1 having an amino acid sequence of SEQ ID NO:24. In some embodiments, the humanized antibody comprises a VH region that includes a VH FR2 having an amino acid sequence of SEQ ID NO: 20. In some embodiments, the humanized antibody comprises a VH region that includes a VH FR3 having an amino acid sequence selected from the group consisting of SEQ ID NOS:21 and 23. In one embodiment, the humanized antibody comprises a VH region that includes a VH FR3 having an amino acid sequence of SEQ ID NO:21. In one embodiment, the humanized antibody comprises a VH region that includes a VH FR3 having an amino acid sequence of SEQ ID NO:23. In other embodiments, the humanized antibody comprises a VH region that includes a VH FR4 having an amino acid sequence of SEQ ID NO:22.

In some embodiments, the various methods provided herein comprise administering an antibody comprising a VL region that comprises: (1) a VL FR1 having an amino acid sequence of SEQ ID NO:14; (2) a VL FR2 having an amino acid sequence of SEQ ID NO:15; (3) a VL FR3 having an amino acid sequence selected from the group consisting of SEQ ID NOS:16 and 18; and/or (4) a VL FR4 having an amino acid sequence of SEQ ID NO:17. In some embodiments, the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NOS:16; and/or (4) a VL FR4 having an amino acid sequence of SEQ ID NO:17. In other embodiments, the VL region that comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO: 18; and/or (4) a VL FR4 having an amino acid sequence of SEQ ID NO:17.

Accordingly, in some embodiments, the various methods provided herein comprise administering a humanized antibody that comprises a VL region that includes a VL FR1 having an amino acid sequence of SEQ ID NO:14. In certain embodiments, the humanized antibody comprises a VL region that includes a VL FR2 having an amino acid sequence of SEQ ID NO:15. In other embodiments, the humanized antibody comprises a VL region that includes a VL FR3 having an amino acid sequence selected from the group consisting of SEQ ID NOS:16 and 18. In one embodiment, the humanized antibody comprises a VL region that includes a VL FR3 having an amino acid sequence of SEQ ID NOS:16. In other embodiments, the humanized antibody comprises a VL region that includes a VL FR3 having an amino acid sequence of SEQ ID NO: 18. In yet other embodiments, the humanized antibody comprises a VL region that includes a VL FR4 having an amino acid sequence of SEQ ID NO:17.

In other embodiments, the various methods provided herein comprise administering an antibody comprising a VH region and a VL region, wherein the VH region comprises: (1) a VH FR1 having an amino acid sequence selected from the group consisting of SEQ ID NOS:19 and 24; (2) a VH FR2 having an amino acid sequence of SEQ ID NO:20; (3) a VH FR3 having an amino acid sequence selected from the group consisting of SEQ ID NOS:21 and 23; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence selected from the group consisting of SEQ ID NOS:16 and 18; and/or (4) a VL FR4 having an amino acid sequence of SEQ ID NO:17. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

In certain embodiments, the various methods provided herein comprise administering an antibody comprising a VH region and a VL region, wherein the VH region comprises: (1) a VH FR1 having an amino acid sequence of SEQ ID NO:19; (2) a VH FR2 having an amino acid sequence of SEQ ID NO:20; (3) a VH FR3 having an amino acid sequence of SEQ ID NO:21; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO:16; and/or (4) a VL FR4 having an amino acid sequence of SEQ ID NO:17. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

In some embodiments, the various methods provided herein comprise administering an antibody comprising a VH region and a VL region, wherein the VH region comprises: (1) a VH FR1 having an amino acid sequence of SEQ ID NO:19; (2) a VH FR2 having an amino acid sequence of SEQ ID NO:20; (3) a VH FR3 having an amino acid sequence of SEQ ID NO:21; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO:18; and/or (4) a VL FR4 having an amino acid sequence of SEQ ID NO:17. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

In other embodiments, the various methods provided herein comprise administering an antibody comprising a VH region and a VL region, wherein the VH region comprises: (1) a VH FR1 having an amino acid sequence of SEQ ID NO:19; (2) a VH FR2 having an amino acid sequence of SEQ ID NO:20; (3) a VH FR3 having an amino acid sequence of SEQ ID NO:23; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO:16; and/or (4) a VL FR4 having an amino acid sequence of SEQ ID NO:17. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

In some embodiments, the various methods provided herein comprise administering an antibody comprising a VH region and a VL region, wherein the VH region comprises: (1) a VH FR1 having an amino acid sequence of SEQ ID NO:19; (2) a VH FR2 having an amino acid sequence of SEQ ID NO:20; (3) a VH FR3 having an amino acid sequence of SEQ ID NO:23; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO:18; and/or (4) a VL FR4 having an amino acid sequence of SEQ ID NO:17. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

In certain embodiments, the various methods provided herein comprise administering an antibody comprising a VH region and a VL region, wherein the VH region comprises: (1) a VH FR1 having an amino acid sequence of SEQ ID NO:24; (2) a VH FR2 having an amino acid sequence of SEQ ID NO:20; (3) a VH FR3 having an amino acid sequence of SEQ ID NO:21; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO:16; and/or (4) a VL FR4 having an amino acid sequence of SEQ ID NO:17. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

In some embodiments, the various methods provided herein comprise administering an antibody comprising a VH region and a VL region, wherein the VH region comprises: (1) a VH FR1 having an amino acid sequence of SEQ ID NO:24; (2) a VH FR2 having an amino acid sequence of SEQ ID NO:20; (3) a VH FR3 having an amino acid sequence of SEQ ID NO:21; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO:18; and/or (4) a VL FR4 having an amino acid sequence of SEQ ID NO:17. In some embodiments, the antibody comprises a VH region comprising all four of the above-referenced VH FR1, VH FR2, VH FR3 and VH FR4. In other embodiments, the antibody comprises a VL region comprising all four of the above-referenced VL FR1, VL FR2, VL FR3 and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

In other embodiments, the various methods provided herein comprise administering an antibody comprising a VH region and a VL region, wherein the VH region comprises: (1) a VH FR1 having an amino acid sequence of SEQ ID NO:24; (2) a VH FR2 having an amino acid sequence of SEQ ID NO:20; (3) a VH FR3 having an amino acid sequence of SEQ ID NO:23; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO:16; and/or (4) a VL FR4 having an amino acid sequence of SEQ ID NO:17. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

In certain embodiments, the various methods provided herein comprise administering an antibody comprising a VH region and a VL region, wherein the VH region comprises: (1) a VH FR1 having an amino acid sequence of SEQ ID NO:24; (2) a VH FR2 having an amino acid sequence of SEQ ID NO:20; (3) a VH FR3 having an amino acid sequence of SEQ ID NO:23; and/or (4) a VH FR4 having an amino acid sequence of SEQ ID NO:22; and wherein the VL region comprises: (1) a VL FR1 having an amino acid sequence of SEQ ID NO:14; (2) a VL FR2 having an amino acid sequence of SEQ ID NO:15; (3) a VL FR3 having an amino acid sequence of SEQ ID NO:18; and/or (4) a VL FR4 having an amino acid sequence of SEQ ID NO:17. In some embodiments, the antibody comprises a VH region comprising all four of the above-referenced VH FR1, VH FR2, VH FR3, and VH FR4. In other embodiments, the antibody comprises a VL region comprising all four of the above-referenced VL FR1, VL FR2, VL FR3, and VL FR4. In yet other embodiments, the antibody comprises a VH region comprising all four of the above-referenced VH FR1, VH FR2, VH FR3, and VH FR4, and a VL region comprising all four of the above-referenced VL FR1, VL FR2, VL FR3, and VL FR4.

The methods provided herein, in certain embodiments, comprise administering an antibody comprising one or more (e.g., one, two, three, or four) VH FRs and one or more (e.g., one, two, three, or four) VL FRs listed in Tables 3-4. In particular, in some embodiments, the antibody comprises a VH FR1 (SEQ ID NOS:19 or 24) and a VL FR1 (SEQ ID NO:14). In one embodiment, the antibody comprises a VH FR1 (SEQ ID NOS:19 or 24) and a VL FR2 (SEQ ID NO:15). In some embodiments, the antibody comprises a VH FR1 (SEQ ID NOS:19 or 24) and a VL FR3 (SEQ ID NOS:16 or 18). In another embodiment, the antibody comprises a VH FR1 (SEQ ID NOS:19 or 24) and a VL FR4 (SEQ ID NO:17). In other embodiments, the antibody comprises a VH FR2 (SEQ ID NO:20) and a VL FR1 (SEQ ID NO:14). In one embodiment, the antibody comprises a VH FR2 (SEQ ID NO:20) and a VL FR2 (SEQ ID NO:15). In some embodiments, the antibody comprises a VH FR2 (SEQ ID NO:20) and a VL FR3 (SEQ ID NOS:16 or 18). In another embodiment, the antibody comprises a VH FR2 (SEQ ID NO:20) and a VL FR4 (SEQ ID NO:17). In one embodiment, the antibody comprises a VH FR3 (SEQ ID NO:21) and a VL FR1 (SEQ ID NO:14). In other embodiments, the antibody comprises a VH FR3 (SEQ ID NO:21) and a VL FR2 (SEQ ID NO:15). In another embodiment, the antibody comprises a VH FR3 (SEQ ID NO:21) and a VL FR3 (SEQ ID NOS:16 or 18). In some embodiments, the antibody comprises a VH FR3 (SEQ ID NO:21) and a VL FR4 (SEQ ID NO:17). In one embodiment, the antibody comprises a VH FR4 (SEQ ID NO:22) and a VL FR1 (SEQ ID NO:14). In another embodiment, the antibody comprises a VH FR4 (SEQ ID NO:22) and a VL FR2 (SEQ ID NO:15). In one embodiment, the antibody comprises a VH FR4 (SEQ ID NO:22) and a VL FR3 (SEQ ID NOS:16 or 18). In some embodiments, the antibody comprises a VH FR4 (SEQ ID NO:22) and a VL FR4 (SEQ ID NO:17). In another embodiment, the antibody comprises a VH FR1 (SEQ ID NOS:19 or 24), a VH FR2 (SEQ ID NO:20), and a VL FR1 (SEQ ID NO:14). In other embodiments, the antibody comprises a VH FR1 (SEQ ID NOS:19 or 24), a VH FR2 (SEQ ID NO:20), and a VL FR2 (SEQ ID NO:15). In one embodiment, the antibody comprises a VH FR1 (SEQ ID NOS:19 or 24), a VH FR2 (SEQ ID NO:20), and a VL FR3 (SEQ ID NOS:16 or 18). In another embodiment, the antibody comprises a VH FR1 (SEQ ID NOS:19 or 24), a VH FR2 (SEQ ID NO:20), and a VL FR4 (SEQ ID NO:17). In some embodiments, the antibody comprises a VH FR2 (SEQ ID NO:20), a VH FR3 (SEQ ID NOS:21 or 23), and a VL FR1 (SEQ ID NO:14). In one embodiment, the antibody comprises a VH FR2 (SEQ ID NO:20), a VH FR3 (SEQ ID NOS:21 or 23), and a VL FR2 (SEQ ID NO:15). In another embodiment, the antibody comprises a VH FR2 (SEQ ID NO:20), a VH FR3 (SEQ ID NOS:21 or 23), and a VL FR3 (SEQ ID NOS:16 or 18). In other embodiments, the antibody comprises a VH FR2 (SEQ ID NO:20), a VH FR3 (SEQ ID NOS:21 or 23), and a VL FR4 (SEQ ID NO:17). In some embodiments, the antibody comprises a VH FR1 (SEQ ID NOS:19 or 24), a VL FR1 (SEQ ID NO:14), and a VL FR2 (SEQ ID NO:15). In another embodiment, the antibody comprises a VH FR1 (SEQ ID NOS:19 or 24), a VL FR1 (SEQ ID NO:14), and a VL FR3 (SEQ ID NOS:16 or 18). In one embodiment, the antibody comprises a VH FR1 (SEQ ID NOS:19 or 24), a VL FR1 (SEQ ID NO:14), and a VL FR4 (SEQ ID NO:17). In one embodiment, the antibody comprises a VH FR1 (SEQ ID NOS:19 or 24), a VL FR2 (SEQ ID NO:15) and a VL FR3 (SEQ ID NOS:16 or 18). In another embodiment, the antibody comprises a VH FR1 (SEQ ID NOS:19 or 24), a VL FR2 (SEQ ID NO:15) and a VL FR4 (SEQ ID NO:17). In some embodiments, the antibody comprises a VH FR1 (SEQ ID NO:19 or 24), a VL FR3 (SEQ ID NOS:16 or 18), and a VL FR4 (SEQ ID NO:17). In other embodiments, the antibody comprises a VH FR2 (SEQ ID NO:20), a VL FR1 (SEQ ID NO:14), and a VL FR2 (SEQ ID NO:15). In another embodiment, the antibody comprises a VH FR2 (SEQ ID NO:20), a VL FR1 (SEQ ID NO:14), and a VL FR3 (SEQ ID NOS:16 or 18). In one embodiment, the antibody comprises a VH FR2 (SEQ ID NO:20), a VL FR1 (SEQ ID NO:14), and a VL FR4 (SEQ ID NO:17). In some embodiments, the antibody comprises a VH FR2 (SEQ ID NO:20), a VL FR2 (SEQ ID NO:15) and a VL FR3 (SEQ ID NOS:16 or 18). In another embodiment, the antibody comprises a VH FR2 (SEQ ID NO:20), a VL FR2 (SEQ ID NO:15) and a VL FR4 (SEQ ID NO:17). In one embodiment, the antibody comprises a VH FR2 (SEQ ID NO:20), a VL FR3 (SEQ ID NOS:16 or 18), and a VL FR4 (SEQ ID NO:17). In another embodiment, the antibody comprises a VH FR3 (SEQ ID NOS:21 or 23), a VL FR1 (SEQ ID NO:14), and a VL FR2 (SEQ ID NO:15). In other embodiments, the antibody comprises a VH FR3 (SEQ ID NOS:21 or 23), a VL FR1 (SEQ ID NO:14), and a VL FR3 (SEQ ID NOS:16 or 18). In some embodiments, the antibody comprises a VH FR3 (SEQ ID NOS:21 or 23), a VL FR1 (SEQ ID NO:14), and a VL FR4 (SEQ ID NO:17). In another embodiment, the antibody comprises a VH FR3 (SEQ ID NOS:21 or 23), a VL FR2 (SEQ ID NO:15) and a VL FR3 (SEQ ID NOS:16 or 18). In one embodiment, the antibody comprises a VH FR3 (SEQ ID NOS:21 or 23), a VL FR2 (SEQ ID NO:15) and a VL FR4 (SEQ ID NO:17). In one embodiment, the antibody comprises a VH FR3 (SEQ ID NOS:21 or 23), a VL FR3 (SEQ ID NOS:16 or 18), and a VL FR4 (SEQ ID NO:17). In another embodiment, the antibody comprises a VH FR4 (SEQ ID NO:22), a VL FR1 (SEQ ID NO:14), and a VL FR2 (SEQ ID NO:15). In some embodiments, the antibody comprises a VH FR4 (SEQ ID NO:22), a VL FR1 (SEQ ID NO:14), and a VL FR3 (SEQ ID NOS:16 or 18). In other embodiments, the antibody comprises a VH FR4 (SEQ ID NO:22), a VL FR1 (SEQ ID NO:14), and a VL FR4 (SEQ ID NO:17). In another embodiment, the antibody comprises a VH FR4 (SEQ ID NO:22), a VL FR2 (SEQ ID NO:15) and a VL FR3 (SEQ ID NOS:16 or 18). In one embodiment, the antibody comprises a VH FR4 (SEQ ID NO:22), a VL FR2 (SEQ ID NO:15) and a VL FR4 (SEQ ID NO:17). In some embodiments, the antibody comprises a VH FR4 (SEQ ID NO:22), a VL FR3 (SEQ ID NOS:16 or 18), and a VL FR4 (SEQ ID NO:17). In another embodiment, the antibody comprises a VH FR1 (SEQ ID NOS:19 or 24), a VH FR2 (SEQ ID NO:20), a VH FR3 (SEQ ID NO:21), and a VL FR1 (SEQ ID NO:14). In one embodiment, the antibody comprises a VH FR1 (SEQ ID NOS:19 or 24), a VH FR2 (SEQ ID NO:20), a VH FR3 (SEQ ID NO:21), and a VL FR2 (SEQ ID NO:15). In other embodiments, the antibody comprises a VH FR1 (SEQ ID NOS:19 or 24), a VH FR2 (SEQ ID NO:20), a VH FR3 (SEQ ID NO:21), and a VL FR3 (SEQ ID NOS:16 or 18). In another embodiment, the antibody comprises a VH FR1 (SEQ ID NOS:19 or 24), a VH FR2 (SEQ ID NO:20), a VH FR3 (SEQ ID NO:21), and a VL FR4 (SEQ ID NO:17). In some embodiments, the antibody comprises a VH FR1 (SEQ ID NOS:19 or 24), a VH FR2 (SEQ ID NO:20), a VH FR4 (SEQ ID NO:22), and a VL FR1 (SEQ ID NO:14). In one embodiment, the antibody comprises a VH FR1 (SEQ ID NOS:19 or 24), a VH FR2 (SEQ ID NO:20), a VH FR4 (SEQ ID NO:22), and a VL FR2 (SEQ ID NO:15). In another embodiment, the antibody comprises a VH FR1 (SEQ ID NOS:19 or 24), a VH FR2 (SEQ ID NO:20), a VH FR4 (SEQ ID NO:22), and a VL FR3 (SEQ ID NOS:16 or 18). In one embodiment, the antibody comprises a VH FR1 (SEQ ID NOS:19 or 24), a VH FR2 (SEQ ID NO:20), a VH FR4 (SEQ ID NO:22), and a VL FR4 (SEQ ID NO:17). In some embodiments, the antibody comprises a VH FR1 (SEQ ID NOS:19 or 24), a VH FR3 (SEQ ID NOS:21 or 23), a VH FR4 (SEQ ID NO:22), and a VL FR1 (SEQ ID NO:14). In another embodiment, the antibody comprises a VH FR1 (SEQ ID NOS:19 or 24), a VH FR3 (SEQ ID NOS:21 or 23), a VH FR4 (SEQ ID NO:22), and a VL FR2 (SEQ ID NO:15). In other embodiments, the antibody comprises a VH FR1 (SEQ ID NOS:19 or 24), VH FR3 (SEQ ID NOS:21 or 23), a VH FR4 (SEQ ID NO:22), and a VL FR3 (SEQ ID NOS:16 or 18). In one embodiment, the antibody comprises a VH FR1 (SEQ ID NOS:19 or 24), a VH FR3 (SEQ ID NOS:21 or 23), a VH FR4 (SEQ ID NO:22), and a VL FR4 (SEQ ID NO:17). In another embodiment, the antibody comprises a VH FR2 (SEQ ID NO:20), a VH FR3 (SEQ ID NOS:21 or 23), a VH FR4 (SEQ ID NO:22), and a VL FR1 (SEQ ID NO:14). In some embodiments, the antibody comprises a VH FR2 (SEQ ID NO:20), a VH FR3 (SEQ ID NOS:21 or 23), a VH FR4 (SEQ ID NO:22), and a VL FR2 (SEQ ID NO:15). In one embodiment, the antibody comprises a VH FR2 (SEQ ID NO:20), VH FR3 (SEQ ID NOS:21 or 23), a VH FR4 (SEQ ID NO:22), and a VL FR3 (SEQ ID NOS:16 or 18). In another embodiment, the antibody comprises a VH FR2 (SEQ ID NO:20), a VH FR3 (SEQ ID NOS:21 or 23), a VH FR4 (SEQ ID NO:22), and a VL FR4 (SEQ ID NO:17). In other embodiments, the antibody comprises a VH FR1 (SEQ ID NOS:19 or 24), a VH FR2 (SEQ ID NO:20), a VL FR1 (SEQ ID NO:14), and a VL FR2 (SEQ ID NO:15). In some embodiments, the antibody comprises a VH FR1 (SEQ ID NOS:19 or 24), a VH FR2 (SEQ ID NO:20), a VL FR1 (SEQ ID NO:14), and a VL FR3 (SEQ ID NOS:16 or 18). In another embodiment, the antibody comprises a VH FR1 (SEQ ID NOS:19 or 24), a VH FR2 (SEQ ID NO:20), a VL FR1 (SEQ ID NO:14), and a VL FR4 (SEQ ID NO:17). In one embodiment, the antibody comprises a VH FR1 (SEQ ID NOS:19 or 24), a VH FR2 (SEQ ID NO:20), a VL FR2 (SEQ ID NO:15), and a VL FR3 (SEQ ID NOS: 16 or 18). In one embodiment, the antibody comprises a VH FR1 (SEQ ID NOS:19 or 24), a VH FR2 (SEQ ID NO:20), a VL FR2 (SEQ ID NO:15), and a VL FR4 (SEQ ID NO:17). In another embodiment, the antibody comprises a VH FR1 (SEQ ID NOS:19 or 24), a VH FR2 (SEQ ID NO:20), a VL FR3 (SEQ ID NOS:16 or 18), and a VL FR4 (SEQ ID NO:17). In some embodiments, the antibody comprises a VH FR1 (SEQ ID NOS:19 or 24), a VH FR3 (SEQ ID NO:21), a VL FR1 (SEQ ID NO:14), and a VL FR2 (SEQ ID NO:15). In other embodiments, the antibody comprises a VH FR1 (SEQ ID NOS:19 or 24), a VH FR3 (SEQ ID NO:21), a VL FR1 (SEQ ID NO:14), and a VL FR3 (SEQ ID NOS:16 or 18). In another embodiment, the antibody comprises a VH FR1 (SEQ ID NOS:19 or 24), a VH FR3 (SEQ ID NO:21), a VL FR1 (SEQ ID NO:14), and a VL FR4 (SEQ ID NO:17). In one embodiment, the antibody comprises a VH FR1 (SEQ ID NOS:19 or 24), a VH FR3 (SEQ ID NO:21), a VL FR2 (SEQ ID NO:15), and a VL FR3 (SEQ ID NOS:16 or 18). In some embodiments, the antibody comprises a VH FR1 (SEQ ID NOS:19 or 24), a VH FR3 (SEQ ID NO:21), a VL FR2 (SEQ ID NO:15), and a VL FR4 (SEQ ID NO:17). In another embodiment, the antibody comprises a VH FR1 (SEQ ID NOS:19 or 24), a VH FR3 (SEQ ID NO:21), a VL FR3 (SEQ ID NOS:16 or 18), and a VL FR4 (SEQ ID NO:17). In one embodiment, the antibody comprises a VH FR1 (SEQ ID NOS:19 or 24), a VH FR4 (SEQ ID NO:22), a VL FR1 (SEQ ID NO:14), and a VL FR2 (SEQ ID NO:15). In other embodiments, the antibody comprises a VH FR1 (SEQ ID NOS:19 or 24), a VH FR4 (SEQ ID NO:22), a VL FR1 (SEQ ID NO:14), and a VL FR3 (SEQ ID NOS:16 or 18). In another embodiment, the antibody comprises a VH FR1 (SEQ ID NOS:19 or 24), a VH FR4 (SEQ ID NO:22), a VL FR1 (SEQ ID NO:14), and a VL FR4 (SEQ ID NO:17). In some embodiments, the antibody comprises a VH FR1 (SEQ ID NOS:19 or 24), a VH FR4 (SEQ ID NO:22), a VL FR2 (SEQ ID NO:15), and a VL FR3 (SEQ ID NOS:16 or 18). In one embodiment, the antibody comprises a VH FR1 (SEQ ID NOS:19 or 24), a VH FR4 (SEQ ID NO:22), a VL FR2 (SEQ ID NO:15), and a VL FR4 (SEQ ID NO:17). In another embodiment, the antibody comprises a VH FR1 (SEQ ID NOS:19 or 24), a VH FR4 (SEQ ID NO:22), a VL FR3 (SEQ ID NOS:16 or 18), and a VL FR4 (SEQ ID NO:17). In one embodiment, the antibody comprises a VH FR2 (SEQ ID NO:20), a VH FR3 (SEQ ID NO:21), a VL FR1 (SEQ ID NO:14), and a VL FR2 (SEQ ID NO:15). In some embodiments, the antibody comprises a VH FR2 (SEQ ID NO:20), a VH FR3 (SEQ ID NO:21), a VL FR1 (SEQ ID NO:14), and a VL FR3 (SEQ ID NOS:16 or 18). In another embodiment, the antibody comprises a VH FR2 (SEQ ID NO:20), a VH FR3 (SEQ ID NO:21), a VL FR1 (SEQ ID NO:14), and a VL FR4 (SEQ ID NO:17). In other embodiments, the antibody comprises a VH FR2 (SEQ ID NO:20), a VH FR3 (SEQ ID NO:21), a VL FR2 (SEQ ID NO:15), and a VL FR3 (SEQ ID NOS:16 or 18). In one embodiment, the antibody comprises a VH FR2 (SEQ ID NO:20), a VH FR3 (SEQ ID NO:21), a VL FR2 (SEQ ID NO:15), and a VL FR4 (SEQ ID NO:17). In another embodiment, the antibody comprises a VH FR2 (SEQ ID NO:20), a VH FR3 (SEQ ID NO:21), a VL FR3 (SEQ ID NOS:16 or 18), and a VL FR4 (SEQ ID NO:17). In some embodiments, the antibody comprises a VH FR2 (SEQ ID NO:20), a VH FR4 (SEQ ID NO:22), a VL FR1 (SEQ ID NO:14), and a VL FR2 (SEQ ID NO:15). In one embodiment, the antibody comprises a VH FR2 (SEQ ID NO:20), a VH FR4 (SEQ ID NO:22), a VL FR1 (SEQ ID NO:14), and a VL FR3 (SEQ ID NOS:16 or 18). In another embodiment, the antibody comprises a VH FR2 (SEQ ID NO:20), a VH FR4 (SEQ ID NO:22), a VL FR1 (SEQ ID NO:14), and a VL FR4 (SEQ ID NO:17). In other embodiments, the antibody comprises a VH FR2 (SEQ ID NO:20), a VH FR4 (SEQ ID NO:22), a VL FR2 (SEQ ID NO:15), and a VL FR3 (SEQ ID NOS:16 or 18). In some embodiments, the antibody comprises a VH FR2 (SEQ ID NO:20), a VH FR4 (SEQ ID NO:22), a VL FR2 (SEQ ID NO:15), and a VL FR4 (SEQ ID NO:17). In another embodiment, the antibody comprises a VH FR2 (SEQ ID NO:20), a VH FR4 (SEQ ID NO:22), a VL FR3 (SEQ ID NOS:16 or 18), and a VL FR4 (SEQ ID NO:17). In one embodiment, the antibody comprises a VH FR3 (SEQ ID NOS:21 or 23), a VH FR4 (SEQ ID NO:22), a VL FR1 (SEQ ID NO:14), and a VL FR2 (SEQ ID NO:15). In one embodiment, the antibody comprises a VH FR3 (SEQ ID NOS:21 or 23), a VH FR4 (SEQ ID NO:22), a VL FR1 (SEQ ID NO:14), and a VL FR3 (SEQ ID NOS:16 or 18). In another embodiment, the antibody comprises a VH FR3 (SEQ ID NOS:21 or 23), a VH FR4 (SEQ ID NO:22), a VL FR1 (SEQ ID NO:14), and a VL FR4 (SEQ ID NO:17). In some embodiments, the antibody comprises a VH FR3 (SEQ ID NOS:21 or 23), a VH FR4 (SEQ ID NO:22), a VL FR2 (SEQ ID NO:15), and a VL FR3 (SEQ ID NOS:16 or 18). In other embodiments, the antibody comprises a VH FR3 (SEQ ID NOS:21 or 23), a VH FR4 (SEQ ID NO:22), a VL FR2 (SEQ ID NO:15), and a VL FR4 (SEQ ID NO:17). In another embodiment, the antibody comprises a VH FR3 (SEQ ID NOS:21 or 23), a VH FR4 (SEQ ID NO:22), a VL FR3 (SEQ ID NOS:16 or 18), and a VL FR4 (SEQ ID NO:17). In one embodiment, the antibody comprises a VH FR1 (SEQ ID NOS:19 or 24), a VL FR1 (SEQ ID NO:14), a VL FR2 (SEQ ID NO:15), and a VL FR3 (SEQ ID NOS:16 or 18). In some embodiments, the antibody comprises a VH FR1 (SEQ ID NOS:19 or 24), a VL FR1 (SEQ ID NO:14), a VL FR2 (SEQ ID NO:15), and a VL FR4 (SEQ ID NO:17). In another embodiment, the antibody comprises a VH FR1 (SEQ ID NOS:19 or 24), a VL FR1 (SEQ ID NO:14), a VL FR3 (SEQ ID NOS:16 or 18), and a VL FR4 (SEQ ID NO:17). In one embodiment, the antibody comprises a VH FR1 (SEQ ID NOS:19 or 24), a VL FR2 (SEQ ID NO:15), a VL FR3 (SEQ ID NOS:16 or 18), and a VL FR4 (SEQ ID NO:17). In other embodiments, the antibody comprises a VH FR2 (SEQ ID NO:20), a VL FR1 (SEQ ID NO:14), a VL FR2 (SEQ ID NO:15), and a VL FR3 (SEQ ID NOS:16 or 18). In another embodiment, the antibody comprises a VH FR2 (SEQ ID NO:20), a VL FR1 (SEQ ID NO:14), a VL FR2 (SEQ ID NO:15), and a VL FR4 (SEQ ID NO:17). In some embodiments, the antibody comprises a VH FR2 (SEQ ID NO:20), a VL FR1 (SEQ ID NO:14), a VL FR3 (SEQ ID NOS:16 or 18), and a VL FR4 (SEQ ID NO:17). In one embodiment, the antibody comprises a VH FR2 (SEQ ID NO:20), a VL FR2 (SEQ ID NO:15), a VL FR3 (SEQ ID NOS:16 or 18), and a VL FR4 (SEQ ID NO:17). In another embodiment, the antibody comprises a VH FR3 (SEQ ID NOS:21 or 23), a VL FR1 (SEQ ID NO:14), a VL FR2 (SEQ ID NO:15), and a VL FR3 (SEQ ID NOS:16 or 18). In one embodiment, the antibody comprises a VH FR3 (SEQ ID NOS:21 or 23), a VL FR1 (SEQ ID NO:14), a VL FR2 (SEQ ID NO:15), and a VL FR4 (SEQ ID NO:17). In some embodiments, the antibody comprises a VH FR3 (SEQ ID NOS:21 or 23), a VL FR1 (SEQ ID NO:14), a VL FR3 (SEQ ID NOS:16 or 18), and a VL FR4 (SEQ ID NO:17). In another embodiment, the antibody comprises a VH FR3 (SEQ ID NOS:21 or 23), a VL FR2 (SEQ ID NO:15), a VL FR3 (SEQ ID NOS:16 or 18), and a VL FR4 (SEQ ID NO:17). In other embodiments, the antibody comprises a VH FR4 (SEQ ID NO:22), a VL FR1 (SEQ ID NO:14), a VL FR2 (SEQ ID NO:15), and a VL FR3 (SEQ ID NOS:16 or 18). In one embodiment, the antibody comprises a VH FR4 (SEQ ID NO:22), a VL FR1 (SEQ ID NO:14), a VL FR2 (SEQ ID NO:15), and a VL FR4 (SEQ ID NO:17). In another embodiment, the antibody comprises a VH FR4 (SEQ ID NO:22), a VL FR1 (SEQ ID NO:14), a VL FR3 (SEQ ID NOS:16 or 18), and a VL FR4 (SEQ ID NO:17). In some embodiments, the antibody comprises a VH FR4 (SEQ ID NO:22), a VL FR2 (SEQ ID NO:15), a VL FR3 (SEQ ID NOS:16 or 18), and a VL FR4 (SEQ ID NO:17). In one embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), and a VL FR1 (SEQ ID NO:14). In another embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), and a VL FR2 (SEQ ID NO:15). In other embodiments, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), and a VL FR3 (SEQ ID NOS:16 or 18). In some embodiments, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), and a VL FR4 (SEQ ID NO:17). In another embodiment, the antibody comprises a VH FR1 (SEQ ID NOS:19 or 24), a VH FR2 (SEQ ID NO:20), a VH FR3 (SEQ ID NOS:21 or 23), a VL FR1 (SEQ ID NO:14), and a VL FR2 (SEQ ID NO:15). In one embodiment, the antibody comprises a VH FR1 (SEQ ID NOS:19 or 24), a VH FR2 (SEQ ID NO:20), a VH FR3 (SEQ ID NOS:21 or 23), a VL FR1 (SEQ ID NO:14), and a VL FR3 (SEQ ID NOS:16 or 18). In one embodiment, the antibody comprises a VH FR1 (SEQ ID NOS:19 or 24), a VH FR2 (SEQ ID NO:20), a VH FR3 (SEQ ID NOS:21 or 23), a VL FR1 (SEQ ID NO:14), and a VL FR4 (SEQ ID NO:17). In another embodiment, the antibody comprises a VH FR1 (SEQ ID NOS:19 or 24), a VH FR2 (SEQ ID NO:20), a VH FR3 (SEQ ID NOS:21 or 23), a VL FR2 (SEQ ID NO:15), and a VL FR3 (SEQ ID NOS:16 or 18). In some embodiments, the antibody comprises a VH FR1 (SEQ ID NOS:19 or 24), a VH FR2 (SEQ ID NO:20), a VH FR3 (SEQ ID NOS:21 or 23), a VL FR2 (SEQ ID NO:15), and a VL FR4 (SEQ ID NO:17). In other embodiments, the antibody comprises a VH FR1 (SEQ ID NOS:19 or 24), a VH FR2 (SEQ ID NO:20), a VH FR3 (SEQ ID NOS:21 or 23), a VL FR3 (SEQ ID NOS:16 or 18), and a VL FR4 (SEQ ID NO:17). In another embodiment, the antibody comprises a VH FR1 (SEQ ID NOS:19 or 24), a VH FR2 (SEQ ID NO:20), a VH FR4 (SEQ ID NO:22), a VL FR1 (SEQ ID NO:14), and a VL FR2 (SEQ ID NO:15). In some embodiments, the antibody comprises a VH FR1 (SEQ ID NOS:19 or 24), a VH FR2 (SEQ ID NO:20), a VH FR4 (SEQ ID NO:22), a VL FR1 (SEQ ID NO:14), and a VL FR4 (SEQ ID NO:17). In another embodiment, the antibody comprises a VH FR1 (SEQ ID NOS:19 or 24), a VH FR2 (SEQ ID NO:20), a VH FR4 (SEQ ID NO:22), a VL FR2 (SEQ ID NO:15), a VL FR3 (SEQ ID NOS:16 or 18). In one embodiment, the antibody comprises a VH FR1 (SEQ ID NOS:19 or 24), a VH FR2 (SEQ ID NO:20), a VH FR4 (SEQ ID NO:22), a VL FR2 (SEQ ID NO:15), and a VL FR4 (SEQ ID NO:17). In other embodiments, the antibody comprises a VH FR1 (SEQ ID NOS:19 or 24), a VH FR2 (SEQ ID NO:20), a VH FR4 (SEQ ID NO:22), a VL FR3 (SEQ ID NOS:16 or 18), and a VL FR4 (SEQ ID NO:17). In another embodiment, the antibody comprises a VH FR1 (SEQ ID NOS:19 or 24), a VH FR3 (SEQ ID NOS:21 or 23), a VH FR4 (SEQ ID NO:22), a VL FR1 (SEQ ID NO:14), and a VL FR2 (SEQ ID NO:15). In some embodiments, the antibody comprises a VH FR1 (SEQ ID NOS:19 or 24), a VH FR3 (SEQ ID NOS:21 or 23), a VH FR4 (SEQ ID NO:22), a VL FR1 (SEQ ID NO:14), and a VL FR3 (SEQ ID NOS:16 or 18). In one embodiment, the antibody comprises a VH FR1 (SEQ ID NOS:19 or 24), a VH FR3 (SEQ ID NOS:21 or 23), a VH FR4 (SEQ ID NO:22), a VL FR1 (SEQ ID NO:14), and a VL FR4 (SEQ ID NO:17). In another embodiment, the antibody comprises a VH FR1 (SEQ ID NOS:19 or 24), a VH FR3 (SEQ ID NOS:21 or 23), a VH FR4 (SEQ ID NO:22), a VL FR2 (SEQ ID NO:15), and a VL FR3 (SEQ ID NOS:16 or 18). In one embodiment, the antibody comprises a VH FR1 (SEQ ID NOS:19 or 24), a VH FR3 (SEQ ID NOS:21 or 23), a VH FR4 (SEQ ID NO:22), a VL FR2 (SEQ ID NO:15), and a VL FR4 (SEQ ID NO:17). In some embodiments, the antibody comprises a VH FR1 (SEQ ID NOS:19 or 24), a VH FR3 (SEQ ID NOS:21 or 23), a VH FR4 (SEQ ID NO:22), a VL FR3 (SEQ ID NOS:16 or 18), and a VL FR4 (SEQ ID NO:17). In another embodiment, the antibody comprises a VH FR2 (SEQ ID NO:20), a VH FR3 (SEQ ID NOS:21 or 23), a VH FR4 (SEQ ID NO:22), a VL FR1 (SEQ ID NO:14), and a VL FR2 (SEQ ID NO:15). In other embodiments, the antibody comprises a VH FR2 (SEQ ID NO:20), a VH FR3 (SEQ ID NOS:21 or 23), a VH FR4 (SEQ ID NO:22), a VL FR1 (SEQ ID NO:14), and a VL FR3 (SEQ ID NOS:16 or 18). In one embodiment, the antibody comprises a VH FR2 (SEQ ID NO:20), a VH FR3 (SEQ ID NOS:21 or 23), a VH FR4 (SEQ ID NO:22), a VL FR1 (SEQ ID NO:14), and a VL FR4 (SEQ ID NO:17). In another embodiment, the antibody comprises a VH FR2 (SEQ ID NO:20), a VH FR3 (SEQ ID NOS:21 or 23), a VH FR4 (SEQ ID NO:22), a VL FR2 (SEQ ID NO:15), and a VL FR3 (SEQ ID NOS:16 or 18). In some embodiments, the antibody comprises a VH FR2 (SEQ ID NO:20), a VH FR3 (SEQ ID NOS:21 or 23), a VH FR4 (SEQ ID NO:22), a VL FR2 (SEQ ID NO:15), and a VL FR4 (SEQ ID NO:17). In one embodiment, the antibody comprises a VH FR2 (SEQ ID NO:20), a VH FR3 (SEQ ID NOS:21 or 23), a VH FR4 (SEQ ID NO:22), a VL FR3 (SEQ ID NOS:16 or 18), and a VL FR4 (SEQ ID NO:17). In another embodiment, the antibody comprises a VH FR1 (SEQ ID NOS:19 or 24), a VH FR2 (SEQ ID NO:20), a VL FR1 (SEQ ID NO:14), a VL FR2 (SEQ ID NO:15), and a VL FR3 (SEQ ID NOS:16 or 18). In other embodiments, the antibody comprises a VH FR1 (SEQ ID NOS:19 or 24), a VH FR2 (SEQ ID NO:20), a VL FR1 (SEQ ID NO:14), a VL FR2 (SEQ ID NO:15), and a VL FR4 (SEQ ID NO:17). In some embodiments, the antibody comprises a VH FR1 (SEQ ID NOS:19 or 24), a VH FR2 (SEQ ID NO:20), a VL FR1 (SEQ ID NO:14), a VL FR3 (SEQ ID NOS:16 or 18), and a VL FR4 (SEQ ID NO:17). In another embodiment, the antibody comprises a VH FR1 (SEQ ID NOS:19 or 24), a VH FR2 (SEQ ID NO:20), a VL FR2 (SEQ ID NO:15), a VL FR3 (SEQ ID NOS:16 or 18), and a VL FR4 (SEQ ID NO:17). In one embodiment, the antibody comprises a VH FR1 (SEQ ID NOS:19 or 24), a VH FR3 (SEQ ID NOS:21 or 23), a VL FR1 (SEQ ID NO:14), a VL FR2 (SEQ ID NO:15), and a VL FR3 (SEQ ID NOS:16 or 18). In one embodiment, the antibody comprises a VH FR1 (SEQ ID NOS:19 or 24), a VH FR3 (SEQ ID NOS:21 or 23), a VL FR1 (SEQ ID NO:14), a VL FR2 (SEQ ID NO:15), and a VL FR4 (SEQ ID NO:17). In another embodiment, the antibody comprises a VH FR1 (SEQ ID NOS:19 or 24), a VH FR3 (SEQ ID NOS:21 or 23), a VL FR1 (SEQ ID NO:14), a VL FR3 (SEQ ID NOS:16 or 18), and a VL FR4 (SEQ ID NO:17). In some embodiments, the antibody comprises a VH FR1 (SEQ ID NOS:19 or 24), a VH FR3 (SEQ ID NOS:21 or 23), a VL FR2 (SEQ ID NO:15), a VL FR3 (SEQ ID NOS:16 or 18), and a VL FR4 (SEQ ID NO:17). In other embodiments, the antibody comprises a VH FR1 (SEQ ID NOS:19 or 24), a VH FR4 (SEQ ID NO:22), a VL FR1 (SEQ ID NO:14), a VL FR2 (SEQ ID NO:15), and a VL FR3 (SEQ ID NOS:16 or 18). In another embodiment, the antibody comprises a VH FR1 (SEQ ID NOS:19 or 24), a VH FR4 (SEQ ID NO:22), a VL FR1 (SEQ ID NO:14), a VL FR2 (SEQ ID NO:15), and a VL FR4 (SEQ ID NO:17). In one embodiment, the antibody comprises a VH FR1 (SEQ ID NOS:19 or 24), a VH FR4 (SEQ ID NO:22), a VL FR1 (SEQ ID NO:14), a VL FR3 (SEQ ID NOS:16 or 18), and a VL FR4 (SEQ ID NO:17). In some embodiments, the antibody comprises a VH FR1 (SEQ ID NOS:19 or 24), a VH FR4 (SEQ ID NO:22), a VL FR2 (SEQ ID NO:15), a VL FR3 (SEQ ID NOS:16 or 18), and a VL FR4 (SEQ ID NO:17). In another embodiment, the antibody comprises a VH FR2 (SEQ ID NO:20), a VH FR3 (SEQ ID NOS:21 or 23), a VL FR1 (SEQ ID NO:14), a VL FR2 (SEQ ID NO:15), and a VL FR3 (SEQ ID NOS:16 or 18). In one embodiment, the antibody comprises a VH FR2 (SEQ ID NO:20), a VH FR3 (SEQ ID NOS:21 or 23), a VL FR1 (SEQ ID NO:14), a VL FR2 (SEQ ID NO:15), and a VL FR4 (SEQ ID NO:17). In other embodiments, the antibody comprises a VH FR2 (SEQ ID NO:20), a VH FR3 (SEQ ID NOS:21 or 23), a VL FR1 (SEQ ID NO:14), a VL FR3 (SEQ ID NOS:16 or 18), and a VL FR4 (SEQ ID NO:17). In another embodiment, the antibody comprises a VH FR2 (SEQ ID NO:20), a VH FR3 (SEQ ID NOS:21 or 23), a VL FR2 (SEQ ID NO:15), a VL FR3 (SEQ ID NOS:16 or 18), and a VL FR4 (SEQ ID NO:17). In some embodiments, the antibody comprises a VH FR2 (SEQ ID NO:20), a VH FR4 (SEQ ID NO:22), a VL FR1 (SEQ ID NO:14), a VL FR2 (SEQ ID NO:15), and a VL FR3 (SEQ ID NOS:16 or 18). In one embodiment, the antibody comprises a VH FR2 (SEQ ID NO:20), a VH FR4 (SEQ ID NO:22), a VL FR1 (SEQ ID NO:14), a VL FR2 (SEQ ID NO:15), and a VL FR4 (SEQ ID NO:17). In another embodiment, the antibody comprises a VH FR2 (SEQ ID NO:20), a VH FR4 (SEQ ID NO:22), a VL FR1 (SEQ ID NO:14), a VL FR3 (SEQ ID NOS:16 or 18), and a VL FR4 (SEQ ID NO:17). In one embodiment, the antibody comprises a VH FR2 (SEQ ID NO:20), a VH FR4 (SEQ ID NO:22), a VL FR2 (SEQ ID NO:15), a VL FR3 (SEQ ID NOS:16 or 18), and a VL FR4 (SEQ ID NO:17). In some embodiments, the antibody comprises a VH FR3 (SEQ ID NOS:21 or 23), a VH FR4 (SEQ ID NO:22), a VL FR1 (SEQ ID NO:14), a VL FR2 (SEQ ID NO:15), and a VL FR3 (SEQ ID NOS:16 or 18). In another embodiment, the antibody comprises a VH FR3 (SEQ ID NOS:21 or 23), a VH FR4 (SEQ ID NO:22), a VL FR1 (SEQ ID NO:14), a VL FR2 (SEQ ID NO:15), and a VL FR4 (SEQ ID NO:17). In other embodiments, the antibody comprises a VH FR3 (SEQ ID NOS:21 or 23), a VH FR4 (SEQ ID NO:22), a VL FR1 (SEQ ID NO:14), a VL FR3 (SEQ ID NOS:16 or 18), and a VL FR4 (SEQ ID NO:17). In one embodiment, the antibody comprises a VH FR3 (SEQ ID NOS:21 or 23), a VH FR4 (SEQ ID NO:22), a VL FR2 (SEQ ID NO:15), a VL FR3 (SEQ ID NOS:16 or 18), and a VL FR4 (SEQ ID NO:17). In another embodiment, the antibody comprises a VH FR1 (SEQ ID NOS:19 or 24), a VL FR1 (SEQ ID NO:14), a VL FR2 (SEQ ID NO:15), a VL FR3 (SEQ ID NOS:16 or 18), and a VL FR4 (SEQ ID NO:17). In some embodiments, the antibody comprises a VH FR2 (SEQ ID NO:20), a VL FR1 (SEQ ID NO:14), a VL FR2 (SEQ ID NO:15), a VL FR3 (SEQ ID NOS:16 or 18), and a VL FR4 (SEQ ID NO:17). In one embodiment, the antibody comprises a VH FR3 (SEQ ID NOS:21 or 23), a VL FR1 (SEQ ID NO:14), a VL FR2 (SEQ ID NO:15), a VL FR3 (SEQ ID NOS:16 or 18), and a VL FR4 (SEQ ID NO:17). In another embodiment, the antibody comprises a VH FR4 (SEQ ID NO:22), a VL FR1 (SEQ ID NO:14), a VL FR2 (SEQ ID NO:15), a VL FR3 (SEQ ID NOS:16 or 18), and a VL FR4 (SEQ ID NO:17). In other embodiments, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR1 (SEQ ID NO:14), and a VL FR2 (SEQ ID NO:15). In some embodiments, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR1 (SEQ ID NO:14), and a VL FR3 (SEQ ID NOS:16 or 18). In another embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR1 (SEQ ID NO:14), and a VL FR4 (SEQ ID NO:17). In one embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR2 (SEQ ID NO:15), and a VL FR3 (SEQ ID NOS:16 or 18). In one embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR3 (SEQ ID NOS:16 or 18), and a VL FR4 (SEQ ID NO:17). In some embodiments, the antibody comprises a VH FR1 (SEQ ID NOS:19 or 24), a VH FR2 (SEQ ID NO:20), a VH FR3 (SEQ ID NOS:21 or 23), a VL FR1 (SEQ ID NO:14), a VL FR2 (SEQ ID NO:15), and a VL FR3 (SEQ ID NOS:16 or 18). In other embodiments, the antibody comprises a VH FR1 (SEQ ID NOS:19 or 24), a VH FR2 (SEQ ID NO:20), a VH FR3 (SEQ ID NOS:21 or 23), a VL FR1 (SEQ ID NO:14), a VL FR2 (SEQ ID NO:15), and a VL FR4 (SEQ ID NO:17). In another embodiment, the antibody comprises a VH FR1 (SEQ ID NOS:19 or 24), a VH FR2 (SEQ ID NO:20), a VH FR3 (SEQ ID NOS:21 or 23), a VL FR1 (SEQ ID NO:14), a VL FR3 (SEQ ID NOS:16 or 18), and a VL FR4 (SEQ ID NO:17). In one embodiment, the antibody comprises a VH FR1 (SEQ ID NOS:19 or 24), a VH FR2 (SEQ ID NO:20), a VH FR3 (SEQ ID NOS:21 or 23), a VL FR2 (SEQ ID NO:15), a VL FR3 (SEQ ID NOS:16 or 18), and a VL FR4 (SEQ ID NO:17). In some embodiments, the antibody comprises a VH FR1 (SEQ ID NOS:19 or 24), a VH FR2 (SEQ ID NO:20), a VH FR4 (SEQ ID NO:22), a VL FR1 (SEQ ID NO:14), a VL FR2 (SEQ ID NO:15), and a VL FR3 (SEQ ID NOS:16 or 18). In another embodiment, the antibody comprises a VH FR1 (SEQ ID NOS:19 or 24), a VH FR2 (SEQ ID NO:20), a VH FR4

(SEQ ID NO:22), a VL FR1 (SEQ ID NO:14), a VL FR2 (SEQ ID NO:15), and a VL FR4 (SEQ ID NO:17). In one embodiment, the antibody comprises a VH FR1 (SEQ ID NOS:19 or 24), a VH FR2 (SEQ ID NO:20), a VH FR4 (SEQ ID NO:22), a VL FR1 (SEQ ID NO:14), a VL FR3 (SEQ ID NOS:16 or 18), and a VL FR4 (SEQ ID NO:17). In other embodiments, the antibody comprises a VH FR1 (SEQ ID NOS:19 or 24), a VH FR2 (SEQ ID NO:20), a VH FR4 (SEQ ID NO:22), a VL FR2 (SEQ ID NO:15), a VL FR3 (SEQ ID NOS:16 or 18), and a VL FR4 (SEQ ID NO:17). In another embodiment, the antibody comprises a VH FR1 (SEQ ID NOS:19 or 24), a VH FR3 (SEQ ID NOS:21 or 23), a VH FR4 (SEQ ID NO:22), a VL FR1 (SEQ ID NO:14), a VL FR2 (SEQ ID NO:15), and a VL FR3 (SEQ ID NOS:16 or 18). In some embodiments, the antibody comprises a VH FR1 (SEQ ID NOS:19 or 24), a VH FR3 (SEQ ID NOS:21 or 23), a VH FR4 (SEQ ID NO:22), a VL FR1 (SEQ ID NO:14), a VL FR2 (SEQ ID NO:15), and a VL FR4 (SEQ ID NO:17). In one embodiment, the antibody comprises a VH FR1 (SEQ ID NOS:19 or 24), a VH FR3 (SEQ ID NOS:21 or 23), a VH FR4 (SEQ ID NO:22), a VL FR1 (SEQ ID NO:14), a VL FR3 (SEQ ID NOS:16 or 18), and a VL FR4 (SEQ ID NO:17). In another embodiment, the antibody comprises a VH FR1 (SEQ ID NOS:19 or 24), a VH FR3 (SEQ ID NOS:21 or 23), a VH FR4 (SEQ ID NO:22), a VL FR2 (SEQ ID NO:15), a VL FR3 (SEQ ID NOS:16 or 18), and a VL FR4 (SEQ ID NO:17). In one embodiment, the antibody comprises a VH FR2 (SEQ ID NO:20), a VH FR3 (SEQ ID NOS:21 or 23), a VH FR4 (SEQ ID NO:22), a VL FR1 (SEQ ID NO:14), a VL FR2 (SEQ ID NO:15), and a VL FR3 (SEQ ID NOS:16 or 18). In some embodiments, the antibody comprises a VH FR2 (SEQ ID NO:20), a VH FR3 (SEQ ID NOS:21 or 23), a VH FR4 (SEQ ID NO:22), a VL FR1 (SEQ ID NO:14), a VL FR2 (SEQ ID NO:15), and a VL FR4 (SEQ ID NO:17). In another embodiment, the antibody comprises a VH FR2 (SEQ ID NO:20), a VH FR3 (SEQ ID NOS:21 or 23), a VH FR4 (SEQ ID NO:22), a VL FR1 (SEQ ID NO:14), a VL FR3 (SEQ ID NOS:16 or 18), and a VL FR4 (SEQ ID NO:17). In other embodiments, the antibody comprises a VH FR2 (SEQ ID NO:20), a VH FR3 (SEQ ID NOS:21 or 23), a VH FR4 (SEQ ID NO:22), a VL FR2 (SEQ ID NO:15), a VL FR3 (SEQ ID NOS:16 or 18), and a VL FR4 (SEQ ID NO:17). In one embodiment, the antibody comprises a VH FR1 (SEQ ID NOS:19 or 24), a VH FR2 (SEQ ID NO:20), a VL FR1 (SEQ ID NO:14), a VL FR2 (SEQ ID NO:15), a VL FR3 (SEQ ID NOS:16 or 18), and a VL FR4 (SEQ ID NO:17). In another embodiment, the antibody comprises a VH FR1 (SEQ ID NOS:19 or 24), a VH FR3 (SEQ ID NOS:21 or 23), a VL FR1 (SEQ ID NO:14), a VL FR2 (SEQ ID NO:15), a VL FR3 (SEQ ID NOS:16 or 18), and a VL FR4 (SEQ ID NO:17). In some embodiments, the antibody comprises a VH FR1 (SEQ ID NOS:19 or 24), a VH FR4 (SEQ ID NO:22), a VL FR1 (SEQ ID NO:14), a VL FR2 (SEQ ID NO:15), a VL FR3 (SEQ ID NOS:16 or 18), and a VL FR4 (SEQ ID NO:17). In one embodiment, the antibody comprises a VH FR2 (SEQ ID NO:20), a VH FR3 (SEQ ID NOS:21 or 23), a VL FR1 (SEQ ID NO:14), a VL FR2 (SEQ ID NO:15), a VL FR3 (SEQ ID NOS:16 or 18), and a VL FR4 (SEQ ID NO:17). In another embodiment, the antibody comprises a VH FR2 (SEQ ID NO:20), a VH FR4 (SEQ ID NO:22), a VL FR1 (SEQ ID NO:14), a VL FR2 (SEQ ID NO:15), a VL FR3 (SEQ ID NOS:16 or 18), and a VL FR4 (SEQ ID NO:17). In other embodiments, the antibody comprises a VH FR3 (SEQ ID NOS:21 or 23), a VH FR4 (SEQ ID NO:22), a VL FR1 (SEQ ID NO:14), a VL FR2 (SEQ ID NO:15), a VL FR3 (SEQ ID NOS:16 or 18), and a VL FR4 (SEQ ID NO:17). In some embodiments, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR1 (SEQ ID NO:14), a VL FR2 (SEQ ID NO:15), and a VL FR3 (SEQ ID NOS:16 or 18). In another embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR1 (SEQ ID NO:14), a VL FR2 (SEQ ID NO:15), and a VL FR4 (SEQ ID NO:17). In one embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR1 (SEQ ID NO:14), a VL FR3 (SEQ ID NOS:16 or 18), and a VL FR4 (SEQ ID NO:17). In one embodiment, the antibody comprises a VH FR1 (SEQ ID NOS:19 or 24), a VH FR2 (SEQ ID NO:20), a VH FR3 (SEQ ID NOS:21 or 23), a VH FR4 (SEQ ID NO:22), a VL FR2 (SEQ ID NO:15), a VL FR3 (SEQ ID NOS:16 or 18), and a VL FR4 (SEQ ID NO:17). In another embodiment, the antibody comprises a VH FR1 (SEQ ID NOS:19 or 24), a VH FR2 (SEQ ID NO:20), a VH FR3 (SEQ ID NOS:21 or 23), a VL FR1 (SEQ ID NO:14), a VL FR2 (SEQ ID NO:15), a VL FR3 (SEQ ID NOS:16 or 18), and a VL FR4 (SEQ ID NO:17). In some embodiments, the antibody comprises a VH FR1 (SEQ ID NOS:19 or 24), a VH FR2 (SEQ ID NO:20), a VH FR4 (SEQ ID NO:22), a VL FR1 (SEQ ID NO:14), a VL FR2 (SEQ ID NO:15), a VL FR3 (SEQ ID NOS:16 or 18), and a VL FR4 (SEQ ID NO:17). In other embodiments, the antibody comprises a VH FR1 (SEQ ID NOS:19 or 24), a VH FR3 (SEQ ID NOS:21 or 23), a VH FR4 (SEQ ID NO:22), a VL FR1 (SEQ ID NO:14), a VL FR2 (SEQ ID NO:15), a VL FR3 (SEQ ID NOS:16 or 18), and a VL FR4 (SEQ ID NO:17). In one embodiment, the antibody comprises a VH FR2 (SEQ ID NO:20), a VH FR3 (SEQ ID NOS:21 or 23), a VH FR4 (SEQ ID NO:22), a VL FR1 (SEQ ID NO:14), a VL FR2 (SEQ ID NO:15), a VL FR3 (SEQ ID NOS:16 or 18), and a VL FR4 (SEQ ID NO:17). In some embodiments, the antibody comprises any combination thereof of the VH FRs (SEQ ID NOS:19-24) and the VL FRs (SEQ ID NOS:14-18) listed in Tables 3-4.

In some embodiments, the various methods provided herein comprise administering an antibody comprising a VH region or VH domain. In other embodiments, the antibodies comprise a VL region or VL domain. In certain embodiments, the antibodies have a combination of (i) a VH domain or VH region; and/or (ii) a VL domain or VL region. Exemplary VH regions, VH domains, VL regions and VL domains of antibodies useful in the methods are set forth elsewhere herein. In some embodiments, the antibodies have a combination of (i) a VH domain or VH region; and/or (ii) a VL domain or VL region selected from the group consisting of SEQ ID NOS: 8-13 as set forth in Tables 5-6. In other embodiments, the antibodies provided herein have a combination of (i) a VH domain or VH region; and/or (ii) a VL domain or VL region of any one of antibodies PD1AB-1, PD1AB-2, PD1AB-3, PD1AB-4, PD1AB-5, or PD1AB-6, as set forth in Tables 5-6.

In some embodiments, the various methods provided herein comprise administering an antibody comprising a VH region comprising: (1) a VH CDR1 having an amino acid sequence of SEQ ID NO:4; (2) a VH CDR2 having an amino acid sequence of SEQ ID NO:5; and (3) a VH CDR3 having an amino acid sequence of SEQ ID NO:6; and a VL region selected from the group consisting of SEQ ID NOS:8-10 as set forth in Table 5. In some embodiments, the VL region has an amino acid sequence of SEQ ID NO:8. In other embodiments, the VL region has an amino acid sequence of SEQ ID NO:9. In some embodiments, the VL region has an amino acid sequence of SEQ ID NO:10.

In other embodiments, the various methods provided herein comprise administering an antibody comprising a VH region selected from the group consisting of SEQ ID NOS: 11-13 as set forth in Table 6; and a VL region comprising: (1) a VL CDR1 having an amino acid sequence selected from the group consisting of SEQ ID NOS:1 and 7; (2) a VL CDR2 having an amino acid sequence of SEQ ID NO:2; and (3) a VL CDR3 having an amino acid sequence of SEQ ID NO:3. In other embodiments, the various methods provided herein comprise administering an antibody comprising a VH region selected from the group consisting of SEQ ID NOS: 11-13 as set forth in Table 6; and a VL region comprising: (1) a VL CDR1 having an amino acid sequence of SEQ ID NO:1; (2) a VL CDR2 having an amino acid sequence of SEQ ID NO:2; and (3) a VL CDR3 having an amino acid sequence of SEQ ID NO:3. In yet other embodiments, the various methods provided herein comprise administering an antibody comprising a VH region selected from the group consisting of SEQ ID NOS:11-13 as set forth in Table 6; and a VL region comprising: (1) a VL CDR1 having an amino acid sequence of SEQ ID NO:7; (2) a VL CDR2 having an amino acid sequence of SEQ ID NO:2; and (3) a VL CDR3 having an amino acid sequence of SEQ ID NO:3. In some embodiments, the VH region has an amino acid sequence of SEQ ID NO:11. In some embodiments, the VH region has an amino acid sequence of SEQ ID NO:12. In some embodiments, the VH region has an amino acid sequence of SEQ ID NO:13.

In some embodiments, the various methods provided herein comprise administering an antibody comprising a VH and a VL amino acid sequence of PD1AB-1. In some embodiments, an antibody comprises a VH amino acid sequence of SEQ ID NO:11, and a VL amino acid sequence of SEQ ID NO:8. In other embodiments, the antibody has a VH and a VL amino acid sequence of PD1AB-2. In some embodiments, an antibody comprises a VH amino acid sequence of SEQ ID NO:11, and a VL amino acid sequence of SEQ ID NO:9. In some embodiments, the antibody has a VH and a VL amino acid sequence of PD1AB-3. In some embodiments, an antibody comprises a VH amino acid sequence of SEQ ID NO:12, and a VL amino acid sequence of SEQ ID NO:10. In other embodiments, the antibody has a VH and a VL amino acid sequence of PD1AB-4. In some embodiments, an antibody comprises a VH amino acid sequence of SEQ ID NO:12, and a VL amino acid sequence of SEQ ID NO:9. In some embodiments, the antibody has a VH and a VL amino acid sequence of PD1AB-5. In some embodiments, an antibody comprises a VH amino acid sequence of SEQ ID NO:13, and a VL amino acid sequence of SEQ ID NO:9. In other embodiments, the antibody has a VH and a VL amino acid sequence of PD1AB-6. In some embodiments, an antibody comprises a VH amino acid sequence of SEQ ID NO:13, and a VL amino acid sequence of SEQ ID NO:8. In certain embodiments, the various methods provided herein comprise administering an antibody, which specifically binds to a PD-1 polypeptide (e.g., an ECD of PD-1, for example human PD-1), comprising a light chain and a heavy chain, wherein the light chain comprises a constant region having an amino acid sequence of SEQ ID NO:41. In other embodiments, the antibody comprises a light chain and a heavy chain, wherein the heavy chain comprises a human IgG1 Fc region having an amino acid sequence of SEQ ID NO:36. In some embodiments, the antibody comprises a light chain and a heavy chain, wherein the heavy chain does not comprise a human IgG1 Fc region having an amino acid sequence of SEQ ID NO:36. In certain embodiments, the antibody comprises a light chain and a heavy chain, wherein the heavy chain comprises a human IgG1-K322A Fc region having an amino acid sequence of SEQ ID NO:37. In some embodiments, the antibody comprises a light chain and a heavy chain, wherein the heavy chain comprises a human IgG4 Fc region having an amino acid sequence of SEQ ID NO:38. In another embodiment, the antibody comprises a light chain and a heavy chain, wherein the heavy chain comprises a human IgG4P Fc region having an amino acid sequence of SEQ ID NO:39. In yet another embodiment the antibody comprises a light chain and a heavy chain, wherein the heavy chain comprises a human IgG4PE Fc region having an amino acid sequence of SEQ ID NO:40. In some embodiments, the antibody comprises a light chain and a heavy chain, wherein the heavy chain does not comprise a human IgG4PE Fc region having an amino acid sequence of SEQ ID NO:40. In still another embodiment, the antibody comprises a light chain and a heavy chain, wherein the light chain comprises a constant region having an amino acid sequence of SEQ ID NO:41; and the heavy chain comprises an Fc region having an amino acid sequence selected from the group consisting of SEQ ID NOS:36-40.

In some embodiments, the various methods provided herein comprise administering an antibody comprising a light chain and a heavy chain, wherein the light chain comprises an amino acid sequence of SEQ ID NO:31. In some embodiments, the antibody comprises a light chain and a heavy chain, wherein the heavy chain comprises an amino acid sequence of SEQ ID NO:32. In other embodiments, the antibody comprises a light chain and a heavy chain, wherein the heavy chain comprises an amino acid sequence of SEQ ID NO:33. In another embodiment, the antibody comprises a light chain and a heavy chain, wherein the heavy chain comprises an amino acid sequence of SEQ ID NO:34. In yet another embodiment, the antibody comprises a light chain and a heavy chain, wherein the heavy chain comprises an amino acid sequence of SEQ ID NO:35. In one particular embodiment, the antibody comprises a light chain and a heavy chain, wherein (i) the light chain comprises an amino acid sequence of SEQ ID NO:31; and (ii) the heavy chain comprises an amino acid sequence of SEQ ID NO:32. In another particular embodiment, the antibody comprises a light chain and a heavy chain, wherein (i) the light chain comprises an amino acid sequence of SEQ ID NO:31; and (ii) the heavy chain comprises an amino acid sequence of SEQ ID NO:33. In yet another particular embodiment, the antibody comprises a light chain and a heavy chain, wherein (i) the light chain comprises an amino acid sequence of SEQ ID NO:31; and (ii) the heavy chain comprises an amino acid sequence of SEQ ID NO:34. In still another particular embodiment, the antibody comprises a light chain and a heavy chain, wherein (i) the light chain comprises an amino acid sequence of SEQ ID NO:31; and (ii) the heavy chain comprises an amino acid sequence of SEQ ID NO:35.

In yet another embodiment, the various methods provided herein comprise administering an antibody that competes with one of the exemplified antibodies or functional fragments for binding to PD-1 provided herein. Such antibodies may also bind to the same epitope as one of the herein exemplified antibodies, or an overlapping epitope. Antibodies and fragments that compete with or bind to the same epitope as the exemplified antibodies are expected to show similar functional properties. The exemplified antigen-binding proteins and fragments include those with the VH and VL regions, and CDRs provided herein, including those in Tables 1-6. Thus, as a specific example, the antibodies useful in the methods provided herein include those that compete with an antibody comprising: (a) 1, 2, 3, 4, 5, or all 6 of the CDRs listed for an antibody listed in Tables 1-2; (b) a VH and a VL selected from the VH and the VL regions listed for an antibody listed in Tables 5-6; or (c) two light chains and two heavy chains comprising a VH and a VL as specified for an antibody listed in Tables 5-6. In some embodiments, the antibody is PD1AB-1. In some embodiments, the antibody is PD1AB-2. In some embodiments, the antibody is PD1AB-3. In some embodiments, the antibody is PD1AB-4. In some embodiments, the antibody is PD1AB-5. In some embodiments, the antibody is PD1AB-6.

Accordingly, provided herein is a method of treating vitiligo in a subject, comprising administering to the subject an effective amount of an anti-PD-1 antibody. In some embodiments, the anti-PD-1 antibody is PD1AB-1, PD1AB-2, PD1AB-3, PD1AB-4, PD1AB-5 or PD1AB-6. In some embodiments, the anti-PD-1 antibody is PD1AB-1. In some embodiments, the anti-PD-1 antibody is PD1AB-2. In some embodiments, the anti-PD-1 antibody is PD1AB-3. In some embodiments, the anti-PD-1 antibody is PD1AB-4. In some embodiments, the anti-PD-1 antibody is PD1AB-5. In some embodiments, the anti-PD-1 antibody is PD1AB-6. Also provided herein is a method of treating vitiligo in a subject, comprising administering to the subject an effective amount of an antigen binding fragment of an anti-PD-1 antibody. In certain embodiments, the antigen binding fragment is a fragment of a PD1AB-1, PD1AB-2, PD1AB-3, PD1AB-4, PD1AB-5 or PD1AB-6 antibody. In some embodiments, the anti-PD-1 antibody fragment is a fragment of PD1AB-1. In some embodiments, the anti-PD-1 antibody fragment is a fragment of PD1AB-2. In some embodiments, the anti-PD-1 antibody fragment is a fragment of PD1AB-3. In some embodiments, the anti-PD-1 antibody fragment is a fragment of PD1AB-4. In some embodiments, the anti-PD-1 antibody fragment is a fragment of PD1AB-5. In some embodiments, the anti-PD-1 antibody fragment is a fragment of PD1AB-6. In one embodiment, the VL of the anti-PD-1 antibody, or antigen binding fragment thereof, comprises VL CDR1, VL CDR2, and VL CDR3 of PD1AB-1. In some embodiments, the VH of the anti-PD-1 antibody, or antigen binding fragment thereof, comprises VH CDR1, VH CDR2, and VH CDR3 of PD1AB-1. In certain embodiments, the VL of the anti-PD-1 antibody, or antigen binding fragment thereof, comprises VL CDR1, VL CDR2, and VL CDR3 of PD1AB-1, and the VH of the anti-PD-1 antibody, or antigen binding fragment thereof, comprises VH CDR1, VH CDR2, and VH CDR3 of PD1AB-1. In one embodiment, the VL of the anti-PD-1 antibody, or antigen binding fragment thereof, comprises VL CDR1, VL CDR2, and VL CDR3 of PD1AB-2. In some embodiments, the VH of the anti-PD-1 antibody, or antigen binding fragment thereof, comprises VH CDR1, VH CDR2, and VH CDR3 of PD1AB-2. In certain embodiments, the VL of the anti-PD-1 antibody, or antigen binding fragment thereof, comprises VL CDR1, VL CDR2, and VL CDR3 of PD1AB-2, and the VH of the anti-PD-1 antibody, or antigen binding fragment thereof, comprises VH CDR1, VH CDR2, and VH CDR3 of PD1AB-2. In one embodiment, the VL of the anti-PD-1 antibody, or antigen binding fragment thereof, comprises VL CDR1, VL CDR2, and VL CDR3 of PD1AB-3. In some embodiments, the VH of the anti-PD-1 antibody, or antigen binding fragment thereof, comprises VH CDR1, VH CDR2, and VH CDR3 of PD1AB-3. In certain embodiments, the VL of the anti-PD-1 antibody, or antigen binding fragment thereof, comprises VL CDR1, VL CDR2, and VL CDR3 of PD1AB-3, and the VH of the anti-PD-1 antibody, or antigen binding fragment thereof, comprises VH CDR1, VH CDR2, and VH CDR3 of PD1AB-3. In one embodiment, the VL of the anti-PD-1 antibody, or antigen binding fragment thereof, comprises VL CDR1, VL CDR2, and VL CDR3 of PD1AB-4. In some embodiments, the VH of the anti-PD-1 antibody, or antigen binding fragment thereof, comprises VH CDR1, VH CDR2, and VH CDR3 of PD1AB-4. In certain embodiments, the VL of the anti-PD-1 antibody, or antigen binding fragment thereof, comprises VL CDR1, VL CDR2, and VL CDR3 of PD1AB-4, and the VH of the anti-PD-1 antibody, or antigen binding fragment thereof, comprises VH CDR1, VH CDR2, and VH CDR3 of PD1AB-4. In one embodiment, the VL of the anti-PD-1 antibody, or antigen binding fragment thereof, comprises VL CDR1, VL CDR2, and VL CDR3 of PD1AB-5. In some embodiments, the VH of the anti-PD-1 antibody, or antigen binding fragment thereof, comprises VH CDR1, VH CDR2, and VH CDR3 of PD1AB-5. In certain embodiments, the VL of the anti-PD-1 antibody, or antigen binding fragment thereof, comprises VL CDR1, VL CDR2, and VL CDR3 of PD1AB-5, and the VH of the anti-PD-1 antibody, or antigen binding fragment thereof, comprises VH CDR1, VH CDR2, and VH CDR3 of PD1AB-5. In one embodiment, the VL of the anti-PD-1 antibody, or antigen binding fragment thereof, comprises VL CDR1, VL CDR2, and VL CDR3 of PD1AB-6. In some embodiments, the VH of the anti-PD-1 antibody, or antigen binding fragment thereof, comprises VH CDR1, VH CDR2, and VH CDR3 of PD1AB-6. In certain embodiments, the VL of the anti-PD-1 antibody, or antigen binding fragment thereof, comprises VL CDR1, VL CDR2, and VL CDR3 of PD1AB-6, and the VH of the anti-PD-1 antibody, or antigen binding fragment thereof, comprises VH CDR1, VH CDR2, and VH CDR3 of PD1AB-6. In one embodiment, the VL of the anti-PD-1 antibody, or antigen binding fragment thereof, comprises an amino acid sequence of SEQ ID NO:8. In another embodiment, the VH of the anti-PD-1 antibody, or antigen binding fragment thereof, comprises an amino acid sequence of SEQ ID NO:13. In yet another embodiment, the VL of the anti-PD-1 antibody, or antigen binding fragment thereof, comprises an amino acid sequence of SEQ ID NO:8, and the VH of the anti-PD-1 antibody, or antigen binding fragment thereof, comprises an amino acid sequence of SEQ ID NO:13. In another embodiment, the anti-PD-1 antibody, or antigen-binding fragment thereof, comprises a light chain constant region comprising an amino acid sequence of SEQ ID NO:41. In yet another embodiment, the anti-PD-1 antibody, or antigen-binding fragment thereof, comprises a heavy chain constant region comprising an amino acid sequence of SEQ ID NO:37. In still another embodiment, the anti-PD-1 antibody, or antigen-binding fragment thereof, comprises a light chain constant region comprising an amino acid sequence of SEQ ID NO:41 and a heavy chain constant region comprising an amino acid sequence of SEQ ID NO:37. In one embodiment, the anti-PD-1 antibody, or antigen-binding fragment thereof, comprises a light chain comprising an amino acid sequence of SEQ ID NO:31. In another embodiment, the anti-PD-1 antibody, or antigen-binding fragment thereof, comprises a heavy chain comprising an amino acid sequence of SEQ ID NO:33. In yet another embodiment, the anti-PD-1 antibody, or antigen-binding fragment, thereof comprises a light chain comprising an amino acid sequence of SEQ ID NO:31 and a heavy chain comprising an amino acid sequence of SEQ ID NO:33. In certain embodiments, the anti-PD-1 antibody comprises a human IgG1 constant region. In a specific embodiment, the IgG1 constant region comprises a K322A substitution. In one embodiment, the anti PD-1 antibody is PD1AB-6-K3 (PD1AB-6-K322A). In some embodiments, the subject has vitiligo. In other embodiments, the subject is at risk of having vitiligo. In certain embodiments of the methods provided herein, the method results in the alleviation of one or more symptoms of vitiligo in a subject. In one embodiment, the subject is a subject in need thereof.

Also provided herein is a method of managing vitiligo in a subject, comprising administering to the subject an effective amount of an anti-PD-1 antibody. In some embodiments, the anti-PD-1 antibody is PD1AB-1, PD1AB-2, PD1AB-3, PD1AB-4, PD1AB-5 or PD1AB-6. In some embodiments, the anti-PD-1 antibody is PD1AB-1. In some embodiments, the anti-PD-1 antibody is PD1AB-2. In some embodiments, the anti-PD-1 antibody is PD1AB-3. In some embodiments, the anti-PD-1 antibody is PD1AB-4. In some embodiments, the anti-PD-1 antibody is PD1AB-5. In some embodiments, the anti-PD-1 antibody is PD1AB-6. Also provided herein is a method of managing vitiligo in a subject, comprising administering to the subject an effective amount of an antigen binding fragment of an anti-PD-1 antibody. In certain embodiments, the antigen binding fragment is a fragment of a PD1AB-1, PD1AB-2, PD1AB-3, PD1AB-4, PD1AB-5 or PD1AB-6 antibody. In some embodiments, the anti-PD-1 antibody fragment is a fragment of PD1AB-1. In some embodiments, the anti-PD-1 antibody fragment is a fragment of PD1AB-2. In some embodiments, the anti-PD-1 antibody fragment is a fragment of PD1AB-3. In some embodiments, the anti-PD-1 antibody fragment is a fragment of PD1AB-4. In some embodiments, the anti-PD-1 antibody fragment is a fragment of PD1AB-5. In some embodiments, the anti-PD-1 antibody fragment is a fragment of PD1AB-6. In one embodiment, the VL of the anti-PD-1 antibody, or antigen binding fragment thereof, comprises VL CDR1, VL CDR2, and VL CDR3 of PD1AB-1. In some embodiments, the VH of the anti-PD-1 antibody, or antigen binding fragment thereof, comprises VH CDR1, VH CDR2, and VH CDR3 of PD1AB-1. In certain embodiments, the VL of the anti-PD-1 antibody, or antigen binding fragment thereof, comprises VL CDR1, VL CDR2, and VL CDR3 of PD1AB-1, and the VH of the anti-PD-1 antibody, or antigen binding fragment thereof, comprises VH CDR1, VH CDR2, and VH CDR3 of PD1AB-1. In one embodiment, the VL of the anti-PD-1 antibody, or antigen binding fragment thereof, comprises VL CDR1, VL CDR2, and VL CDR3 of PD1AB-2. In some embodiments, the VH of the anti-PD-1 antibody, or antigen binding fragment thereof, comprises VH CDR1, VH CDR2, and VH CDR3 of PD1AB-2. In certain embodiments, the VL of the anti-PD-1 antibody, or antigen binding fragment thereof, comprises VL CDR1, VL CDR2, and VL CDR3 of PD1AB-2, and the VH of the anti-PD-1 antibody, or antigen binding fragment thereof, comprises VH CDR1, VH CDR2, and VH CDR3 of PD1AB-2. In one embodiment, the VL of the anti-PD-1 antibody, or antigen binding fragment thereof, comprises VL CDR1, VL CDR2, and VL CDR3 of PD1AB-3. In some embodiments, the VH of the anti-PD-1 antibody, or antigen binding fragment thereof, comprises VH CDR1, VH CDR2, and VH CDR3 of PD1AB-3. In certain embodiments, the VL of the anti-PD-1 antibody, or antigen binding fragment thereof, comprises VL CDR1, VL CDR2, and VL CDR3 of PD1AB-3, and the VH of the anti-PD-1 antibody, or antigen binding fragment thereof, comprises VH CDR1, VH CDR2, and VH CDR3 of PD1AB-3. In one embodiment, the VL of the anti-PD-1 antibody, or antigen binding fragment thereof, comprises VL CDR1, VL CDR2, and VL CDR3 of PD1AB-4. In some embodiments, the VH of the anti-PD-1 antibody, or antigen binding fragment thereof, comprises VH CDR1, VH CDR2, and VH CDR3 of PD1AB-4. In certain embodiments, the VL of the anti-PD-1 antibody, or antigen binding fragment thereof, comprises VL CDR1, VL CDR2, and VL CDR3 of PD1AB-4, and the VH of the anti-PD-1 antibody, or antigen binding fragment thereof, comprises VH CDR1, VH CDR2, and VH CDR3 of PD1AB-4. In one embodiment, the VL of the anti-PD-1 antibody, or antigen binding fragment thereof, comprises VL CDR1, VL CDR2, and VL CDR3 of PD1AB-5. In some embodiments, the VH of the anti-PD-1 antibody, or antigen binding fragment thereof, comprises VH CDR1, VH CDR2, and VH CDR3 of PD1AB-5. In certain embodiments, the VL of the anti-PD-1 antibody, or antigen binding fragment thereof, comprises VL CDR1, VL CDR2, and VL CDR3 of PD1AB-5, and the VH of the anti-PD-1 antibody, or antigen binding fragment thereof, comprises VH CDR1, VH CDR2, and VH CDR3 of PD1AB-5. In one embodiment, the VL of the anti-PD-1 antibody, or antigen binding fragment thereof, comprises VL CDR1, VL CDR2, and VL CDR3 of PD1AB-6. In some embodiments, the VH of the anti-PD-1 antibody, or antigen binding fragment thereof, comprises VH CDR1, VH CDR2, and VH CDR3 of PD1AB-6. In certain embodiments, the VL of the anti-PD-1 antibody, or antigen binding fragment thereof, comprises VL CDR1, VL CDR2, and VL CDR3 of PD1AB-6, and the VH of the anti-PD-1 antibody, or antigen binding fragment thereof, comprises VH CDR1, VH CDR2, and VH CDR3 of PD1AB-6. In one embodiment, the VL of the anti-PD-1 antibody, or antigen binding fragment thereof, comprises an amino acid sequence of SEQ ID NO:8. In another embodiment, the VH of the anti-PD-1 antibody, or antigen binding fragment thereof, comprises an amino acid sequence of SEQ ID NO:13. In yet another embodiment, the VL of the anti-PD-1 antibody, or antigen binding fragment thereof, comprises an amino acid sequence of SEQ ID NO:8, and the VH of the anti-PD-1 antibody, or antigen binding fragment thereof, comprises an amino acid sequence of SEQ ID NO:13. In another embodiment, the anti-PD-1 antibody, or antigen-binding fragment thereof, comprises a light chain constant region comprising an amino acid sequence of SEQ ID NO:41. In yet another embodiment, the anti-PD-1 antibody, or antigen-binding fragment thereof, comprises a heavy chain constant region comprising an amino acid sequence of SEQ ID NO:37. In still another embodiment, the anti-PD-1 antibody, or antigen-binding fragment thereof, comprises a light chain constant region comprising an amino acid sequence of SEQ ID NO:41 and a heavy chain constant region comprising an amino acid sequence of SEQ ID NO:37. In one embodiment, the anti-PD-1 antibody, or antigen-binding fragment thereof, comprises a light chain comprising an amino acid sequence of SEQ ID NO:31. In another embodiment, the anti-PD-1 antibody, or antigen-binding fragment thereof, comprises a heavy chain comprising an amino acid sequence of SEQ ID NO:33. In yet another embodiment, the anti-PD-1 antibody, or antigen-binding fragment, thereof comprises a light chain comprising an amino acid sequence of SEQ ID NO:31 and a heavy chain comprising an amino acid sequence of SEQ ID NO:33. In certain embodiments, the anti-PD-1 antibody comprises a human IgG1 constant region. In a specific embodiment, the IgG1 constant region comprises a K322A substitution. In one embodiment, the anti PD-1 antibody is PD1AB-6-K3 (PD1AB-6-K322A). In some embodiments, the subject has vitiligo. In other embodiments, the subject is at risk of having vitiligo. In certain embodiments of the methods provided herein, the method results in the alleviation of one or more symptoms of vitiligo in a subject. In one embodiment, the subject is a subject in need thereof.

Also provided herein is a method of preventing vitiligo in a subject, comprising administering to the subject an effective amount of an anti-PD-1 antibody. In some embodiments, the anti-PD-1 antibody is PD1AB-1, PD1AB-2, PD1AB-3, PD1AB-4, PD1AB-5 or PD1AB-6. In some embodiments, the anti-PD-1 antibody is PD1AB-1. In some embodiments, the anti-PD-1 antibody is PD1AB-2. In some embodiments, the anti-PD-1 antibody is PD1AB-3. In some embodiments, the anti-PD-1 antibody is PD1AB-4. In some embodiments, the anti-PD-1 antibody is PD1AB-5. In some embodiments, the anti-PD-1 antibody is PD1AB-6. Also provided herein is a method of preventing vitiligo in a subject, comprising administering to the subject an effective amount of an antigen binding fragment of an anti-PD-1 antibody. In certain embodiments, the antigen binding fragment is a fragment of a PD1AB-1, PD1AB-2, PD1AB-3, PD1AB-4, PD1AB-5 or PD1AB-6 antibody. In some embodiments, the anti-PD-1 antibody fragment is a fragment of PD1AB-1. In some embodiments, the anti-PD-1 antibody fragment is a fragment of PD1AB-2. In some embodiments, the anti-PD-1 antibody fragment is a fragment of PD1AB-3. In some embodiments, the anti-PD-1 antibody fragment is a fragment of PD1AB-4. In some embodiments, the anti-PD-1 antibody fragment is a fragment of PD1AB-5. In some embodiments, the anti-PD-1 antibody fragment is a fragment of PD1AB-6. In one embodiment, the VL of the anti-PD-1 antibody, or antigen binding fragment thereof, comprises VL CDR1, VL CDR2, and VL CDR3 of PD1AB-1. In some embodiments, the VH of the anti-PD-1 antibody, or antigen binding fragment thereof, comprises VH CDR1, VH CDR2, and VH CDR3 of PD1AB-1. In certain embodiments, the VL of the anti-PD-1 antibody, or antigen binding fragment thereof, comprises VL CDR1, VL CDR2, and VL CDR3 of PD1AB-1, and the VH of the anti-PD-1 antibody, or antigen binding fragment thereof, comprises VH CDR1, VH CDR2, and VH CDR3 of PD1AB-1. In one embodiment, the VL of the anti-PD-1 antibody, or antigen binding fragment thereof, comprises VL CDR1, VL CDR2, and VL CDR3 of PD1AB-2. In some embodiments, the VH of the anti-PD-1 antibody, or antigen binding fragment thereof, comprises VH CDR1, VH CDR2, and VH CDR3 of PD1AB-2. In certain embodiments, the VL of the anti-PD-1 antibody, or antigen binding fragment thereof, comprises VL CDR1, VL CDR2, and VL CDR3 of PD1AB-2, and the VH of the anti-PD-1 antibody, or antigen binding fragment thereof, comprises VH CDR1, VH CDR2, and VH CDR3 of PD1AB-2. In one embodiment, the VL of the anti-PD-1 antibody, or antigen binding fragment thereof, comprises VL CDR1, VL CDR2, and VL CDR3 of PD1AB-3. In some embodiments, the VH of the anti-PD-1 antibody, or antigen binding fragment thereof, comprises VH CDR1, VH CDR2, and VH CDR3 of PD1AB-3. In certain embodiments, the VL of the anti-PD-1 antibody, or antigen binding fragment thereof, comprises VL CDR1, VL CDR2, and VL CDR3 of PD1AB-3, and the VH of the anti-PD-1 antibody, or antigen binding fragment thereof, comprises VH CDR1, VH CDR2, and VH CDR3 of PD1AB-3. In one embodiment, the VL of the anti-PD-1 antibody, or antigen binding fragment thereof, comprises VL CDR1, VL CDR2, and VL CDR3 of PD1AB-4. In some embodiments, the VH of the anti-PD-1 antibody, or antigen binding fragment thereof, comprises VH CDR1, VH CDR2, and VH CDR3 of PD1AB-4. In certain embodiments, the VL of the anti-PD-1 antibody, or antigen binding fragment thereof, comprises VL CDR1, VL CDR2, and VL CDR3 of PD1AB-4, and the VH of the anti-PD-1 antibody, or antigen binding fragment thereof, comprises VH CDR1, VH CDR2, and VH CDR3 of PD1AB-4. In one embodiment, the VL of the anti-PD-1 antibody, or antigen binding fragment thereof, comprises VL CDR1, VL CDR2, and VL CDR3 of PD1AB-5. In some embodiments, the VH of the anti-PD-1 antibody, or antigen binding fragment thereof, comprises VH CDR1, VH CDR2, and VH CDR3 of PD1AB-5. In certain embodiments, the VL of the anti-PD-1 antibody, or antigen binding fragment thereof, comprises VL CDR1, VL CDR2, and VL CDR3 of PD1AB-5, and the VH of the anti-PD-1 antibody, or antigen binding fragment thereof, comprises VH CDR1, VH CDR2, and VH CDR3 of PD1AB-5. In one embodiment, the VL of the anti-PD-1 antibody, or antigen binding fragment thereof, comprises VL CDR1, VL CDR2, and VL CDR3 of PD1AB-6. In some embodiments, the VH of the anti-PD-1 antibody, or antigen binding fragment thereof, comprises VH CDR1, VH CDR2, and VH CDR3 of PD1AB-6. In certain embodiments, the VL of the anti-PD-1 antibody, or antigen binding fragment thereof, comprises VL CDR1, VL CDR2, and VL CDR3 of PD1AB-6, and the VH of the anti-PD-1 antibody, or antigen binding fragment thereof, comprises VH CDR1, VH CDR2, and VH CDR3 of PD1AB-6. In one embodiment, the VL of the anti-PD-1 antibody, or antigen binding fragment thereof, comprises an amino acid sequence of SEQ ID NO:8. In another embodiment, the VH of the anti-PD-1 antibody, or antigen binding fragment thereof, comprises an amino acid sequence of SEQ ID NO:13. In yet another embodiment, the VL of the anti-PD-1 antibody, or antigen binding fragment thereof, comprises an amino acid sequence of SEQ ID NO:8, and the VH of the anti-PD-1 antibody, or antigen binding fragment thereof, comprises an amino acid sequence of SEQ ID NO:13. In another embodiment, the anti-PD-1 antibody, or antigen-binding fragment thereof, comprises a light chain constant region comprising an amino acid sequence of SEQ ID NO:41. In yet another embodiment, the anti-PD-1 antibody, or antigen-binding fragment thereof, comprises a heavy chain constant region comprising an amino acid sequence of SEQ ID NO:37. In still another embodiment, the anti-PD-1 antibody, or antigen-binding fragment thereof, comprises a light chain constant region comprising an amino acid sequence of SEQ ID NO:41 and a heavy chain constant region comprising an amino acid sequence of SEQ ID NO:37. In one embodiment, the anti-PD-1 antibody, or antigen-binding fragment thereof, comprises a light chain comprising an amino acid sequence of SEQ ID NO:31. In another embodiment, the anti-PD-1 antibody, or antigen-binding fragment thereof, comprises a heavy chain comprising an amino acid sequence of SEQ ID NO:33. In yet another embodiment, the anti-PD-1 antibody, or antigen-binding fragment, thereof comprises a light chain comprising an amino acid sequence of SEQ ID NO:31 and a heavy chain comprising an amino acid sequence of SEQ ID NO:33. In certain embodiments, the anti-PD-1 antibody comprises a human IgG1 constant region. In a specific embodiment, the IgG1 constant region comprises a K322A substitution. In one embodiment, the anti PD-1 antibody is PD1AB-6-K3 (PD1AB-6-K322A). In some embodiments, the subject has vitiligo. In other embodiments, the subject is at risk of having vitiligo. In certain embodiments of the methods provided herein, the method results in the alleviation of one or more symptoms of vitiligo in a subject. In one embodiment, the subject is a subject in need thereof.

In yet another embodiment, the various methods provided herein comprise administering an antibody or antigen-binding fragments thereof described herein that binds to a region, including an epitope, of human PD-1 or cyno PD-1. For example, in some embodiments, the antibody binds to a region of human PD-1 (SEQ ID NO:42) comprising amino acid residues 33 to 109 of human PD-1. In still another aspect, antibodies bind to a specific epitope of human PD-1.

In certain embodiments, the various methods provided herein comprise administering an antibody or antigen-binding fragment thereof that, when bound to PD-1, binds to at least one of residues 100-109 (SEQ ID NO:43) within an amino acid sequence of SEQ ID NO:42. In some embodiments, the antibody or antigen-binding fragment thereof, when bound to PD-1, binds to at least one of residues 100-105 (SEQ ID NO:44) within an amino acid sequence of SEQ ID NO:42. In particular embodiments, the antibody or antigen-binding fragment thereof, when bound to PD-1, binds to at least one residue selected from the group consisting of N33, T51, S57, L100, N102, G103, R104, D105, H107, and S109 within an amino acid sequence of SEQ ID NO:42. In some embodiments, the antibody or antigen-binding fragment thereof, when bound to PD-1, binds to at least one residue selected from the group consisting of L100, N102, G103, R104, D105, H107, and S109 within an amino acid sequence of SEQ ID NO:42. In some embodiments, the antibody or antigen-binding fragment thereof, when bound to PD-1, binds to two or more residues selected from the group consisting of N33, T51, S57, L100, N102, G103, R104, D105, H107, and S109 within an amino acid sequence of SEQ ID NO:42. In other embodiments, the antibody or antigen-binding fragment thereof, when bound to PD-1, binds to three or more residues selected from the group consisting of N33, T51, S57, L100, N102, G103, R104, D105, H107, and S109 within an amino acid sequence of SEQ ID NO:42. In certain embodiments, the antibody or antigen-binding fragment thereof, when bound to PD-1, binds to four or more residues selected from the group consisting of N33, T51, S57, L100, N102, G103, R104, D105, H107, and S109 within an amino acid sequence of SEQ ID NO:42. In one embodiment, the antibody or antigen-binding fragment thereof, when bound to PD-1, binds to five or more residues selected from the group consisting of N33, T51, S57, L100, N102, G103, R104, D105, H107, and S109 within an amino acid sequence of SEQ ID NO:42. In another embodiment, the antibody or antigen-binding fragment thereof, when bound to PD-1, binds to six or more residues selected from the group consisting of N33, T51, S57, L100, N102, G103, R104, D105, H107, and S109 within an amino acid sequence of SEQ ID NO:42. In yet another embodiment, the antibody or antigen-binding fragment thereof, when bound to PD-1, binds to seven or more residues selected from the group consisting of N33, T51, S57, L100, N102, G103, R104, D105, H107, and S109 within an amino acid sequence of SEQ ID NO:42. In still another embodiment, the antibody or antigen-binding fragment thereof, when bound to PD-1, binds to eight or more residues selected from the group consisting of N33, T51, S57, L100, N102, G103, R104, D105, H107, and S109 within an amino acid sequence of SEQ ID NO:42. In certain embodiments, the antibody or antigen-binding fragment thereof, when bound to PD-1, binds to nine or more residues selected from the group consisting of N33, T51, S57, L100, N102, G103, R104, D105, H107, and S109 within an amino acid sequence of SEQ ID NO:42. In other embodiments, the antibody or antigen-binding fragment thereof, when bound to PD-1, binds to all ten residues from the group consisting of N33, T51, S57, L100, N102, G103, R104, D105, H107, and S109 within an amino acid sequence of SEQ ID NO:42. In another embodiment, the antibody or antigen-binding fragment thereof, when bound to PD-1, binds to N33 within an amino acid sequence of SEQ ID NO:42. In another embodiment, the antibody or antigen-binding fragment thereof, when bound to PD-1, binds to T51 within an amino acid sequence of SEQ ID NO:42. In a particular embodiment, the antibody or antigen-binding fragment thereof, when bound to PD-1, binds to S57 within an amino acid sequence of SEQ ID NO:42. In one specific embodiment, the antibody or antigen-binding fragment thereof, when bound to PD-1, binds to L100 within an amino acid sequence of SEQ ID NO:42. In some embodiments, the antibody or antigen-binding fragment thereof, when bound to PD-1, binds to N102 within an amino acid sequence of SEQ ID NO:42. In other embodiments, the antibody or antigen-binding fragment thereof, when bound to PD-1, binds to G103 within an amino acid sequence of SEQ ID NO:42. In another embodiment, the antibody or antigen-binding fragment thereof, when bound to PD-1, binds to R104 within an amino acid sequence of SEQ ID NO:42. In yet another embodiment, the antibody or antigen-binding fragment thereof, when bound to PD-1, binds to G103 and R104 within an amino acid sequence of SEQ ID NO:42. In still another embodiment, the antibody or antigen-binding fragment thereof, when bound to PD-1, binds to D105 within an amino acid sequence of SEQ ID NO:42. In some embodiments, the antibody or antigen-binding fragment thereof, when bound to PD-1, binds to H107 within an amino acid sequence of SEQ ID NO:42. In certain embodiments, the antibody or antigen-binding fragment thereof, when bound to PD-1, binds to S109 within an amino acid sequence of SEQ ID NO:42. Any combination of two, three, four, five, six, seven, eight, nine, ten or more of the above-referenced amino acid PD-1 binding sites is also contemplated.

In some embodiments of the various methods provided herein, the PD-1 binding protein (e.g., an anti-PD-1 antibody as described herein) is administered in an amount effective to treat T cell hypersensitivity. In some embodiments of the various methods provided herein, the PD-1 binding protein (e.g., an anti-PD-1 antibody as described herein) is administered in an amount effective to reduce undesirable or abnormally elevated levels of serum/plasma proinflammatory cytokines. In some embodiments of the various methods provided herein, the PD-1 binding protein (e.g., an anti-PD-1 antibody as described herein) is administered in an amount effective to activate PD-1 signaling in the subject.

In some embodiments of the various methods provided herein, the PD-1 binding protein (e.g., an anti-PD-1 antibody as described herein) is administered in an amount effective to downregulate PD-1 expression in the subject. In some embodiments of the various methods provided herein, the PD-1 binding protein (e.g., an anti-PD-1 antibody as described herein) is administered in an amount effective to attenuate T cell activity in the subject. In some embodiments, the effects of treatment are measured by (a) attenuating T cell activity; and/or (b) downregulating PD-1 expression. In certain embodiments, the effects of treatment are measured by attenuating T cell activity. In other embodiments, the effects of treatment are measured by downregulating PD-1 expression. In some embodiments, the effects of treatment are measured by (a) attenuating T cell activity; and (b) downregulating PD-1 expression. In certain embodiments, the attenuation of T cell activity is measured by inhibiting secretion of a cytokine. In some embodiments, the cytokine is IL-1, IL-2, IL-6, IL-12, IL-17, IL-22, IL-23, GM-CSF, TNF-α, IFN-γ, or a combination thereof. In one embodiment, the attenuation of T cell activity is measured by inhibiting secretion of IL-1. In some embodiments, the attenuation of T cell activity is measured by inhibiting secretion of IL-2. In another embodiment, the attenuation of T cell activity is measured by inhibiting secretion of IL-6. In yet another embodiment, the attenuation of T cell activity is measured by inhibiting secretion of IL-12. In still another embodiment, the attenuation of T cell activity is measured by inhibiting secretion of IL-17. In one embodiment, the attenuation of T cell activity is measured by inhibiting secretion of IL-22. In some embodiments, the attenuation of T cell activity is measured by inhibiting secretion of IL-23. In another embodiment, the attenuation of T cell activity is measured by inhibiting secretion of GM-CSF. In yet another embodiment, the attenuation of T cell activity is measured by inhibiting secretion of TNF-α. In still another embodiment, the attenuation of T cell activity is measured by inhibiting secretion of IFN-γ. In certain embodiments, the attenuation of T cell activity is measured by inhibition of T cell proliferation. In some embodiments, the inhibition of T cell proliferation is inhibition of CD4+ T cell proliferation. In other embodiments, the inhibition of T cell proliferation is inhibition of CD8+ T cell proliferation. In yet another embodiment, the attenuation of T cell activity is measured by downregulation of T cell activation markers. In one embodiment, the T cell activation marker is CD25. In another embodiment, the T cell activation marker is CD69. In still another embodiment, the attenuation of T cell activity is measured by upregulation of regulatory T cell biomarker. In one embodiment, the regulatory T cell biomarker is Foxp3. In still another embodiment, the attenuation of T cell activity is measured by increase of regulatory T cell numbers. In one embodiment, the regulatory T cell is induced Foxp3+ regulatory T cell. In one embodiment, the regulatory T cell is induced CD25+Foxp3+ regulatory T cell.

Moreover, an anti-PD-1 antibody or fragment thereof can be administered to a non-human mammal expressing PD-1 with which the antibody cross-reacts (e.g., a primate) for veterinary purposes or as an animal model of human disease. Regarding the latter, such animal models may be useful for evaluating the therapeutic efficacy of antibodies of the present disclosure (e.g., testing of dosages and time courses of administration).

In certain embodiments of the various methods provided herein, a therapeutically or prophylactically effective amount of an anti-PD-1 antibody or antigen-binding fragment thereof is administered to the subject. A therapeutically or prophylactically effective amount of an anti-PD-1 antibody or antigen-binding fragment thereof is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day.

In certain embodiments, the therapeutically or prophylactically effective amount of an anti-PD-1 antibody or antigen-binding fragment thereof is about 0.1, about 0.2, about 0.5, about 1, about 2, about 5, about 10, about 15, about 20, about 25, about 30, about 40, about 45, about 50, about 60, about 70, about 80, about 90, about 100, or about 150 mg per day.

In one embodiment, the recommended daily dose range of an anti-PD-1 antibody or antigen-binding fragment thereof for the conditions described herein lie within the range of from about 0.5 mg to about 50 mg per day, preferably given as a single once-α-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a specific embodiment, the recommended starting dosage may be 0.5, 1, 2, 3, 4, 5, 10, 15, 20, 25 or 50 mg per day. In another embodiment, the recommended starting dosage may be 0.5, 1, 2, 3, 4, or 5 mg per day. The dose may be escalated to 15, 20, 25, 30, 35, 40, 45 and 50 mg/day.

In certain embodiments, the therapeutically or prophylactically effective amount of an anti-PD-1 antibody or antigen-binding fragment thereof is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

The administered dose can also be expressed in units other than mg/kg/day. For example, doses for parenteral administration can be expressed as mg/m2/day. One of ordinary skill in the art would readily know how to convert doses from mg/kg/day to mg/m2/day to given either the height or weight of a subject or both (see, www.fda.gov/cder/cancer/animalframe.htm). For example, a dose of 1 mg/kg/day for a 65 kg human is approximately equal to 38 mg/m2/day.

In certain embodiments, the amount of the anti-PD-1 antibody or antigen-binding fragment thereof administered is sufficient to provide a plasma concentration of the antibody at steady state, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In other embodiments, the amount of the anti-PD-1 antibody or antigen-binding fragment thereof administered is sufficient to provide a plasma concentration of the antibody at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a anti-PD-1 antibody or antigen-binding fragment thereof provided herein, e.g., PD1AB-6-K3. Once steady state is reached, there are minor peaks and troughs on the time dependent curve of the plasma concentration of the antibody.

In certain embodiments, the amount of the anti-PD-1 antibody or antigen-binding fragment thereof administered is sufficient to provide a maximum plasma concentration (peak concentration) of the antibody, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In certain embodiments, the amount of the anti-PD-1 antibody or antigen-binding fragment thereof administered is sufficient to provide a minimum plasma concentration (trough concentration) of the antibody, ranging from about 0.001 to about 500 µM, about 0.002 to about 200 µM, about 0.005 to about 100 µM, about 0.01 to about 50 µM, from about 1 to about 50 µM, about 0.01 to about 25 µM, from about 0.01 to about 20 µM, from about 0.02 to about 20 µM, from about 0.02 to about 20 µM, or from about 0.01 to about 20 µM.

In certain embodiments, the amount of the anti-PD-1 antibody or antigen-binding fragment thereof administered is sufficient to provide an area under the curve (AUC) of the antibody, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

The anti-PD-1 antibody or antigen-binding fragment thereof provided herein, e.g., PD1AB-6-K3, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic antibody, such as PD1AB-6-K3, is administered once or more than once each day, for example, for a period of time. The term "continuous" is intended to mean that a therapeutic antibody, such as PD1AB-6-K3, is administered daily for an uninterrupted period of at least 10 days to 52 weeks. The term "intermittent" or "intermittently" as used herein is intended to mean stopping and starting at either regular or irregular intervals. For example, intermittent administration of the antibody, such as PD1AB-6-K3, is administration for one to six days per week, administration in cycles (e.g., daily administration for two to eight consecutive weeks, then a rest period with no administration for up to one week), or administration on alternate days. The term "cycling" as used herein is intended to mean that a therapeutic antibody, such as PD1AB-6-K3, is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the antibody, such as PD1AB-6-K3, is administered once a day. In another embodiment, the antibody, such as PD1AB-6-K3, is administered twice a day. In yet another embodiment, the antibody, such as PD1AB-6-K3, is administered three times a day. In still another embodiment, the antibody, such as PD1AB-6-K3, is administered four times a day.

In certain embodiments, the anti-PD-1 antibody, such as PD1AB-6-K3, is administered once per day from one day to six months, from one week to three months, from one week to four weeks, from one week to three weeks, or from one week to two weeks. In certain embodiments, the antibody, such as PD1AB-6-K3, is administered once per day for one week, two weeks, three weeks, or four weeks. In one embodiment, the antibody, such as PD1AB-6-K3, is administered once per day for one week. In another embodiment, antibody, such as PD1AB-6-K3, is administered once per day for two weeks. In yet another embodiment, the antibody, such as PD1AB-6-K3, is administered once per day for three weeks. In still another embodiment, the antibody, such as PD1AB-6-K3, is administered once per day for four weeks.

In some embodiments, the therapeutically or prophylactically effective amount of an anti-PD-1 antibody or antigen-binding fragment thereof is from about 0.001 to about 50 mg/kg, from about 0.01 to about 50 mg/kg, from about 0.01 to about 25 mg/kg, from about 0.01 to about 10 mg/kg, from about 0.01 to about 9 mg/kg, from about 0.01 to about 8 mg/kg, from about 0.01 to about 7 mg/kg, from about 0.01 to about 6 mg/kg, from about 0.01 to about 5 mg/kg, from about 0.01 to about 4 mg/kg, from about 0.01 to about 3 mg/kg, from about 0.01 to about 2 mg/kg, or from about 0.01 to about 1 mg/kg. In certain embodiments, the therapeutically or prophylactically effective amount of an anti-PD-1 antibody or antigen-binding fragment thereof is about 0.001, about 0.003, about 0.005, about 0.01, about 0.03, about 0.05, about 0.1, about 0.3, about 0.5, about 1, about 3, about 5, about 10, about 30, or about 50 mg/kg. In one embodiment, the therapeutically or prophylactically effective amount of an anti-PD-1 antibody or antigen-binding fragment thereof is 0.001 mg/kg. In one embodiment, the therapeutically or prophylactically effective amount of an anti-PD-1 antibody or antigen-binding fragment thereof is 0.01 mg/kg. In one embodiment, the therapeutically or prophylactically effective amount of an anti-PD-1 antibody or antigen-binding fragment thereof is 0.1 mg/kg. In another embodiment, the therapeutically or prophylactically effective amount of an anti-PD-1 antibody or antigen-binding fragment thereof is 0.3 mg/kg. In another embodiment, the therapeutically or prophylactically effective amount of an anti-PD-1 antibody or antigen-binding fragment thereof is 0.5 mg/kg. In yet another embodiment, the therapeutically or prophylactically effective amount of an anti-PD-1 antibody or antigen-binding fragment thereof is 1 mg/kg. In still another embodiment, the therapeutically or prophylactically effective amount of an anti-PD-1 antibody or antigen-binding fragment thereof is 3 mg/kg. In one embodiment, the therapeutically or prophylactically effective amount of an anti-PD-1 antibody or antigen-binding fragment thereof is 5 mg/kg. In another embodiment, the therapeutically or prophylactically effective amount of an anti-PD-1 antibody or antigen-binding fragment thereof is 10 mg/kg. In yet another embodiment, the therapeutically or prophylactically effective amount of an anti-PD-1 antibody or antigen-binding fragment thereof is 30 mg/kg. In yet another embodiment, the therapeutically or prophylactically effective amount of an anti-PD-1 antibody or antigen-binding fragment thereof is 50 mg/kg.

In some embodiments, the frequency of administration is once every week, once every two weeks, once every three weeks, or once every four weeks. In one embodiment, the antibody, such as PD1AB-6-K3, is administered once every week. In another embodiment, the antibody, such as PD1AB-6-K3, is administered once every two weeks. In yet another embodiment, the antibody, such as PD1AB-6-K3, is administered once every three weeks. In still another embodiment, the antibody, such as PD1AB-6-K3, is administered once every four weeks.

In one embodiment, the antibody, such as PD1AB-6-K3, is administered once every week at a dosage of 0.1 mg/kg. In another embodiment, the antibody, such as PD1AB-6-K3, is administered once every week at a dosage of 0.3 mg/kg. In yet another embodiment, the antibody, such as PD1AB-6-K3, is administered once every week at a dosage of 0.5 mg/kg. In still another embodiment, the antibody, such as PD1AB-6-K3, is administered once every week at a dosage of 1 mg/kg. In one embodiment, the antibody, such as PD1AB-6-K3, is administered once every week at a dosage of 3 mg/kg. In another embodiment, the antibody, such as PD1AB-6-K3, is administered once every week at a dosage of 5 mg/kg. In yet another embodiment, the antibody, such as PD1AB-6-K3, is administered once every week at a dosage of 10 mg/kg. In still another embodiment, the antibody, such as PD1AB-6-K3, is administered once every week at a dosage of 30 mg/kg.

In one embodiment, the antibody, such as PD1AB-6-K3, is administered once every two weeks at a dosage of 0.1 mg/kg. In another embodiment, the antibody, such as PD1AB-6-K3, is administered once every two weeks at a dosage of 0.3 mg/kg. In yet another embodiment, the antibody, such as PD1AB-6-K3, is administered once every two weeks at a dosage of 0.5 mg/kg. In still another embodiment, the antibody, such as PD1AB-6-K3, is administered once every two weeks at a dosage of 1 mg/kg. In one embodiment, the antibody, such as PD1AB-6-K3, is administered once every two weeks at a dosage of 3 mg/kg. In another embodiment, the antibody, such as PD1AB-6-K3, is administered once every two weeks at a dosage of 5 mg/kg. In yet another embodiment, the antibody, such as PD1AB-6-K3, is administered once every two weeks at a dosage of 10 mg/kg. In still another embodiment, the antibody, such as PD1AB-6-K3, is administered once every two weeks at a dosage of 30 mg/kg.

In one embodiment, the antibody, such as PD1AB-6-K3, is administered once every three weeks at a dosage of 0.1 mg/kg. In another embodiment, the antibody, such as PD1AB-6-K3, is administered once every three weeks at a dosage of 0.3 mg/kg. In yet another embodiment, the antibody, such as PD1AB-6-K3, is administered once every three weeks at a dosage of 0.5 mg/kg. In still another embodiment, the antibody, such as PD1AB-6-K3, is administered once every three weeks at a dosage of 1 mg/kg. In one embodiment, the antibody, such as PD1AB-6-K3, is administered once every three weeks at a dosage of 3 mg/kg. In another embodiment, the antibody, such as PD1AB-6-K3, is administered once every three weeks at a dosage of 5 mg/kg. In yet another embodiment, the antibody, such as PD1AB-6-K3, is administered once every three weeks at a dosage of 10 mg/kg. In still another embodiment, the antibody, such as PD1AB-6-K3, is administered once every three weeks at a dosage of 30 mg/kg.

In one embodiment, the antibody, such as PD1AB-6-K3, is administered once every four weeks at a dosage of 0.1 mg/kg. In another embodiment, the antibody, such as PD1AB-6-K3, is administered once every four weeks at a dosage of 0.3 mg/kg. In yet another embodiment, the antibody, such as PD1AB-6-K3, is administered once every four weeks at a dosage of 0.5 mg/kg. In still another embodiment, the antibody, such as PD1AB-6-K3, is administered once every four weeks at a dosage of 1 mg/kg. In one embodiment, the antibody, such as PD1AB-6-K3, is administered once every four weeks at a dosage of 3 mg/kg. In another embodiment, the antibody, such as PD1AB-6-K3, is administered once every four weeks at a dosage of 5 mg/kg. In yet another embodiment, the antibody, such as PD1AB-6-K3, is administered once every four weeks at a dosage of 10 mg/kg. In still another embodiment, the antibody, such as PD1AB-6-K3, is administered once every four weeks at a dosage of 30 mg/kg.

Depending on the disease to be treated and the subject's condition, the antibody provided herein, e.g., PD1AB-6-K3, may be administered by parenteral (e.g., intramuscular, intraperitoneal, intravenous, continuous intravenous, intracistemal injection or infusion, subcutaneous injection, or implant), inhalation, nasal, vaginal, rectal, sublingual, or topical (e.g., transdermal or local) routes of administration. In one embodiment, the administration route is subcutaneous. In another embodiment, the administration route is intravenous. In yet another embodiment, the administration route is intramuscular. In still another embodiment, the administration route is intraperitoneal. In one embodiment, the administration route is continuous intravenous. In another embodiment, the administration route is intracistemal injection or infusion. In yet another embodiment, the administration route is implant. In still another embodiment, the administration route is inhalation. In one embodiment, the administration route is nasal. In another embodiment, the administration route is rectal. In yet another embodiment, the administration route is sublingual. In still another embodiment, the administration route is transdermal. Any anti-PD-1 antibody provided herein, e.g., PD1AB-6-K3, may be formulated, alone or together, in suitable dosage unit with pharmaceutically acceptable excipients, carriers, adjuvants, and vehicles, appropriate for each route of administration.

In some embodiments of the various methods provided herein, the method further comprises administering a therapeutically effective amount of a second active agent or a support care therapy. Second active agents can be large molecules (e.g., proteins) or small molecules (e.g., synthetic inorganic, organometallic, or organic molecules). In some embodiments, the second active agents are small molecules that can alleviate adverse effects associated with the administration of an antibody provided herein. However, like some large molecules, many are believed to be capable of providing a synergistic effect when administered with (e.g., before, after or simultaneously) an antibody provided herein. Examples of small molecule second active agents include, but are not limited to, anti-cancer agents, anti-inflammatory agents, immunosuppressive agents, and steroids.

4.5 Pharmaceutical Compositions

In one aspect, the present disclosure further describes pharmaceutical compositions for use in the various methods provided herein comprising at least one anti-PD-1 antibody of the present disclosure. In some embodiments, a pharmaceutical composition comprises 1) an anti-PD-1 antibody, and 2) a pharmaceutically acceptable carrier.

Pharmaceutical compositions comprising an antibody are prepared for storage by mixing the antibody having the desired degree of purity with optional physiologically acceptable carriers, excipients, or stabilizers (see, e.g., Remington, *Remington's Pharmaceutical Sciences* (18th ed. 1980)) in the form of aqueous solutions or lyophilized or other dried forms.

The antibodies of the present disclosure may be formulated in any suitable form for delivery to a target cell/tissue, e.g., as microcapsules or macroemulsions (Remington, supra; Park et al., 2005, Molecules 10:146-61; Malik et al., 2007, Curr. Drug. Deliv. 4:141-51), as sustained release formulations (Putney and Burke, 1998, Nature Biotechnol. 16:153-57), or in liposomes (Maclean et al., 1997, Int. J. Oncol. 11:325-32; Kontermann, 2006, Curr. Opin. Mol. Ther. 8:39-45).

An antibody provided herein can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles, and nano-capsules) or in macroemulsions. Such techniques are disclosed, for example, in Remington, supra.

Various compositions and delivery systems are known and can be used with an antibody that binds to PD-1 as described herein, including, but not limited to, encapsulation in liposomes, microparticles, microcapsules, recombinant cells capable of expressing the antibody, receptor-mediated endocytosis (see, e.g., Wu and Wu, 1987, J. Biol. Chem. 262:4429-32), construction of a nucleic acid as part of a retroviral or other vector, etc. In another embodiment, a composition can be provided as a controlled release or sustained release system. In one embodiment, a pump may be used to achieve controlled or sustained release (see, e.g., Langer, supra; Sefton, 1987, Crit. Ref. Biomed. Eng. 14:201-40; Buchwald et al., 1980, Surgery 88:507-16; and Saudek et al., 1989, N. Engl. J. Med. 321:569-74). In another embodiment, polymeric materials can be used to achieve controlled or sustained release of a prophylactic or therapeutic agent (e.g., an antibody that binds to PD-1 as described herein) or a composition of the invention (see, e.g., *Medical Applications of Controlled Release* (Langer and Wise eds., 1974); *Controlled Drug Bioavailability, Drug Product Design and Performance* (Smolen and Ball eds., 1984); Ranger and Peppas, 1983, J. Macromol. Sci. Rev. Macromol. Chem. 23:61-126; Levy et al., 1985, Science 228:190-92; During et al., 1989, Ann. Neurol. 25:351-56; Howard et al., 1989, J. Neurosurg. 71:105-12; U.S. Pat. Nos. 5,679,377; 5,916,597; 5,912,015; 5,989,463; and 5,128,326; PCT Publication Nos. WO 99/15154 and WO 99/20253). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable.

In yet another embodiment, a controlled or sustained release system can be placed in proximity of a particular target tissue, for example, the nasal passages or lungs, thus requiring only a fraction of the systemic dose (see, e.g., Goodson, *Medical Applications of Controlled Release* Vol. 2, 115-38 (1984)). Controlled release systems are discussed, for example, by Langer, 1990, Science 249:1527-33. Any technique known to one of skill in the art can be used to produce sustained release formulations comprising one or more antibodies that bind to PD-1 as described herein (see, e.g., U.S. Pat. No. 4,526,938, PCT publication Nos. WO 91/05548 and WO 96/20698, Ning et al., 1996, Radiotherapy & Oncology 39:179-89; Song et al., 1995, PDA J. of Pharma. Sci. & Tech. 50:372-97; Cleek et al., 1997, Pro. Int'l. Symp. Control. Rel. Bioact. Mater. 24:853-54; and Lam et al., 1997, Proc. Int'l. Symp. Control Rel. Bioact. Mater. 24:759-60).

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a," "and," and "the" include plural referents unless the context clearly indicates otherwise. Thus, for example, reference to "a peptide sequence" includes a plurality of such sequences and so forth.

As used herein, numerical values are often presented in a range format throughout this document. The use of a range format is merely for convenience and brevity and should not be construed as an inflexible limitation on the scope of the invention unless the context clearly indicates otherwise. Accordingly, the use of a range expressly includes all possible subranges, all individual numerical values within that range, and all numerical values or numerical ranges including integers within such ranges and fractions of the values or the integers within ranges unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100% also includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

In addition, reference to a range of 1-3, 3-5, 5-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, 190-200, 200-225, 225-250 includes 1, 2, 3, 4, 5, 6, 7, 8, 9, 10, 11, 12, 13, 14, 15, 16, 17, 18, 19, 20, etc. In a further example, reference to a range of 25-250, 250-500, 500-1,000, 1,000-2,500, 2,500-5,000, 5,000-25,000, 25,000-50,000 includes any numerical value or range within or encompassing such values, e.g., 25, 26, 27, 28, 29 . . . 250, 251, 252, 253, 254 . . . 500, 501, 502, 503, 504 . . . , etc.

As also used herein a series of ranges are disclosed throughout this document. The use of a series of ranges include combinations of the upper and lower ranges to provide another range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, includes ranges such as 5-20, 5-30, 5-40, 5-50, 5-75, 5-100, 5-150, and 10-30, 10-40, 10-50, 10-75, 10-100, 10-150, and 20-40, 20-50, 20-75, 20-100, 20-150, and so forth.

For the sake of conciseness, certain abbreviations are used herein. One example is the single letter abbreviation to represent amino acid residues. The amino acids and their corresponding three letter and single letter abbreviations are as follows:

| | | |
|---|---|---|
| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |

| | | |
|---|---|---|
| isoleucine | Ile | (I) |
| leucine | Leu | (L) |
| lysine | Lys | (K) |
| methionine | Met | (M) |
| phenylalanine | Phe | (F) |
| proline | Pro | (P) |
| serine | Ser | (S) |
| threonine | Thr | (T) |
| tryptophan | Trp | (W) |
| tyrosine | Tyr | (Y) |
| valine | Val | (V) |

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include, aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

core® to soluble antigen. The mouse $V_H$ and $V_L$ genes from the PD1Sub1 hybridoma were sequenced and used for human CDR-grafting into human γ1 and κ constant regions of the most homologous human $V_H$ and $V_L$ framework genes (IgH1-f and Vκ4-1, respectively) utilizing the closest J regions (IgH J6 and Igκ J2, respectively). For human germline HG1 $V_H$ and $V_L$ regions only, the mouse CDR3 segments were placed into the human $V_H$ and $V_L$ framework germline genes, IgH 1-f and Vκ 4-1, respectively.

Stable HEK-293c18 cell lines expressing either CDR-grafted or germline HG1 antibodies in Deciduous™ constructs with stable AID (Activation-Induced Deaminase) were generated for use in a SHM-XEL™ affinity maturation platform (AnaptysBio, San Diego, Calif.). In situ generation of genetic diversity in the antibody variable domain resulted in cells expressing higher affinity variants of the parental antibody. These were isolated by flow cytometry using monomeric or dimeric hPD-1. Multiple rounds of affinity purification and selection yielded 6 corridors and 45 clones. Sanger and deep sequencing of these clones, along with additional "in silico SHM" events, resulted in rounds of site directed mutagenesis incorporating enriching mutations into $V_H$ and $V_L$ CDRs. The highest affinity binding 12 muteins were further characterized biochemically, biophysically for binding kinetics to PD-1, and for binding to full length PD-1 expressed on the surface of CHO cells. Functional characterization of the purified antibodies was performed in two assays: PD-L1 competition for binding to cell surface PD-1 and inhibitory activity in IL-2 production from reactivation of activated human CD4+ T cells.

Based on these methods, anti-PD-1 antibodies PD1AB-1, PD1AB-2, PD1AB-3, PD1AB-4, PD1AB-5, or PD1AB-6 were generated, as shown in Table 9.

TABLE 9

Characterization of anti-PD-1 antibodies

| Antibody ID | HC/LC TOPO Vector ID | CDR-grafted HG1 HC/LC mutations | $K_D$ (Biacore) $K_D$ (KinExA) | PD-L1 Competition ($IC_{50}$) | CD4+ T cell IL-2 inhibition ($EC_{50}$) |
|---|---|---|---|---|---|
| PD1AB-1 | 3015/3017 | parental/parental | 5 nM (n = 4) 575 pM (n = 2) | >100 nM (n = 4) | 22 ± 4 nM (n = 5) |
| PD1AB-2 | 3015/3193 | parental/germline | 5 nM (n = 2) 425 pM (n = 1) | >100 nM (n = 2) | 27 ± 4 nM (n = 3) |
| PD1AB-3 | 3653/3646 | D76N/S77N | 7 nM (n = 2) 350 pM (n = 1) | >100 nM (n = 1) | 21 nM (n = 1) |
| PD1AB-4 | 3653/3193 | D76N/germline | 6 nM (n = 2) 500 pM (n = 1) | >100 nM (n = 1) | 23 nM (n = 1) |
| PD1AB-5 | 3650/3193 | V24A/germline | 6 nM (n = 2) 400 pM (n = 1) | >100 nM (n = 1) | 15 nM (n = 1) |
| PD1AB-6 | 3650/3017 | V24A/parental | 6 nM (n = 2) 450 pM (n = 1) | >100 nM (n = 1) | 16 ± 3 nM (n = 3) |

5. EXAMPLES

The examples in this section (i.e., Section 5) are offered by way of illustration, and not by way of limitation.

5.1 Example 1: Generation of Anti-PD-1 Antibodies 5.1.1 Generation of Anti-PD-1 Antibodies The parental PD-1-IgG1 mAb was initially generated by mouse immunization methods using human PD-1 extracellular domain (ECD) antigen or CHO-hPD-1 transfected cells. Initial characterization of a hybridoma pool identified a subclone designated PD1Sub1 producing an anti-human PD-1, PD-L1 non-blocking and PD-L2 non-blocking antibody (data not shown) with $K_D$~6 nM measured by Biacore® to soluble antigen.

5.1.2 CD4+ Reactivation Assay in Human PBMCs or Human Whole Blood

PD-1 expression was induced on human PBMCs isolated from leukocyte reduction system (LRS) with PHA activation 48 hours at 37° C. CD4+ T cells were purified from the PBMCs using CD4 isolation kits (Miltenyi Biotec, San Diego, Calif.) and replated onto 96-wells with immobilized anti-CD3 or anti-CD3 plus titrated anti-PD-1 or hIgG1 isotype control antibodies. Supernatants were collected at 24 and 48 hours for IL-2, IFN-γ, and IL-17 cytokine determinations. All six anti-PD-1 clones showed similar inhibition $EC_{50}$s, ranging from 20-36 nM for IL-2, 34-58 nM for IFN-γ, and 27-41 nM for IL-17, as shown in Table 10.

TABLE 10

Comparison of T cell attenuating activity of 6 lead antibodies in PBMC reactivation assay

| | nM | PD1AB-1 | PD1AB-3 | PD1AB-2 | PD1AB-4 | PD1AB-5 | PD1AB-6 | hIgG1 |
|---|---|---|---|---|---|---|---|---|
| IL-2 | $EC_{50}$ | 21 ± 9 | 24 ± 5 | 24 ± 8 | 20 ± 7 | 36 ± 11 | 24 ± 7 | >133 |
| | $EC_{75}$ | 40 ± 9 | 46 ± 9 | 42 ± 9 | 39 ± 8 | 58 ± 18 | 33 ± 5 | |
| | nM | (n = 6) | (n = 2) | (n = 6) | (n = 6) | (n = 2) | (n = 6) | |
| IFN-γ | $EC_{50}$ | 46 ± 21 | ND | 58 ± 14 | 34 ± 21 | ND | 36 ± 22 | >133 |
| | $EC_{75}$ | 85 ± 31 | | 91 ± 29 | 64 ± 29 | | 67 ± 30 | |
| | nM | (n = 3) | | (n = 3) | (n = 3) | | (n = 3) | |
| IL-17 | $EC_{50}$ | 41 ± 9 | ND | 36 ± 12 | 27 ± 11 | ND | 37 ± 11 | >133 |
| | $EC_{75}$ | 65 ± 9 | | 59 ± 10 | 52 ± 11 | | 56 ± 13 | |
| | nM | (n = 5) | | (n = 5) | (n = 5) | | (n = 5) | |

Inhibition of specific T cell function was then assessed in a human whole-blood matrix. Freshly drawn and heparinized human blood was plated onto wells immobilized with either anti-CD3 or anti-CD3 plus titrated anti-PD-1 or hIgG1 isotype control antibodies. Collected plasma at 24 and 48 hours were measured for IL-2 (24 hours) and IFN-γ/IL-17 (48 hours). Compared to three other tested antibody clones, PD1AB-6 showed a 2-3 fold increased potency in specific IL-2 ($EC_{50}$ 4.0+0.9 nM, n=4), IFN-γ ($EC_{50}$ 4.1+2.2 nM, n=2), and IL-17 ($EC_{50}$ 3.6+1.2 nM, n=3) inhibition, as shown in Table 11.

TABLE 11

Comparison of T cell attenuating activity of 4 lead molecules in whole blood assay

| $EC_{50}$ nM | | PD1AB-1 | PD1AB-2 | PD1AB-4 | PD1AB-6 | hIgG1 |
|---|---|---|---|---|---|---|
| IL-2 | Hu (n = 4) | 8.3 ± 2.7 | 8.4 ± 1.1 | 10.2 ± 2.0 | 4.0 ± 0.9 | >133 |
| hIFN-γ | Hu (n = 2) | 5.9 ± 0.8 | 7.6 ± 0.9 | 9.2 ± 1.3 | 4.1 ± 2.2 | >133 |
| hIL-17 | Hu (n = 3) | 7.2 ± 1.3 | 8.9 ± 2.3 | 9.9 ± 3.7 | 3.6 ± 1.2 | >133 |

5.1.3 Cell-Based Ligand Binding Assay

Figure 1A:
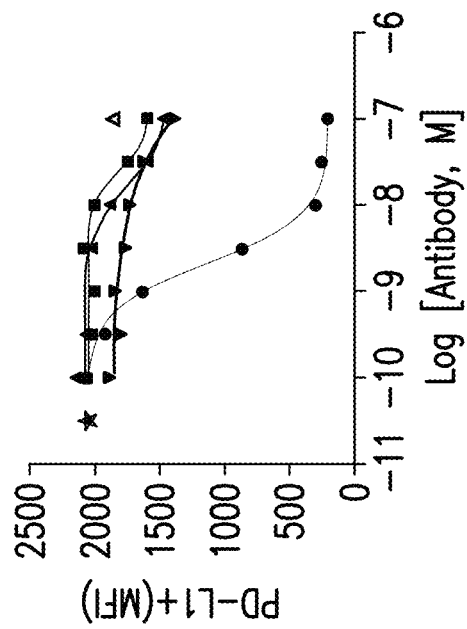
FIGS. 1A-1B show that the T cell attenuating anti-PD-1 antibodies (PD1AB) do not compete with PD-L1 (PD-L1-DyL650 denotes PD-L1 conjugated with the dye DyL650) binding to PD-1: (A) PD1AB-1, PD1AB-2, and PD1AB-6; (B) PD1AB-1, PD1AB-2, PD1AB-3, PD1AB-4, and PD1AB-5. MDX 4H1, an antagonist antibody, blocks PD-L1 binding to PD-1.
Figure 1B:
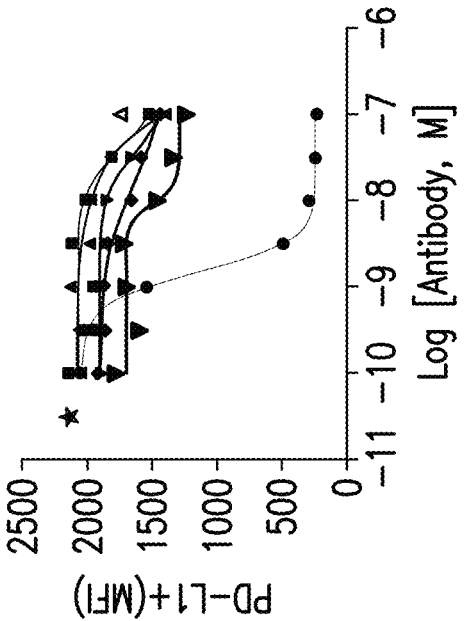

To assess ligand competition, a cell binding assay was put in-place to evaluate the identified six antibody clones. Briefly, individual antibody clones at semi-log concentrations from 100 nM to 100 pM were pre-mixed with 10 nM DyL650-PD-L1 before adding to human PD-1-CHO cells ($2 \times 10^5$ cells) for 45 minutes on ice. Cells were then washed before DyL650-PD-L1 binding was analyzed on a BD FACSArray™ and median fluorescence intensity relative to isotype control antibody was plotted at each concentration. As shown in FIGS. 1A-1B, PD1AB-6, as well as the other five clones, including the parental clone PD1AB-1, showed no significant competition against DyL650-PD-L1 binding up to 100 nM. In contrast, MDX 4H1 (AnaptysBio, San Diego, Calif.), an antagonist, ligand-blocking, PD-1 antibody dose-dependently blocked labeled PD-L1 binding, generating a binding EC50~5-10 nM.

5.1.4 Epitope Mapping

Figure 2:
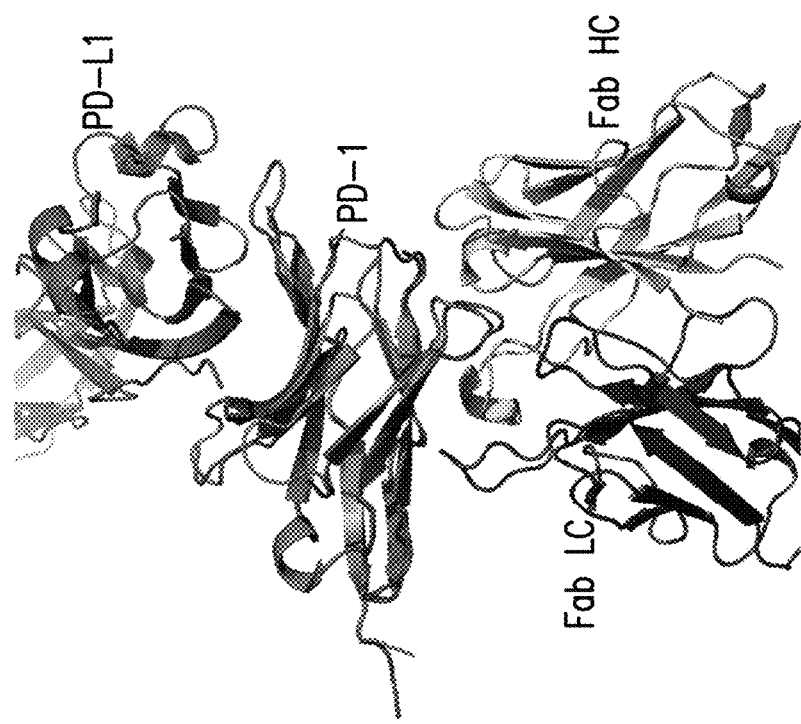
FIG. 2 depicts that the PD-1:PD1AB-6 Fab interaction site is at a distal side of PD-1 relative to the PD-1:PD-L1 interaction site.
Figure 3:
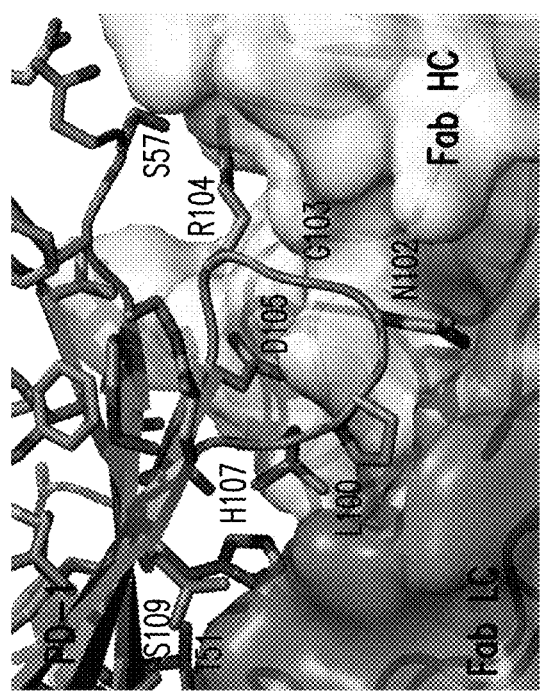
FIG. 3 depicts that PD1AB-6 Fab binds against a PD-1 β sheet, with substantial interactions formed with a PD-1 loop composed of residues 100-105.

The PD-1 epitope was determined by solving the crystal structure of the PD1AB-6 Fab in complex with the human PD-1 extracellular domain to 1.8 Å resolution. The PD-1:PD1AB-6 Fab interaction site occurs on a distal side of PD-1 relative to the PD-1:PD-L1 interaction site (FIG. 2), consistent with the observation that PD-L1 and PD1AB-6 do not compete for PD-1 binding. PD1AB-6 Fab binds against a PD-1 β sheet, with substantial interactions formed with a PD-1 loop composed of residues 100-105 (FIG. 3). R104 on PD-1 engages multiple polar interactions with residues on the Fab CDR H1. The adjacent residue G103 also makes a tight polar interaction with the Fab. Both R104 and G103 are mutated in mouse PD-1 (to a histidine and arginine, respectively), providing a structural rationale for the lack of binding of PD1AB-6 to murine PD-1. The PD1AB-6 Fab regions that interact with PD-1 are the CDR H1, H2, H3, L1 and L2. Atomic details of the PD-1:PD1AB-6 Fab interactions are described in the Table 12. HC and LC residues that interact with PD-1 epitope are described. Abbreviations are as follows: HB-hydrogen bond, HYD-hydrophobic interaction, ION-ionic interaction.

TABLE 12

Atomic details of PD1AB-6:PD-1 interaction

| Type | Chain | Pos | Chain | Pos |
|---|---|---|---|---|
| HB | PD-1 | ASN33.Nδ2 | H | ALA71.O |
| HB | PD-1 | THR51.Oγ1 | L | SER50.O |
| HB | PD-1 | SER57.Oγ | H | ASP69.Oδ2 |
| HYD | PD-1 | LEU100.Cδ1 | H | PHE55.Cζ |
| HYD | PD-1 | LEU100.Cδ1 | L | LEU115.CD1 |
| HB | PD-1 | ASN102.Nδ2 | L | TYR114.O |
| HB | PD-1 | ASN102.Oδ1 | L | SER117.N |
| HB | PD-1 | ASN102.O | H | TYR50.Oη |
| HB | PD-1 | GLY103.O | H | TYR126.Oη |
| HB | PD-1 | ARG104.Nη2 | H | LYS47.O |
| HB | PD-1 | ARG104.Nη1 | H | ASP48.O |
| HB | PD-1 | ARG104.Nη1 | H | ASP69.Oδ1 |
| ION | PD-1 | ARG104.Nη2 | H | ASP69.Oδ1 |
| HB | PD-1 | ASP105.Oδ1 | H | SER125.Oγ |
| HB | PD-1 | HIS107.Nδ1 | L | SER50.Oγ |
| HB | PD-1 | SER109.Oγ | L | SER50.O |

5.1.5 Generation of Variants of PD1AB-6

PD1AB-6 IgG1 antibody (PD1AB-6-IgG1) and Fc modified IgG4PE antibody (PD1AB-6-4PE) were generated. PD1AB-6-4PE was designed to have significantly lower Fc-mediated effector function. The CH region, γ4 contains two non-standard amino acids substitutions, S228P and L235E (EU numbering systems, Kabat and Wu 1991). Serine 228, a common amino acid type in the hinge of IgG4, was changed to proline, a less commonly observed amino acid type in IgG4 and highly conserved amino acid in IgG1. This change significantly reduced the level of "half-antibody" that is commonly observed in the production of IgG4-subclass antibody. Leucine 235, one of the critical amino acids involved in heavy chain interactions with Fcγ receptors was changed to glutamic acid. The L235E substitution significantly reduced the interaction of γ4 chain to FcγR, eliminating ADCC and Fc-receptor-mediated elimination of PD-1-expressing normal cells. In addition, inherent lack of complement binding by γ4 heavy chain renders the PD1AB-6-4PE molecule devoid of CDC function. Two other variants were generated to minimize binding affinity to C1q for reduced CDC (FIG. 4). To generate PD1AB-6-K3, lysine 322 was substituted with alanine in PD1AB-6-IgG1. The K322A substitution is reported to suppress C1q binding on rituximab, a chimeric antibody with a human IgG1 Fc (Idusogie et al., 2000, J. Immunol. 164(8):4178-84). PD1AB-6-4P was generated by converting the Fc-backbone of the PD1AB-6-IgG1 to the Fc-backbone of IgG4 with S228P substitution. Serine 228, a common amino acid type in the hinge of IgG4, was changed to proline, a less commonly observed amino acid type in IgG4 and highly conserved amino acid in IgG1. This change significantly reduces the level of half-antibody that is frequently observed in the production of IgG4-subclass antibody. IgG4 antibody was reported to have attenuated ADCC and CDC function (Overdijk et al., 2012, J. Immunol. 189(7):3430-38). All changes were created in the CH region with no changes in the variable regions. The amino acid sequences of the heavy and light chains of PD1AB-6-IgG1 are labeled LC_PD1AB-6-IgG1 and HC_PD1AB-6-IgG1, respectively (FIG. 4). The two heavy chain variants include HC_PD1AB-6-IgG1-K322A and HC_PD1AB-6-IgG4P. The light chain LC_PD1AB-6-IgG1 is paired with the three individual heavy chains to generate PD1AB-6-IgG1, PD1AB-6-K3, and PD1AB-6-4P, respectively.

5.1.6 Cell Line Development and Antibody Manufacturing from Transient Transfection 5.1.6.1 Molecular Cloning of the Heavy and Light Chains IgG LC expression vector pFUSE2ss-CLIg-hk and IgG HC expression vector pFUSEss-CHIg-hG1 were purchased from InvivoGen (San Diego, Calif.).

The amino acid sequence encoding LC_PD1AB-6-IgG1 (FIG. 4) was converted into a codon-optimized gene sequence for protein expression in mammalian cells. Restriction enzyme sites EcoRI at the 5'-end and NheI at the 3'-end were added to the optimized gene. The optimized LC gene with EcoRI and NheI sites were synthesized producing an insert fragment. The IgG LC expression vector pFUSE2ss-CLIg-hk was digested with EcoRI and NheI producing approximately a 3.5 kb pFUSE2ss-CLIg-hk-EcoRI/NheI fragment. The insert fragment was ligated into pFUSE2ss-CLIg-hk-EcoRI/NheI fragment resulting in production of pJS-1 which is pFUSE2ss-CLIg-hk-LC_PD1AB-6-IgG1.

The amino acid sequence encoding HC_PD1AB-6-IgG1, HC_PD1AB-6-IgG1-K322A, or HC_PD1AB-6-IgG4P (FIG. 4) was converted into a codon-optimized gene sequence for protein expression in mammalian cells. Restriction enzyme sites EcoRI at the 5'-end, a constant region from a stop codon (after the 3'-end of HC sequence in pFUSEss-CHIg-hG1) to HpaI at the 3'-end were added. The optimized genes with EcoRI and HpaI sites were synthesized producing insert fragments containing the genes encoding HC_PD1AB-6-IgG1, HC_PD1AB-6-IgG1-K322A, and HC_PD1AB-6-IgG4P, respectively. The IgG HC expression vector pFUSEss-CHIg-hG1 was digested with EcoRI and HpaI producing approximately a 3.4 kb pFUSEss-CHIg-hG1-EcoRT/HpaI fragment. The insert fragments were ligated into pFUSEss-CHIg-hG1-EcoRT/HpaI fragment resulting in production of pJS-2, pJS-3, and pJS-12, which are pFUSEss-CHIg-hG1-HC_PD1AB-6-IgG1, pFUSEss-CHIg-hG1-HC_PD1AB-6-IgG1-K322A, and pFUSEss-CHIg-hG1-HC_PD1AB-6-IgG4P, respectively.

5.1.6.2 Protein Production

All three variants of PD1AB-6-IgG1, PD1AB-6-K3, and PD1AB-6-4P were manufactured at the laboratory scale in shake-flasks for in vitro and in vivo efficacy studies. PD1AB-6-4P and PD1AB-6-K3 antibodies for non-GLP toxicology studies and additional characterization were manufactured in 50 L bioreactors (50 L stirred tanks and 50 L wave bags) using FreeStyle™ MAX CHO expression system as well as Expi293™ expression system from Life Technologies (Carlsbad, Calif.). FreeStyle™ MAX CHO expression system was used for transient transfection of CHO-S cells using manufacturer's standard protocol. Expi293™ expression system was used for transient transfection of Expi293 cells using manufacturer's standard protocol. A 3:2 ratio of light chain versus heavy chain was used for DNA mixture at 1 mg per 1 L of culture during the transfection. Cells were seeded at 0.5 million cells/mL in a 50 L bioreactor at 37° C. and grew over night to reach 1 million cell/mL. Cells then were transfected using manufacturer's standard protocols. On day one post-transfection, 1 mM sodium butyrate plus 1% v/v of feed media (Yeastolate, CHO CD EfficientFeed™ A, Glutamax and Glucose) was added to bioreactor, and temperature was dropped to 32° C. Forty liters of cells plus additives were seeded for a 50 L stirred tank, and 25 L of cells plus additives were seeded for a 50 L wave bioreactor. Cell viability and titer were monitored every day, and batches were harvested when cell viability dropped below 50%. Vi-Cell™ instrument was used for viability analysis, and Octet RED equipped with Anti-Human IgG sensor was used for titer analysis using purified antibody for the standard curve. Cells and supernatant were harvested using GE Life Sciences depth filtration and sterilization columns, ULTA Prime GF 5 μm capsules were used for depth filtration followed by ULTA Pure HC 0.6/0.2 μm sterilization capsules. Clarified supernatant were concentrated 5-8 fold using cross flow filtration, 50 Kd cut off Kvick™ Lab SCU from GE Life Science were used for TFF. The titer and maximum cell densities obtained for each isotype at harvest are given in Table 13.

TABLE 13

Productivity in Fed-batch Bioreactor (50 Liter)

| Isotype Cell pool | Cell Line/ Volume | Titer (mg/l) | Cell density at harvest (1 × 10⁶ cells/mL) |
|---|---|---|---|
| PD1AB-6-4P | Expi293/25 L | 22 | 3.2 |
| PD1AB-6-4P | CHO—S/50 L | 9 | 3 |
| PD1AB-6-K3 | Expi293/50 L | 31 | 4.5 |
| PD1AB-6-K3 | CHO—S/50 L | 15 | 2 |

5.1.6.3 Protein Purification

Purification of the materials produced was performed by a series of downstream purification steps including protein A affinity chromatography and low pH virus inactivation, followed by IEX interaction (Capto™ Adhere & Capto™ SP ImpRes) chromatography steps. The purified antibody is bulk formulated by buffer exchanged against (10 mM Succinate pH 5.5, 9% sucrose, 0.05% PS20) buffer, filtered through 0.2 μm filter, and aliquoted.

The protein A affinity chromatography was carried out with MabSelect SuRe™, designed to capture the product and to remove process related impurities. The subsequent virus inactivation step was performed under acidic conditions (pH 3.4±0.1 for 45 min.) followed by conditioning of the inactivation pool to pH 5.5±0.1. After virus inactivation, an anion exchanger was used in a flow-through mode for intermediate polishing step using Capto™ Adhere to remove impurities such as aggregates, DNA, host cell protein, and endotoxin. The product pool was conditioned to pH 6.5±0.1, and the conductivity was reduced to 2 mS/cm prior to the next process step. Cation exchanger Capto™ SP ImpRes was used as a polishing step, and the product was resolved at 10 mS/cm. The antibody was then buffer exchanged in stock solution (10 mM Succinate, 9% sucrose, 0.05% PS20, pH 5.5) and concentrated to 20 mg/mL. The product pool was then filtered through 0.2 μm filter and aliquoted.

5.1.7 Cell-Based PD-1 Binding Assay

Figure 5B:
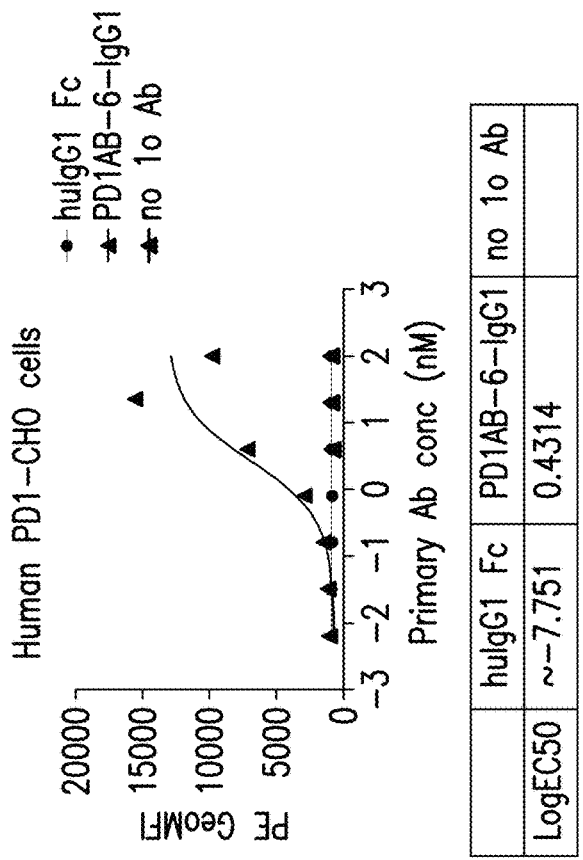
FIGS. 5A-5B depict the PD1AB-6-IgG1 affinity for cyno (A) or human (B) PD-1 expressed on CHO cells.
Figure 5A:
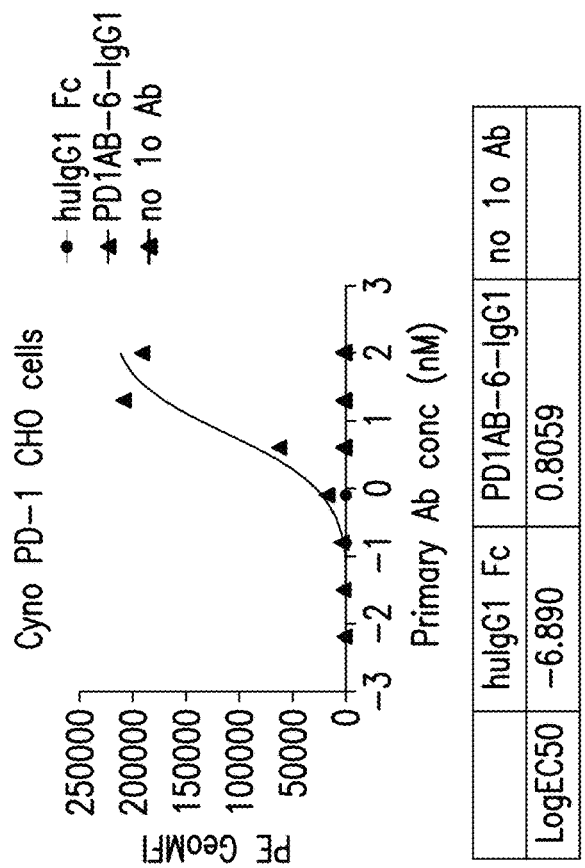
Figure 6:
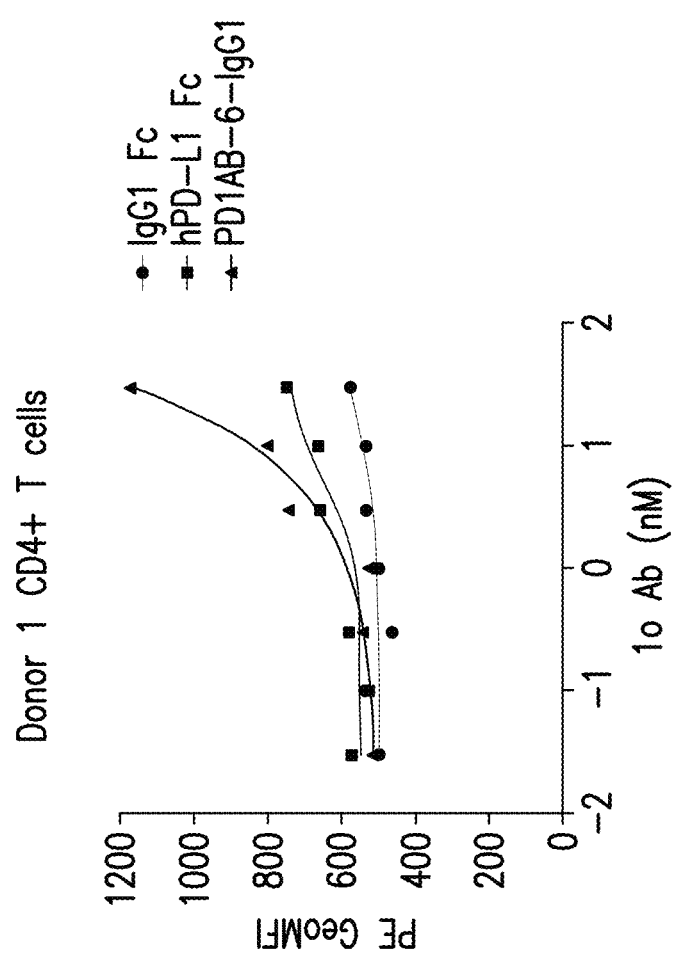
FIG. 6 depicts the binding of PD1AB-6-IgG1, isotype control, and human PD-L1 Fc fusion protein (hPD-L1 Fc) to activated human PBMC gated on CD4+ T cells.
Figure 7:
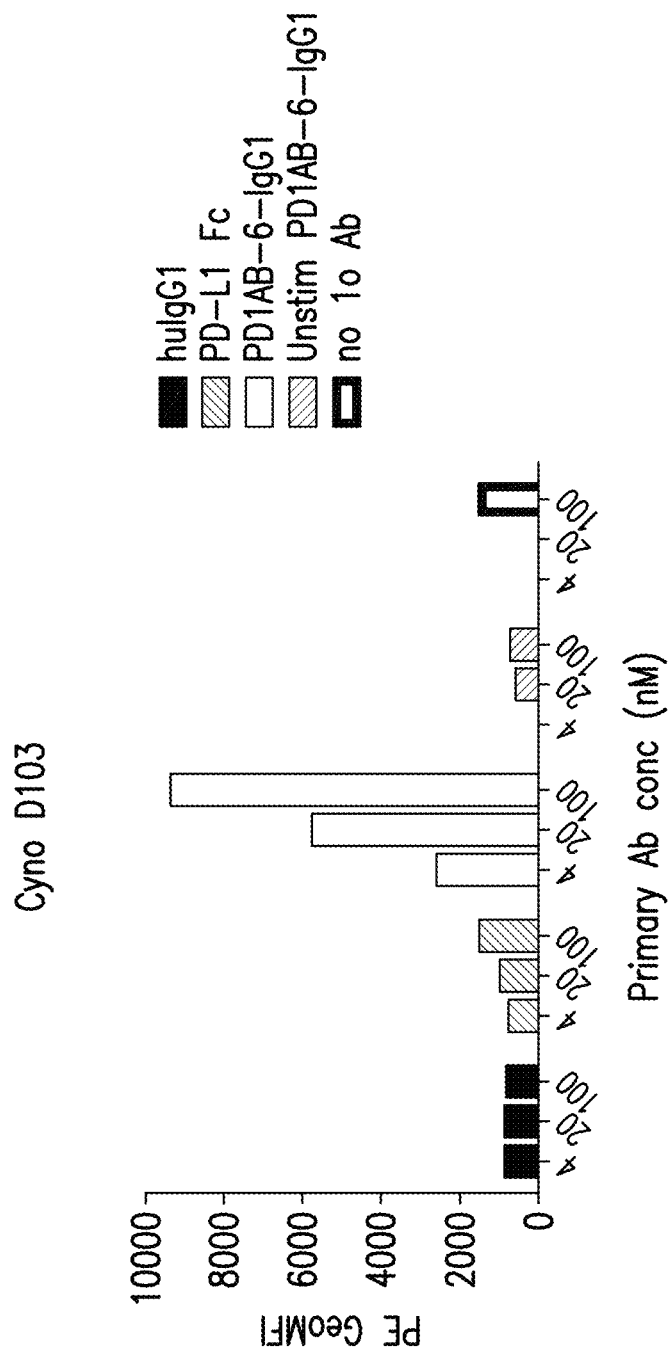
FIG. 7 depicts the binding of PD1AB-6-IgG1, isotype control, and human PD-L1 Fc fusion protein (hPD-L1 Fc) to activated cyno PBMC gated on CD4+ T cells.

PD1AB-6-IgG1 binding was evaluated on CHO cells expressing human PD-1 and cyno PD-1 (FIGS. 5A-5B), and on primary human PBMC (FIG. 6) and cyno PBMC (FIG. 7).

CHO cells expressing human PD-1 and cyno PD-1 were incubated with various concentration of unlabeled PD1AB-6-IgG1 antibody for 30 minutes at 4° C., washed, and stained with anti-human IgG Fc (eBioscience, San Diego, Calif.) for 30 minute at 4° C. Human IgG1 Fc was used as a negative control. PD1AB-6-IgG1 binds to human PD-1 expressed on CHO cells with an $EC_{50}$=0.4 nM and binds to Cyno PD-1 expressed on CHO cells with an $EC_{50}$=0.8 nM (FIG. 5).

Human PBMCs were activated with 1 μg/mL plate bound anti-CD3 for 3 days to induce PD-1 expression on T cells. Cells were incubated with various concentration of unlabeled PD1AB-6-IgG1 antibody for 30 minutes at 4° C., washed, and stained with anti-human IgG Fc (eBioscience, San Diego, Calif.) for 30 minute at 4° C. Human IgG1 Fc was used as a negative control. Geometric MFI was determined on CD4+ T cells. Data from 1 of 2 human healthy donors are shown in FIG. 6.

Cyno PBMCs were activated with 1 μg/mL anti-cyno CD3/CD28 for 2 days to induce PD-1 expression on T cells. Cells were incubated with various concentration of unlabeled PD1AB-6-IgG1 antibody for 30 minutes at 4° C., washed, and stained with anti-human IgG Fc (eBioscience) for 30 minute at 4° C. Human IgG1 Fc was used as a negative control. Geometric MFI was determined on CD4+ T cells. Data from 1 of 2 cyno donors are shown in FIG. 7.

5.1.8 Fc Receptor Binding Assay

To confirm the objectives of variants generation, i.e., decreased FcγR-mediated effector function, FcγR binding to the PD1AB-6-K3 and PD1AB-6-4P variants were analyzed by two methodologies. First, binding was tested with displacement FcγR assays using Cisbio Tag-lite® detection (FIGS. 8A-8D). HEK293 cells engineered to express specific FcγRs (FcγRI, FcγRIIIa, or FcγRIIb) prelabeled with a terbium (Tb) donor dye were mixed with reference controls or PD1AB-6-IgG1, PD1AB-6-K3, and PD1AB-6-4P antibodies over log concentrations ranging from 10000 nM to 0.1 pM. A second, human-hIgG-d2 (acceptor) was then added to compete for receptor binding. Detection of a Fluorescence Resonance Energy Transfer (FRET) signal generated by Tb-d2 proximity is measured and is inversely proportional to PD1AB-6 variant-bound FcγR. As shown in FIGS. 8A-8D, the PD1AB-6-K3 variant showed decreased binding to FcγRIIIa (CD16), the low affinity receptor on NK cells responsible for ADCC activity. Binding to FcγRI (expressed on granulocytes, dendritic cells (DCs), or monocytes) was similar to parental PD1AB-6-IgG1 molecule.

Figures 9A, 9B, 9C:
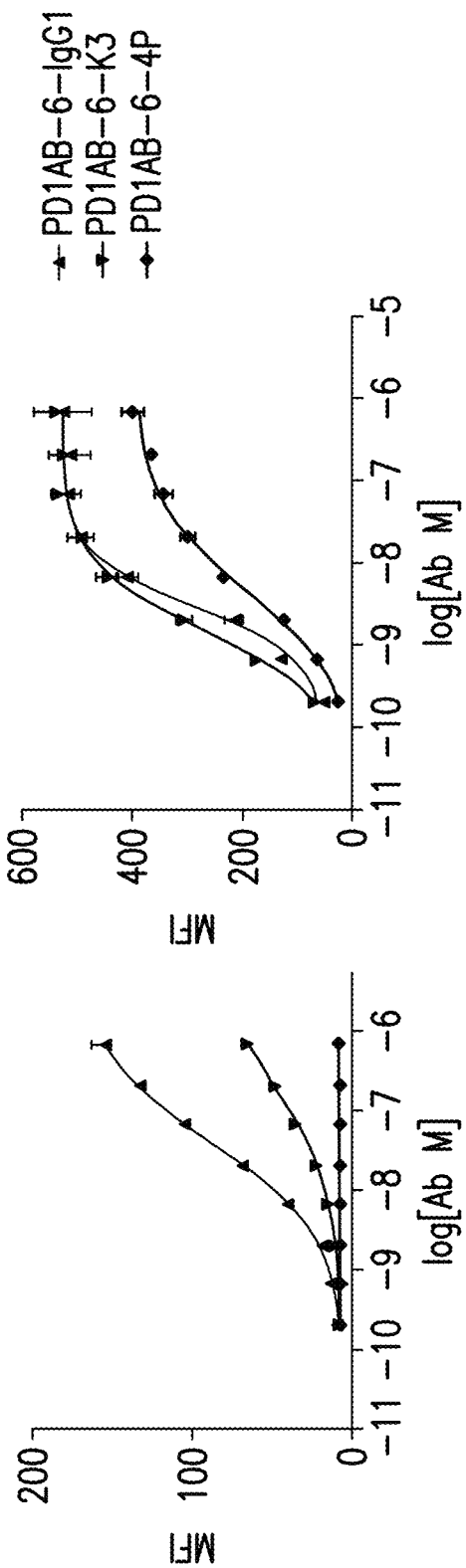
FIGS. 9A-9C depict the PD1AB-6 variants binding to FcγRIIIa (V158) (A) or FcγRI (B) expressed on CHO cells using FACS, and (C) the $EC_{50}$ values of the PD-1 antibody variants binding to FcγRI or FcγRIIIa.

Second, both PD1AB-6-K3 and PD1AB-6-4P variants were tested in FACS-based binding assays (FIGS. 9A-9C). Briefly, FcγRI-CHO or FcγRIIIaV158-CHO expressing cell lines were detached and washed prior to mixing with the PD1AB-6-K3 and PD1AB-6-4P variants over different concentrations for 1 hour on ice. PD1AB-6 variant-bound cells were detected with a labeled PE-conjugated F(ab')$_2$ goat anti-human secondary antibody for an additional hour on ice, washed, and fixed prior to analysis by FACS, and mean fluorescence intensity was plotted at each concentration. The PD1AB-6-4P variant returned significantly higher binding $EC_{50}$s (>15× and >21×) against FcγRI and FcγRIIIa lines, respectively (FIGS. 9A-9C).

5.1.9 In Vitro ADCC Assay

Figure 10B:
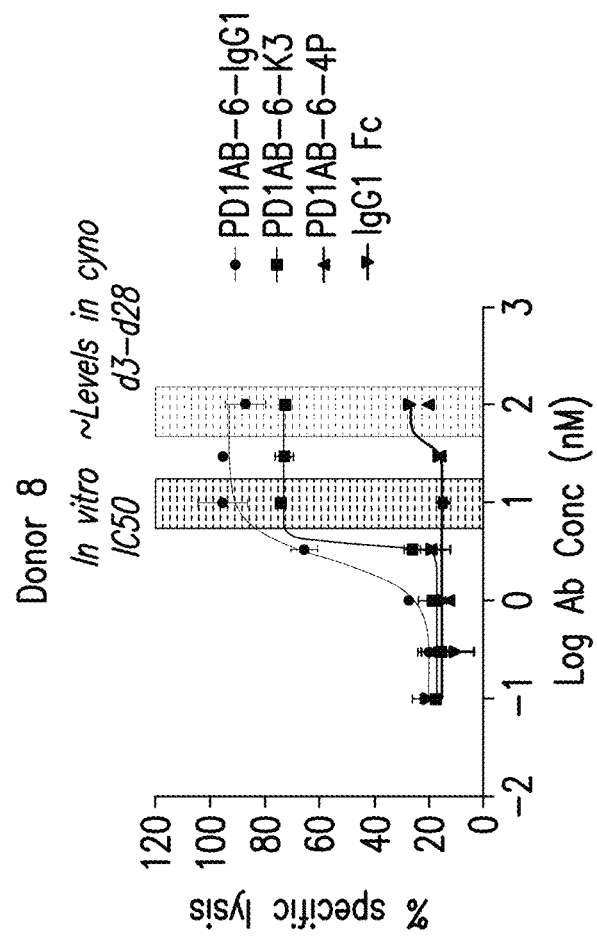
FIGS. 10A-10B depict the ADCC activity of the PD1AB-6 variants and a control human IgG1 Fc among two representatives of four individual healthy donors: (A) Donor 7 and (B) Donor 8.
Figure 10A:
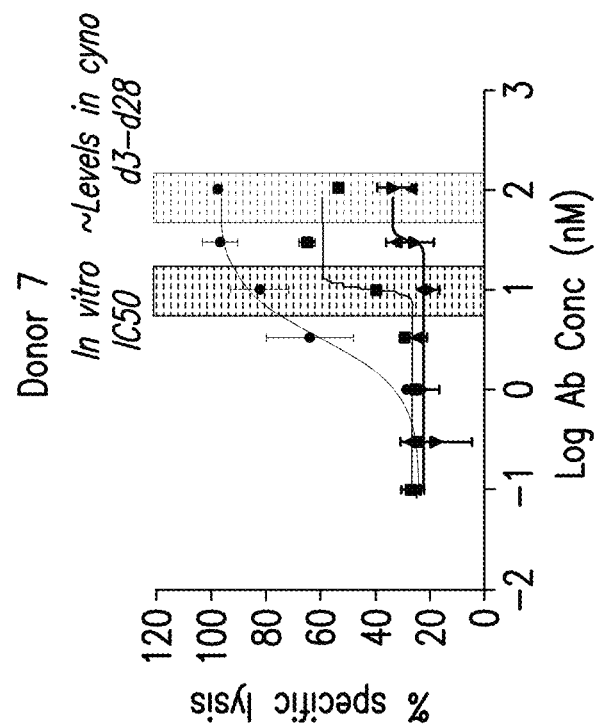

The ability of PD1AB-6 variants to induce ADCC was evaluated in co-culture assay involving natural killer (NK) cells from healthy donors and PD-1 expressing target cells. Target cells (NCI-OCI-Ly3) pre-treated with PD1AB-6 variants were co-cultured with activated NK cells for 4 hours. Supernatant LDH concentration was used to calculate specific lysis. $EC_{50}$ (nM) was calculated using Prism. Error bar represents experimental triplicates. Data are 2 representatives of 4 individual healthy donors. As shown in FIGS. 10A-10B, titration of PD1AB-6-IgG1 induced dose dependent ADCC, while PD1AB-6-K3 showed reduced ADCC activity.

5.1.10 In Vitro CDC Assay

Figure 11:
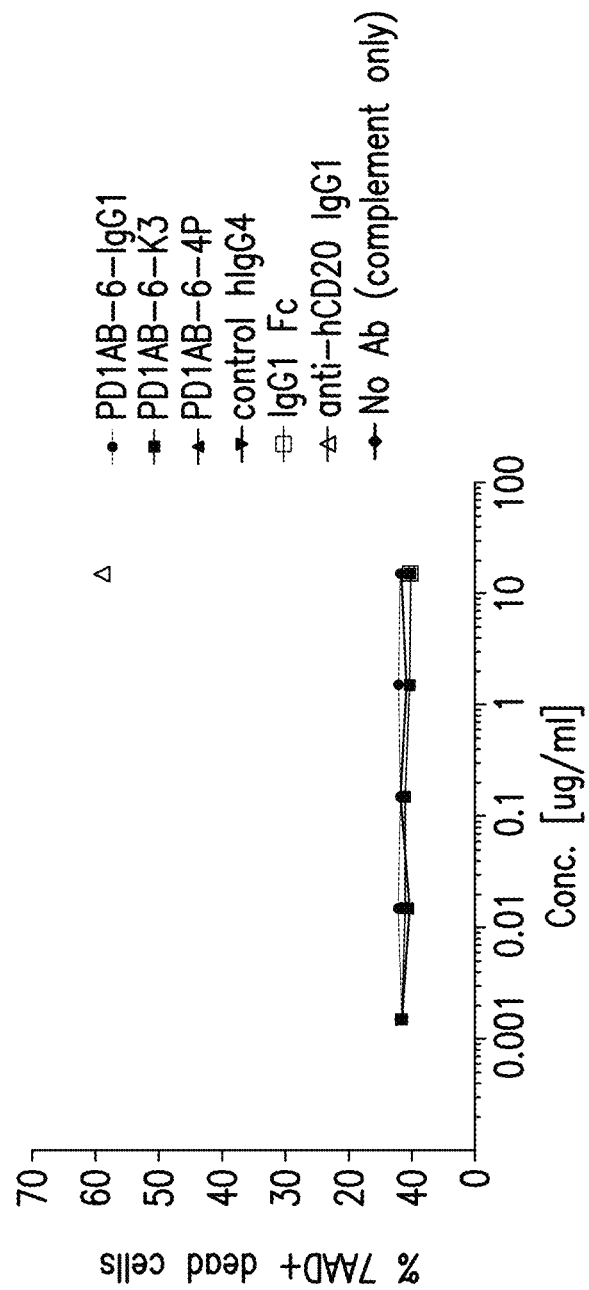
FIG. 11 depicts the CDC activity of the PD1AB-6 variants. Data are representative of 3 independent experiments: (i) CDC activity of PD1AB-6-IgG1 and anti-human CD20 IgG1; (ii) CDC activity of PD1AB-6-IgG1 and PD1AB-6-K3; (iii) CDC activity of PD1AB-6-4P and commercial human IgG4 isotype control antibody and human IgG1 Fc protein.

The ability of PD1AB-6 variants to induce CDC was evaluated using PD-1 expressing CD20$^+$ NCI-OCI-Ly3 cells. Target cells (NCI-OCI-Ly3) pre-treated with antibodies were cultured in serum-free media supplemented with 5% rabbit complement for 4 hours. Cell lysis was determined by 7-AAD$^+$ cells by FACS. Data are representative of 3 independent experiments: (i) CDC activity of PD1AB-6-IgG1 and anti-CD20 IgG1; (ii) CDC activity of PD1AB-6-IgG1 and PD1AB-6-K3; (iii) CDC activity of PD1AB-6-4P and commercial mouse anti-PD-1 IgG1 antibody. As shown in FIG. 11, PD1AB-6-K3 consistently did not induce CDC (n=3). Parental PD1AB-6-IgG1 and PD1AB-6-4P also did not induce CDC. This was not due to resistance of the target cell line to complement killing, since anti-CD20 IgG1 repeatedly induced dose dependent CDC on NCI-OCI-Ly3 cells in presence of 5% rabbit complement.

5.2 Example 2: Activity Assays 5.2.1 Human T Cell Activation Assay

Figure 12:
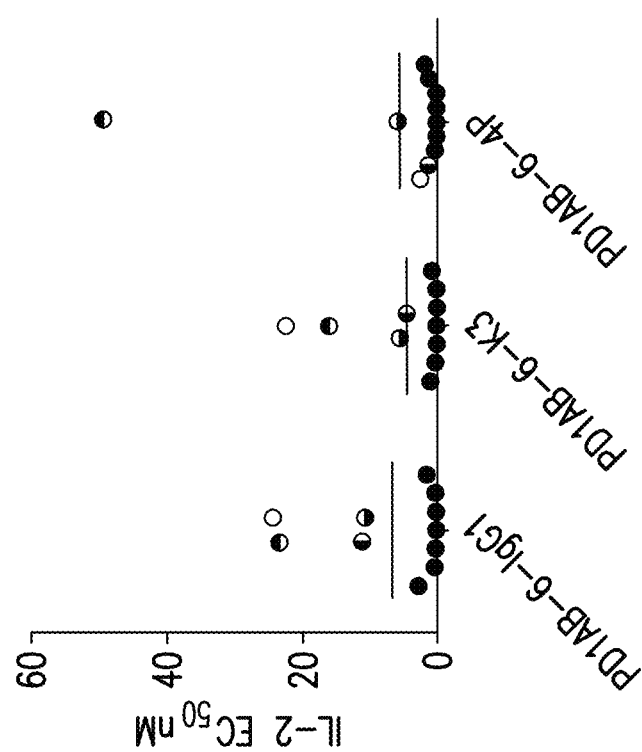
FIG. 12 depicts the potent attenuating activity of PD1AB-6 variants in human PBMC assay, measured by IL-2 levels in culture supernatants at 24 hours post-stimulation.

Functional assessment of PD1AB-6 variants on inhibiting T cell effector function was performed by two methods. In one assay, the peripheral blood mononuclear cells were preactivated to express PD-1 and restimulated in the presence of soluble PD1AB-6-K3 (FIG. 12). Peripheral blood mononuclear cells (PBMCs), from healthy donors were preactivated with the mitogen, PHA, for 48 h to upregulate PD-1 expression. These cells were then restimulated using anti-CD3 conjugated Dynabeads® (Life Technologies' Carlsbad, Calif.) in the presence of diluted PD1AB-6 variants over a range of 100 nM to 0.1 nM final concentration. T cell activation was measured using IL-2 levels in culture supernatants at 24 h post-stimulation. As shown in FIG. 12, PD1AB-6-K3 and the two other variants showed potent T cell inhibitory activity in this assay with an $EC_{50}$ of 5-25 nM.

A second assay was used for direct ex vivo measurement of PD1AB-6-K3 in inhibiting T cell function (FIG. 13). This was done by directly plating fresh human whole blood in 96-well plates co-coated with anti-CD3+/−PD1AB-6-K3, and measuring IL-17 and IFN-γ levels as readouts of T cell activation. CTLA4Ig (Orencia®) was used as a positive control in these assays, and human IgG Fc fragment was used as a negative control. As shown in FIG. 13, overall, PD1AB-6-K3 trended towards better efficacy than PD1AB-6-4P. Negative control, hIgG Fc, showed no activity with an $EC_{50}>100$ nM.

5.2.2 Cynomolgus Monkey Crossreactivity Assay

Determination of functional cynomolgus monkey cross reactivity with lead PD1AB-6-K3 was performed similarly to human samples, using freshly isolated cynomolgus PBMCs, activated with anti-cyno CD3, CD28, and PD1AB-6 variants as indicated. CTLA4Ig was used as a positive control in these assays, and hIgG1 Fc was used as a negative control. Culture supernatants were removed after 48 hours for cytokine determinations using cynomolgus IL-2 MSD assays. As shown in Table 14, these assays demonstrated that PD1AB-6-K3 attenuated cyno T cells cytokine secretion to levels comparable to the positive control, CTLA4Ig, and the activity was comparable to that seen in human assays.

TABLE 14

PD1AB-6-K3 activity in cyno PBMC assay

| | PD1AB-6-IgG1 | PD1AB-6-K3 | PD1AB-6-4P | CTLA4Ig |
|---|---|---|---|---|
| | | IL-2 EC50 (nM) | | |
| NHP1 | 0.28 | 0.24 | <0.1 | Not done |
| NHP2 | 4.9 | 2.5 | 1.24 | Not done |
| NHP3 | N.D. | 9.24 | 16.5 | 14 |
| NHP4 | N.D. | 1.22 | 1.23 | 6 |

5.2.3 In Vitro Mechanism of Action

Several antibodies that bind to T cell surface molecules, such as CD3 and CD4, lead to signaling and subsequent downregulation of surface expression of those molecules. Since PD1AB-6 antibody is designed to provide an agonist signal via PD-1, it was of interest to evaluate PD-1 expression after PD1AB-6 treatment in vitro.

5.2.3.1 Decreased PD-1 Expression after PD1AB-6 Treatment

Human PBMC from different donors were activated with 1 μg/mL plate bound anti-CD3+0.25 μg/mL plate bound anti-CD28 with various concentration of soluble control IgG1 or PD1AB-6-IgG1. After 4 hours to 72 hours incubation, cells were stained for CD3, CD45RO, and PD-1 to assess PD-1 expression on T cells. FIGS. 14A-14C show reduced expression of PD-1 on human CD3+ T cells after 48 hours PD1AB-6-IgG1 treatment. Analysis of PD-1 expression showed that PD1AB-6-IgG1 treatment led to downregulation of PD-1 expression on the surface of T cells (representative histogram from one donor in FIGS. 14A-14B and analysis of mean fluorescence intensity at 48 hours, across three donors and various antibody concentrations in FIG. 14C). PD-1 downregulation was seen as early as 4 hours of incubation with PD1AB-6-IgG1. Downregulation of surface PD-1 expression was likely due to PD1AB-6 induced signaling via PD-1, and was through similar mechanism to what is observed with T cell receptor signaling (San Jose et al., 2000, Immunity 12(2):161-70).

5.3 Example 3: Physicochemical Characterization of PD1AB-6 Variants 5.3.1 Biacore Binding Analysis Purified PD1AB-6 variant antibodies were analyzed on Biacore® T200 for binding to hPD1 antigen using capture method. Fc-specific anti-human IgG was immobilized on Fc2, and Fc1 was left blank as reference channel. Purified PD1 antibodies were captured on anti-Human IgG, and internally produced hPD1 antigen (PD1_002) was flowed over both channels using two fold dilution series from 100 nM to 200 pM to determine kinetics of binding. The PD-1 used was the extracellular domain of human PD-1 (residues 32-160) expressed in E. coli as inclusion bodies and refolded. Surface was regenerated between each antigen concentration using 3M Magnesium Chloride. Examples of binding kinetics as well as values of $k_{on}$, $k_{on}$, and $K_D$ for PD1AB-6-IgG1, PD1AB-6-4P, and PD1AB-6-K3 are shown in FIG. 15A-15C. All three variants had similar rates of association and dissociation to the PD-1 antigen with comparable $K_D$ values of 19-22 nM.

5.4 Example 4. Effect of PD-1 Antibodies in a Vitiligo Mouse Model

In order to test the effectiveness of PD-1 antibodies in the treatment of vitiligo, a mouse model of the disease is used. KRT14-Kitl*4XTG2Bj1 (Krt14-Kitl*) mice express a non-cleavable, membrane-bound form of Kit ligand under the keratin 14 promoter, limiting its expression to the epidermis (Harris et al., 2012, J. Invest. Dermatol. 132(7):1869-76). Consequently, the Krt14-Kitl* mice have black skin, black hair, and elevated levels of melanocytes (Kunisada et al., 1998, Development 125(15):2915-23). Vitiligo is induced in the mouse through the adoptive transfer of human melanocyte-specific CD8+ T cells that are subsequently activated in vivo (Harris et al., 2012, J. Invest. Dermatol. 132(7):1869-76).

KRT14-Kitl*4XTG2Bj1 (Krt14-Kitl*) mice are obtained from Jackson Laboratories (Bar Harbor, Me., stock no. 009687, Tg(KRT14-Kitl*)4XTG2Bj1). Thy1.1+PMEL TCR transgenic mice are obtained from Jackson Laboratories (Bar Harbor, Me., stock no. 005023, B6.Cg Thy1$^a$/CyTg (TcraTcrb)8Rest/J). Thy1.1+PMEL TCR transgenic mice are crossed with humanized PD-1 knock-in mice (Oxford University Innovation, product code 4460) to obtain Thy1.1+ PMEL TCR transgenic humanized PD-1 knock-in mice (PMEL-hPD-1 KI). All mice are on a C57BL/6J background, and are maintained in pathogen-free facilities.

CD8+ T cells are isolated from PMEL-hPD-1 KI mice. Vitiligo is induced through adoptive transfer of PMEL-hPD-1 KI CD8+ T cells as described previously (Harris et al., 2012, J. Invest. Dermatol. 132:1869-76). Briefly, PMEL CD8+ T cells are isolated from the spleens of PMEL-hPD-1 KI mice through negative selection on microbeads (Miltenyi Biotec, Auburn, Calif.) according to the manufacturer's instructions. Purified CD8+ T cells (1×10$^6$) are injected intravenously into sub-lethally irradiated (100-500 rads 1 day before transfer) Krt14-Kitl* hosts (12 to 16 weeks of age). Recipient mice are challenged with human PMEL antigen (either as purified protein or expressed in a viral vector such as described in P. Agarwal et al., 2015, J Invest Dermatol. 135(4):1080-88) on the same day of transfer. Treatment with anti-PD-1 antibodies (e.g., PD1AB-6, PD1AB-6-K3, or a murine surrogate of PD1AB-6 or PD1AB-6-K3, which retains the PD-1 binding variable region, with Fc region switched to murine IgG2a or murine IgG2a with mutations comparable to K322A) is performed by i.p. injection of a dose (range of 0.1 mpk-10 mpk) at a frequency of daily to once a week for the duration of the study. Control mice receive either no treatment or are treated with an equal volume of saline or isotype control. A "vitiligo score" is objectively quantified, using a point scale based on the extent of depigmentation at four easily visible locations, including the ears, nose, rear footpads, and tails as described previously (Harris et al., 2012, J. Invest. Dermatol. 132: 1869-76). Each location is examined, and the extent of depigmentation is estimated as a percentage of the anatomic site; both left and right ears and left and right rear footpads are estimated together and therefore evaluated as single sites. Specifically, points are awarded as follows:

TABLE 15

Mouse dipigmentation scale for vitiligo score

| Depigmentation (%) | Score |
| --- | --- |
| 0 | 0 |
| >0-10 | 1 |
| >10-25 | 2 |
| >25-75 | 3 |
| >75-<100 | 4 |
| 100 | 5 |

The vitiligo score is the sum of the scores at all four sites, with a maximum score of 20 points. Antibodies to PD-1 (e.g., PD1AB-6, PD1AB-6-K3, or a murine surrogate of PD1AB-6 or PD1AB-6-K3, which retains the PD-1 binding variable region, with Fc region switched to murine IgG2a or murine IgG2a with mutations comparable to K322A) reduce the vitiligo score and the extent of depigmentation of the mice.

Cells are isolated from ears, tails, spleens, and skin-draining lymph nodes at the indicated times (30 min to 14 days post antibody treatment) and processed for flow cytometric analysis for quantifying T cell numbers, activation markers (such as CD25 and CD69), proliferation, intracellular cytokines (such as IFN-γ), and markers for cytotoxic activity (such as Granzyme B and Perforin). The cells are also processed for gene expression analysis, using techniques such as Nanostring, qPCR or RNAseq. Anti-PD-1 antibodies decrease T cell numbers, activation markers on T cells, and IFN-γ, IL-2, TNF-α and GM-CSF levels. The anti-PD-1 antibodies also decrease cytotoxic markers, reduce PD-1 expression on T cells, and inhibit T cell proliferation in vitiligo mice. In addition, the anti-PD1 antibodies increase CD25+Foxp3+ regulatory T cells. For microscopic examination of affected skin, mouse tails or ears are excised and fixed in 10% neutral-buffered formalin. Tissues are embedded in paraffin, sectioned, and stained with hematoxylin and eosin (H+E). Anti-PD-1 antibodies reduce the T cell infiltration in skin.

6. SEQUENCE LISTING

The present specification is being filed with a computer readable form (CRF) copy of the Sequence Listing. The CRF entitled 10624-418-999 SEQLIST.txt, which was created on Sep. 11, 2017 and is 50,874 bytes in size, is identical to the paper copy of the Sequence Listing and is incorporated herein by reference in its entirety.

What is claimed:

1. A method of managing or treating vitiligo in a subject, comprising administering to the subject a therapeutically effective amount of an antibody or antigen-binding fragment thereof that binds to PD-1, wherein the antibody or antigen-binding fragment comprises:
 a light chain variable region (VL) comprising:
  a VL complementarity determining region 1 (CDR1) comprising SEQ ID NO:1,
  a VL CDR2 comprising SEQ ID NO:2, and
  a VL CDR3 comprising SEQ ID NO:3; and
 a heavy chain variable region (VH) comprising:
  a VH CDR1 comprising SEQ ID NO:4,
  a VH CDR2 comprising SEQ ID NO:5, and
  a VH CDR3 comprising SEQ ID NO:6.

2. The method of claim 1, wherein the antibody or antigen-binding fragment comprises a VL comprising an amino acid sequence of SEQ ID NO:8.

3. The method of claim 1, wherein the antibody or antigen-binding fragment comprises a VL comprising an amino acid sequence of SEQ ID NO:10.

4. The method of claim 1, wherein the antibody or antigen-binding fragment comprises a VH comprising an amino acid sequence of SEQ ID NO:11.

5. The method of claim 1, wherein the antibody or antigen-binding fragment comprises a VH comprising an amino acid sequence of SEQ ID NO:12.

6. The method of claim 1, wherein the antibody or antigen-binding fragment comprises a VH comprising an amino acid sequence of SEQ ID NO:13.

7. The method of claim 1, wherein the antibody or antigen-binding fragment comprises
 a VL comprising an amino acid sequence of SEQ ID NO:8; and
 a VH comprising an amino acid sequence of SEQ ID NO:11.

8. The method of claim 1, wherein the antibody or antigen-binding fragment comprises
 a VL comprising an amino acid sequence of SEQ ID NO:8; and
 a VH comprising an amino acid sequence of SEQ ID NO:12.

9. The method of claim 1, wherein the antibody or antigen-binding fragment comprises
 a VL comprising an amino acid sequence of SEQ ID NO:8; and
 a VH comprising an amino acid sequence of SEQ ID NO:13.

10. The method of claim 1, wherein the antibody or antigen-binding fragment comprises
 a VL comprising an amino acid sequence of SEQ ID NO:10; and
 a VH comprising an amino acid sequence of SEQ ID NO:11.

11. The method of claim 1, wherein the antibody or antigen-binding fragment comprises
 a VL comprising an amino acid sequence of SEQ ID NO:10; and
 a VH comprising an amino acid sequence of SEQ ID NO:12.

12. The method of claim 1, wherein the antibody or antigen-binding fragment comprises
 a VL comprising an amino acid sequence of SEQ ID NO:10; and
 a VH comprising an amino acid sequence of SEQ ID NO:13.

13. The method of claim 1, wherein the antibody or antigen-binding fragment comprises a human IgG1 Fc region, or a mutant thereof.

14. The method of claim 9, wherein the antibody or antigen-binding fragment comprises a human IgG1 Fc region, or a mutant thereof.

15. The method of claim 1, wherein the antibody or antigen-binding fragment comprises a human IgG1-K322A Fc region.

16. The method of claim 9, wherein the antibody or antigen-binding fragment comprises a human IgG1-K322A Fc region.

17. The method of 1, wherein the antibody or antigen-binding fragment comprises a human IgG4 Fc region, or a mutant thereof.

18. The method of 9, wherein the antibody or antigen-binding fragment comprises a human IgG4 Fc region, or a mutant thereof.

19. The method of claim 1, wherein the antibody or antigen-binding fragment comprises a human IgG4P Fc region.

20. The method of claim 9, wherein the antibody or antigen-binding fragment comprises a human IgG4P Fc region.

21. The method of claim 1, wherein the antibody or antigen-binding fragment comprises a human IgG4PE Fc region.

22. The method of claim 9, wherein the antibody or antigen-binding fragment comprises a human IgG4PE Fc region.

23. The method of claim 1, wherein the antibody or antigen-binding fragment comprises a heavy chain Fc region comprising an amino acid sequence selected from the group consisting of SEQ ID NO:36, SEQ ID NO:37, SEQ ID NO:38, SEQ ID NO:39 or SEQ ID NO:40.

24. The method of claim 7, wherein the antibody or antigen-binding fragment comprises a heavy chain Fc region comprising an amino acid sequence selected from the group consisting of SEQ ID NO:36, SEQ ID NO:37, SEQ ID NO:38, SEQ ID NO:39 or SEQ ID NO:40.

25. The method of claim 8, wherein the antibody or antigen-binding fragment comprises a heavy chain Fc region comprising an amino acid sequence selected from the group consisting of SEQ ID NO:36, SEQ ID NO:37, SEQ ID NO:38, SEQ ID NO:39 or SEQ ID NO:40.

26. The method of claim 9, wherein the antibody or antigen-binding fragment comprises a heavy chain Fc region comprising an amino acid sequence selected from the group consisting of SEQ ID NO:36, SEQ ID NO:37, SEQ ID NO:38, SEQ ID NO:39 or SEQ ID NO:40.

27. The method of claim 10, wherein the antibody or antigen-binding fragment comprises a heavy chain Fc region comprising an amino acid sequence selected from the group consisting of SEQ ID NO:36, SEQ ID NO:37, SEQ ID NO:38, SEQ ID NO:39 or SEQ ID NO:40.

28. The method of claim 11, wherein the antibody or antigen-binding fragment comprises a heavy chain Fc region comprising an amino acid sequence selected from the group consisting of SEQ ID NO:36, SEQ ID NO:37, SEQ ID NO:38, SEQ ID NO:39 or SEQ ID NO:40.

29. The method of claim 12, wherein the antibody or antigen-binding fragment comprises a heavy chain Fc region comprising an amino acid sequence selected from the group consisting of SEQ ID NO:36, SEQ ID NO:37, SEQ ID NO:38, SEQ ID NO:39 or SEQ ID NO:40.

30. The method of claim 1, wherein the antibody or antigen-binding fragment comprises a light chain constant region comprising an amino acid sequence of SEQ ID NO:41.

31. The method of claim 7, wherein the antibody or antigen-binding fragment comprises a light chain constant region comprising an amino acid sequence of SEQ ID NO:41.

32. The method of claim 8, wherein the antibody or antigen-binding fragment comprises a light chain constant region comprising an amino acid sequence of SEQ ID NO:41.

33. The method of claim 9, wherein the antibody or antigen-binding fragment comprises a light chain constant region comprising an amino acid sequence of SEQ ID NO:41.

34. The method of claim 10, wherein the antibody or antigen-binding fragment comprises a light chain constant region comprising an amino acid sequence of SEQ ID NO:41.

35. The method of claim 11, wherein the antibody or antigen-binding fragment comprises a light chain constant region comprising an amino acid sequence of SEQ ID NO:41.

36. The method of claim 12, wherein the antibody or antigen-binding fragment comprises a light chain constant region comprising an amino acid sequence of SEQ ID NO:41.

37. The method of claim 23, wherein the antibody or antigen-binding fragment further comprises a light chain constant region comprising an amino acid sequence of SEQ ID NO:41.

38. The method of claim 24, wherein the antibody or antigen-binding fragment comprises a light chain constant region comprising an amino acid sequence of SEQ ID NO:41.

39. The method of claim 25, wherein the antibody or antigen-binding fragment comprises a light chain constant region comprising an amino acid sequence of SEQ ID NO:41.

40. The method of claim 26, wherein the antibody or antigen-binding fragment comprises a light chain constant region comprising an amino acid sequence of SEQ ID NO:41.

41. The method of claim 27, wherein the antibody or antigen-binding fragment comprises a light chain constant region comprising an amino acid sequence of SEQ ID NO:41.

42. The method of claim 28, wherein the antibody or antigen-binding fragment comprises a light chain constant region comprising an amino acid sequence of SEQ ID NO:41.

43. The method of claim 29, wherein the antibody or antigen-binding fragment comprises a light chain constant region comprising an amino acid sequence of SEQ ID NO:41.

44. The method of claim 1, wherein the antibody or antigen-binding fragment comprises a light chain comprising an amino acid sequence of SEQ ID NO:31.

45. The method of claim 1, wherein the antibody or antigen-binding fragment comprises a heavy chain comprising an amino acid sequence of SEQ ID NO:32.

46. The method of claim 1, wherein the antibody or antigen-binding fragment comprises:
a light chain comprising an amino acid sequence of SEQ ID NO:31; and
a heavy chain comprising an amino acid sequence of SEQ ID NO:32.

47. The method of claim 1, wherein the antibody or antigen-binding fragment comprises a heavy chain comprising an amino acid sequence of SEQ ID NO:33.

48. The method of claim 1, wherein the antibody or antigen-binding fragment comprises:
a light chain comprising an amino acid sequence of SEQ ID NO:31; and
a heavy chain comprising an amino acid sequence of SEQ ID NO:33.

49. The method of claim 1, wherein the antibody or antigen-binding fragment comprises a heavy chain comprising an amino acid sequence of SEQ ID NO:34.

50. The method of claim 1, wherein the antibody or antigen-binding fragment comprises:
a light chain comprising an amino acid sequence of SEQ ID NO:31; and
a heavy chain comprising an amino acid sequence of SEQ ID NO:34.

51. The method of claim 1, wherein the antibody or antigen-binding fragment comprises a heavy chain comprising an amino acid sequence of SEQ ID NO:35.

52. The method of claim 1, wherein the antibody or antigen-binding fragment comprises:
a light chain comprising an amino acid sequence of SEQ ID NO:31; and
a heavy chain comprising an amino acid sequence of SEQ ID NO:35.

53. The method of claim 1, wherein the antibody or antigen-binding fragment specifically binds to human PD-1 and/or monkey PD-1, but not rodent PD-1.

54. The method of claim 53, wherein the $K_D$ for binding to purified human PD-1 is from about 100 pM to about 10 nM, and the $K_D$ for binding to human PD-1 expressed on cell surface and monkey PD-1 expressed on cell surface is from about 100 pM to about 10 nM.

55. The method of claim 1, wherein the antibody or antigen-binding fragment has attenuated ADCC activity and/or attenuated CDC activity.

56. The method of claim 1, wherein the antibody is a monoclonal antibody.

57. The method of claim 1, wherein the antibody is a humanized antibody.

58. The method of claim 1, wherein the antibody is a human antibody.

59. The method of claim 1, wherein the antibody is a chimeric antibody.

60. The method of claim 57, wherein the humanized antibody is a deimmunized antibody.

61. The method of claim 57, wherein the humanized antibody is a composite human antibody.

62. The method of claim 1 wherein the antibody or antigen-binding fragment is a Fab, a Fab', a F(ab')$_2$, a Fv, a scFv, a dsFv, a diabody, a triabody, a tetrabody, or a multispecific antibody formed from antibody fragments.

63. The method of claim 1, wherein the antibody or antigen-binding fragment is conjugated to an agent.

64. The method of claim 63, wherein the agent is selected from the group consisting of a radioisotope, a metal chelator, an enzyme, a fluorescent compound, a bioluminescent compound, and a chemiluminescent compound.

65. The method of claim 1, wherein the antibody or antigen-binding fragment further comprises a pharmaceutically acceptable carrier.

66. The method of claim 1, wherein the immune cells in the subject express PD-1.

\* \* \* \* \*